United States Patent
Nolte et al.

(10) Patent No.: US 10,865,249 B2
(45) Date of Patent: Dec. 15, 2020

(54) ANTIGEN-BINDING POLYPEPTIDES DIRECTED AGAINST CD38

(71) Applicant: University Medical Center Hamburg-Eppendorf, Hamburg (DE)

(72) Inventors: Friedrich Nolte, Hamburg (DE); Peter Bannas, Hamburg (DE); Kerstin Schütze, Hamburg (DE); William Fumey, Hamburg (DE); Levin Schriewer, Hamburg (DE); Stephan Menzel, Hamburg (DE); Catelijne Stortelers, Ghent (BE)

(73) Assignee: University Medical Center Hamburg-Eppendorf, Hamburg (DE)

( * ) Notice: Subject to any disclaimer, the term of this patent is extended or adjusted under 35 U.S.C. 154(b) by 0 days.

(21) Appl. No.: 15/774,919

(22) PCT Filed: Nov. 10, 2016

(86) PCT No.: PCT/EP2016/077361
§ 371 (c)(1),
(2) Date: May 9, 2018

(87) PCT Pub. No.: WO2017/081211
PCT Pub. Date: May 18, 2017

(65) Prior Publication Data
US 2019/0276551 A1    Sep. 12, 2019

Related U.S. Application Data

(60) Provisional application No. 62/253,318, filed on Nov. 10, 2015.

(51) Int. Cl.
| | | |
|---|---|---|
| *C07K 16/28* | (2006.01) |
| *G01N 33/53* | (2006.01) |
| *A61P 37/06* | (2006.01) |
| *C12N 15/86* | (2006.01) |
| *C12Q 1/25* | (2006.01) |
| *A61K 39/00* | (2006.01) |

(52) U.S. Cl.
CPC .......... *C07K 16/2896* (2013.01); *A61P 37/06* (2018.01); *C12N 15/86* (2013.01); *C12Q 1/25* (2013.01); *G01N 33/53* (2013.01); *A61K 2039/505* (2013.01); *C07K 2317/22* (2013.01); *C07K 2317/31* (2013.01); *C07K 2317/64* (2013.01); *C07K 2317/732* (2013.01); *C07K 2317/734* (2013.01); *C07K 2317/75* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | | |
|---|---|---|---|
| CN | 103421115 A | | 12/2013 |
| WO | WO 2007/066109 | * | 6/2007 |
| WO | WO 2007/066109 A1 | | 6/2007 |

OTHER PUBLICATIONS

Unger et al (Nano Temper Technologies, Application Note NT0011, 2012, 3 pages, IDS).*
Revets et al (Expert Opinion on Biological Therapy, 2005, 5:1, 111-124).*
Ausiello et al., Functional topography of discrete domains of human CD38. Tissue Antigens. Dec. 2000;56(6):539-47.
Bannas et al., Vergleich von CD38-spezifischen Nanobodies and konventionellen Antikörpern für die Nah-Infrarot-Fluoreszenz Bildgebung von Lymphomen in vitro. Fortschr Röntgenstr 2013. Retrieved from https://www.thieme-connect.de/DOI/DOI?10.1055/s-0033-1346241 on Jan. 19, 2017. 5-6.
Hoshino et al., Mapping of the catalytic and epitopic sites of human CD38/NAD+ glycohydrolase to a functional domain in the carboxyl terminus. J Immunol. Jan. 15, 1997;158(2):741-7.
Unger et al., Antibody-antigen interaction analysis using MST to analyse the binding of nanobodies and nanobody-Fc fusion proteins to human CD38. Jan. 1, 2012. www.nanotemper.de.

* cited by examiner

*Primary Examiner* — Laura B Goddard
(74) *Attorney, Agent, or Firm* — Hovey Williams LLP

(57) ABSTRACT

The invention relates to polypeptides specifically binding to CD38 and are therefore suitable for the diagnosis and for the therapeutic and prophylactic treatment of diseases which are characterized by increased CD38 expression. Conjugates and pharmaceutical compositions comprising the polypeptides are disclosed as well. In addition, the invention relates to the use of such polypeptides in methods for the detection of CD38 and/or CD38-expressing cells in a biological sample. A process for the purification and concentration of CD38 and/or CD38-expressing cells in which the antigen-binding polypeptides are used are also described.

17 Claims, 18 Drawing Sheets
Specification includes a Sequence Listing.

Figure 2
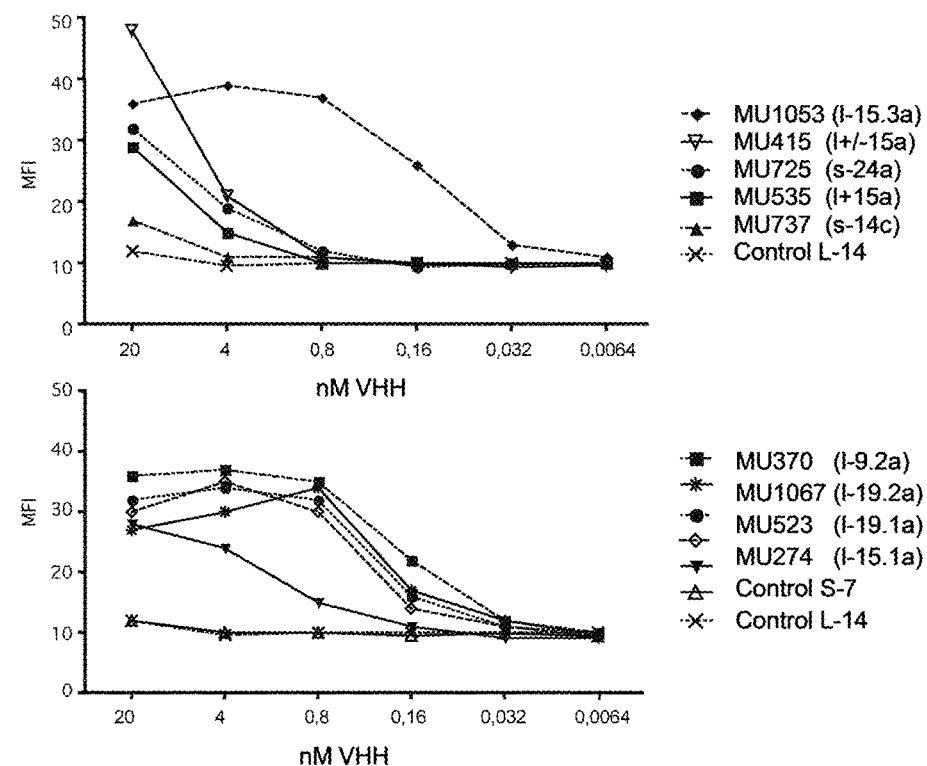
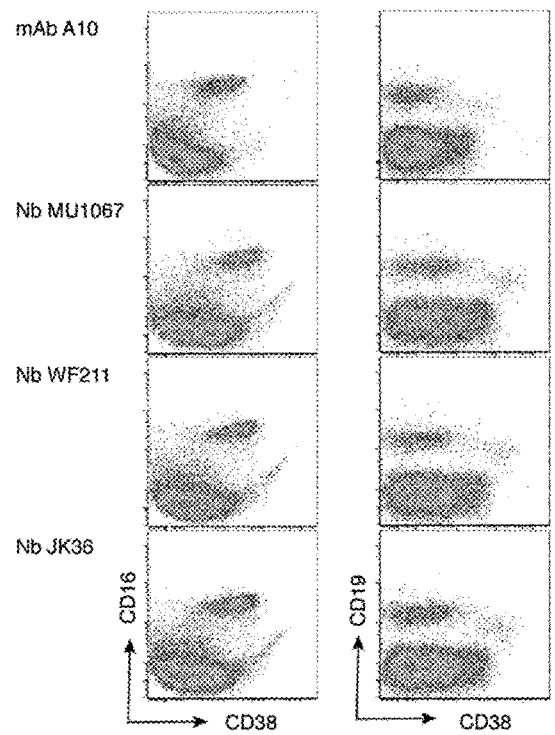

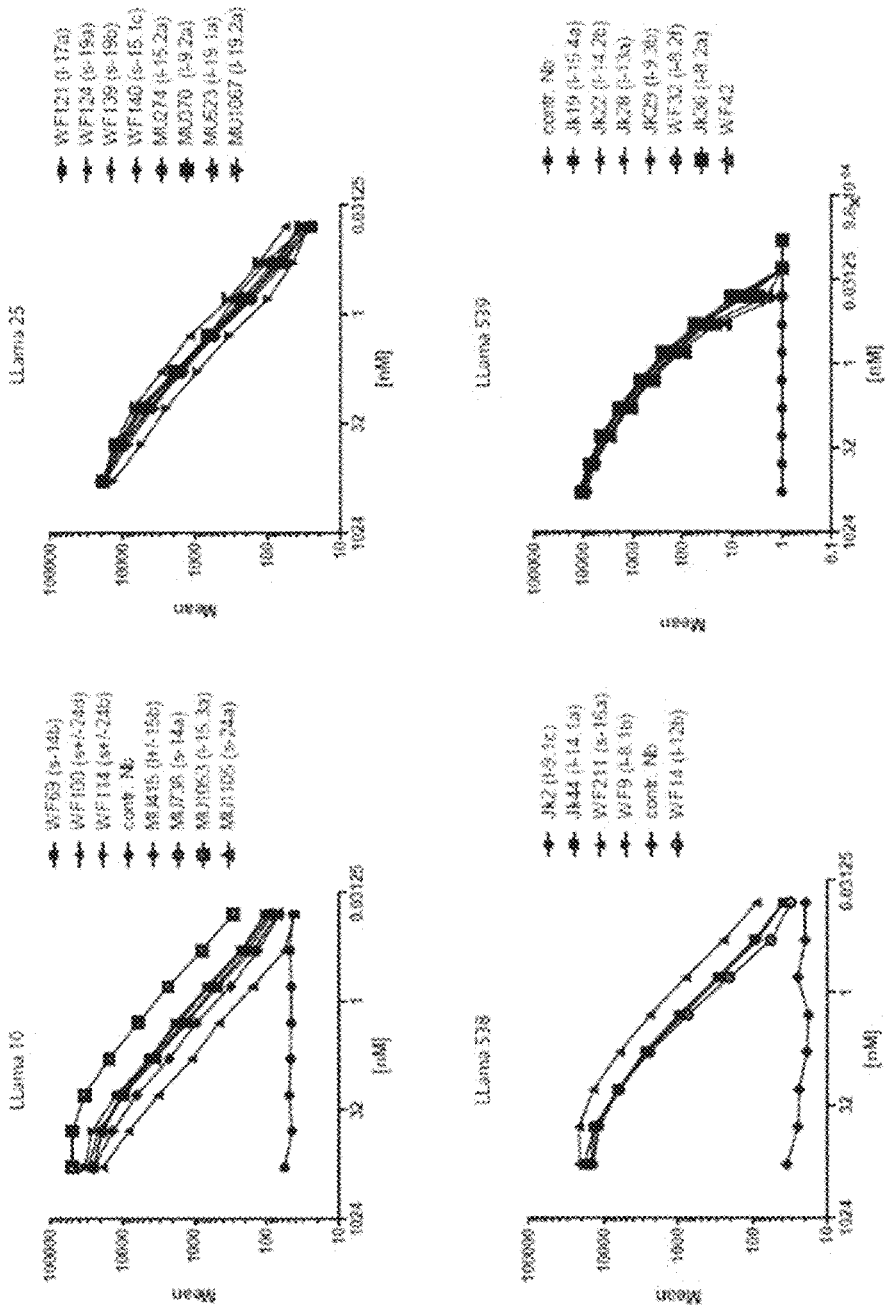
(Figure 2 continued)

Figure 3

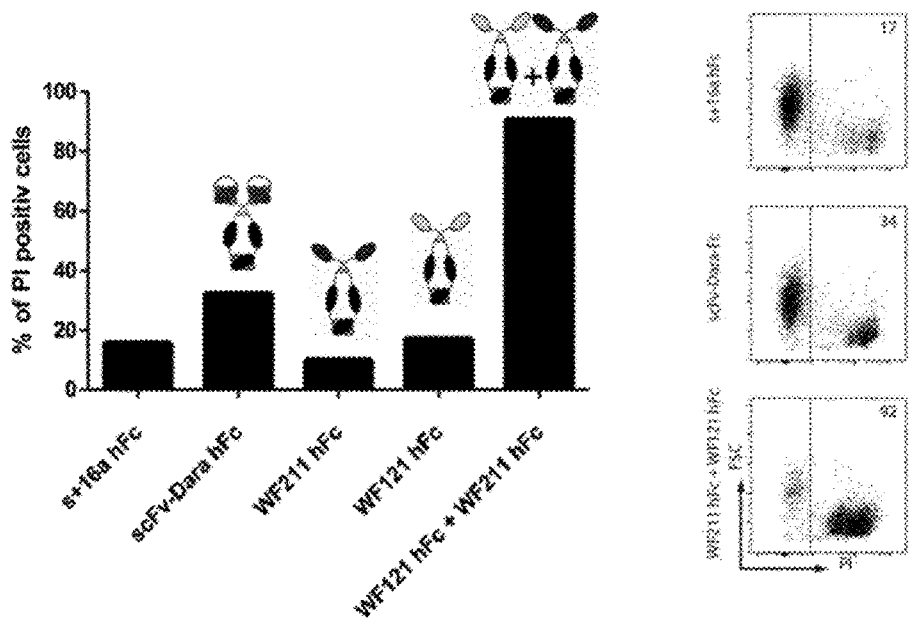

LP-1 myeloma cells were incubated with 2 µg Fc-fusion proteins in the presence of 20% pooled human serum as a source of complement for 1 hour at 37°. Cell death was determined by uptake of propidium iodide.

Figure 4

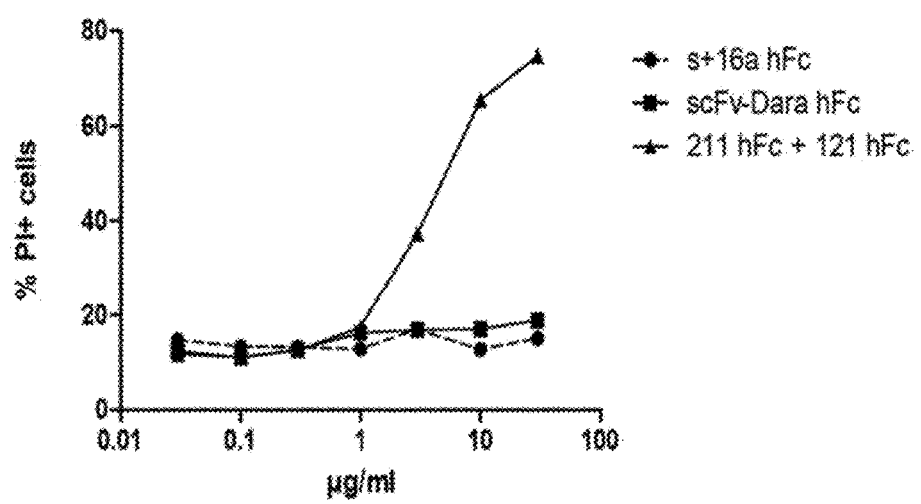

LP-1 myeloma cells were incubated with different concentrations of Fc-Fusionprotein in the presence of 20% pooled human serum as a source of complement for 2 hours at 37°. Cell death was determined by propidium iodide staining.

A

B

Figure 16
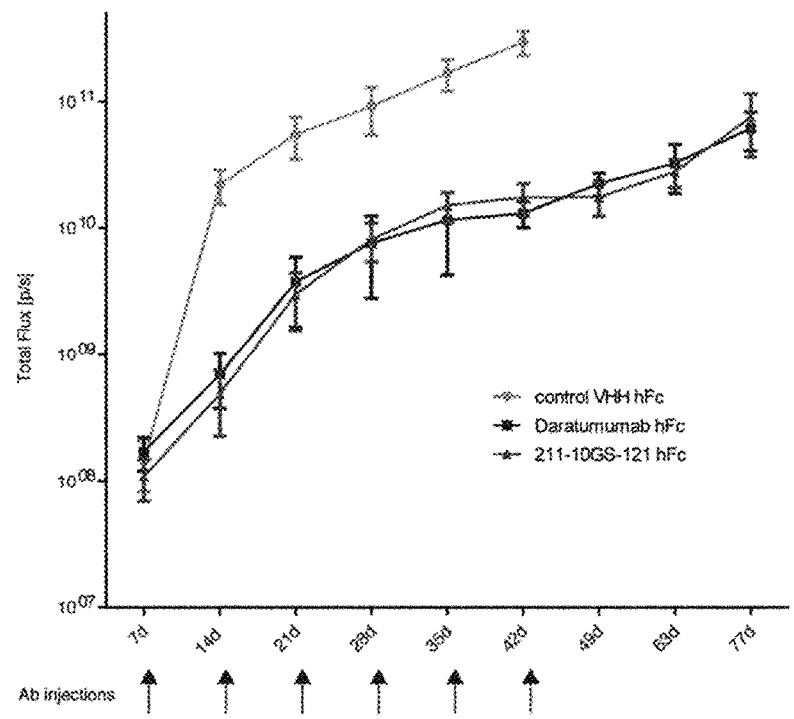
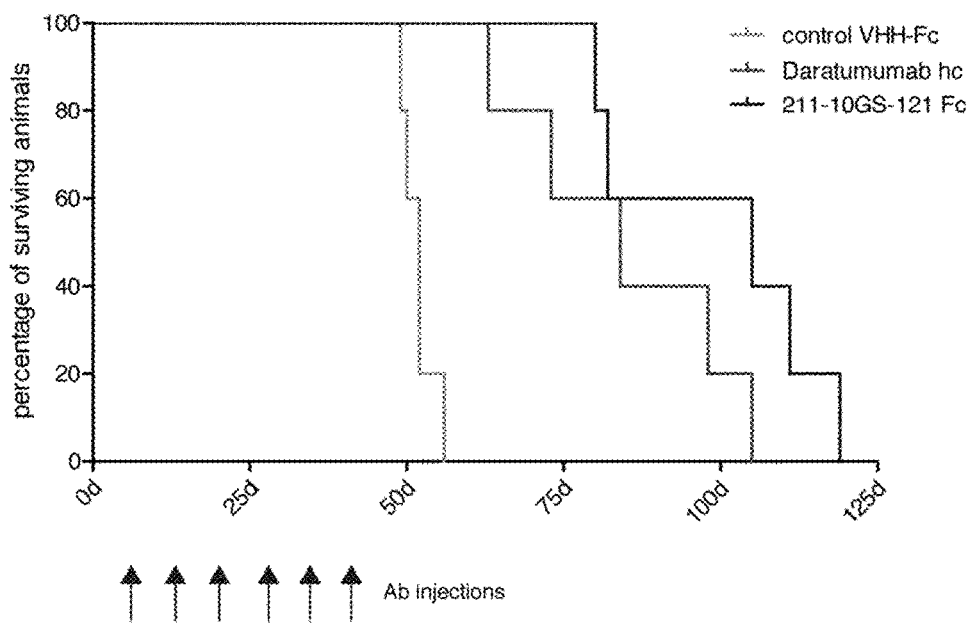

SEQUENCE LISTING

<160> NUMBER OF SEQ ID NOS: 494

<210> SEQ ID NO 1
<211> LENGTH: 116
<212> TYPE: PRT
<213> ORGANISM: Artificial Sequence
<220> FEATURE:
<223> OTHER INFORMATION: CDR sequence

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Gly Ala Thr Gly Ile Ile Phe Ser Ile Asn
            20                  25                  30

```
Asp Met Gly Trp Tyr Arg Gln Ala Pro Gly Lys Gln Arg Glu Leu Val
        35                  40                  45

Ala Glu Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Asn Pro Glu Asp Thr Ala Val Tyr Tyr Cys Asn
                 85                  90                  95

Ala Ala His Thr Phe Ser Gly Ser Phe Trp Gly Gln Gly Thr Gln Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: CDR sequence

<400> SEQUENCE: 2

Gln Val Gln Leu Gln Glu Ser Gly Gly Gly Leu Val Gln Pro Gly Gly
 1               5                  10                  15

Ser Leu Arg Leu Ser Cys Gly Ala Thr Gly Ile Ile Phe Ser Ile Asn
             20                  25                  30

Asp Met Gly Trp Tyr Arg Gln Ala Pro Gly Lys Gln Arg Glu Leu Val
        35                  40                  45

Ala Glu Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Asn Pro Glu Asp Thr Ala Val Tyr Tyr Cys Asn
                 85                  90                  95

Ala Ala His Thr Phe Ser Gly Ser Phe Trp Gly Gln Gly Thr Gln Val
            100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: CDR sequence

<400> SEQUENCE: 3

Gln Val Lys Leu Gln Glu Ser Gly Gly Gly Leu Val Gln Pro Gly Gly
 1               5                  10                  15

Ser Leu Arg Leu Ser Cys Gly Ala Thr Gly Ile Ile Phe Ser Ile Asn
             20                  25                  30

Asp Met Gly Trp Tyr Arg Gln Ala Pro Gly Lys Gln Arg Glu Leu Val
        35                  40                  45

Ala Glu Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Asn Pro Glu Asp Thr Ala Val Tyr Tyr Cys Asn
```

```
                    85                  90                  95
Ala Ala His Thr Phe Ser Gly Ser Phe Trp Gly Gln Gly Thr Gln Val
                   100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: CDR sequence

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Ile Leu Arg Ile Tyr
            20                  25                  30

Asp Met Gly Trp Tyr Arg Gln Ala Pro Gly Lys Gln Arg Glu Leu Val
        35                  40                  45

Ala Ala Ile Thr Ser Arg Gly Ser Thr Asn Tyr Ala Asp Ser Val Lys
50                  55                  60

Gly Arg Phe Thr Ile Ser Arg Asp Asn Ala Glu Asn Thr Val Ser Leu
65                  70                  75                  80

Gln Met Asn Ser Leu Lys Pro Gly Asp Thr Ala Val Tyr Tyr Cys Asn
                85                  90                  95

Ala Asp His Thr Phe Ala Gly Val Tyr Trp Gly Gln Gly Thr Gln Val
                   100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: CDR sequence

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Ile Leu Arg Ile Tyr
            20                  25                  30

Asp Met Gly Trp Tyr Arg Gln Ala Pro Gly Lys Gln Arg Glu Leu Val
        35                  40                  45

Ala Ala Ile Thr Ser Gly Gly Arg Thr Asn Tyr Ala Asp Ser Val Lys
50                  55                  60

Gly Arg Phe Thr Ile Ser Arg Asp Asn Ala Glu Asn Thr Val Ser Leu
65                  70                  75                  80

Gln Met Asn Ser Leu Lys Ser Gly Asp Thr Ala Val Tyr Tyr Cys Asn
                85                  90                  95

Ala Asp His Thr Phe Ala Gly Val Tyr Trp Gly Gln Gly Thr Gln Val
                   100                 105                 110

Thr Val Ser Ser
        115

<210> SEQ ID NO 6
<211> LENGTH: 116
```

```
<212> TYPE: PRT
<213> ORGANISM: Artificial Sequence
<220> FEATURE:
<223> OTHER INFORMATION: CDR sequence

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Ile Leu Arg Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Gly Gly Ser Thr Asn Tyr Ala Asp Ser Val Lys
    50                  55                  60

Gly Arg Phe Thr Ile Ser Arg Asp Asn Ala Glu Asn Thr Val Ser Leu
65                  70                  75                  80

Gln Met Asn Ser Leu Lys Pro Gly Asp Thr Ala Val Tyr Tyr Cys Asn
                85                  90                  95

Ala His His Thr Phe Ala Gly Ala Tyr Trp Gly Gln Gly Thr Gln Val
            100                 105                 110

Thr Val Ser Ser
            115

<210> SEQ ID NO 7
<211> LENGTH: 116
<212> TYPE: PRT
<213> ORGANISM: Artificial Sequence
<220> FEATURE:
<223> OTHER INFORMATION: CDR sequence

<400> SEQUENCE: 7

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Ile Leu Arg Leu Tyr
            20                  25                  30

Asp Met Gly Trp Tyr Arg Gln Thr Pro Gly Lys Gln Arg Glu Leu Val
        35                  40                  45

Ala Glu Ile Thr Ser Gly Gly Ser Thr Asn Tyr Ala Asp Ser Val Lys
    50                  55                  60

Gly Arg Phe Thr Ile Ser Arg Asp Asn Ala Glu Asn Thr Val Ser Leu
65                  70                  75                  80

Gln Met Asn Ser Leu Lys Ser Gly Asp Thr Ala Val Tyr Tyr Cys Asn
                85                  90                  95

Ala Asp His Thr Phe Ala Gly Val Tyr Trp Gly Gln Gly Thr Gln Val
            100                 105                 110

Thr Val Ser Ser
            115

<210> SEQ ID NO 8
<211> LENGTH: 116
<212> TYPE: PRT
<213> ORGANISM: Artificial Sequence
<220> FEATURE:
<223> OTHER INFORMATION: CDR sequence

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Leu Arg Leu Tyr
```

```
                20                  25                  30
Asp Met Gly Trp Tyr Arg Gln Ala Asp Gly Lys Gln Arg Glu Leu Val
        35                  40                  45

Ala Glu Ile Thr Ser Gly Gly Ser Thr Asn Tyr Ala Asn Ser Val Lys
 50                  55                  60

Gly Arg Phe Thr Ile Ser Arg Asp Asn Ala Glu Asn Thr Val Ser Leu
 65                  70                  75                  80

Gln Met Asn Ser Leu Lys Pro Glu Asp Thr Ala Val Tyr Tyr Cys Asn
                85                  90                  95

Ala Glu His Thr Phe Met Gly Ala Tyr Trp Gly Gln Gly Thr Gln Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: CDR sequence

<400> SEQUENCE: 9

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ile Ile Leu Arg Ile Tyr
                20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Ser Met Val Tyr Leu
 65                  70                  75                  80

Gln Met Asn Ser Leu Lys Pro Glu Asp Thr Ala Val Tyr Tyr Cys Asn
                85                  90                  95

Ala Trp His Val Phe Arg Gly Asn Tyr Trp Gly Gln Gly Thr Gln Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: CDR sequence

<400> SEQUENCE: 10

Gln Val Gln Leu Gln Glu Ser Gly Gly Gly Leu Val Gln Ala Gly Gly
  1               5                  10                  15

Ser Leu Thr Leu Ser Cys Ala Ala Ser Arg Asn Thr Asp Ser Ile Glu
                20                  25                  30

Ile Met Gly Trp Tyr Arg Gln Ala Pro Gly Lys Gln Arg Glu Trp Val
        35                  40                  45

Ala Thr Ile Asn Thr Gly Gly Asn Thr Gly Tyr Ala Asp Ser Val Lys
 50                  55                  60

Gly Arg Phe Ala Ile Ser Arg Asp Asn Ala Lys Asn Thr Val Tyr Leu
 65                  70                  75                  80
```

Gln Met His Ser Leu Lys Pro Glu Asp Thr Ala Val Tyr Tyr Cys Thr
            85                  90                  95

Ala Val Ile Arg Thr Tyr Ser Thr Tyr Trp Gly Gln Gly Thr Gln Val
            100                 105                 110

Thr Val Ser Ser
            115

<210> SEQ ID NO 11
<211> LENGTH: 117
<212> TYPE: PRT
<213> ORGANISM: Artificial Sequence
<220> FEATURE:
<223> OTHER INFORMATION: CDR sequence

<400> SEQUENCE: 11

Gln Val Gln Leu Gln Glu Ser Gly Gly Gly Leu Val Gln Pro Gly Gly
1               5                   10                  15

Ser Leu Arg Leu Ser Cys Val Ala Ser Glu Arg Ile Phe Ser Arg Asn
            20                  25                  30

Thr Met Gly Trp Tyr Arg Gln Ala Pro Gly Lys Gln Arg Glu Leu Val
            35                  40                  45

Ala Arg Ile Ala Ser Leu Gly Ile Thr Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Asn Leu Lys Pro Glu Asp Thr Ala Val Tyr Tyr Cys Asn
            85                  90                  95

Tyr Trp His Tyr Ala Ala Gly Arg Asp Tyr Trp Gly Gln Gly Thr Gln
            100                 105                 110

Val Thr Val Ser Ser
            115

<210> SEQ ID NO 12
<211> LENGTH: 117
<212> TYPE: PRT
<213> ORGANISM: Artificial Sequence
<220> FEATURE:
<223> OTHER INFORMATION: CDR sequence

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Val Ala Ser Glu Arg Ile Phe Ser Arg Asn
            20                  25                  30

Thr Met Gly Trp Tyr Arg Gln Ala Pro Gly Lys Gln Arg Glu Leu Val
            35                  40                  45

Ala Arg Ile Ala Ser Leu Gly Ile Thr Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Asn Leu Lys Pro Glu Asp Thr Ala Val Tyr Tyr Cys Asn
            85                  90                  95

Tyr Trp His Tyr Ala Ala Gly Arg Asp Tyr Trp Gly Gln Gly Thr Gln
            100                 105                 110

Val Thr Val Ser Ser
            115

<210> SEQ ID NO 13

```
<211> LENGTH: 117
<212> TYPE: PRT
<213> ORGANISM: Artificial Sequence
<220> FEATURE:
<223> OTHER INFORMATION: CDR sequence

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Val Gly Ser Glu Arg Ile Phe Ser Arg Asn
            20                  25                  30

Thr Met Gly Trp Tyr Arg Gln Ala Pro Gly Lys Gln Arg Glu Leu Val
        35                  40                  45

Gly Tyr Val Gly Ser Met Gly Ile Thr Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Tyr Trp His Tyr Ala Ala Gly Arg Asp Tyr Trp Gly Gln Gly Thr Gln
            100                 105                 110

Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: CDR sequence

<400> SEQUENCE: 14

Gln Val Lys Leu Gln Glu Ser Gly Gly Gly Leu Val Gln Pro Gly Gly
1               5                   10                  15

Ser Leu Arg Leu Ser Cys Val Ala Ser Glu Arg Ile Phe Ser Arg Asn
            20                  25                  30

Thr Met Gly Trp Tyr Arg Gln Ala Pro Gly Lys Gln Arg Glu Leu Val
        35                  40                  45

Ala Tyr Ile Thr Ser Leu Gly Ile Ala Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Asn Leu Lys Ser Glu Asp Thr Ala Val Tyr Asn Cys Asn
                85                  90                  95

Tyr Trp His Tyr Ala Ala Gly Arg Asp Tyr Trp Gly Gln Gly Thr Gln
            100                 105                 110

Val Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: CDR sequence

<400> SEQUENCE: 15

Asp Val Gln Leu Gln Ala Ser Gly Gly Gly Ser Val Gln Ala Gly Gly
1               5                   10                  15
```

```
Ser Leu Thr Leu Ser Cys Arg Tyr Ser Gly Phe Val Phe Arg Val
            20                  25                  30

Ser Ser Met Gly Trp Tyr Arg Gln Ala Pro Gly Asn Gln Arg Glu Leu
        35                  40                  45

Ile Ala Thr Ile Thr Val Gly Gly Lys Thr Asn Tyr Lys Asp Ser Val
50                  55                  60

Gln Gly Arg Phe Ile Ile Ser Arg Asn Asp Thr Val Thr Leu Gln
65                  70                  75                  80

Met Asn Arg Leu Gln Pro Glu Asp Thr Ala Val Tyr Tyr Cys Asn Leu
                85                  90                  95

Ala Ser Thr Ala Val Gly Ala Asp Thr Trp Gly Gln Gly Thr Arg Val
            100                 105                 110

Thr Val Ser Ser
        115
```

<210> SEQ ID NO 16
<211> LENGTH: 121
<212> TYPE: PRT
<213> ORGANISM: Artificial Sequence
<220> FEATURE:
<223> OTHER INFORMATION: CDR sequence

<400> SEQUENCE: 16

```
Asp Val Gln Leu Gln Glu Ser Gly Gly Gly Ser Val Gln Ala Gly Gly
1               5                   10                  15

Ser Leu Thr Leu Ser Cys Thr Ala Ser Gly Leu Leu Phe Arg Leu Ala
            20                  25                  30

Ser Met Gly Trp Tyr Arg Gln Ala Pro Gly Lys Glu Arg Glu Leu Ile
        35                  40                  45

Ala Thr Ile Thr Val Gly Gly Lys Thr Asn Tyr Lys Asp Ser Val Gln
50                  55                  60

Gly Arg Phe Ile Ile Thr Arg Asp Asn Thr Gly Asp Asn Thr Lys Ser
65                  70                  75                  80

Thr Val Thr Leu Gln Met Asn Arg Leu Lys Pro Glu Asp Thr Ala Val
                85                  90                  95

Tyr Tyr Cys Asn Thr Ala Ser Pro Ala Val Gly Ala Asp Thr Trp Gly
            100                 105                 110

Gln Gly Thr Arg Val Thr Val Ser Ser
        115                 120
```

<210> SEQ ID NO 17
<211> LENGTH: 117
<212> TYPE: PRT
<213> ORGANISM: Artificial Sequence
<220> FEATURE:
<223> OTHER INFORMATION: CDR sequence

<400> SEQUENCE: 17

```
Gln Val Lys Leu Gln Glu Ser Gly Gly Gly Leu Val Gln Pro Gly Gly
1               5                   10                  15

Ser Leu Arg Leu Ser Cys Val Ala Ser Gly Ser Ile Ser Ser Ile Ile
            20                  25                  30

Thr Met Gly Trp Tyr Arg Gln Ala Pro Gly Lys Gln Arg Glu Phe Val
        35                  40                  45

Ala Arg Val Ile Ile Gly Gly Ser Thr Gly Tyr Ala Asp Ser Val Lys
50                  55                  60

Gly Arg Phe Thr Ile Ser Arg Asp Asn Thr Lys Asn Thr Val Tyr Leu
65                  70                  75                  80
```

Glu Met Asn Ser Leu Lys Pro Glu Asp Thr Ala Val Tyr Tyr Cys Asn
            85                  90                  95

Ala Gly Asn Pro Gly Thr Ser Tyr His Tyr Trp Gly Gln Gly Thr Gln
            100                 105                 110

Val Thr Val Ser Ser
            115

<210> SEQ ID NO 18
<211> LENGTH: 117
<212> TYPE: PRT
<213> ORGANISM: Artificial Sequence
<220> FEATURE:
<223> OTHER INFORMATION: CDR sequence

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Ile Ser Asn Ile Ile
            20                  25                  30

Thr Met Gly Trp Tyr Arg Gln Ala Pro Gly Lys Gln Arg Glu Phe Val
            35                  40                  45

Ala Arg Ile Ile Gly Gly Ser Thr Gly Tyr Ser Asp Ser Val Lys
    50                  55                  60

Gly Arg Phe Thr Ile Ser Arg Asp Asn Thr Gly Asn Thr Trp Tyr Leu
65                  70                  75                  80

Gln Met Asn Ser Leu Lys Pro Glu Asp Thr Ala Val Tyr Tyr Cys Asn
            85                  90                  95

Ala Gly Asn Pro Gly Thr Arg Tyr Ile Tyr Trp Gly Gln Gly Thr Gln
            100                 105                 110

Val Thr Val Ser Ser
            115

<210> SEQ ID NO 19
<211> LENGTH: 121
<212> TYPE: PRT
<213> ORGANISM: Artificial Sequence
<220> FEATURE:
<223> OTHER INFORMATION: CDR sequence

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Val
            20                  25                  30

Ala Met Gly Trp Phe Arg Gln Ala Pro Gly Lys Glu Arg Glu Phe Val
            35                  40                  45

Ala Thr Ile Asn Trp Ser Gly Gly Arg Thr Thr Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Arg Phe Ser Val Val Ala Val Glu Tyr Asp Tyr Trp Gly
            100                 105                 110

Gln Gly Thr Gln Val Thr Val Ser Ser
            115                 120

```
<210> SEQ ID NO 20
<211> LENGTH: 121
<212> TYPE: PRT
<213> ORGANISM: Artificial Sequence
<220> FEATURE:
<223> OTHER INFORMATION: CDR sequence

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Val
                20                  25                  30

Ala Met Gly Trp Phe Arg Gln Ala Pro Gly Arg Glu Arg Glu Phe Val
            35                  40                  45

Ala Thr Ile Asn Trp Ser Gly Arg Thr Thr Tyr Ala Asp Ser Val
        50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Arg Phe Ser Val Val Ala Val Glu Tyr Asp Tyr Trp Gly
            100                 105                 110

Gln Gly Thr Gln Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: CDR sequence

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ile Ser Gly Arg Thr Phe Ile Ala Asp
                20                  25                  30

Met Gly Trp Phe Arg Gln Ala Pro Gly Lys Glu Arg Glu Phe Gln Ala
            35                  40                  45

Gly Ile Thr Trp Phe Gly Ser Thr Tyr Tyr Ala Asp Ser Val Lys
        50                  55                  60

Gly Arg Phe Thr Ile Ser Arg Asp Asn Thr Lys Asn Thr Leu Tyr Leu
65                  70                  75                  80

Gln Met Asn Ser Leu Lys Pro Glu Asp Thr Ala Ile Tyr Tyr Cys Ala
                85                  90                  95

Ala Gly Leu Lys Arg Ile Gly Asp Gln Arg Glu Ala Asp Tyr Trp Gly
            100                 105                 110

Gln Gly Thr Gln Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: CDR sequence

<400> SEQUENCE: 22

Glu Val Gln Leu Val Glu Ser Gly Gly Gly Leu Val Gln Ala Gly Gly
1               5                   10                  15
```

-continued

```
Ser Leu Arg Leu Ser Cys Ala Ile Ser Gly Arg Thr Phe Ile Ala Asp
        20                  25                  30

Met Gly Trp Phe Arg Gln Ala Pro Gly Lys Glu Arg Glu Phe Gln Ala
            35                  40                  45

Gly Ile Thr Trp Phe Gly Gly Ser Thr Tyr Tyr Ala Asp Ser Val Lys
    50                  55                  60

Gly Arg Phe Thr Ile Ser Arg Asp Asn Thr Lys Asn Thr Leu Tyr Leu
65                  70                  75                  80

Gln Met Asn Ser Leu Lys Pro Glu Asp Thr Ala Ile Tyr Tyr Cys Ala
                85                  90                  95

Ala Gly Leu Lys Arg Ile Gly Asp Gln Arg Glu Ala Asp Tyr Trp Gly
            100                 105                 110

Gln Gly Thr Gln Val Thr Val Ala Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: CDR sequence

<400> SEQUENCE: 23

Gln Val Gln Leu Gln Glu Ser Gly Gly Leu Val Gln Ala Gly Gly
1               5                   10                  15

Ser Val Arg Leu Ser Cys Ala Ile Ser Gly Arg Thr Phe Ile Asn Asp
        20                  25                  30

Met Gly Trp Phe Arg Gln Ala Pro Gly Lys Glu Arg Glu Phe Gln Ala
            35                  40                  45

Gly Ile Thr Trp Phe Gly Gly Ser Thr Tyr Tyr Ala Asp Ser Val Lys
    50                  55                  60

Gly Arg Phe Thr Ile Ser Arg Asp Asn Thr Lys Asn Thr Leu Tyr Leu
65                  70                  75                  80

Gln Met Asn Ser Leu Lys Pro Glu Asp Thr Ala Ile Tyr Tyr Cys Ala
                85                  90                  95

Ala Gly Leu Lys Arg Ile Gly Asp Gln Arg Glu Ala Asp Tyr Trp Gly
            100                 105                 110

Gln Gly Thr Gln Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: CDR sequence

<400> SEQUENCE: 24

Asp Val Gln Leu Gln Ala Ser Gly Gly Gly Leu Val Gln Ala Gly Gly
1               5                   10                  15

Ser Leu Arg Leu Ser Cys Ala Gly Ser Gly Arg Thr Phe Thr Asn Tyr
        20                  25                  30

Asp Met Gly Trp Phe Arg Gln Ala Pro Gly Lys Glu Arg Phe Val
            35                  40                  45

Ala Ala Ile Ser Gly Ser Gly Gly Ser Ala Arg Tyr Ala Val Pro Val
    50                  55                  60

Lys Gly Arg Phe Thr Ile Thr Arg Asp Asn Ala Lys Asn Thr Val Tyr
```

```
                65                  70                  75                  80
Leu Gln Met Ser Ser Leu Lys Pro Glu Asp Thr Ala Val Tyr Tyr Cys
                    85                  90                  95

Ala Ala Asp Arg Phe Val Val Ala Ala Gly Thr His Asp Leu Asp Tyr
                100                 105                 110

Trp Gly Gln Gly Thr Gln Val Thr Val Ser Ser
            115                 120

<210> SEQ ID NO 25
<211> LENGTH: 123
<212> TYPE: PRT
<213> ORGANISM: Artificial Sequence
<220> FEATURE:
<223> OTHER INFORMATION: CDR sequence

<400> SEQUENCE: 25

Asp Val Gln Leu Gln Glu Ser Gly Gly Gly Leu Val Gln Ala Gly Gly
1               5                   10                  15

Ser Leu Arg Leu Ser Cys Ala Gly Ser Gly Arg Thr Phe Thr Asn Tyr
                20                  25                  30

Asp Met Gly Trp Phe Arg Gln Ala Pro Gly Lys Glu Arg Arg Phe Val
            35                  40                  45

Ala Ala Ile Ser Gly Gly Gly Ser Ala Arg Tyr Ala Val Pro Val
        50                  55                  60

Lys Gly Arg Phe Thr Ile Thr Arg Asp Asn Ala Lys Asn Thr Val Tyr
65                  70                  75                  80

Leu Gln Met Ser Ser Leu Lys Pro Glu Asp Thr Ala Val Tyr Tyr Cys
                    85                  90                  95

Ala Ala Asp Arg Phe Val Val Ala Ala Gly Thr His Asp Leu Asp Tyr
                100                 105                 110

Trp Gly Gln Gly Thr Gln Val Thr Val Ser Ser
            115                 120

<210> SEQ ID NO 26
<211> LENGTH: 123
<212> TYPE: PRT
<213> ORGANISM: Artificial Sequence
<220> FEATURE:
<223> OTHER INFORMATION: CDR sequence

<400> SEQUENCE: 26

Asp Val Gln Leu Gln Ala Ser Gly Gly Gly Leu Val Gln Ala Gly Gly
1               5                   10                  15

Ser Leu Arg Leu Ser Cys Ala Gly Ser Gly Arg Ser Phe Ser Ser Tyr
                20                  25                  30

Ala Met Gly Trp Phe Arg Gln Ala Pro Gly Lys Ala Arg Glu Ile Val
            35                  40                  45

Ala Thr Ile Thr Arg Ser Gly Gly Ser Thr Asn Tyr Ala Val Pro Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                    85                  90                  95

Ala Ala Asp Arg Phe Ala Val Ala Ser Gly Thr His Asp Leu Asp Tyr
                100                 105                 110

Trp Gly Gln Gly Thr Gln Val Thr Val Ser Ser
            115                 120
```

<210> SEQ ID NO 27
<211> LENGTH: 123
<212> TYPE: PRT
<213> ORGANISM: Artificial Sequence
<220> FEATURE:
<223> OTHER INFORMATION: CDR sequence

<400> SEQUENCE: 27

```
Asp Val Gln Leu Gln Ala Ser Gly Gly Gly Leu Val Gln Ala Gly Gly
1               5                   10                  15

Ser Leu Arg Leu Ser Cys Ala Gly Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ser Ile Ser Trp Ser Gly Ser Arg Thr Asn Tyr Gly Val Pro Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Arg Phe Ala Val Ala Ile Gly Thr His Asp Leu Asp Tyr
            100                 105                 110

Trp Gly Gln Gly Thr Gln Val Thr Val Ser Ser
        115                 120
```

<210> SEQ ID NO 28
<211> LENGTH: 122
<212> TYPE: PRT
<213> ORGANISM: Artificial Sequence
<220> FEATURE:
<223> OTHER INFORMATION: CDR sequence

<400> SEQUENCE: 28

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Asp Thr Arg Tyr
            20                  25                  30

Thr Met Gly Trp Phe Arg Gln Ala Pro Gly Lys Glu Arg Glu Phe Val
        35                  40                  45

Ser Gly Ile Thr Trp Asn Gly Thr Ser Tyr Ala Asp Ser Val Lys
    50                  55                  60

Gly Arg Phe Thr Ile Ser Arg Asp Asn Gly Lys Asn Ser Val Tyr Leu
65                  70                  75                  80

Gln Met Asn Ser Leu Lys Pro Glu Asp Thr Ala Val Tyr Tyr Cys Ala
                85                  90                  95

Ala Asp Arg Phe Thr Leu Val Pro Thr Thr Ser Asp Leu Asp Tyr Trp
            100                 105                 110

Gly Gln Gly Thr Gln Val Thr Val Ser Ser
        115                 120
```

<210> SEQ ID NO 29
<211> LENGTH: 122
<212> TYPE: PRT
<213> ORGANISM: Artificial Sequence
<220> FEATURE:
<223> OTHER INFORMATION: CDR sequence

<400> SEQUENCE: 29

Gln Val Gln Leu Gln Glu Ser Gly Gly Arg Leu Val Gln Pro Gly Gly

```
1               5                   10                  15
Ser Leu Arg Leu Ser Cys Ala Ala Ser Gly Arg Thr Leu Ser Asn Tyr
            20                  25                  30

Ala Met Ala Trp Phe Arg Gln Gly Pro Gly Lys Glu Arg Glu Phe Val
        35                  40                  45

Ala Ser Ile Ser Ala Ser Asp Ser Thr Leu Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Thr Val Tyr Tyr Cys Ala
            85                  90                  95

Ala Arg Phe Trp Ile Gly Val Arg Ala Pro Ala Glu Tyr Asn Tyr Trp
        100                 105                 110

Gly Gln Gly Thr Gln Val Thr Val Ser Ser
            115                 120

<210> SEQ ID NO 30
<211> LENGTH: 122
<212> TYPE: PRT
<213> ORGANISM: Artificial Sequence
<220> FEATURE:
<223> OTHER INFORMATION: CDR sequence

<400> SEQUENCE: 30

Gln Val Lys Leu Gln Glu Ser Gly Gly Arg Leu Val Gln Pro Gly Gly
1               5                   10                  15

Ser Leu Arg Leu Ser Cys Ala Ala Ser Gly Arg Thr Leu Ser Asn Tyr
            20                  25                  30

Ala Met Ala Trp Phe Arg Gln Gly Pro Gly Lys Glu Arg Glu Phe Val
        35                  40                  45

Ala Ser Ile Ser Ala Ser Asp Ser Thr Leu Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Thr Val Tyr Tyr Cys Ala
            85                  90                  95

Ala Arg Phe Trp Ile Gly Val Arg Ala Pro Ala Glu Tyr Asn Tyr Trp
        100                 105                 110

Gly Gln Gly Thr Gln Val Thr Val Ser Ser
            115                 120

<210> SEQ ID NO 31
<211> LENGTH: 122
<212> TYPE: PRT
<213> ORGANISM: Artificial Sequence
<220> FEATURE:
<223> OTHER INFORMATION: CDR sequence

<400> SEQUENCE: 31

Gln Val Lys Leu Gln Glu Ser Gly Gly Arg Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Gly Pro Gly Lys Glu Arg Glu Phe Val
        35                  40                  45

Ala Ala Ile Ser Ala Ala Asp Ser Thr Leu Tyr Ala Asp Phe Val Lys
    50                  55                  60
```

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Trp Trp Ile Ala Val Arg Ala Pro Ala Glu Tyr Asn Tyr Trp
            100                 105                 110

Gly Gln Gly Thr Gln Val Thr Val Ser Ser
            115                 120

<210> SEQ ID NO 32
<211> LENGTH: 122
<212> TYPE: PRT
<213> ORGANISM: Artificial Sequence
<220> FEATURE:
<223> OTHER INFORMATION: CDR sequence

<400> SEQUENCE: 32

Gln Val Gln Leu Gln Glu Ser Gly Gly Arg Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Gly Pro Gly Lys Glu Arg Glu Phe Val
        35                  40                  45

Ala Ala Ile Ser Ala Ala Asp Ser Thr Leu Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Trp Trp Ile Ala Val Arg Ala Pro Ala Glu Tyr Asn Tyr Trp
            100                 105                 110

Gly Gln Gly Thr Gln Val Thr Val Ser Ser
            115                 120

<210> SEQ ID NO 33
<211> LENGTH: 124
<212> TYPE: PRT
<213> ORGANISM: Artificial Sequence
<220> FEATURE:
<223> OTHER INFORMATION: CDR sequence

<400> SEQUENCE: 33

Asp Val Gln Leu Gln Ala Ser Gly Gly Gly Leu Val Gln Ala Gly Gly
1               5                   10                  15

Ser Leu Arg Leu Ser Cys Ala Pro Ser Gly Gly Thr Phe Asp Ala Tyr
            20                  25                  30

Asp Met Gly Trp Tyr Arg Glu Ala Pro Gly Lys Lys Arg Gln Phe Val
        35                  40                  45

Ala Ala Val Arg Ser Gly Gly Gly Thr Arg Tyr Ala Asp Ser Val
    50                  55                  60

Lys Gly Arg Phe Thr Ile Ser Arg Asp Asp Ala Lys Asp Thr Val Phe
65                  70                  75                  80

Leu Gln Met Asn Ser Leu Lys Pro Glu Asp Thr Ala Leu Tyr Tyr Cys
                85                  90                  95

Ala Ala Asp Arg Trp Gly Leu Phe Ser Leu Ser Ile Ala Thr Pro Thr
            100                 105                 110

His Trp Gly Gln Gly Thr Gln Val Thr Val Ser Ser
            115                 120

<210> SEQ ID NO 34
<211> LENGTH: 126
<212> TYPE: PRT
<213> ORGANISM: Artificial Sequence
<220> FEATURE:
<223> OTHER INFORMATION: CDR sequence

<400> SEQUENCE: 34

Asp Val Gln Leu Gln Ala Ser Gly Gly Gly Ser Val Gln Glu Gly Glu
1               5                   10                  15

Ser Leu Lys Leu Ser Cys Val Gly Ser Gly Arg Thr Phe Ser Asp Trp
            20                  25                  30

Ala Met Gly Trp Tyr Arg Gln Ala Pro Gly Lys Asp Arg Glu Phe Val
        35                  40                  45

Ala Ala Val Ser Gly Ala Gly Arg Gly Lys Pro Ser Tyr Ala Asn
    50                  55                  60

Ser Val Lys Gly Arg Phe Thr Val Ser Arg Asp Asn Ala Lys Asn Thr
65                  70                  75                  80

Val Tyr Leu Gln Met Asp Asn Leu Lys Pro Glu Asp Thr Ala Val Tyr
                85                  90                  95

Tyr Cys Ala Ala Asp Arg Leu Val Leu Val Ala Leu Ser Ile Ala Asp
            100                 105                 110

Pro Gly Phe Trp Gly Gln Gly Thr Arg Val Thr Val Ser Ser
        115                 120                 125

<210> SEQ ID NO 35
<211> LENGTH: 125
<212> TYPE: PRT
<213> ORGANISM: Artificial Sequence
<220> FEATURE:
<223> OTHER INFORMATION: CDR sequence

<400> SEQUENCE: 35

Asp Val Gln Leu Gln Glu Ser Gly Gly Gly Leu Val Gln Ala Gly Gly
1               5                   10                  15

Ser Leu Arg Leu Ser Cys Ala Ala Ser Gly Val Ser Phe Ser Arg Tyr
            20                  25                  30

Thr Met Gly Trp Tyr Arg Glu Val Pro Gly Lys Glu Arg Arg Glu Phe
        35                  40                  45

Val Ala Ala Val Arg Pro Ser Gly Asp Ser Thr Tyr Tyr Gly Asn Ser
    50                  55                  60

Val Lys Gly Arg Phe Ser Ile Ser Arg Asp Asp Lys Asn Ile Val
65                  70                  75                  80

Tyr Leu Gln Met Asn Ser Leu Lys Pro Glu Asp Thr Ala Val Tyr Tyr
                85                  90                  95

Cys Ala Ala Gly Phe Pro Val Leu Val Ala Leu Ser Ile Ala Asp Pro
            100                 105                 110

Asp Tyr Trp Gly Gln Gly Thr Gln Val Thr Val Ser Thr
        115                 120                 125

<210> SEQ ID NO 36
<211> LENGTH: 125
<212> TYPE: PRT
<213> ORGANISM: Artificial Sequence
<220> FEATURE:
<223> OTHER INFORMATION: CDR sequence

<400> SEQUENCE: 36

-continued

```
Asp Val Gln Leu Gln Ala Ser Gly Gly Gly Leu Val Gln Thr Gly Asp
1               5                   10                  15

Ser Leu Thr Val Ser Cys Ala Ala Ser Gly Leu Ser Phe Thr Arg Tyr
            20                  25                  30

Thr Met Gly Trp Tyr Arg Glu Val Pro Gly Lys Glu Arg Arg Glu Phe
        35                  40                  45

Val Ala Ala Val Lys Pro Ala Gly Asp Ser Ala Tyr Tyr Gly Ala Ser
    50                  55                  60

Val Lys Gly Arg Phe Thr Ala Ser Arg Asp Asn Ala Lys Asn Thr Val
65                  70                  75                  80

Thr Leu Gln Met Asn Ser Leu Lys Pro Glu Asp Thr Ala Ile Tyr Tyr
                85                  90                  95

Cys Ala Ala Gly Phe Pro Val Leu Thr Ala Leu His Ile Ala Asp Pro
            100                 105                 110

Asp Tyr Trp Gly Gln Gly Thr Gln Val Thr Val Ser Pro
            115                 120                 125

<210> SEQ ID NO 37
<211> LENGTH: 124
<212> TYPE: PRT
<213> ORGANISM: Artificial Sequence
<220> FEATURE:
<223> OTHER INFORMATION: CDR sequence

<400> SEQUENCE: 37

Asp Val Gln Leu Gln Glu Ser Gly Gly Gly Leu Val Gln Ala Gly Gly
1               5                   10                  15

Ser Leu Arg Leu Ser Cys Thr Gly Ser Gly Arg Thr Phe Arg Asn Tyr
            20                  25                  30

Pro Met Ala Trp Phe Arg Gln Ala Pro Gly Lys Glu Arg Glu Phe Val
        35                  40                  45

Ala Gly Ile Thr Trp Val Gly Ala Ser Thr Leu Tyr Ala Asp Phe Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ala Ala Gly Arg Gly Ile Val Ala Gly Arg Ile Pro Ala Glu Tyr Ala
            100                 105                 110

Asp Trp Gly Gln Gly Thr Gln Val Thr Val Ser Ser
            115                 120

<210> SEQ ID NO 38
<211> LENGTH: 124
<212> TYPE: PRT
<213> ORGANISM: Artificial Sequence
<220> FEATURE:
<223> OTHER INFORMATION: CDR sequence

<400> SEQUENCE: 38

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Val Ser Phe
            20                  25                  30

Gly Met Gly Trp Phe Arg Gln Ala Pro Gly Lys Glu Arg Glu Phe Val
        35                  40                  45

Ala Ala Ile Asn Trp Arg Gly Ser Thr Thr Ala Tyr Ala Asp Ser Val
    50                  55                  60
```

```
Lys Gly Arg Phe Thr Ile Ser Arg Asp Val Thr Lys Asn Thr Ile Tyr
 65                  70                  75                  80

Leu Gln Met Asn Ser Leu Lys Pro Glu Asp Thr Ala Ile Tyr Tyr Cys
                 85                  90                  95

Ala Glu Gly Arg Thr Ala Ser Ala Ser Thr Met Ile Arg Glu Tyr Asp
            100                 105                 110

Ser Trp Gly Gln Gly Thr Gln Val Thr Val Ser Glu
        115                 120

<210> SEQ ID NO 39
<211> LENGTH: 123
<212> TYPE: PRT
<213> ORGANISM: Artificial Sequence
<220> FEATURE:
<223> OTHER INFORMATION: CDR sequence

<400> SEQUENCE: 39

Asp Val Gln Leu Gln Ala Ser Gly Gly Gly Ser Val Gln Ala Gly Gly
 1               5                  10                  15

Ser Leu Arg Leu Ser Cys Ala Ala Ser Gly Leu Ser Phe Ser Asp Tyr
                 20                  25                  30

Ala Met Gly Trp Phe Arg Gln Glu Pro Gly Lys Glu Arg Arg Phe Val
             35                  40                  45

Ala Ser Ile Arg Ser Ser Gly Gly Thr Thr Tyr Ala Glu Ser Val Lys
 50                  55                  60

Gly Arg Phe Thr Ile Ser Arg Asp Asn Ala Lys Asn Thr Met Tyr Leu
 65                  70                  75                  80

Gln Met Asn Asn Leu Lys Pro Glu Asp Thr Ala Val Tyr Tyr Cys Ala
                 85                  90                  95

Ala Asp Arg Leu Val Ile Thr Lys Leu Ser Ile Ala Asp Pro Gly Tyr
            100                 105                 110

Trp Gly Gln Gly Thr Gln Val Thr Val Ser Ser
        115                 120

<210> SEQ ID NO 40
<211> LENGTH: 123
<212> TYPE: PRT
<213> ORGANISM: Artificial Sequence
<220> FEATURE:
<223> OTHER INFORMATION: CDR sequence
<220> FEATURE:
<221> NAME/KEY: SITE
<222> LOCATION: (70)..(70)
<223> OTHER INFORMATION: Xaa can be any naturally occurring amino acid
<220> FEATURE:
<221> NAME/KEY: SITE
<222> LOCATION: (74)..(74)
<223> OTHER INFORMATION: Xaa can be any naturally occurring amino acid
<220> FEATURE:
<221> NAME/KEY: SITE
<222> LOCATION: (89)..(89)
<223> OTHER INFORMATION: Xaa can be any naturally occurring amino acid
<220> FEATURE:
<221> NAME/KEY: SITE
<222> LOCATION: (93)..(93)
<223> OTHER INFORMATION: Xaa can be any naturally occurring amino acid

<400> SEQUENCE: 40

Val Gln Leu Gln Ala Ser Gly Gly Gly Leu Val Gln Ala Gly Gly Ser
 1               5                  10                  15

Leu Arg Leu Ser Cys Thr Val Ser Gly Phe Thr Ser Asp Asp Tyr Thr
                 20                  25                  30
```

Val Gly Trp Phe Arg Gln Ala Pro Gly Leu Lys Arg Glu Gly Leu Ser
        35                  40                  45

Cys Leu Ser Arg Arg Asp Gly Arg Phe Tyr His Ser Asn Ser Val Lys
 50                  55                  60

Gly Arg Phe Thr Met Xaa Ser Asp Asp Xaa Lys Asn Thr Val Tyr Leu
 65                  70                  75                  80

Gln Leu Asp Ser Leu Lys Pro Asp Xaa Thr Ala Val Xaa Tyr Cys Ala
                 85                  90                  95

Ala Cys Thr Ser Val Val Val Leu Leu Ala Pro Asn Trp Tyr Glu Tyr
                100                 105                 110

Trp Gly Gln Gly Thr Gln Val Thr Val Ser Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: CDR sequence

<400> SEQUENCE: 41

Val Gln Leu Gln Ala Ser Gly Gly Gly Leu Val Gln Ala Gly Gly Ser
  1               5                  10                  15

Leu Arg Leu Ser Cys Thr Val Ser Gly Phe Thr Ser Asp Asp Tyr Thr
                 20                  25                  30

Val Gly Trp Phe Arg Gln Ala Pro Gly Leu Lys Arg Glu Gly Leu Ser
            35                  40                  45

Cys Leu Ser Arg Arg Asp Gly Arg Phe Tyr His Ser Asn Ser Val Lys
 50                  55                  60

Gly Arg Phe Thr Met Ser Ser Asp Asp Asn Lys Asn Thr Val Tyr Leu
 65                  70                  75                  80

Gln Leu Asp Ser Leu Lys Pro Asp Asp Thr Ala Val Tyr Tyr Cys Ala
                 85                  90                  95

Ala Thr Thr Ser Val Val Val Leu Leu Ala Pro Asn Trp Tyr Glu Tyr
                100                 105                 110

Trp Gly Gln Gly Thr Gln Val Thr Val Ser Ser
            115                 120

<210> SEQ ID NO 42
<211> LENGTH: 124
<212> TYPE: PRT
<213> ORGANISM: Artificial Sequence
<220> FEATURE:
<223> OTHER INFORMATION: CDR sequence

<400> SEQUENCE: 42

Glu Val Gln Leu Val Glu Ser Gly Gly Gly Leu Val Gln Ala Gly Glu
  1               5                  10                  15

Ser Leu Arg Leu Ser Cys Ala Ala Gly Arg Thr Phe Thr Asn Leu Gly
                 20                  25                  30

Met Gly Trp Phe Arg Gln Ala Pro Gly Lys Glu Arg Glu Phe Val Ala
            35                  40                  45

Ala Asp Thr Trp Ser Gly Thr Ser Thr Trp Tyr Gly Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Asn Leu Lys Pro Glu Asp Thr Ala Val Tyr Tyr Cys Ala
                 85                  90                  95

Ala Arg Leu Arg Gly Trp Ile Thr Thr Arg Lys Pro Asn Glu Tyr Asp
            100                 105                 110

Tyr Trp Gly Gln Gly Thr Gln Val Thr Val Ala Ser
        115                 120

<210> SEQ ID NO 43
<211> LENGTH: 126
<212> TYPE: PRT
<213> ORGANISM: Artificial Sequence
<220> FEATURE:
<223> OTHER INFORMATION: CDR sequence

<400> SEQUENCE: 43

Asp Val Gln Leu Gln Glu Ser Gly Gly Gly Leu Val Gln Ala Gly Asp
1               5                   10                  15

Ser Leu Arg Leu Ser Cys Glu Phe Ser Gly Arg Thr Phe Ser Gly Phe
            20                  25                  30

Ala Met Gly Trp Phe Arg Gln Phe Pro Gly Lys Glu Arg Glu Phe Val
        35                  40                  45

Ala Ala Ile Asn Trp Ser Gly Ser Asp Thr Asp Tyr Ser Asp Ser Val
    50                  55                  60

Lys Gly Arg Phe Thr Ile Ser Arg Asp Asn Val Lys Gln Met Met Tyr
65                  70                  75                  80

Leu Ala Met Asn Ser Leu Lys Pro Glu Asp Thr Ala Val Tyr Phe Cys
                85                  90                  95

Ala Glu Ala Arg Ser Ala Gly Leu Gly Ser Ser Arg Arg Ile Glu Gly
            100                 105                 110

Tyr Asp Lys Trp Gly Arg Gly Thr Gln Val Thr Val Ser Ser
        115                 120                 125

<210> SEQ ID NO 44
<211> LENGTH: 126
<212> TYPE: PRT
<213> ORGANISM: Artificial Sequence
<220> FEATURE:
<223> OTHER INFORMATION: CDR sequence

<400> SEQUENCE: 44

Asp Val Gln Leu Gln Glu Ser Gly Gly Gly Leu Val Gln Ala Gly Asp
1               5                   10                  15

Ser Leu Arg Leu Ser Cys Glu Phe Ser Gly Arg Thr Phe Ser Gly Phe
            20                  25                  30

Ala Met Gly Trp Phe Arg Gln Phe Pro Gly Lys Glu Arg Glu Phe Val
        35                  40                  45

Ala Ala Ile Asn Trp Ser Gly Ser Asp Thr Asp Tyr Ser Asp Ser Val
    50                  55                  60

Lys Gly Arg Phe Thr Ile Ser Arg Asp Asn Val Lys Gln Met Met Tyr
65                  70                  75                  80

Leu Ala Met Asn Ser Leu Lys Pro Glu Asp Thr Ala Val Tyr Phe Cys
                85                  90                  95

Ala Glu Ala Arg Ser Ala Gly Leu Gly Ser Ser Arg Arg Ile Glu Gly
            100                 105                 110

Tyr Asp Lys Trp Gly Arg Gly Thr Gln Val Thr Val Ser Ser
        115                 120                 125

<210> SEQ ID NO 45
<211> LENGTH: 126
<212> TYPE: PRT

<213> ORGANISM: Artificial Sequence
<220> FEATURE:
<223> OTHER INFORMATION: CDR sequence

<400> SEQUENCE: 45

Asp Val Gln Leu Gln Ala Ser Gly Gly Gly Leu Val Gln Ala Gly Gly
1               5                   10                  15

Ser Leu Arg Leu Ser Cys Glu Phe Ser Gly Arg Thr Phe Ser Gly Phe
            20                  25                  30

Ala Met Gly Trp Phe Arg Gln Phe Pro Gly Lys Glu Arg Glu Phe Val
        35                  40                  45

Ala Ala Ile Asn Trp Ser Gly Ser Ser Val Asp Tyr Ser Asp Ser Val
    50                  55                  60

Lys Gly Arg Phe Thr Ile Ser Arg Asp Asn Val Lys Ser Thr Met Tyr
65                  70                  75                  80

Leu Val Met Asn Ser Leu Lys Pro Glu Asp Thr Ala Val Tyr Tyr Cys
                85                  90                  95

Ala Glu Ala Arg Ser Ala Glu Leu Gly Ser Ser Arg Lys Ile Gln Gly
            100                 105                 110

Tyr Asp Gln Trp Gly Arg Gly Thr Gln Val Thr Val Ser Ser
        115                 120                 125

<210> SEQ ID NO 46
<211> LENGTH: 126
<212> TYPE: PRT
<213> ORGANISM: Artificial Sequence
<220> FEATURE:
<223> OTHER INFORMATION: CDR sequence

<400> SEQUENCE: 46

Asp Val Gln Leu Gln Ala Ser Gly Gly Gly Leu Val Gln Ala Gly Gly
1               5                   10                  15

Ser Leu Arg Leu Ser Cys Glu Phe Ser Gly Arg Thr Phe Ser Gly Phe
            20                  25                  30

Ala Met Gly Trp Phe Arg Gln Phe Pro Gly Lys Glu Arg Glu Phe Val
        35                  40                  45

Ala Ala Ile Asn Trp Ser Gly Ser Ser Val Asp Tyr Ser Asp Ser Val
    50                  55                  60

Lys Gly Arg Phe Thr Ile Ser Arg Asp Asn Val Lys Ser Thr Met Tyr
65                  70                  75                  80

Leu Val Met Asn Ser Leu Lys Pro Glu Asp Thr Ala Val Tyr Tyr Cys
                85                  90                  95

Ala Glu Ala Arg Ser Ala Glu Leu Gly Ser Ser Arg Lys Ile Gln Gly
            100                 105                 110

Tyr Asp Gln Trp Gly Arg Gly Thr Arg Val Thr Val Ser Ser
        115                 120                 125

<210> SEQ ID NO 47
<211> LENGTH: 128
<212> TYPE: PRT
<213> ORGANISM: Artificial Sequence
<220> FEATURE:
<223> OTHER INFORMATION: CDR sequence

<400> SEQUENCE: 47

Asp Val Gln Leu Gln Glu Ser Gly Gly Gly Leu Val Gln Ala Gly Ser
1               5                   10                  15

Ser Leu Arg Ile Ser Cys Ala Val Ser Gly Val Arg Leu Asp Asn Tyr
            20                  25                  30

```
Ala Met Gly Trp Phe Arg Gln Ala Pro Gly Lys Glu Arg Glu Ser Val
            35                  40                  45

Ala Gly Ile Ser Trp Ser Ser Gly Thr Leu Leu Tyr Ser Asp Ser Val
        50                  55                  60

Lys Gly Arg Phe Ala Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Gln Tyr Gln Asp Arg Tyr Tyr Asp Glu Phe Thr Trp Lys Glu
            100                 105                 110

Lys Asp Met Asp Tyr Trp Gly Lys Gly Thr Leu Val Thr Val Ser Ser
            115                 120                 125

<210> SEQ ID NO 48
<211> LENGTH: 128
<212> TYPE: PRT
<213> ORGANISM: Artificial Sequence
<220> FEATURE:
<223> OTHER INFORMATION: CDR sequence

<400> SEQUENCE: 48

Asp Val Gln Leu Gln Glu Ser Gly Gly Gly Leu Val Gln Ala Gly Asp
  1               5                  10                  15

Ser Leu Arg Leu Ser Cys Ala Ala Ser Gly Pro His Phe Asn Asn Tyr
                20                  25                  30

Ala Ile Gly Trp Phe Arg Gln Ala Pro Gly Lys Glu Arg Glu Phe Val
            35                  40                  45

Ala Gly Ile Ser Trp Ser Ser Gly Ser Leu Leu Tyr Ser Asp Ser Val
        50                  55                  60

Lys Gly Arg Phe Thr Ile Ser Arg Asp Asn Asp Lys Asn Thr Ala Tyr
 65                  70                  75                  80

Leu Gln Met Asn Ser Leu Lys Pro Glu Asp Thr Ala Leu Tyr Tyr Cys
                85                  90                  95

Ala Ala Gln Tyr Gln Glu Arg Tyr Tyr Ser Asp Phe Ser Leu Lys Glu
            100                 105                 110

Lys Gly Met Glu Tyr Trp Gly Lys Gly Thr Leu Val Thr Val Ser Ser
            115                 120                 125

<210> SEQ ID NO 49
<211> LENGTH: 128
<212> TYPE: PRT
<213> ORGANISM: Artificial Sequence
<220> FEATURE:
<223> OTHER INFORMATION: CDR sequence

<400> SEQUENCE: 49

Asp Val Gln Leu Gln Glu Ser Gly Gly Gly Leu Val Gln Ala Gly Asp
  1               5                  10                  15

Ser Leu Arg Leu Ser Cys Val Gly Ser Gly Arg Arg Phe Asp Asn Tyr
                20                  25                  30

Ala Met Ala Trp Phe Arg Gln Ala Pro Gly Lys Glu Arg Thr Phe Val
            35                  40                  45

Ala Ala Ile Ser Trp Ser Ser Gly Thr Thr Arg Tyr Leu Asp Thr Val
        50                  55                  60

Lys Gly Arg Phe Thr Ile Ser Arg Asp Asn Ala Lys Ser Thr Val Tyr
 65                  70                  75                  80

Leu Gln Met Asn Ser Leu Lys Pro Glu Asp Thr Ala Val Tyr Tyr Cys
```

```
                    85                  90                  95

Ala Ala Arg Tyr Gln Pro Arg Tyr Tyr Asp Ser Gly Asp Met Asp Gly
                   100                 105                 110

Tyr Glu Tyr Glu Phe Trp Gly Gln Gly Thr Gln Val Thr Val Ser Ser
            115                 120                 125

<210> SEQ ID NO 50
<211> LENGTH: 128
<212> TYPE: PRT
<213> ORGANISM: Artificial Sequence
<220> FEATURE:
<223> OTHER INFORMATION: CDR sequence

<400> SEQUENCE: 50

Asp Val Gln Leu Gln Glu Ser Gly Gly Gly Leu Val Gln Ala Gly His
1               5                  10                  15

Ser Leu Arg Leu Ser Cys Val Gly Ser Gly Ser Arg Phe Asp Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Ser Gly Thr Thr Arg Tyr Leu Asp Thr Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Arg Tyr Gln Pro Arg Tyr Tyr Asp Ser Gly Asp Met Asp Gly
                   100                 105                 110

Tyr Glu Tyr Asp Asn Trp Gly Gln Gly Thr Gln Val Thr Val Ser Ser
            115                 120                 125

<210> SEQ ID NO 51
<211> LENGTH: 128
<212> TYPE: PRT
<213> ORGANISM: Artificial Sequence
<220> FEATURE:
<223> OTHER INFORMATION: CDR sequence

<400> SEQUENCE: 51

Asp Val Gln Leu Gln Ala Ser Gly Gly Gly Leu Val Gln Ala Gly Gly
1               5                  10                  15

Ser Gln Arg Leu Ser Cys Ala Ala Ser Gly His Thr Phe Ser Ser Tyr
            20                  25                  30

Ser Met Ala Trp Phe Arg Gln Ala Pro Gly Lys Glu Arg Glu Phe Val
        35                  40                  45

Ala Ala Asn Ser Met Ser Gly Thr Lys Thr Ala Tyr Ser Asp Ser Val
    50                  55                  60

Lys Gly Arg Phe Thr Ile Ser Arg Asp Ile Pro Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Val Asp Arg Ser Thr Gly Trp Asp Ser Trp Arg Asp Pro
                   100                 105                 110

Asp Gln Tyr Asp Tyr Trp Asp Gln Gly Thr Gln Val Thr Val Ser Ser
            115                 120                 125

<210> SEQ ID NO 52
<211> LENGTH: 122
```

-continued

```
<212> TYPE: PRT
<213> ORGANISM: Artificial Sequence
<220> FEATURE:
<223> OTHER INFORMATION: CDR sequence

<400> SEQUENCE: 52

Ser Gly Gly Gly Leu Val Gln Ala Gly Gly Ser Gln Arg Leu Ser Cys
1               5                   10                  15

Ala Ala Ser Gly His Thr Phe Ser Ser Tyr Ser Met Ala Trp Phe Arg
            20                  25                  30

Gln Ala Pro Gly Lys Glu Arg Glu Phe Val Ala Ala Asn Ile Met Ser
        35                  40                  45

Gly Thr Asn Thr Tyr Tyr Ala Asp Ser Val Arg Gly Arg Phe Thr Met
    50                  55                  60

Ser Arg Asp Ile Ala Lys Asn Thr Val Tyr Leu Gln Met Asn Ser Leu
65                  70                  75                  80

Lys Glu Glu Asp Thr Ala Leu Tyr Tyr Cys Ala Ala Ala Asp Arg Phe
                85                  90                  95

Arg Gly Trp Ala Thr Trp Arg Asp Asp Pro Asp Gln Tyr Asp Tyr Trp
            100                 105                 110

Asp Gln Gly Thr Gln Val Thr Val Ser Ser
        115                 120

<210> SEQ ID NO 53
<211> LENGTH: 132
<212> TYPE: PRT
<213> ORGANISM: Artificial Sequence
<220> FEATURE:
<223> OTHER INFORMATION: CDR sequence

<400> SEQUENCE: 53

Asp Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Val Ile Gly Trp Phe Arg Gln Ala Pro Gly Lys Glu Arg Glu Gly Val
        35                  40                  45

Ser Ser Ile Ser Asn Asn Asn Ser Thr Tyr Tyr Ala Asp Ser Val Lys
    50                  55                  60

Gly Arg Phe Thr Ile Ala Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Val Thr Leu Asn Pro Phe Thr Gly Trp Asn Thr Arg Ser Gly
            100                 105                 110

Pro Met Tyr Arg Tyr Glu Tyr Asp Tyr Trp Gly Gln Gly Thr Gln Val
        115                 120                 125

Thr Val Ser Ser
    130

<210> SEQ ID NO 54
<211> LENGTH: 131
<212> TYPE: PRT
<213> ORGANISM: Artificial Sequence
<220> FEATURE:
<223> OTHER INFORMATION: CDR sequence

<400> SEQUENCE: 54

Val Gln Leu Gln Glu Ser Gly Gly Gly Leu Val Gln Ala Gly Gly Ser
```

```
                1               5                   10                  15
            Leu Arg Leu Ser Cys Ala Ala Ser Gly Phe Thr Phe Asp Asp Tyr Val
                        20                  25                  30

Ile Gly Trp Phe Arg Gln Ala Pro Gly Lys Glu Cys Glu Gly Val Ser
                        35                  40                  45

Ser Ile Ser Asn Asn Ser Thr Tyr Tyr Ala Asp Ser Val Lys Gly
                        50                  55                  60

Arg Phe Thr Ile Ala Ser Asp Asn Ala Lys Asn Thr Val Tyr Leu Gln
            65                      70                  75                  80

Met Asn Ser Leu Lys Pro Glu Asp Thr Ala Val Tyr Tyr Cys Ala Ala
                            85                  90                  95

Asp Val Thr Leu Asn Pro Phe Thr Gly Trp Asn Thr Arg Ser Gly Pro
                            100                 105                 110

Met Tyr Arg Tyr Glu Tyr Asp Tyr Trp Gly Gln Gly Thr Gln Val Thr
                            115                 120                 125

Val Ser Ser
                130
```

<210> SEQ ID NO 55
<211> LENGTH: 132
<212> TYPE: PRT
<213> ORGANISM: Artificial Sequence
<220> FEATURE:
<223> OTHER INFORMATION: CDR sequence

<400> SEQUENCE: 55

```
            Asp Val Gln Leu Gln Ala Ser Gly Gly Gly Leu Val Gln Ala Gly Gly
            1               5                   10                  15

Ser Leu Arg Leu Ser Cys Ala Ala Ser Glu Phe Thr Phe Asp Asp Tyr
                        20                  25                  30

Val Ile Gly Trp Phe Arg Gln Ala Pro Gly Lys Glu Arg Glu Gly Val
                        35                  40                  45

Ser Ser Ile Ser Ser Asp Gly Ser Thr Tyr Tyr Ala Asp Ser Val Lys
                        50                  55                  60

Gly Arg Phe Thr Ile Ser Ser Asp Asn Ala Lys Asn Thr Val Tyr Leu
            65                      70                  75                  80

His Met Asn Ser Leu Lys Pro Glu Asp Thr Ala Val Tyr Tyr Cys Ala
                            85                  90                  95

Ala Asp Val Thr Leu Asn Pro Phe Thr Gly Trp Thr Thr Arg Ser Gly
                            100                 105                 110

Pro Met Tyr Arg Tyr Glu Tyr Asp Tyr Trp Gly Gln Gly Thr Gln Val
                            115                 120                 125

Thr Val Ser Ser
                130
```

<210> SEQ ID NO 56
<211> LENGTH: 131
<212> TYPE: PRT
<213> ORGANISM: Artificial Sequence
<220> FEATURE:
<223> OTHER INFORMATION: CDR sequence

<400> SEQUENCE: 56

```
            Val Gln Leu Gln Ala Ser Gly Gly Gly Leu Val Gln Ala Gly Gly Ser
            1               5                   10                  15

Leu Arg Leu Ser Cys Ala Ala Ser Gly Phe Thr Phe Asp Asp Tyr Val
                        20                  25                  30
```

-continued

Ile Gly Trp Phe Arg Gln Ser Pro Gly Lys Glu Arg Glu Gly Val Ser
             35                  40                  45

Cys Ile Ser Ser Ala Gly Ser Thr Tyr Tyr Ala Asp Ser Val Lys Gly
 50                  55                  60

Arg Phe Thr Ile Ser Ser Asp Asn Ala Lys Asn Met Val Tyr Leu Gln
 65                  70                  75                  80

Met Asp Asn Leu Lys Pro Glu Asp Thr Ala Val Tyr Cys Ala Ala
                 85                  90                  95

Asp Val Thr Leu Asn Pro Phe Thr Gly Trp Asp Thr Arg Ser Gly Pro
                100                 105                 110

Met Tyr Arg Tyr Glu Tyr Asp Tyr Trp Gly Gln Gly Thr Gln Val Thr
            115                 120                 125

Val Ser Ser
    130

<210> SEQ ID NO 57
<211> LENGTH: 132
<212> TYPE: PRT
<213> ORGANISM: Artificial Sequence
<220> FEATURE:
<223> OTHER INFORMATION: CDR sequence

<400> SEQUENCE: 57

Asp Val Gln Leu Gln Ala Ser Gly Gly Gly Leu Val Gln Ala Gly Gly
 1               5                  10                  15

Ser Leu Arg Leu Ser Cys Ala Ala Ser Gly Phe Thr Phe Asp Asp Tyr
             20                  25                  30

Val Ile Gly Trp Phe Arg Gln Ala Pro Gly Lys Glu Arg Glu Gly Val
             35                  40                  45

Ser Ser Ile Ser Ser Ser Gly Ser Ile Tyr Tyr Ala Asp Ser Val Lys
 50                  55                  60

Gly Arg Phe Thr Ile Ser Ser Asp Asn Ala Lys Asn Thr Val Tyr Leu
 65                  70                  75                  80

Gln Met Asn Ser Leu Lys Pro Glu Asp Thr Ala Val Tyr Phe Cys Ala
                 85                  90                  95

Ala Asp Val Thr Leu Asn Pro Phe Thr Gly Trp Asp Thr Arg Ser Gly
                100                 105                 110

Pro Met Tyr Arg Tyr Glu Tyr Asp Tyr Trp Gly Gln Gly Thr Gln Val
            115                 120                 125

Thr Val Ser Ser
    130

<210> SEQ ID NO 58
<211> LENGTH: 132
<212> TYPE: PRT
<213> ORGANISM: Artificial Sequence
<220> FEATURE:
<223> OTHER INFORMATION: CDR sequence

<400> SEQUENCE: 58

Asp Val Gln Leu Gln Ala Ser Gly Gly Gly Leu Val Gln Ala Gly Gly
 1               5                  10                  15

Ser Leu Arg Leu Ser Cys Ala Ala Ser Gly Phe Thr Phe Asp Asp Tyr
             20                  25                  30

Val Ile Gly Trp Phe Arg Gln Ala Pro Gly Lys Glu Arg Glu Gly Val
             35                  40                  45

Ser Ser Ile Ser Ser Ser Gly Ser Ile Tyr Tyr Ala Asp Ser Val Lys
 50                  55                  60

```
Gly Arg Phe Thr Ile Ser Ser Asp Asn Ala Lys Asn Thr Val Tyr Leu
 65                  70                  75                  80

Gln Met Asn Ser Leu Lys Pro Glu Asp Thr Ala Val Tyr Phe Cys Ala
                 85                  90                  95

Ala Asp Val Thr Leu Asn Pro Phe Thr Gly Trp Asp Thr Arg Ser Gly
            100                 105                 110

Pro Met Tyr Arg Tyr Glu Tyr Asp Tyr Trp Gly Gln Gly Thr Gln Val
        115                 120                 125

Thr Val Ser Ser
        130

<210> SEQ ID NO 59
<211> LENGTH: 25
<212> TYPE: PRT
<213> ORGANISM: Artificial Sequence
<220> FEATURE:
<223> OTHER INFORMATION: FW sequence

<400> SEQUENCE: 59

Gln Val Gln Leu Gln Glu Ser Gly Gly Gly Leu Val Gln Pro Gly Gly
 1               5                  10                  15

Ser Leu Arg Leu Ser Cys Gly Ala Thr
            20                  25

<210> SEQ ID NO 60
<211> LENGTH: 25
<212> TYPE: PRT
<213> ORGANISM: Artificial Sequence
<220> FEATURE:
<223> OTHER INFORMATION: FW sequence

<400> SEQUENCE: 60

Gln Val Gln Leu Gln Glu Ser Gly Gly Gly Leu Val Gln Pro Gly Gly
 1               5                  10                  15

Ser Leu Arg Leu Ser Cys Gly Ala Thr
            20                  25

<210> SEQ ID NO 61
<211> LENGTH: 25
<212> TYPE: PRT
<213> ORGANISM: Artificial Sequence
<220> FEATURE:
<223> OTHER INFORMATION: FW sequence

<400> SEQUENCE: 61

Gln Val Lys Leu Gln Glu Ser Gly Gly Gly Leu Val Gln Pro Gly Gly
 1               5                  10                  15

Ser Leu Arg Leu Ser Cys Gly Ala Thr
            20                  25

<210> SEQ ID NO 62
<211> LENGTH: 25
<212> TYPE: PRT
<213> ORGANISM: Artificial Sequence
<220> FEATURE:
<223> OTHER INFORMATION: FW sequence

<400> SEQUENCE: 62

Gln Val Gln Leu Gln Glu Ser Gly Gly Gly Leu Val Gln Pro Gly Gly
 1               5                  10                  15

Ser Leu Arg Leu Ser Cys Ala Ala Ser
            20                  25
```

<210> SEQ ID NO 63
<211> LENGTH: 25
<212> TYPE: PRT
<213> ORGANISM: Artificial Sequence
<220> FEATURE:
<223> OTHER INFORMATION: FW sequence

<400> SEQUENCE: 63

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 64
<211> LENGTH: 25
<212> TYPE: PRT
<213> ORGANISM: Artificial Sequence
<220> FEATURE:
<223> OTHER INFORMATION: FW sequence

<400> SEQUENCE: 64

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 65
<211> LENGTH: 25
<212> TYPE: PRT
<213> ORGANISM: Artificial Sequence
<220> FEATURE:
<223> OTHER INFORMATION: FW sequence

<400> SEQUENCE: 65

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 66
<211> LENGTH: 25
<212> TYPE: PRT
<213> ORGANISM: Artificial Sequence
<220> FEATURE:
<223> OTHER INFORMATION: FW sequence

<400> SEQUENCE: 66

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 67
<211> LENGTH: 25
<212> TYPE: PRT
<213> ORGANISM: Artificial Sequence
<220> FEATURE:
<223> OTHER INFORMATION: FW sequence

<400> SEQUENCE: 67

Gln Val Gln Leu Gln Glu Ser Gly Gly Gly Leu Val Gln Ala Gly Gly
1               5                   10                  15

Ser Leu Arg Leu Ser Cys Ala Ala Ser

```
                 20                  25

<210> SEQ ID NO 68
<211> LENGTH: 25
<212> TYPE: PRT
<213> ORGANISM: Artificial Sequence
<220> FEATURE:
<223> OTHER INFORMATION: FW sequence

<400> SEQUENCE: 68

Gln Val Gln Leu Gln Glu Ser Gly Gly Gly Leu Val Gln Ala Gly Gly
1               5                   10                  15

Ser Leu Thr Leu Ser Cys Ala Ala Ser
                 20                  25

<210> SEQ ID NO 69
<211> LENGTH: 25
<212> TYPE: PRT
<213> ORGANISM: Artificial Sequence
<220> FEATURE:
<223> OTHER INFORMATION: FW sequence

<400> SEQUENCE: 69

Gln Val Gln Leu Gln Glu Ser Gly Gly Gly Leu Val Gln Pro Gly Gly
1               5                   10                  15

Ser Leu Arg Leu Ser Cys Val Ala Ser
                 20                  25

<210> SEQ ID NO 70
<211> LENGTH: 25
<212> TYPE: PRT
<213> ORGANISM: Artificial Sequence
<220> FEATURE:
<223> OTHER INFORMATION: FW sequence

<400> SEQUENCE: 70

Glu Val Gln Leu Val Glu Ser Gly Gly Gly Leu Val Gln Ala Gly Gly
1               5                   10                  15

Ser Leu Arg Leu Ser Cys Val Ala Ser
                 20                  25

<210> SEQ ID NO 71
<211> LENGTH: 25
<212> TYPE: PRT
<213> ORGANISM: Artificial Sequence
<220> FEATURE:
<223> OTHER INFORMATION: FW sequence

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Val Gly Ser
                 20                  25

<210> SEQ ID NO 72
<211> LENGTH: 25
<212> TYPE: PRT
<213> ORGANISM: Artificial Sequence
<220> FEATURE:
<223> OTHER INFORMATION: FW sequence

<400> SEQUENCE: 72

Gln Val Lys Leu Gln Glu Ser Gly Gly Gly Leu Val Gln Pro Gly Gly
1               5                   10                  15
```

```
Ser Leu Arg Leu Ser Cys Val Ala Ser
            20                  25

<210> SEQ ID NO 73
<211> LENGTH: 25
<212> TYPE: PRT
<213> ORGANISM: Artificial Sequence
<220> FEATURE:
<223> OTHER INFORMATION: FW sequence

<400> SEQUENCE: 73

Asp Val Gln Leu Gln Ala Ser Gly Gly Gly Ser Val Gln Ala Gly Gly
1               5                   10                  15

Ser Leu Thr Leu Ser Cys Arg Tyr Ser
            20                  25

<210> SEQ ID NO 74
<211> LENGTH: 25
<212> TYPE: PRT
<213> ORGANISM: Artificial Sequence
<220> FEATURE:
<223> OTHER INFORMATION: FW sequence

<400> SEQUENCE: 74

Asp Val Gln Leu Gln Glu Ser Gly Gly Gly Ser Val Gln Ala Gly Gly
1               5                   10                  15

Ser Leu Thr Leu Ser Cys Thr Ala Ser
            20                  25

<210> SEQ ID NO 75
<211> LENGTH: 25
<212> TYPE: PRT
<213> ORGANISM: Artificial Sequence
<220> FEATURE:
<223> OTHER INFORMATION: FW sequence

<400> SEQUENCE: 75

Gln Val Lys Leu Gln Glu Ser Gly Gly Gly Leu Val Gln Pro Gly Gly
1               5                   10                  15

Ser Leu Arg Leu Ser Cys Val Ala Ser
            20                  25

<210> SEQ ID NO 76
<211> LENGTH: 25
<212> TYPE: PRT
<213> ORGANISM: Artificial Sequence
<220> FEATURE:
<223> OTHER INFORMATION: FW sequence

<400> SEQUENCE: 76

Gln Val Gln Leu Gln Glu Ser Gly Gly Gly Leu Val Gln Pro Gly Gly
1               5                   10                  15

Ser Leu Arg Leu Ser Cys Val Ala Ser
            20                  25

<210> SEQ ID NO 77
<211> LENGTH: 25
<212> TYPE: PRT
<213> ORGANISM: Artificial Sequence
<220> FEATURE:
<223> OTHER INFORMATION: FW sequence

<400> SEQUENCE: 77

Gln Val Gln Leu Gln Glu Ser Gly Gly Gly Leu Val Gln Ala Gly Gly
1               5                   10                  15
```

Ser Leu Arg Leu Ser Cys Ala Ala Ser
            20                  25

<210> SEQ ID NO 78
<211> LENGTH: 25
<212> TYPE: PRT
<213> ORGANISM: Artificial Sequence
<220> FEATURE:
<223> OTHER INFORMATION: FW sequence

<400> SEQUENCE: 78

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 79
<211> LENGTH: 25
<212> TYPE: PRT
<213> ORGANISM: Artificial Sequence
<220> FEATURE:
<223> OTHER INFORMATION: FW sequence

<400> SEQUENCE: 79

Gln Val Gln Leu Gln Glu Ser Gly Gly Gly Leu Val Gln Ala Gly Gly
1               5                   10                  15

Ser Leu Arg Leu Ser Cys Ala Ile Ser
            20                  25

<210> SEQ ID NO 80
<211> LENGTH: 25
<212> TYPE: PRT
<213> ORGANISM: Artificial Sequence
<220> FEATURE:
<223> OTHER INFORMATION: FW sequence

<400> SEQUENCE: 80

Glu Val Gln Leu Val Glu Ser Gly Gly Gly Leu Val Gln Ala Gly Gly
1               5                   10                  15

Ser Leu Arg Leu Ser Cys Ala Ile Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: FW sequence

<400> SEQUENCE: 81

Gln Val Gln Leu Gln Glu Ser Gly Gly Gly Leu Val Gln Ala Gly Gly
1               5                   10                  15

Ser Val Arg Leu Ser Cys Ala Ile Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: FW sequence

<400> SEQUENCE: 82

Asp Val Gln Leu Gln Ala Ser Gly Gly Gly Leu Val Gln Ala Gly Gly

```
1               5                   10                  15
Ser Leu Arg Leu Ser Cys Ala Gly Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: FW sequence

<400> SEQUENCE: 83

Asp Val Gln Leu Gln Glu Ser Gly Gly Gly Leu Val Gln Ala Gly Gly
1               5                   10                  15

Ser Leu Arg Leu Ser Cys Ala Gly Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: FW sequence

<400> SEQUENCE: 84

Asp Val Gln Leu Gln Ala Ser Gly Gly Gly Leu Val Gln Ala Gly Gly
1               5                   10                  15

Ser Leu Arg Leu Ser Cys Ala Gly Ser
            20                  25

<210> SEQ ID NO 85
<211> LENGTH: 25
<212> TYPE: PRT
<213> ORGANISM: Artificial Sequence
<220> FEATURE:
<223> OTHER INFORMATION: FW sequence

<400> SEQUENCE: 85

Asp Val Gln Leu Gln Ala Ser Gly Gly Gly Leu Val Gln Ala Gly Gly
1               5                   10                  15

Ser Leu Arg Leu Ser Cys Ala Gly Ser
            20                  25

<210> SEQ ID NO 86
<211> LENGTH: 25
<212> TYPE: PRT
<213> ORGANISM: Artificial Sequence
<220> FEATURE:
<223> OTHER INFORMATION: FW sequence

<400> SEQUENCE: 86

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 87
<211> LENGTH: 25
<212> TYPE: PRT
<213> ORGANISM: Artificial Sequence
<220> FEATURE:
<223> OTHER INFORMATION: FW sequence

<400> SEQUENCE: 87
```

-continued

Gln Val Gln Leu Gln Glu Ser Gly Gly Arg Leu Val Gln Pro Gly Gly
1               5                   10                  15

Ser Leu Arg Leu Ser Cys Ala Ala Ser
            20                  25

<210> SEQ ID NO 88
<211> LENGTH: 25
<212> TYPE: PRT
<213> ORGANISM: Artificial Sequence
<220> FEATURE:
<223> OTHER INFORMATION: FW sequence

<400> SEQUENCE: 88

Gln Val Lys Leu Gln Glu Ser Gly Gly Arg Leu Val Gln Pro Gly Gly
1               5                   10                  15

Ser Leu Arg Leu Ser Cys Ala Ala Ser
            20                  25

<210> SEQ ID NO 89
<211> LENGTH: 25
<212> TYPE: PRT
<213> ORGANISM: Artificial Sequence
<220> FEATURE:
<223> OTHER INFORMATION: FW sequence

<400> SEQUENCE: 89

Gln Val Lys Leu Gln Glu Ser Gly Gly Arg Leu Val Gln Pro Gly Gly
1               5                   10                  15

Ser Leu Arg Leu Ser Cys Ala Ala Ser
            20                  25

<210> SEQ ID NO 90
<211> LENGTH: 25
<212> TYPE: PRT
<213> ORGANISM: Artificial Sequence
<220> FEATURE:
<223> OTHER INFORMATION: FW sequence

<400> SEQUENCE: 90

Gln Val Gln Leu Gln Glu Ser Gly Gly Arg Leu Val Gln Pro Gly Gly
1               5                   10                  15

Ser Leu Arg Leu Ser Cys Ala Ala Ser
            20                  25

<210> SEQ ID NO 91
<211> LENGTH: 25
<212> TYPE: PRT
<213> ORGANISM: Artificial Sequence
<220> FEATURE:
<223> OTHER INFORMATION: FW sequence

<400> SEQUENCE: 91

Asp Val Gln Leu Gln Ala Ser Gly Gly Gly Leu Val Gln Ala Gly Gly
1               5                   10                  15

Ser Leu Arg Leu Ser Cys Ala Pro Ser
            20                  25

<210> SEQ ID NO 92
<211> LENGTH: 25
<212> TYPE: PRT
<213> ORGANISM: Artificial Sequence
<220> FEATURE:
<223> OTHER INFORMATION: FW sequence

<400> SEQUENCE: 92

Asp Val Gln Leu Gln Ala Ser Gly Gly Gly Ser Val Gln Glu Gly Glu
1               5                   10                  15

Ser Leu Lys Leu Ser Cys Val Gly Ser
            20                  25

<210> SEQ ID NO 93
<211> LENGTH: 25
<212> TYPE: PRT
<213> ORGANISM: Artificial Sequence
<220> FEATURE:
<223> OTHER INFORMATION: FW sequence

<400> SEQUENCE: 93

Asp Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 94
<211> LENGTH: 25
<212> TYPE: PRT
<213> ORGANISM: Artificial Sequence
<220> FEATURE:
<223> OTHER INFORMATION: FW sequence

<400> SEQUENCE: 94

Asp Val Gln Leu Gln Ala Ser Gly Gly Gly Leu Val Gln Thr Gly Asp
1               5                   10                  15

Ser Leu Thr Val Ser Cys Ala Ala Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: FW sequence

<400> SEQUENCE: 95

Asp Val Gln Leu Gln Glu Ser Gly Gly Gly Leu Val Gln Ala Gly Gly
1               5                   10                  15

Ser Leu Arg Leu Ser Cys Thr Gly Ser
            20                  25

<210> SEQ ID NO 96
<211> LENGTH: 25
<212> TYPE: PRT
<213> ORGANISM: Artificial Sequence
<220> FEATURE:
<223> OTHER INFORMATION: FW sequence

<400> SEQUENCE: 96

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 97
<211> LENGTH: 25
<212> TYPE: PRT
<213> ORGANISM: Artificial Sequence
<220> FEATURE:
<223> OTHER INFORMATION: FW sequence

```
<400> SEQUENCE: 97

Asp Val Gln Leu Gln Ala Ser Gly Gly Gly Ser Val Gln Ala Gly Gly
1               5                   10                  15

Ser Leu Arg Leu Ser Cys Ala Ala Ser
            20                  25

<210> SEQ ID NO 98
<211> LENGTH: 24
<212> TYPE: PRT
<213> ORGANISM: Artificial Sequence
<220> FEATURE:
<223> OTHER INFORMATION: FW sequence

<400> SEQUENCE: 98

Val Gln Leu Gln Ala Ser Gly Gly Gly Leu Val Gln Ala Gly Gly Ser
1               5                   10                  15

Leu Arg Leu Ser Cys Thr Val Ser
            20

<210> SEQ ID NO 99
<211> LENGTH: 24
<212> TYPE: PRT
<213> ORGANISM: Artificial Sequence
<220> FEATURE:
<223> OTHER INFORMATION: FW sequence

<400> SEQUENCE: 99

Val Gln Leu Gln Ala Ser Gly Gly Gly Leu Val Gln Ala Gly Gly Ser
1               5                   10                  15

Leu Arg Leu Ser Cys Thr Val Ser
            20

<210> SEQ ID NO 100
<211> LENGTH: 25
<212> TYPE: PRT
<213> ORGANISM: Artificial Sequence
<220> FEATURE:
<223> OTHER INFORMATION: FW sequence

<400> SEQUENCE: 100

Glu Val Gln Leu Val Glu Ser Gly Gly Gly Leu Val Gln Ala Gly Glu
1               5                   10                  15

Ser Leu Arg Leu Ser Cys Ala Ala Ser
            20                  25

<210> SEQ ID NO 101
<211> LENGTH: 25
<212> TYPE: PRT
<213> ORGANISM: Artificial Sequence
<220> FEATURE:
<223> OTHER INFORMATION: FW sequence

<400> SEQUENCE: 101

Asp Val Gln Leu Gln Glu Ser Gly Gly Gly Leu Val Gln Ala Gly Asp
1               5                   10                  15

Ser Leu Arg Leu Ser Cys Glu Phe Ser
            20                  25

<210> SEQ ID NO 102
<211> LENGTH: 25
<212> TYPE: PRT
<213> ORGANISM: Artificial Sequence
<220> FEATURE:
<223> OTHER INFORMATION: FW sequence
```

```
<400> SEQUENCE: 102

Asp Val Gln Leu Gln Glu Ser Gly Gly Gly Leu Val Gln Ala Gly Asp
1               5                   10                  15

Ser Leu Arg Leu Ser Cys Glu Phe Ser
            20                  25

<210> SEQ ID NO 103
<211> LENGTH: 25
<212> TYPE: PRT
<213> ORGANISM: Artificial Sequence
<220> FEATURE:
<223> OTHER INFORMATION: FW sequence

<400> SEQUENCE: 103

Asp Val Gln Leu Gln Ala Ser Gly Gly Gly Leu Val Gln Ala Gly Gly
1               5                   10                  15

Ser Leu Arg Leu Ser Cys Glu Phe Ser
            20                  25

<210> SEQ ID NO 104
<211> LENGTH: 25
<212> TYPE: PRT
<213> ORGANISM: Artificial Sequence
<220> FEATURE:
<223> OTHER INFORMATION: FW sequence

<400> SEQUENCE: 104

Asp Val Gln Leu Gln Ala Ser Gly Gly Gly Leu Val Gln Ala Gly Gly
1               5                   10                  15

Ser Leu Arg Leu Ser Cys Glu Phe Ser
            20                  25

<210> SEQ ID NO 105
<211> LENGTH: 25
<212> TYPE: PRT
<213> ORGANISM: Artificial Sequence
<220> FEATURE:
<223> OTHER INFORMATION: FW sequence

<400> SEQUENCE: 105

Asp Val Gln Leu Gln Glu Ser Gly Gly Gly Leu Val Gln Ala Gly Ser
1               5                   10                  15

Ser Leu Arg Ile Ser Cys Ala Val Ser
            20                  25

<210> SEQ ID NO 106
<211> LENGTH: 25
<212> TYPE: PRT
<213> ORGANISM: Artificial Sequence
<220> FEATURE:
<223> OTHER INFORMATION: FW sequence

<400> SEQUENCE: 106

Asp Val Gln Leu Gln Glu Ser Gly Gly Gly Leu Val Gln Ala Gly Asp
1               5                   10                  15

Ser Leu Arg Leu Ser Cys Ala Ala Ser
            20                  25

<210> SEQ ID NO 107
<211> LENGTH: 25
<212> TYPE: PRT
<213> ORGANISM: Artificial Sequence
<220> FEATURE:
```

```
<223> OTHER INFORMATION: FW sequence

<400> SEQUENCE: 107

Asp Val Gln Leu Gln Glu Ser Gly Gly Gly Leu Val Gln Ala Gly Asp
1               5                   10                  15

Ser Leu Arg Leu Ser Cys Val Gly Ser
            20                  25

<210> SEQ ID NO 108
<211> LENGTH: 25
<212> TYPE: PRT
<213> ORGANISM: Artificial Sequence
<220> FEATURE:
<223> OTHER INFORMATION: FW sequence

<400> SEQUENCE: 108

Asp Val Gln Leu Gln Glu Ser Gly Gly Gly Leu Val Gln Ala Gly His
1               5                   10                  15

Ser Leu Arg Leu Ser Cys Val Gly Ser
            20                  25

<210> SEQ ID NO 109
<211> LENGTH: 25
<212> TYPE: PRT
<213> ORGANISM: Artificial Sequence
<220> FEATURE:
<223> OTHER INFORMATION: FW sequence

<400> SEQUENCE: 109

Asp Val Gln Leu Gln Ala Ser Gly Gly Gly Leu Val Gln Ala Gly Gly
1               5                   10                  15

Ser Gln Arg Leu Ser Cys Ala Ala Ser
            20                  25

<210> SEQ ID NO 110
<211> LENGTH: 19
<212> TYPE: PRT
<213> ORGANISM: Artificial Sequence
<220> FEATURE:
<223> OTHER INFORMATION: FW sequence

<400> SEQUENCE: 110

Ser Gly Gly Gly Leu Val Gln Ala Gly Ser Gln Arg Leu Ser Cys
1               5                   10                  15

Ala Ala Ser

<210> SEQ ID NO 111
<211> LENGTH: 25
<212> TYPE: PRT
<213> ORGANISM: Artificial Sequence
<220> FEATURE:
<223> OTHER INFORMATION: FW sequence

<400> SEQUENCE: 111

Asp Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 112
<211> LENGTH: 24
<212> TYPE: PRT
<213> ORGANISM: Artificial Sequence
<220> FEATURE:
```

<223> OTHER INFORMATION: FW sequence

<400> SEQUENCE: 112

Val Gln Leu Gln Glu Ser Gly Gly Gly Leu Val Gln Ala Gly Gly Ser
1               5                   10                  15

Leu Arg Leu Ser Cys Ala Ala Ser
            20

<210> SEQ ID NO 113
<211> LENGTH: 25
<212> TYPE: PRT
<213> ORGANISM: Artificial Sequence
<220> FEATURE:
<223> OTHER INFORMATION: FW sequence

<400> SEQUENCE: 113

Asp Val Gln Leu Gln Ala Ser Gly Gly Gly Leu Val Gln Ala Gly Gly
1               5                   10                  15

Ser Leu Arg Leu Ser Cys Ala Ala Ser
            20                  25

<210> SEQ ID NO 114
<211> LENGTH: 24
<212> TYPE: PRT
<213> ORGANISM: Artificial Sequence
<220> FEATURE:
<223> OTHER INFORMATION: FW sequence

<400> SEQUENCE: 114

Val Gln Leu Gln Ala Ser Gly Gly Gly Leu Val Gln Ala Gly Gly Ser
1               5                   10                  15

Leu Arg Leu Ser Cys Ala Ala Ser
            20

<210> SEQ ID NO 115
<211> LENGTH: 25
<212> TYPE: PRT
<213> ORGANISM: Artificial Sequence
<220> FEATURE:
<223> OTHER INFORMATION: FW sequence

<400> SEQUENCE: 115

Asp Val Gln Leu Gln Ala Ser Gly Gly Gly Leu Val Gln Ala Gly Gly
1               5                   10                  15

Ser Leu Arg Leu Ser Cys Ala Ala Ser
            20                  25

<210> SEQ ID NO 116
<211> LENGTH: 25
<212> TYPE: PRT
<213> ORGANISM: Artificial Sequence
<220> FEATURE:
<223> OTHER INFORMATION: FW sequence

<400> SEQUENCE: 116

Asp Val Gln Leu Gln Ala Ser Gly Gly Gly Leu Val Gln Ala Gly Gly
1               5                   10                  15

Ser Leu Arg Leu Ser Cys Ala Ala Ser
            20                  25

<210> SEQ ID NO 117
<211> LENGTH: 10
<212> TYPE: PRT
<213> ORGANISM: Artificial Sequence

```
<220> FEATURE:
<223> OTHER INFORMATION: CDR sequence

<400> SEQUENCE: 117

Gly Ile Ile Phe Ser Ile Asn Asp Met Gly
1               5                   10

<210> SEQ ID NO 118
<211> LENGTH: 10
<212> TYPE: PRT
<213> ORGANISM: Artificial Sequence
<220> FEATURE:
<223> OTHER INFORMATION: CDR sequence

<400> SEQUENCE: 118

Gly Ile Ile Phe Ser Ile Asn Asp Met Gly
1               5                   10

<210> SEQ ID NO 119
<211> LENGTH: 10
<212> TYPE: PRT
<213> ORGANISM: Artificial Sequence
<220> FEATURE:
<223> OTHER INFORMATION: CDR sequence

<400> SEQUENCE: 119

Gly Ile Ile Phe Ser Ile Asn Asp Met Gly
1               5                   10

<210> SEQ ID NO 120
<211> LENGTH: 10
<212> TYPE: PRT
<213> ORGANISM: Artificial Sequence
<220> FEATURE:
<223> OTHER INFORMATION: CDR sequence

<400> SEQUENCE: 120

Gly Ile Ile Leu Arg Ile Tyr Asp Met Gly
1               5                   10

<210> SEQ ID NO 121
<211> LENGTH: 10
<212> TYPE: PRT
<213> ORGANISM: Artificial Sequence
<220> FEATURE:
<223> OTHER INFORMATION: CDR sequence

<400> SEQUENCE: 121

Gly Ile Ile Leu Arg Ile Tyr Asp Met Gly
1               5                   10

<210> SEQ ID NO 122
<211> LENGTH: 10
<212> TYPE: PRT
<213> ORGANISM: Artificial Sequence
<220> FEATURE:
<223> OTHER INFORMATION: CDR sequence

<400> SEQUENCE: 122

Gly Ile Ile Leu Arg Ile Tyr Asp Met Gly
1               5                   10

<210> SEQ ID NO 123
<211> LENGTH: 10
<212> TYPE: PRT
<213> ORGANISM: Artificial Sequence
<220> FEATURE:
```

<223> OTHER INFORMATION: CDR sequence

<400> SEQUENCE: 123

Gly Ile Ile Leu Arg Leu Tyr Asp Met Gly
1               5                   10

<210> SEQ ID NO 124
<211> LENGTH: 10
<212> TYPE: PRT
<213> ORGANISM: Artificial Sequence
<220> FEATURE:
<223> OTHER INFORMATION: CDR sequence

<400> SEQUENCE: 124

Gly Ser Thr Leu Arg Leu Tyr Asp Met Gly
1               5                   10

<210> SEQ ID NO 125
<211> LENGTH: 10
<212> TYPE: PRT
<213> ORGANISM: Artificial Sequence
<220> FEATURE:
<223> OTHER INFORMATION: CDR sequence

<400> SEQUENCE: 125

Gly Ile Ile Leu Arg Ile Tyr Asp Met Gly
1               5                   10

<210> SEQ ID NO 126
<211> LENGTH: 10
<212> TYPE: PRT
<213> ORGANISM: Artificial Sequence
<220> FEATURE:
<223> OTHER INFORMATION: CDR sequence

<400> SEQUENCE: 126

Arg Asn Thr Asp Ser Ile Glu Ile Met Gly
1               5                   10

<210> SEQ ID NO 127
<211> LENGTH: 10
<212> TYPE: PRT
<213> ORGANISM: Artificial Sequence
<220> FEATURE:
<223> OTHER INFORMATION: CDR sequence

<400> SEQUENCE: 127

Glu Arg Ile Phe Ser Arg Asn Thr Met Gly
1               5                   10

<210> SEQ ID NO 128
<211> LENGTH: 10
<212> TYPE: PRT
<213> ORGANISM: Artificial Sequence
<220> FEATURE:
<223> OTHER INFORMATION: CDR sequence

<400> SEQUENCE: 128

Glu Arg Ile Phe Ser Arg Asn Thr Met Gly
1               5                   10

<210> SEQ ID NO 129
<211> LENGTH: 10
<212> TYPE: PRT
<213> ORGANISM: Artificial Sequence
<220> FEATURE:
<223> OTHER INFORMATION: CDR sequence

<400> SEQUENCE: 129

Glu Arg Ile Phe Ser Arg Asn Thr Met Gly
1               5                   10

<210> SEQ ID NO 130
<211> LENGTH: 10
<212> TYPE: PRT
<213> ORGANISM: Artificial Sequence
<220> FEATURE:
<223> OTHER INFORMATION: CDR sequence

<400> SEQUENCE: 130

Glu Arg Ile Phe Ser Arg Asn Thr Met Gly
1               5                   10

<210> SEQ ID NO 131
<211> LENGTH: 11
<212> TYPE: PRT
<213> ORGANISM: Artificial Sequence
<220> FEATURE:
<223> OTHER INFORMATION: CDR sequence

<400> SEQUENCE: 131

Gly Gly Phe Val Phe Arg Val Ser Ser Met Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: CDR sequence

<400> SEQUENCE: 132

Gly Leu Leu Phe Arg Leu Ala Ser Met Gly
1               5                   10

<210> SEQ ID NO 133
<211> LENGTH: 10
<212> TYPE: PRT
<213> ORGANISM: Artificial Sequence
<220> FEATURE:
<223> OTHER INFORMATION: CDR sequence

<400> SEQUENCE: 133

Gly Ser Ile Ser Ser Ile Ile Thr Met Gly
1               5                   10

<210> SEQ ID NO 134
<211> LENGTH: 10
<212> TYPE: PRT
<213> ORGANISM: Artificial Sequence
<220> FEATURE:
<223> OTHER INFORMATION: CDR sequence

<400> SEQUENCE: 134

Gly Ser Ile Ser Asn Ile Ile Thr Met Gly
1               5                   10

<210> SEQ ID NO 135
<211> LENGTH: 10
<212> TYPE: PRT
<213> ORGANISM: Artificial Sequence
<220> FEATURE:
<223> OTHER INFORMATION: CDR sequence

```
<400> SEQUENCE: 135

Gly Arg Thr Phe Ser Ser Val Ala Met Gly
1               5                   10

<210> SEQ ID NO 136
<211> LENGTH: 10
<212> TYPE: PRT
<213> ORGANISM: Artificial Sequence
<220> FEATURE:
<223> OTHER INFORMATION: CDR sequence

<400> SEQUENCE: 136

Gly Arg Thr Phe Ser Ser Val Ala Met Gly
1               5                   10

<210> SEQ ID NO 137
<211> LENGTH: 9
<212> TYPE: PRT
<213> ORGANISM: Artificial Sequence
<220> FEATURE:
<223> OTHER INFORMATION: CDR sequence

<400> SEQUENCE: 137

Gly Arg Thr Phe Ile Ala Asp Met Gly
1               5

<210> SEQ ID NO 138
<211> LENGTH: 9
<212> TYPE: PRT
<213> ORGANISM: Artificial Sequence
<220> FEATURE:
<223> OTHER INFORMATION: CDR sequence

<400> SEQUENCE: 138

Gly Arg Thr Phe Ile Ala Asp Met Gly
1               5

<210> SEQ ID NO 139
<211> LENGTH: 9
<212> TYPE: PRT
<213> ORGANISM: Artificial Sequence
<220> FEATURE:
<223> OTHER INFORMATION: CDR sequence

<400> SEQUENCE: 139

Gly Arg Thr Phe Ile Asn Asp Met Gly
1               5

<210> SEQ ID NO 140
<211> LENGTH: 10
<212> TYPE: PRT
<213> ORGANISM: Artificial Sequence
<220> FEATURE:
<223> OTHER INFORMATION: CDR sequence

<400> SEQUENCE: 140

Gly Arg Thr Phe Thr Asn Tyr Asp Met Gly
1               5                   10

<210> SEQ ID NO 141
<211> LENGTH: 10
<212> TYPE: PRT
<213> ORGANISM: Artificial Sequence
<220> FEATURE:
<223> OTHER INFORMATION: CDR sequence

<400> SEQUENCE: 141
```

Gly Arg Thr Phe Thr Asn Tyr Asp Met Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: CDR sequence

<400> SEQUENCE: 142

Gly Arg Ser Phe Ser Ser Tyr Ala Met Gly
1               5                   10

<210> SEQ ID NO 143
<211> LENGTH: 10
<212> TYPE: PRT
<213> ORGANISM: Artificial Sequence
<220> FEATURE:
<223> OTHER INFORMATION: CDR sequence

<400> SEQUENCE: 143

Gly Arg Thr Phe Ser Ser Tyr Ala Met Gly
1               5                   10

<210> SEQ ID NO 144
<211> LENGTH: 10
<212> TYPE: PRT
<213> ORGANISM: Artificial Sequence
<220> FEATURE:
<223> OTHER INFORMATION: CDR sequence

<400> SEQUENCE: 144

Gly Arg Thr Asp Thr Arg Tyr Thr Met Gly
1               5                   10

<210> SEQ ID NO 145
<211> LENGTH: 10
<212> TYPE: PRT
<213> ORGANISM: Artificial Sequence
<220> FEATURE:
<223> OTHER INFORMATION: CDR sequence

<400> SEQUENCE: 145

Gly Arg Thr Leu Ser Asn Tyr Ala Met Ala
1               5                   10

<210> SEQ ID NO 146
<211> LENGTH: 10
<212> TYPE: PRT
<213> ORGANISM: Artificial Sequence
<220> FEATURE:
<223> OTHER INFORMATION: CDR sequence

<400> SEQUENCE: 146

Gly Arg Thr Leu Ser Asn Tyr Ala Met Ala
1               5                   10

<210> SEQ ID NO 147
<211> LENGTH: 10
<212> TYPE: PRT
<213> ORGANISM: Artificial Sequence
<220> FEATURE:
<223> OTHER INFORMATION: CDR sequence

<400> SEQUENCE: 147

```
Gly Arg Thr Phe Ser Asn Tyr Ala Met Ala
1               5                   10
```

<210> SEQ ID NO 148
<211> LENGTH: 10
<212> TYPE: PRT
<213> ORGANISM: Artificial Sequence
<220> FEATURE:
<223> OTHER INFORMATION: CDR sequence

<400> SEQUENCE: 148

```
Gly Arg Thr Phe Ser Asn Tyr Ala Met Ala
1               5                   10
```

<210> SEQ ID NO 149
<211> LENGTH: 10
<212> TYPE: PRT
<213> ORGANISM: Artificial Sequence
<220> FEATURE:
<223> OTHER INFORMATION: CDR sequence

<400> SEQUENCE: 149

```
Gly Gly Thr Phe Asp Ala Tyr Asp Met Gly
1               5                   10
```

<210> SEQ ID NO 150
<211> LENGTH: 10
<212> TYPE: PRT
<213> ORGANISM: Artificial Sequence
<220> FEATURE:
<223> OTHER INFORMATION: CDR sequence

<400> SEQUENCE: 150

```
Gly Arg Thr Phe Ser Asp Trp Ala Met Gly
1               5                   10
```

<210> SEQ ID NO 151
<211> LENGTH: 10
<212> TYPE: PRT
<213> ORGANISM: Artificial Sequence
<220> FEATURE:
<223> OTHER INFORMATION: CDR sequence

<400> SEQUENCE: 151

```
Gly Val Ser Phe Ser Arg Tyr Thr Met Gly
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: CDR sequence

<400> SEQUENCE: 152

```
Gly Leu Ser Phe Thr Arg Tyr Thr Met Gly
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: CDR sequence

<400> SEQUENCE: 153

```
Gly Arg Thr Phe Arg Asn Tyr Pro Met Ala
```

```
1               5                   10
```

<210> SEQ ID NO 154
<211> LENGTH: 10
<212> TYPE: PRT
<213> ORGANISM: Artificial Sequence
<220> FEATURE:
<223> OTHER INFORMATION: CDR sequence

<400> SEQUENCE: 154

```
Gly Arg Thr Phe Val Ser Phe Gly Met Gly
1               5                   10
```

<210> SEQ ID NO 155
<211> LENGTH: 10
<212> TYPE: PRT
<213> ORGANISM: Artificial Sequence
<220> FEATURE:
<223> OTHER INFORMATION: CDR sequence

<400> SEQUENCE: 155

```
Gly Leu Ser Phe Ser Asp Tyr Ala Met Gly
1               5                   10
```

<210> SEQ ID NO 156
<211> LENGTH: 10
<212> TYPE: PRT
<213> ORGANISM: Artificial Sequence
<220> FEATURE:
<223> OTHER INFORMATION: CDR sequence

<400> SEQUENCE: 156

```
Gly Phe Thr Ser Asp Asp Tyr Thr Val Gly
1               5                   10
```

<210> SEQ ID NO 157
<211> LENGTH: 10
<212> TYPE: PRT
<213> ORGANISM: Artificial Sequence
<220> FEATURE:
<223> OTHER INFORMATION: CDR sequence

<400> SEQUENCE: 157

```
Gly Phe Thr Ser Asp Asp Tyr Thr Val Gly
1               5                   10
```

<210> SEQ ID NO 158
<211> LENGTH: 10
<212> TYPE: PRT
<213> ORGANISM: Artificial Sequence
<220> FEATURE:
<223> OTHER INFORMATION: CDR sequence

<400> SEQUENCE: 158

```
Gly Arg Thr Phe Thr Asn Leu Gly Met Gly
1               5                   10
```

<210> SEQ ID NO 159
<211> LENGTH: 10
<212> TYPE: PRT
<213> ORGANISM: Artificial Sequence
<220> FEATURE:
<223> OTHER INFORMATION: CDR sequence

<400> SEQUENCE: 159

```
Gly Arg Thr Phe Ser Gly Phe Ala Met Gly
1               5                   10
```

<210> SEQ ID NO 160
<211> LENGTH: 10
<212> TYPE: PRT
<213> ORGANISM: Artificial Sequence
<220> FEATURE:
<223> OTHER INFORMATION: CDR sequence

<400> SEQUENCE: 160

Gly Arg Thr Phe Ser Gly Phe Ala Met Gly
1               5                   10

<210> SEQ ID NO 161
<211> LENGTH: 10
<212> TYPE: PRT
<213> ORGANISM: Artificial Sequence
<220> FEATURE:
<223> OTHER INFORMATION: CDR sequence

<400> SEQUENCE: 161

Gly Arg Thr Phe Ser Gly Phe Ala Met Gly
1               5                   10

<210> SEQ ID NO 162
<211> LENGTH: 10
<212> TYPE: PRT
<213> ORGANISM: Artificial Sequence
<220> FEATURE:
<223> OTHER INFORMATION: CDR sequence

<400> SEQUENCE: 162

Gly Arg Thr Phe Ser Gly Phe Ala Met Gly
1               5                   10

<210> SEQ ID NO 163
<211> LENGTH: 10
<212> TYPE: PRT
<213> ORGANISM: Artificial Sequence
<220> FEATURE:
<223> OTHER INFORMATION: CDR sequence

<400> SEQUENCE: 163

Gly Val Arg Leu Asp Asn Tyr Ala Met Gly
1               5                   10

<210> SEQ ID NO 164
<211> LENGTH: 10
<212> TYPE: PRT
<213> ORGANISM: Artificial Sequence
<220> FEATURE:
<223> OTHER INFORMATION: CDR sequence

<400> SEQUENCE: 164

Gly Pro His Phe Asn Asn Tyr Ala Ile Gly
1               5                   10

<210> SEQ ID NO 165
<211> LENGTH: 10
<212> TYPE: PRT
<213> ORGANISM: Artificial Sequence
<220> FEATURE:
<223> OTHER INFORMATION: CDR sequence

<400> SEQUENCE: 165

Gly Arg Arg Phe Asp Asn Tyr Ala Met Ala
1               5                   10

<210> SEQ ID NO 166
<211> LENGTH: 10
<212> TYPE: PRT
<213> ORGANISM: Artificial Sequence
<220> FEATURE:
<223> OTHER INFORMATION: CDR sequence

<400> SEQUENCE: 166

Gly Ser Arg Phe Asp Asn Tyr Ala Met Gly
1               5                   10

<210> SEQ ID NO 167
<211> LENGTH: 10
<212> TYPE: PRT
<213> ORGANISM: Artificial Sequence
<220> FEATURE:
<223> OTHER INFORMATION: CDR sequence

<400> SEQUENCE: 167

Gly His Thr Phe Ser Ser Tyr Ser Met Ala
1               5                   10

<210> SEQ ID NO 168
<211> LENGTH: 10
<212> TYPE: PRT
<213> ORGANISM: Artificial Sequence
<220> FEATURE:
<223> OTHER INFORMATION: CDR sequence

<400> SEQUENCE: 168

Gly His Thr Phe Ser Ser Tyr Ser Met Ala
1               5                   10

<210> SEQ ID NO 169
<211> LENGTH: 10
<212> TYPE: PRT
<213> ORGANISM: Artificial Sequence
<220> FEATURE:
<223> OTHER INFORMATION: CDR sequence

<400> SEQUENCE: 169

Gly Phe Thr Phe Asp Asp Tyr Val Ile Gly
1               5                   10

<210> SEQ ID NO 170
<211> LENGTH: 10
<212> TYPE: PRT
<213> ORGANISM: Artificial Sequence
<220> FEATURE:
<223> OTHER INFORMATION: CDR sequence

<400> SEQUENCE: 170

Gly Phe Thr Phe Asp Asp Tyr Val Ile Gly
1               5                   10

<210> SEQ ID NO 171
<211> LENGTH: 10
<212> TYPE: PRT
<213> ORGANISM: Artificial Sequence
<220> FEATURE:
<223> OTHER INFORMATION: CDR sequence

<400> SEQUENCE: 171

Glu Phe Thr Phe Asp Asp Tyr Val Ile Gly
1               5                   10

```
<210> SEQ ID NO 172
<211> LENGTH: 10
<212> TYPE: PRT
<213> ORGANISM: Artificial Sequence
<220> FEATURE:
<223> OTHER INFORMATION: CDR sequence

<400> SEQUENCE: 172

Gly Phe Thr Phe Asp Asp Tyr Val Ile Gly
1               5                   10

<210> SEQ ID NO 173
<211> LENGTH: 10
<212> TYPE: PRT
<213> ORGANISM: Artificial Sequence
<220> FEATURE:
<223> OTHER INFORMATION: CDR sequence

<400> SEQUENCE: 173

Gly Phe Thr Phe Asp Asp Tyr Val Ile Gly
1               5                   10

<210> SEQ ID NO 174
<211> LENGTH: 10
<212> TYPE: PRT
<213> ORGANISM: Artificial Sequence
<220> FEATURE:
<223> OTHER INFORMATION: CDR sequence

<400> SEQUENCE: 174

Gly Phe Thr Phe Asp Asp Tyr Val Ile Gly
1               5                   10

<210> SEQ ID NO 175
<211> LENGTH: 14
<212> TYPE: PRT
<213> ORGANISM: Artificial Sequence
<220> FEATURE:
<223> OTHER INFORMATION: FW sequence

<400> SEQUENCE: 175

Trp Tyr Arg Gln Ala Pro Gly Lys Gln Arg Glu Leu Val Ala
1               5                   10

<210> SEQ ID NO 176
<211> LENGTH: 14
<212> TYPE: PRT
<213> ORGANISM: Artificial Sequence
<220> FEATURE:
<223> OTHER INFORMATION: FW sequence

<400> SEQUENCE: 176

Trp Tyr Arg Gln Ala Pro Gly Lys Gln Arg Glu Leu Val Ala
1               5                   10

<210> SEQ ID NO 177
<211> LENGTH: 14
<212> TYPE: PRT
<213> ORGANISM: Artificial Sequence
<220> FEATURE:
<223> OTHER INFORMATION: FW sequence

<400> SEQUENCE: 177

Trp Tyr Arg Gln Ala Pro Gly Lys Gln Arg Glu Leu Val Ala
1               5                   10

<210> SEQ ID NO 178
```

```
<211> LENGTH: 14
<212> TYPE: PRT
<213> ORGANISM: Artificial Sequence
<220> FEATURE:
<223> OTHER INFORMATION: FW sequence

<400> SEQUENCE: 178

Trp Tyr Arg Gln Ala Pro Gly Lys Gln Arg Glu Leu Val Ala
1               5                   10

<210> SEQ ID NO 179
<211> LENGTH: 14
<212> TYPE: PRT
<213> ORGANISM: Artificial Sequence
<220> FEATURE:
<223> OTHER INFORMATION: FW sequence

<400> SEQUENCE: 179

Trp Tyr Arg Gln Ala Pro Gly Lys Gln Arg Glu Leu Val Ala
1               5                   10

<210> SEQ ID NO 180
<211> LENGTH: 14
<212> TYPE: PRT
<213> ORGANISM: Artificial Sequence
<220> FEATURE:
<223> OTHER INFORMATION: FW sequence

<400> SEQUENCE: 180

Trp Tyr Arg Gln Ala Pro Gly Lys Gln Arg Glu Leu Val Ala
1               5                   10

<210> SEQ ID NO 181
<211> LENGTH: 14
<212> TYPE: PRT
<213> ORGANISM: Artificial Sequence
<220> FEATURE:
<223> OTHER INFORMATION: FW sequence

<400> SEQUENCE: 181

Trp Tyr Arg Gln Thr Pro Gly Lys Gln Arg Glu Leu Val Ala
1               5                   10

<210> SEQ ID NO 182
<211> LENGTH: 14
<212> TYPE: PRT
<213> ORGANISM: Artificial Sequence
<220> FEATURE:
<223> OTHER INFORMATION: FW sequence

<400> SEQUENCE: 182

Trp Tyr Arg Gln Ala Asp Gly Lys Gln Arg Glu Leu Val Ala
1               5                   10

<210> SEQ ID NO 183
<211> LENGTH: 14
<212> TYPE: PRT
<213> ORGANISM: Artificial Sequence
<220> FEATURE:
<223> OTHER INFORMATION: FW sequence

<400> SEQUENCE: 183

Trp Tyr Arg Gln Ala Pro Gly Lys Gln Arg Glu Leu Val Ala
1               5                   10

<210> SEQ ID NO 184
<211> LENGTH: 14
```

```
<212> TYPE: PRT
<213> ORGANISM: Artificial Sequence
<220> FEATURE:
<223> OTHER INFORMATION: FW sequence

<400> SEQUENCE: 184

Trp Tyr Arg Gln Ala Pro Gly Lys Gln Arg Glu Trp Val Ala
1               5                   10

<210> SEQ ID NO 185
<211> LENGTH: 14
<212> TYPE: PRT
<213> ORGANISM: Artificial Sequence
<220> FEATURE:
<223> OTHER INFORMATION: FW sequence

<400> SEQUENCE: 185

Trp Tyr Arg Gln Ala Pro Gly Lys Gln Arg Glu Leu Val Ala
1               5                   10

<210> SEQ ID NO 186
<211> LENGTH: 14
<212> TYPE: PRT
<213> ORGANISM: Artificial Sequence
<220> FEATURE:
<223> OTHER INFORMATION: FW sequence

<400> SEQUENCE: 186

Trp Tyr Arg Gln Ala Pro Gly Lys Gln Arg Glu Leu Val Ala
1               5                   10

<210> SEQ ID NO 187
<211> LENGTH: 14
<212> TYPE: PRT
<213> ORGANISM: Artificial Sequence
<220> FEATURE:
<223> OTHER INFORMATION: FW sequence

<400> SEQUENCE: 187

Trp Tyr Arg Gln Ala Pro Gly Lys Gln Arg Glu Leu Val Gly
1               5                   10

<210> SEQ ID NO 188
<211> LENGTH: 14
<212> TYPE: PRT
<213> ORGANISM: Artificial Sequence
<220> FEATURE:
<223> OTHER INFORMATION: FW sequence

<400> SEQUENCE: 188

Trp Tyr Arg Gln Ala Pro Gly Lys Gln Arg Glu Leu Val Ala
1               5                   10

<210> SEQ ID NO 189
<211> LENGTH: 14
<212> TYPE: PRT
<213> ORGANISM: Artificial Sequence
<220> FEATURE:
<223> OTHER INFORMATION: FW sequence

<400> SEQUENCE: 189

Trp Tyr Arg Gln Ala Pro Gly Asn Gln Arg Glu Leu Ile Ala
1               5                   10

<210> SEQ ID NO 190
<211> LENGTH: 14
<212> TYPE: PRT
```

<213> ORGANISM: Artificial Sequence
<220> FEATURE:
<223> OTHER INFORMATION: FW sequence

<400> SEQUENCE: 190

Trp Tyr Arg Gln Ala Pro Gly Lys Glu Arg Glu Leu Ile Ala
1               5                   10

<210> SEQ ID NO 191
<211> LENGTH: 14
<212> TYPE: PRT
<213> ORGANISM: Artificial Sequence
<220> FEATURE:
<223> OTHER INFORMATION: FW sequence

<400> SEQUENCE: 191

Trp Tyr Arg Gln Ala Pro Gly Lys Gln Arg Glu Phe Val Ala
1               5                   10

<210> SEQ ID NO 192
<211> LENGTH: 14
<212> TYPE: PRT
<213> ORGANISM: Artificial Sequence
<220> FEATURE:
<223> OTHER INFORMATION: FW sequence

<400> SEQUENCE: 192

Trp Tyr Arg Gln Ala Pro Gly Lys Gln Arg Glu Phe Val Ala
1               5                   10

<210> SEQ ID NO 193
<211> LENGTH: 14
<212> TYPE: PRT
<213> ORGANISM: Artificial Sequence
<220> FEATURE:
<223> OTHER INFORMATION: FW sequence

<400> SEQUENCE: 193

Trp Phe Arg Gln Ala Pro Gly Lys Glu Arg Glu Phe Val Ala
1               5                   10

<210> SEQ ID NO 194
<211> LENGTH: 14
<212> TYPE: PRT
<213> ORGANISM: Artificial Sequence
<220> FEATURE:
<223> OTHER INFORMATION: FW sequence

<400> SEQUENCE: 194

Trp Phe Arg Gln Ala Pro Gly Arg Glu Arg Glu Phe Val Ala
1               5                   10

<210> SEQ ID NO 195
<211> LENGTH: 14
<212> TYPE: PRT
<213> ORGANISM: Artificial Sequence
<220> FEATURE:
<223> OTHER INFORMATION: FW sequence

<400> SEQUENCE: 195

Trp Phe Arg Gln Ala Pro Gly Lys Glu Arg Glu Phe Gln Ala
1               5                   10

<210> SEQ ID NO 196
<211> LENGTH: 14
<212> TYPE: PRT
<213> ORGANISM: Artificial Sequence

```
<220> FEATURE:
<223> OTHER INFORMATION: FW sequence

<400> SEQUENCE: 196

Trp Phe Arg Gln Ala Pro Gly Lys Glu Arg Glu Phe Gln Ala
1               5                   10

<210> SEQ ID NO 197
<211> LENGTH: 14
<212> TYPE: PRT
<213> ORGANISM: Artificial Sequence
<220> FEATURE:
<223> OTHER INFORMATION: FW sequence

<400> SEQUENCE: 197

Trp Phe Arg Gln Ala Pro Gly Lys Glu Arg Glu Phe Gln Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: FW sequence

<400> SEQUENCE: 198

Trp Phe Arg Gln Ala Pro Gly Lys Glu Arg Arg Phe Val Ala
1               5                   10

<210> SEQ ID NO 199
<211> LENGTH: 14
<212> TYPE: PRT
<213> ORGANISM: Artificial Sequence
<220> FEATURE:
<223> OTHER INFORMATION: FW sequence

<400> SEQUENCE: 199

Trp Phe Arg Gln Ala Pro Gly Lys Glu Arg Arg Phe Val Ala
1               5                   10

<210> SEQ ID NO 200
<211> LENGTH: 14
<212> TYPE: PRT
<213> ORGANISM: Artificial Sequence
<220> FEATURE:
<223> OTHER INFORMATION: FW sequence

<400> SEQUENCE: 200

Trp Phe Arg Gln Ala Pro Gly Lys Ala Arg Glu Ile Val Ala
1               5                   10

<210> SEQ ID NO 201
<211> LENGTH: 14
<212> TYPE: PRT
<213> ORGANISM: Artificial Sequence
<220> FEATURE:
<223> OTHER INFORMATION: FW sequence

<400> SEQUENCE: 201

Trp Phe Arg Gln Ala Pro Gly Lys Glu Arg Glu Phe Val Ala
1               5                   10

<210> SEQ ID NO 202
<211> LENGTH: 14
<212> TYPE: PRT
<213> ORGANISM: Artificial Sequence
<220> FEATURE:
```

<223> OTHER INFORMATION: FW sequence

<400> SEQUENCE: 202

Trp Phe Arg Gln Ala Pro Gly Lys Glu Arg Glu Phe Val Ser
1               5                   10

<210> SEQ ID NO 203
<211> LENGTH: 14
<212> TYPE: PRT
<213> ORGANISM: Artificial Sequence
<220> FEATURE:
<223> OTHER INFORMATION: FW sequence

<400> SEQUENCE: 203

Trp Phe Arg Gln Gly Pro Gly Lys Glu Arg Glu Phe Val Ala
1               5                   10

<210> SEQ ID NO 204
<211> LENGTH: 14
<212> TYPE: PRT
<213> ORGANISM: Artificial Sequence
<220> FEATURE:
<223> OTHER INFORMATION: FW sequence

<400> SEQUENCE: 204

Trp Phe Arg Gln Gly Pro Gly Lys Glu Arg Glu Phe Val Ala
1               5                   10

<210> SEQ ID NO 205
<211> LENGTH: 14
<212> TYPE: PRT
<213> ORGANISM: Artificial Sequence
<220> FEATURE:
<223> OTHER INFORMATION: FW sequence

<400> SEQUENCE: 205

Trp Phe Arg Gln Gly Pro Gly Lys Glu Arg Glu Phe Val Ala
1               5                   10

<210> SEQ ID NO 206
<211> LENGTH: 14
<212> TYPE: PRT
<213> ORGANISM: Artificial Sequence
<220> FEATURE:
<223> OTHER INFORMATION: FW sequence

<400> SEQUENCE: 206

Trp Phe Arg Gln Gly Pro Gly Lys Glu Arg Glu Phe Val Ala
1               5                   10

<210> SEQ ID NO 207
<211> LENGTH: 14
<212> TYPE: PRT
<213> ORGANISM: Artificial Sequence
<220> FEATURE:
<223> OTHER INFORMATION: FW sequence

<400> SEQUENCE: 207

Trp Tyr Arg Glu Ala Pro Gly Lys Lys Arg Gln Phe Val Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: FW sequence

<400> SEQUENCE: 208

Trp Tyr Arg Gln Ala Pro Gly Lys Asp Arg Glu Phe Val Ala
1               5                   10

<210> SEQ ID NO 209
<211> LENGTH: 14
<212> TYPE: PRT
<213> ORGANISM: Artificial Sequence
<220> FEATURE:
<223> OTHER INFORMATION: FW sequence

<400> SEQUENCE: 209

Trp Tyr Arg Glu Val Pro Gly Lys Glu Arg Arg Glu Phe Val
1               5                   10

<210> SEQ ID NO 210
<211> LENGTH: 14
<212> TYPE: PRT
<213> ORGANISM: Artificial Sequence
<220> FEATURE:
<223> OTHER INFORMATION: FW sequence

<400> SEQUENCE: 210

Trp Tyr Arg Glu Val Pro Gly Lys Glu Arg Arg Glu Phe Val
1               5                   10

<210> SEQ ID NO 211
<211> LENGTH: 14
<212> TYPE: PRT
<213> ORGANISM: Artificial Sequence
<220> FEATURE:
<223> OTHER INFORMATION: FW sequence

<400> SEQUENCE: 211

Trp Phe Arg Gln Ala Pro Gly Lys Glu Arg Glu Phe Val Ala
1               5                   10

<210> SEQ ID NO 212
<211> LENGTH: 14
<212> TYPE: PRT
<213> ORGANISM: Artificial Sequence
<220> FEATURE:
<223> OTHER INFORMATION: FW sequence

<400> SEQUENCE: 212

Trp Phe Arg Gln Ala Pro Gly Lys Glu Arg Glu Phe Val Ala
1               5                   10

<210> SEQ ID NO 213
<211> LENGTH: 14
<212> TYPE: PRT
<213> ORGANISM: Artificial Sequence
<220> FEATURE:
<223> OTHER INFORMATION: FW sequence

<400> SEQUENCE: 213

Trp Phe Arg Gln Glu Pro Gly Lys Glu Arg Arg Phe Val Ala
1               5                   10

<210> SEQ ID NO 214
<211> LENGTH: 14
<212> TYPE: PRT
<213> ORGANISM: Artificial Sequence
<220> FEATURE:
<223> OTHER INFORMATION: FW sequence -continued

```
<400> SEQUENCE: 214

Trp Phe Arg Gln Ala Pro Gly Leu Lys Arg Glu Gly Leu Ser
1               5                   10

<210> SEQ ID NO 215
<211> LENGTH: 14
<212> TYPE: PRT
<213> ORGANISM: Artificial Sequence
<220> FEATURE:
<223> OTHER INFORMATION: FW sequence

<400> SEQUENCE: 215

Trp Phe Arg Gln Ala Pro Gly Leu Lys Arg Glu Gly Leu Ser
1               5                   10

<210> SEQ ID NO 216
<211> LENGTH: 14
<212> TYPE: PRT
<213> ORGANISM: Artificial Sequence
<220> FEATURE:
<223> OTHER INFORMATION: FW sequence

<400> SEQUENCE: 216

Trp Phe Arg Gln Ala Pro Gly Lys Glu Arg Glu Phe Val Ala
1               5                   10

<210> SEQ ID NO 217
<211> LENGTH: 14
<212> TYPE: PRT
<213> ORGANISM: Artificial Sequence
<220> FEATURE:
<223> OTHER INFORMATION: FW sequence

<400> SEQUENCE: 217

Trp Phe Arg Gln Phe Pro Gly Lys Glu Arg Glu Phe Val Ala
1               5                   10

<210> SEQ ID NO 218
<211> LENGTH: 14
<212> TYPE: PRT
<213> ORGANISM: Artificial Sequence
<220> FEATURE:
<223> OTHER INFORMATION: FW sequence

<400> SEQUENCE: 218

Trp Phe Arg Gln Phe Pro Gly Lys Glu Arg Glu Phe Val Ala
1               5                   10

<210> SEQ ID NO 219
<211> LENGTH: 14
<212> TYPE: PRT
<213> ORGANISM: Artificial Sequence
<220> FEATURE:
<223> OTHER INFORMATION: FW sequence

<400> SEQUENCE: 219

Trp Phe Arg Gln Phe Pro Gly Lys Glu Arg Glu Phe Val Ala
1               5                   10

<210> SEQ ID NO 220
<211> LENGTH: 14
<212> TYPE: PRT
<213> ORGANISM: Artificial Sequence
<220> FEATURE:
<223> OTHER INFORMATION: FW sequence

<400> SEQUENCE: 220
```

Trp Phe Arg Gln Phe Pro Gly Lys Glu Arg Glu Phe Val Ala
1               5                   10

<210> SEQ ID NO 221
<211> LENGTH: 14
<212> TYPE: PRT
<213> ORGANISM: Artificial Sequence
<220> FEATURE:
<223> OTHER INFORMATION: FW sequence

<400> SEQUENCE: 221

Trp Phe Arg Gln Ala Pro Gly Lys Glu Arg Glu Ser Val Ala
1               5                   10

<210> SEQ ID NO 222
<211> LENGTH: 14
<212> TYPE: PRT
<213> ORGANISM: Artificial Sequence
<220> FEATURE:
<223> OTHER INFORMATION: FW sequence

<400> SEQUENCE: 222

Trp Phe Arg Gln Ala Pro Gly Lys Glu Arg Glu Phe Val Ala
1               5                   10

<210> SEQ ID NO 223
<211> LENGTH: 14
<212> TYPE: PRT
<213> ORGANISM: Artificial Sequence
<220> FEATURE:
<223> OTHER INFORMATION: FW sequence

<400> SEQUENCE: 223

Trp Phe Arg Gln Ala Pro Gly Lys Glu Arg Thr Phe Val Ala
1               5                   10

<210> SEQ ID NO 224
<211> LENGTH: 14
<212> TYPE: PRT
<213> ORGANISM: Artificial Sequence
<220> FEATURE:
<223> OTHER INFORMATION: FW sequence

<400> SEQUENCE: 224

Trp Phe Arg Gln Ala Pro Gly Lys Glu Arg Glu Phe Val Ala
1               5                   10

<210> SEQ ID NO 225
<211> LENGTH: 14
<212> TYPE: PRT
<213> ORGANISM: Artificial Sequence
<220> FEATURE:
<223> OTHER INFORMATION: FW sequence

<400> SEQUENCE: 225

Trp Phe Arg Gln Ala Pro Gly Lys Glu Arg Glu Phe Val Ala
1               5                   10

<210> SEQ ID NO 226
<211> LENGTH: 14
<212> TYPE: PRT
<213> ORGANISM: Artificial Sequence
<220> FEATURE:
<223> OTHER INFORMATION: FW sequence

<400> SEQUENCE: 226

```
Trp Phe Arg Gln Ala Pro Gly Lys Glu Arg Glu Phe Val Ala
1               5                   10
```

<210> SEQ ID NO 227
<211> LENGTH: 14
<212> TYPE: PRT
<213> ORGANISM: Artificial Sequence
<220> FEATURE:
<223> OTHER INFORMATION: FW sequence

<400> SEQUENCE: 227

```
Trp Phe Arg Gln Ala Pro Gly Lys Glu Arg Glu Gly Val Ser
1               5                   10
```

<210> SEQ ID NO 228
<211> LENGTH: 14
<212> TYPE: PRT
<213> ORGANISM: Artificial Sequence
<220> FEATURE:
<223> OTHER INFORMATION: FW sequence

<400> SEQUENCE: 228

```
Trp Phe Arg Gln Ala Pro Gly Lys Glu Cys Glu Gly Val Ser
1               5                   10
```

<210> SEQ ID NO 229
<211> LENGTH: 14
<212> TYPE: PRT
<213> ORGANISM: Artificial Sequence
<220> FEATURE:
<223> OTHER INFORMATION: FW sequence

<400> SEQUENCE: 229

```
Trp Phe Arg Gln Ala Pro Gly Lys Glu Arg Glu Gly Val Ser
1               5                   10
```

<210> SEQ ID NO 230
<211> LENGTH: 14
<212> TYPE: PRT
<213> ORGANISM: Artificial Sequence
<220> FEATURE:
<223> OTHER INFORMATION: FW sequence

<400> SEQUENCE: 230

```
Trp Phe Arg Gln Ser Pro Gly Lys Glu Arg Glu Gly Val Ser
1               5                   10
```

<210> SEQ ID NO 231
<211> LENGTH: 14
<212> TYPE: PRT
<213> ORGANISM: Artificial Sequence
<220> FEATURE:
<223> OTHER INFORMATION: FW sequence

<400> SEQUENCE: 231

```
Trp Phe Arg Gln Ala Pro Gly Lys Glu Arg Glu Gly Val Ser
1               5                   10
```

<210> SEQ ID NO 232
<211> LENGTH: 14
<212> TYPE: PRT
<213> ORGANISM: Artificial Sequence
<220> FEATURE:
<223> OTHER INFORMATION: FW sequence

<400> SEQUENCE: 232

```
Trp Phe Arg Gln Ala Pro Gly Lys Glu Arg Glu Gly Val Ser
```

<210> SEQ ID NO 233
<211> LENGTH: 9
<212> TYPE: PRT
<213> ORGANISM: Artificial Sequence
<220> FEATURE:
<223> OTHER INFORMATION: CDR sequence

<400> SEQUENCE: 233

Glu Ile Thr Arg Gly Gly Ser Thr Asn
1               5

<210> SEQ ID NO 234
<211> LENGTH: 9
<212> TYPE: PRT
<213> ORGANISM: Artificial Sequence
<220> FEATURE:
<223> OTHER INFORMATION: CDR sequence

<400> SEQUENCE: 234

Glu Ile Thr Arg Gly Gly Ser Thr Asn
1               5

<210> SEQ ID NO 235
<211> LENGTH: 9
<212> TYPE: PRT
<213> ORGANISM: Artificial Sequence
<220> FEATURE:
<223> OTHER INFORMATION: CDR sequence

<400> SEQUENCE: 235

Glu Ile Thr Arg Gly Gly Ser Thr Asn
1               5

<210> SEQ ID NO 236
<211> LENGTH: 9
<212> TYPE: PRT
<213> ORGANISM: Artificial Sequence
<220> FEATURE:
<223> OTHER INFORMATION: CDR sequence

<400> SEQUENCE: 236

Ala Ile Thr Ser Arg Gly Ser Thr Asn
1               5

<210> SEQ ID NO 237
<211> LENGTH: 9
<212> TYPE: PRT
<213> ORGANISM: Artificial Sequence
<220> FEATURE:
<223> OTHER INFORMATION: CDR sequence

<400> SEQUENCE: 237

Ala Ile Thr Ser Gly Gly Arg Thr Asn
1               5

<210> SEQ ID NO 238
<211> LENGTH: 9
<212> TYPE: PRT
<213> ORGANISM: Artificial Sequence
<220> FEATURE:
<223> OTHER INFORMATION: CDR sequence

<400> SEQUENCE: 238

Glu Ile Thr Ser Gly Gly Ser Thr Asn
1               5

<210> SEQ ID NO 239
<211> LENGTH: 9
<212> TYPE: PRT
<213> ORGANISM: Artificial Sequence
<220> FEATURE:
<223> OTHER INFORMATION: CDR sequence

<400> SEQUENCE: 239

Glu Ile Thr Ser Gly Gly Ser Thr Asn
1               5

<210> SEQ ID NO 240
<211> LENGTH: 9
<212> TYPE: PRT
<213> ORGANISM: Artificial Sequence
<220> FEATURE:
<223> OTHER INFORMATION: CDR sequence

<400> SEQUENCE: 240

Glu Ile Thr Ser Gly Gly Ser Thr Asn
1               5

<210> SEQ ID NO 241
<211> LENGTH: 9
<212> TYPE: PRT
<213> ORGANISM: Artificial Sequence
<220> FEATURE:
<223> OTHER INFORMATION: CDR sequence

<400> SEQUENCE: 241

Ala Ile Thr Ser Gly Gly Ser Thr Asn
1               5

<210> SEQ ID NO 242
<211> LENGTH: 9
<212> TYPE: PRT
<213> ORGANISM: Artificial Sequence
<220> FEATURE:
<223> OTHER INFORMATION: CDR sequence

<400> SEQUENCE: 242

Thr Ile Asn Thr Gly Gly Asn Thr Gly
1               5

<210> SEQ ID NO 243
<211> LENGTH: 9
<212> TYPE: PRT
<213> ORGANISM: Artificial Sequence
<220> FEATURE:
<223> OTHER INFORMATION: CDR sequence

<400> SEQUENCE: 243

Arg Ile Ala Ser Leu Gly Ile Thr Asn
1               5

<210> SEQ ID NO 244
<211> LENGTH: 9
<212> TYPE: PRT
<213> ORGANISM: Artificial Sequence
<220> FEATURE:
<223> OTHER INFORMATION: CDR sequence

<400> SEQUENCE: 244

Arg Ile Ala Ser Leu Gly Ile Thr Asn
1               5

```
<210> SEQ ID NO 245
<211> LENGTH: 9
<212> TYPE: PRT
<213> ORGANISM: Artificial Sequence
<220> FEATURE:
<223> OTHER INFORMATION: CDR sequence

<400> SEQUENCE: 245

Tyr Val Gly Ser Met Gly Ile Thr Asn
1               5

<210> SEQ ID NO 246
<211> LENGTH: 9
<212> TYPE: PRT
<213> ORGANISM: Artificial Sequence
<220> FEATURE:
<223> OTHER INFORMATION: CDR sequence

<400> SEQUENCE: 246

Tyr Ile Thr Ser Leu Gly Ile Ala Asn
1               5

<210> SEQ ID NO 247
<211> LENGTH: 9
<212> TYPE: PRT
<213> ORGANISM: Artificial Sequence
<220> FEATURE:
<223> OTHER INFORMATION: CDR sequence

<400> SEQUENCE: 247

Thr Ile Thr Val Gly Gly Lys Thr Asn
1               5

<210> SEQ ID NO 248
<211> LENGTH: 9
<212> TYPE: PRT
<213> ORGANISM: Artificial Sequence
<220> FEATURE:
<223> OTHER INFORMATION: CDR sequence

<400> SEQUENCE: 248

Thr Ile Thr Val Gly Gly Lys Thr Asn
1               5

<210> SEQ ID NO 249
<211> LENGTH: 9
<212> TYPE: PRT
<213> ORGANISM: Artificial Sequence
<220> FEATURE:
<223> OTHER INFORMATION: CDR sequence

<400> SEQUENCE: 249

Arg Val Ile Ile Gly Gly Ser Thr Gly
1               5

<210> SEQ ID NO 250
<211> LENGTH: 9
<212> TYPE: PRT
<213> ORGANISM: Artificial Sequence
<220> FEATURE:
<223> OTHER INFORMATION: CDR sequence

<400> SEQUENCE: 250

Arg Ile Ile Ile Gly Gly Ser Thr Gly
1               5
```

```
<210> SEQ ID NO 251
<211> LENGTH: 10
<212> TYPE: PRT
<213> ORGANISM: Artificial Sequence
<220> FEATURE:
<223> OTHER INFORMATION: CDR sequence

<400> SEQUENCE: 251

Thr Ile Asn Trp Ser Gly Gly Arg Thr Thr
1               5                   10

<210> SEQ ID NO 252
<211> LENGTH: 10
<212> TYPE: PRT
<213> ORGANISM: Artificial Sequence
<220> FEATURE:
<223> OTHER INFORMATION: CDR sequence

<400> SEQUENCE: 252

Thr Ile Asn Trp Ser Gly Gly Arg Thr Thr
1               5                   10

<210> SEQ ID NO 253
<211> LENGTH: 10
<212> TYPE: PRT
<213> ORGANISM: Artificial Sequence
<220> FEATURE:
<223> OTHER INFORMATION: CDR sequence

<400> SEQUENCE: 253

Gly Ile Thr Trp Phe Gly Gly Ser Thr Tyr
1               5                   10

<210> SEQ ID NO 254
<211> LENGTH: 10
<212> TYPE: PRT
<213> ORGANISM: Artificial Sequence
<220> FEATURE:
<223> OTHER INFORMATION: CDR sequence

<400> SEQUENCE: 254

Gly Ile Thr Trp Phe Gly Gly Ser Thr Tyr
1               5                   10

<210> SEQ ID NO 255
<211> LENGTH: 10
<212> TYPE: PRT
<213> ORGANISM: Artificial Sequence
<220> FEATURE:
<223> OTHER INFORMATION: CDR sequence

<400> SEQUENCE: 255

Gly Ile Thr Trp Phe Gly Gly Ser Thr Tyr
1               5                   10

<210> SEQ ID NO 256
<211> LENGTH: 10
<212> TYPE: PRT
<213> ORGANISM: Artificial Sequence
<220> FEATURE:
<223> OTHER INFORMATION: CDR sequence

<400> SEQUENCE: 256

Ala Ile Ser Gly Ser Gly Gly Ser Ala Arg
1               5                   10

<210> SEQ ID NO 257
```

```
<211> LENGTH: 10
<212> TYPE: PRT
<213> ORGANISM: Artificial Sequence
<220> FEATURE:
<223> OTHER INFORMATION: CDR sequence

<400> SEQUENCE: 257

Ala Ile Ser Gly Ser Gly Gly Ser Ala Arg
1               5                   10

<210> SEQ ID NO 258
<211> LENGTH: 10
<212> TYPE: PRT
<213> ORGANISM: Artificial Sequence
<220> FEATURE:
<223> OTHER INFORMATION: CDR sequence

<400> SEQUENCE: 258

Thr Ile Thr Arg Ser Gly Gly Ser Thr Asn
1               5                   10

<210> SEQ ID NO 259
<211> LENGTH: 10
<212> TYPE: PRT
<213> ORGANISM: Artificial Sequence
<220> FEATURE:
<223> OTHER INFORMATION: CDR sequence

<400> SEQUENCE: 259

Ser Ile Ser Trp Ser Gly Ser Arg Thr Asn
1               5                   10

<210> SEQ ID NO 260
<211> LENGTH: 9
<212> TYPE: PRT
<213> ORGANISM: Artificial Sequence
<220> FEATURE:
<223> OTHER INFORMATION: CDR sequence

<400> SEQUENCE: 260

Gly Ile Thr Trp Asn Gly Gly Thr Ser
1               5

<210> SEQ ID NO 261
<211> LENGTH: 9
<212> TYPE: PRT
<213> ORGANISM: Artificial Sequence
<220> FEATURE:
<223> OTHER INFORMATION: CDR sequence

<400> SEQUENCE: 261

Ser Ile Ser Ala Ser Asp Ser Thr Leu
1               5

<210> SEQ ID NO 262
<211> LENGTH: 9
<212> TYPE: PRT
<213> ORGANISM: Artificial Sequence
<220> FEATURE:
<223> OTHER INFORMATION: CDR sequence

<400> SEQUENCE: 262

Ser Ile Ser Ala Ser Asp Ser Thr Leu
1               5

<210> SEQ ID NO 263
<211> LENGTH: 9
```

<212> TYPE: PRT
<213> ORGANISM: Artificial Sequence
<220> FEATURE:
<223> OTHER INFORMATION: CDR sequence

<400> SEQUENCE: 263

Ala Ile Ser Ala Ala Asp Ser Thr Leu
1               5

<210> SEQ ID NO 264
<211> LENGTH: 9
<212> TYPE: PRT
<213> ORGANISM: Artificial Sequence
<220> FEATURE:
<223> OTHER INFORMATION: CDR sequence

<400> SEQUENCE: 264

Ala Ile Ser Ala Ala Asp Ser Thr Leu
1               5

<210> SEQ ID NO 265
<211> LENGTH: 10
<212> TYPE: PRT
<213> ORGANISM: Artificial Sequence
<220> FEATURE:
<223> OTHER INFORMATION: CDR sequence

<400> SEQUENCE: 265

Ala Val Arg Ser Gly Gly Gly Thr Thr Arg
1               5                   10

<210> SEQ ID NO 266
<211> LENGTH: 12
<212> TYPE: PRT
<213> ORGANISM: Artificial Sequence
<220> FEATURE:
<223> OTHER INFORMATION: CDR sequence

<400> SEQUENCE: 266

Ala Val Ser Gly Ala Gly Arg Gly Gly Lys Pro Ser
1               5                   10

<210> SEQ ID NO 267
<211> LENGTH: 11
<212> TYPE: PRT
<213> ORGANISM: Artificial Sequence
<220> FEATURE:
<223> OTHER INFORMATION: CDR sequence

<400> SEQUENCE: 267

Ala Ala Val Arg Pro Ser Gly Asp Ser Thr Tyr
1               5                   10

<210> SEQ ID NO 268
<211> LENGTH: 11
<212> TYPE: PRT
<213> ORGANISM: Artificial Sequence
<220> FEATURE:
<223> OTHER INFORMATION: CDR sequence

<400> SEQUENCE: 268

Ala Ala Val Lys Pro Ala Gly Asp Ser Ala Tyr
1               5                   10

<210> SEQ ID NO 269
<211> LENGTH: 10
<212> TYPE: PRT

```
<213> ORGANISM: Artificial Sequence
<220> FEATURE:
<223> OTHER INFORMATION: CDR sequence

<400> SEQUENCE: 269

Gly Ile Thr Trp Val Gly Ala Ser Thr Leu
1               5                   10

<210> SEQ ID NO 270
<211> LENGTH: 10
<212> TYPE: PRT
<213> ORGANISM: Artificial Sequence
<220> FEATURE:
<223> OTHER INFORMATION: CDR sequence

<400> SEQUENCE: 270

Ala Ile Asn Trp Arg Gly Ser Thr Thr Ala
1               5                   10

<210> SEQ ID NO 271
<211> LENGTH: 9
<212> TYPE: PRT
<213> ORGANISM: Artificial Sequence
<220> FEATURE:
<223> OTHER INFORMATION: CDR sequence

<400> SEQUENCE: 271

Ser Ile Arg Ser Ser Gly Gly Thr Thr
1               5

<210> SEQ ID NO 272
<211> LENGTH: 10
<212> TYPE: PRT
<213> ORGANISM: Artificial Sequence
<220> FEATURE:
<223> OTHER INFORMATION: CDR sequence

<400> SEQUENCE: 272

Cys Leu Ser Arg Arg Asp Gly Arg Phe Tyr
1               5                   10

<210> SEQ ID NO 273
<211> LENGTH: 10
<212> TYPE: PRT
<213> ORGANISM: Artificial Sequence
<220> FEATURE:
<223> OTHER INFORMATION: CDR sequence

<400> SEQUENCE: 273

Cys Leu Ser Arg Arg Asp Gly Arg Phe Tyr
1               5                   10

<210> SEQ ID NO 274
<211> LENGTH: 10
<212> TYPE: PRT
<213> ORGANISM: Artificial Sequence
<220> FEATURE:
<223> OTHER INFORMATION: CDR sequence

<400> SEQUENCE: 274

Ala Asp Thr Trp Ser Gly Thr Ser Thr Trp
1               5                   10

<210> SEQ ID NO 275
<211> LENGTH: 10
<212> TYPE: PRT
<213> ORGANISM: Artificial Sequence
```

<220> FEATURE:
<223> OTHER INFORMATION: CDR sequence

<400> SEQUENCE: 275

Ala Ile Asn Trp Ser Gly Ser Asp Thr Asp
1               5                   10

<210> SEQ ID NO 276
<211> LENGTH: 10
<212> TYPE: PRT
<213> ORGANISM: Artificial Sequence
<220> FEATURE:
<223> OTHER INFORMATION: CDR sequence

<400> SEQUENCE: 276

Ala Ile Asn Trp Ser Gly Ser Asp Thr Asp
1               5                   10

<210> SEQ ID NO 277
<211> LENGTH: 10
<212> TYPE: PRT
<213> ORGANISM: Artificial Sequence
<220> FEATURE:
<223> OTHER INFORMATION: CDR sequence

<400> SEQUENCE: 277

Ala Ile Asn Trp Ser Gly Ser Ser Val Asp
1               5                   10

<210> SEQ ID NO 278
<211> LENGTH: 10
<212> TYPE: PRT
<213> ORGANISM: Artificial Sequence
<220> FEATURE:
<223> OTHER INFORMATION: CDR sequence

<400> SEQUENCE: 278

Ala Ile Asn Trp Ser Gly Ser Ser Val Asp
1               5                   10

<210> SEQ ID NO 279
<211> LENGTH: 10
<212> TYPE: PRT
<213> ORGANISM: Artificial Sequence
<220> FEATURE:
<223> OTHER INFORMATION: CDR sequence

<400> SEQUENCE: 279

Gly Ile Ser Trp Ser Ser Gly Thr Leu Leu
1               5                   10

<210> SEQ ID NO 280
<211> LENGTH: 10
<212> TYPE: PRT
<213> ORGANISM: Artificial Sequence
<220> FEATURE:
<223> OTHER INFORMATION: CDR sequence

<400> SEQUENCE: 280

Gly Ile Ser Trp Ser Ser Gly Ser Leu Leu
1               5                   10

<210> SEQ ID NO 281
<211> LENGTH: 10
<212> TYPE: PRT
<213> ORGANISM: Artificial Sequence
<220> FEATURE:

<223> OTHER INFORMATION: CDR sequence

<400> SEQUENCE: 281

Ala Ile Ser Trp Ser Ser Gly Thr Thr Arg
1               5                   10

<210> SEQ ID NO 282
<211> LENGTH: 10
<212> TYPE: PRT
<213> ORGANISM: Artificial Sequence
<220> FEATURE:
<223> OTHER INFORMATION: CDR sequence

<400> SEQUENCE: 282

Ala Ile Ser Trp Ser Ser Gly Thr Thr Arg
1               5                   10

<210> SEQ ID NO 283
<211> LENGTH: 10
<212> TYPE: PRT
<213> ORGANISM: Artificial Sequence
<220> FEATURE:
<223> OTHER INFORMATION: CDR sequence

<400> SEQUENCE: 283

Ala Asn Ser Met Ser Gly Thr Lys Thr Ala
1               5                   10

<210> SEQ ID NO 284
<211> LENGTH: 10
<212> TYPE: PRT
<213> ORGANISM: Artificial Sequence
<220> FEATURE:
<223> OTHER INFORMATION: CDR sequence

<400> SEQUENCE: 284

Ala Asn Ile Met Ser Gly Thr Asn Thr Tyr
1               5                   10

<210> SEQ ID NO 285
<211> LENGTH: 9
<212> TYPE: PRT
<213> ORGANISM: Artificial Sequence
<220> FEATURE:
<223> OTHER INFORMATION: CDR sequence

<400> SEQUENCE: 285

Ser Ile Ser Asn Asn Asn Ser Thr Tyr
1               5

<210> SEQ ID NO 286
<211> LENGTH: 9
<212> TYPE: PRT
<213> ORGANISM: Artificial Sequence
<220> FEATURE:
<223> OTHER INFORMATION: CDR sequence

<400> SEQUENCE: 286

Ser Ile Ser Asn Asn Asn Ser Thr Tyr
1               5

<210> SEQ ID NO 287
<211> LENGTH: 9
<212> TYPE: PRT
<213> ORGANISM: Artificial Sequence
<220> FEATURE:
<223> OTHER INFORMATION: CDR sequence

<400> SEQUENCE: 287

Ser Ile Ser Ser Asp Gly Ser Thr Tyr
1               5

<210> SEQ ID NO 288
<211> LENGTH: 9
<212> TYPE: PRT
<213> ORGANISM: Artificial Sequence
<220> FEATURE:
<223> OTHER INFORMATION: CDR sequence

<400> SEQUENCE: 288

Cys Ile Ser Ser Ala Gly Ser Thr Tyr
1               5

<210> SEQ ID NO 289
<211> LENGTH: 9
<212> TYPE: PRT
<213> ORGANISM: Artificial Sequence
<220> FEATURE:
<223> OTHER INFORMATION: CDR sequence

<400> SEQUENCE: 289

Ser Ile Ser Ser Ser Gly Ser Ile Tyr
1               5

<210> SEQ ID NO 290
<211> LENGTH: 9
<212> TYPE: PRT
<213> ORGANISM: Artificial Sequence
<220> FEATURE:
<223> OTHER INFORMATION: CDR sequence

<400> SEQUENCE: 290

Ser Ile Ser Ser Ser Gly Ser Ile Tyr
1               5

<210> SEQ ID NO 291
<211> LENGTH: 39
<212> TYPE: PRT
<213> ORGANISM: Artificial Sequence
<220> FEATURE:
<223> OTHER INFORMATION: FW sequence

<400> SEQUENCE: 291

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Asn Pro Glu Asp Thr
            20                  25                  30

Ala Val Tyr Tyr Cys Asn Ala
        35

<210> SEQ ID NO 292
<211> LENGTH: 39
<212> TYPE: PRT
<213> ORGANISM: Artificial Sequence
<220> FEATURE:
<223> OTHER INFORMATION: FW sequence

<400> SEQUENCE: 292

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Asn Pro Glu Asp Thr
            20                  25                  30

Ala Val Tyr Tyr Cys Asn Ala
        35

<210> SEQ ID NO 293
<211> LENGTH: 39
<212> TYPE: PRT
<213> ORGANISM: Artificial Sequence
<220> FEATURE:
<223> OTHER INFORMATION: FW sequence

<400> SEQUENCE: 293

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Asn Pro Glu Asp Thr
            20                  25                  30

Ala Val Tyr Tyr Cys Asn Ala
        35

<210> SEQ ID NO 294
<211> LENGTH: 39
<212> TYPE: PRT
<213> ORGANISM: Artificial Sequence
<220> FEATURE:
<223> OTHER INFORMATION: FW sequence

<400> SEQUENCE: 294

Tyr Ala Asp Ser Val Lys Gly Arg Phe Thr Ile Ser Arg Asp Asn Ala
1               5                   10                  15

Glu Asn Thr Val Ser Leu Gln Met Asn Ser Leu Lys Pro Gly Asp Thr
            20                  25                  30

Ala Val Tyr Tyr Cys Asn Ala
        35

<210> SEQ ID NO 295
<211> LENGTH: 39
<212> TYPE: PRT
<213> ORGANISM: Artificial Sequence
<220> FEATURE:
<223> OTHER INFORMATION: FW sequence

<400> SEQUENCE: 295

Tyr Ala Asp Ser Val Lys Gly Arg Phe Thr Ile Ser Arg Asp Asn Ala
1               5                   10                  15

Glu Asn Thr Val Ser Leu Gln Met Asn Ser Leu Lys Ser Gly Asp Thr
            20                  25                  30

Ala Val Tyr Tyr Cys Asn Ala
        35

<210> SEQ ID NO 296
<211> LENGTH: 39
<212> TYPE: PRT
<213> ORGANISM: Artificial Sequence
<220> FEATURE:
<223> OTHER INFORMATION: FW sequence

<400> SEQUENCE: 296

Tyr Ala Asp Ser Val Lys Gly Arg Phe Thr Ile Ser Arg Asp Asn Ala
1               5                   10                  15

Glu Asn Thr Val Ser Leu Gln Met Asn Ser Leu Lys Pro Gly Asp Thr
            20                  25                  30

Ala Val Tyr Tyr Cys Asn Ala
        35

<210> SEQ ID NO 297
<211> LENGTH: 39
<212> TYPE: PRT
<213> ORGANISM: Artificial Sequence
<220> FEATURE:
<223> OTHER INFORMATION: FW sequence

<400> SEQUENCE: 297

Tyr Ala Asp Ser Val Lys Gly Arg Phe Thr Ile Ser Arg Asp Asn Ala
1               5                   10                  15

Glu Asn Thr Val Ser Leu Gln Met Asn Ser Leu Lys Ser Gly Asp Thr
            20                  25                  30

Ala Val Tyr Tyr Cys Asn Ala
        35

<210> SEQ ID NO 298
<211> LENGTH: 39
<212> TYPE: PRT
<213> ORGANISM: Artificial Sequence
<220> FEATURE:
<223> OTHER INFORMATION: FW sequence

<400> SEQUENCE: 298

Tyr Ala Asn Ser Val Lys Gly Arg Phe Thr Ile Ser Arg Asp Asn Ala
1               5                   10                  15

Glu Asn Thr Val Ser Leu Gln Met Asn Ser Leu Lys Pro Glu Asp Thr
            20                  25                  30

Ala Val Tyr Tyr Cys Asn Ala
        35

<210> SEQ ID NO 299
<211> LENGTH: 39
<212> TYPE: PRT
<213> ORGANISM: Artificial Sequence
<220> FEATURE:
<223> OTHER INFORMATION: FW sequence

<400> SEQUENCE: 299

Tyr Ala Asp Ser Val Lys Gly Arg Phe Thr Ile Ser Arg Asp Asn Ala
1               5                   10                  15

Lys Ser Met Val Tyr Leu Gln Met Asn Ser Leu Lys Pro Glu Asp Thr
            20                  25                  30

Ala Val Tyr Tyr Cys Asn Ala
        35

<210> SEQ ID NO 300
<211> LENGTH: 39
<212> TYPE: PRT
<213> ORGANISM: Artificial Sequence
<220> FEATURE:
<223> OTHER INFORMATION: FW sequence

<400> SEQUENCE: 300

Tyr Ala Asp Ser Val Lys Gly Arg Phe Ala Ile Ser Arg Asp Asn Ala
1               5                   10                  15

Lys Asn Thr Val Tyr Leu Gln Met His Ser Leu Lys Pro Glu Asp Thr
            20                  25                  30

Ala Val Tyr Tyr Cys Thr Ala
        35

<210> SEQ ID NO 301

```
<211> LENGTH: 39
<212> TYPE: PRT
<213> ORGANISM: Artificial Sequence
<220> FEATURE:
<223> OTHER INFORMATION: FW sequence

<400> SEQUENCE: 301

Tyr Ala Asp Ser Val Lys Gly Arg Phe Thr Ile Ser Ser Asp Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Asn Tyr
        35

<210> SEQ ID NO 302
<211> LENGTH: 39
<212> TYPE: PRT
<213> ORGANISM: Artificial Sequence
<220> FEATURE:
<223> OTHER INFORMATION: FW sequence

<400> SEQUENCE: 302

Tyr Ala Asp Ser Val Lys Gly Arg Phe Thr Ile Ser Ser Asp Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Asn Tyr
        35

<210> SEQ ID NO 303
<211> LENGTH: 39
<212> TYPE: PRT
<213> ORGANISM: Artificial Sequence
<220> FEATURE:
<223> OTHER INFORMATION: FW sequence

<400> SEQUENCE: 303

Tyr Ala Asp Ser Val Lys Gly Arg Phe Thr Ile Ser Ser Asp Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Asn Tyr
        35

<210> SEQ ID NO 304
<211> LENGTH: 39
<212> TYPE: PRT
<213> ORGANISM: Artificial Sequence
<220> FEATURE:
<223> OTHER INFORMATION: FW sequence

<400> SEQUENCE: 304

Tyr Ala Asp Ser Val Lys Gly Arg Phe Thr Ile Ser Ser Asp Asn Ala
1               5                   10                  15

Lys Asn Thr Val Tyr Leu Gln Met Asn Asn Leu Lys Ser Glu Asp Thr
            20                  25                  30

Ala Val Tyr Asn Cys Asn Tyr
        35

<210> SEQ ID NO 305
<211> LENGTH: 37
<212> TYPE: PRT
<213> ORGANISM: Artificial Sequence
```

<220> FEATURE:
<223> OTHER INFORMATION: FW sequence

<400> SEQUENCE: 305

Tyr Lys Asp Ser Val Gln Gly Arg Phe Ile Ile Ser Arg Asn Asp Thr
1               5                   10                  15

Thr Val Thr Leu Gln Met Asn Arg Leu Gln Pro Glu Asp Thr Ala Val
            20                  25                  30

Tyr Tyr Cys Asn Leu
        35

<210> SEQ ID NO 306
<211> LENGTH: 43
<212> TYPE: PRT
<213> ORGANISM: Artificial Sequence
<220> FEATURE:
<223> OTHER INFORMATION: FW sequence

<400> SEQUENCE: 306

Tyr Lys Asp Ser Val Gln Gly Arg Phe Ile Ile Thr Arg Asp Asn Thr
1               5                   10                  15

Gly Asp Asn Thr Lys Ser Thr Val Thr Leu Gln Met Asn Arg Leu Lys
            20                  25                  30

Pro Glu Asp Thr Ala Val Tyr Tyr Cys Asn Thr
        35                  40

<210> SEQ ID NO 307
<211> LENGTH: 39
<212> TYPE: PRT
<213> ORGANISM: Artificial Sequence
<220> FEATURE:
<223> OTHER INFORMATION: FW sequence

<400> SEQUENCE: 307

Tyr Ala Asp Ser Val Lys Gly Arg Phe Thr Ile Ser Arg Asp Asn Thr
1               5                   10                  15

Lys Asn Thr Val Tyr Leu Glu Met Asn Ser Leu Lys Pro Glu Asp Thr
            20                  25                  30

Ala Val Tyr Tyr Cys Asn Ala
        35

<210> SEQ ID NO 308
<211> LENGTH: 39
<212> TYPE: PRT
<213> ORGANISM: Artificial Sequence
<220> FEATURE:
<223> OTHER INFORMATION: FW sequence

<400> SEQUENCE: 308

Tyr Ser Asp Ser Val Lys Gly Arg Phe Thr Ile Ser Arg Asp Asn Thr
1               5                   10                  15

Gly Asn Thr Trp Tyr Leu Gln Met Asn Ser Leu Lys Pro Glu Asp Thr
            20                  25                  30

Ala Val Tyr Tyr Cys Asn Ala
        35

<210> SEQ ID NO 309
<211> LENGTH: 39
<212> TYPE: PRT
<213> ORGANISM: Artificial Sequence
<220> FEATURE:
<223> OTHER INFORMATION: FW sequence

```
<400> SEQUENCE: 309

Tyr Ala Asp Ser Val Lys Gly Arg Phe Thr Ile Ser Arg Asp Ser Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 310
<211> LENGTH: 39
<212> TYPE: PRT
<213> ORGANISM: Artificial Sequence
<220> FEATURE:
<223> OTHER INFORMATION: FW sequence

<400> SEQUENCE: 310

Tyr Ala Asp Ser Val Lys Gly Arg Phe Thr Ile Ser Arg Asp Ser Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 311
<211> LENGTH: 39
<212> TYPE: PRT
<213> ORGANISM: Artificial Sequence
<220> FEATURE:
<223> OTHER INFORMATION: FW sequence

<400> SEQUENCE: 311

Tyr Ala Asp Ser Val Lys Gly Arg Phe Thr Ile Ser Arg Asp Asn Thr
1               5                   10                  15

Lys Asn Thr Leu Tyr Leu Gln Met Asn Ser Leu Lys Pro Glu Asp Thr
            20                  25                  30

Ala Ile Tyr Tyr Cys Ala Ala
        35

<210> SEQ ID NO 312
<211> LENGTH: 39
<212> TYPE: PRT
<213> ORGANISM: Artificial Sequence
<220> FEATURE:
<223> OTHER INFORMATION: FW sequence

<400> SEQUENCE: 312

Tyr Ala Asp Ser Val Lys Gly Arg Phe Thr Ile Ser Arg Asp Asn Thr
1               5                   10                  15

Lys Asn Thr Leu Tyr Leu Gln Met Asn Ser Leu Lys Pro Glu Asp Thr
            20                  25                  30

Ala Ile Tyr Tyr Cys Ala Ala
        35

<210> SEQ ID NO 313
<211> LENGTH: 39
<212> TYPE: PRT
<213> ORGANISM: Artificial Sequence
<220> FEATURE:
<223> OTHER INFORMATION: FW sequence

<400> SEQUENCE: 313

Tyr Ala Asp Ser Val Lys Gly Arg Phe Thr Ile Ser Arg Asp Asn Thr
```

```
1               5                   10                  15
Lys Asn Thr Leu Tyr Leu Gln Met Asn Ser Leu Lys Pro Glu Asp Thr
            20                  25                  30

Ala Ile Tyr Tyr Cys Ala Ala
        35

<210> SEQ ID NO 314
<211> LENGTH: 39
<212> TYPE: PRT
<213> ORGANISM: Artificial Sequence
<220> FEATURE:
<223> OTHER INFORMATION: FW sequence

<400> SEQUENCE: 314

Tyr Ala Val Pro Val Lys Gly Arg Phe Thr Ile Thr Arg Asp Asn Ala
1               5                   10                  15

Lys Asn Thr Val Tyr Leu Gln Met Ser Ser Leu Lys Pro Glu Asp Thr
            20                  25                  30

Ala Val Tyr Tyr Cys Ala Ala
        35

<210> SEQ ID NO 315
<211> LENGTH: 39
<212> TYPE: PRT
<213> ORGANISM: Artificial Sequence
<220> FEATURE:
<223> OTHER INFORMATION: FW sequence

<400> SEQUENCE: 315

Tyr Ala Val Pro Val Lys Gly Arg Phe Thr Ile Thr Arg Asp Asn Ala
1               5                   10                  15

Lys Asn Thr Val Tyr Leu Gln Met Ser Ser Leu Lys Pro Glu Asp Thr
            20                  25                  30

Ala Val Tyr Tyr Cys Ala Ala
        35

<210> SEQ ID NO 316
<211> LENGTH: 39
<212> TYPE: PRT
<213> ORGANISM: Artificial Sequence
<220> FEATURE:
<223> OTHER INFORMATION: FW sequence

<400> SEQUENCE: 316

Tyr Ala Val Pro Val Lys Gly Arg Phe Thr Ile Ser Arg Asp Asn Ala
1               5                   10                  15

Lys Asn Thr Val Tyr Leu Gln Met Ser Ser Leu Lys Pro Glu Asp Thr
            20                  25                  30

Ala Val Tyr Tyr Cys Ala Ala
        35

<210> SEQ ID NO 317
<211> LENGTH: 39
<212> TYPE: PRT
<213> ORGANISM: Artificial Sequence
<220> FEATURE:
<223> OTHER INFORMATION: FW sequence

<400> SEQUENCE: 317

Tyr Gly Val Pro Val Lys Gly Arg Phe Thr Ile Ser Arg Asp Asn Ala
1               5                   10                  15

Lys Asn Thr Val Tyr Leu Gln Met Ser Ser Leu Lys Pro Glu Asp Thr
```

```
                  20                  25                  30

Ala Val Tyr Tyr Cys Ala Ala
        35

<210> SEQ ID NO 318
<211> LENGTH: 39
<212> TYPE: PRT
<213> ORGANISM: Artificial Sequence
<220> FEATURE:
<223> OTHER INFORMATION: FW sequence

<400> SEQUENCE: 318

Tyr Ala Asp Ser Val Lys Gly Arg Phe Thr Ile Ser Arg Asp Asn Gly
1               5                  10                  15

Lys Asn Ser Val Tyr Leu Gln Met Asn Ser Leu Lys Pro Glu Asp Thr
            20                  25                  30

Ala Val Tyr Tyr Cys Ala Ala
        35

<210> SEQ ID NO 319
<211> LENGTH: 39
<212> TYPE: PRT
<213> ORGANISM: Artificial Sequence
<220> FEATURE:
<223> OTHER INFORMATION: FW sequence

<400> SEQUENCE: 319

Tyr Ala Asp Phe Val Lys Gly Arg Phe Thr Ile Ser Arg Asp Asn Ala
1               5                  10                  15

Lys Asn Thr Val Tyr Leu Gln Met Asp Ser Leu Lys Pro Glu Asp Thr
            20                  25                  30

Thr Val Tyr Tyr Cys Ala Ala
        35

<210> SEQ ID NO 320
<211> LENGTH: 39
<212> TYPE: PRT
<213> ORGANISM: Artificial Sequence
<220> FEATURE:
<223> OTHER INFORMATION: FW sequence

<400> SEQUENCE: 320

Tyr Ala Asp Phe Val Lys Gly Arg Phe Thr Ile Ser Arg Asp Asn Ala
1               5                  10                  15

Lys Asn Thr Val Tyr Leu Gln Met Asp Ser Leu Lys Pro Glu Asp Thr
            20                  25                  30

Thr Val Tyr Tyr Cys Ala Ala
        35

<210> SEQ ID NO 321
<211> LENGTH: 39
<212> TYPE: PRT
<213> ORGANISM: Artificial Sequence
<220> FEATURE:
<223> OTHER INFORMATION: FW sequence

<400> SEQUENCE: 321

Tyr Ala Asp Phe Val Lys Gly Arg Phe Thr Ile Ser Arg Asp Asn Ala
1               5                  10                  15

Lys Asn Thr Val Tyr Leu Gln Met Asn Ser Leu Lys Pro Glu Asp Thr
            20                  25                  30

Ala Val Tyr Tyr Cys Ala Ala
```

-continued

<210> SEQ ID NO 322
<211> LENGTH: 39
<212> TYPE: PRT
<213> ORGANISM: Artificial Sequence
<220> FEATURE:
<223> OTHER INFORMATION: FW sequence

<400> SEQUENCE: 322

Tyr Ala Asp Phe Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 323
<211> LENGTH: 39
<212> TYPE: PRT
<213> ORGANISM: Artificial Sequence
<220> FEATURE:
<223> OTHER INFORMATION: FW sequence

<400> SEQUENCE: 323

Tyr Ala Asp Ser Val Lys Gly Arg Phe Thr Ile Ser Arg Asp Asp Ala
1               5                   10                  15

Lys Asp Thr Val Phe Leu Gln Met Asn Ser Leu Lys Pro Glu Asp Thr
            20                  25                  30

Ala Leu Tyr Tyr Cys Ala Ala
        35

<210> SEQ ID NO 324
<211> LENGTH: 39
<212> TYPE: PRT
<213> ORGANISM: Artificial Sequence
<220> FEATURE:
<223> OTHER INFORMATION: FW sequence

<400> SEQUENCE: 324

Tyr Ala Asn Ser Val Lys Gly Arg Phe Thr Val Ser Arg Asp Asn Ala
1               5                   10                  15

Lys Asn Thr Val Tyr Leu Gln Met Asp Asn Leu Lys Pro Glu Asp Thr
            20                  25                  30

Ala Val Tyr Tyr Cys Ala Ala
        35

<210> SEQ ID NO 325
<211> LENGTH: 39
<212> TYPE: PRT
<213> ORGANISM: Artificial Sequence
<220> FEATURE:
<223> OTHER INFORMATION: FW sequence

<400> SEQUENCE: 325

Tyr Gly Asn Ser Val Lys Gly Arg Phe Ser Ile Ser Arg Asp Asp Asp
1               5                   10                  15

Lys Asn Ile Val Tyr Leu Gln Met Asn Ser Leu Lys Pro Glu Asp Thr
            20                  25                  30

Ala Val Tyr Tyr Cys Ala Ala
        35

```
<210> SEQ ID NO 326
<211> LENGTH: 39
<212> TYPE: PRT
<213> ORGANISM: Artificial Sequence
<220> FEATURE:
<223> OTHER INFORMATION: FW sequence

<400> SEQUENCE: 326

Tyr Gly Ala Ser Val Lys Gly Arg Phe Thr Ala Ser Arg Asp Asn Ala
1               5                   10                  15

Lys Asn Thr Val Thr Leu Gln Met Asn Ser Leu Lys Pro Glu Asp Thr
            20                  25                  30

Ala Ile Tyr Tyr Cys Ala Ala
        35

<210> SEQ ID NO 327
<211> LENGTH: 39
<212> TYPE: PRT
<213> ORGANISM: Artificial Sequence
<220> FEATURE:
<223> OTHER INFORMATION: FW sequence

<400> SEQUENCE: 327

Tyr Ala Asp Phe Ala Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Ser Cys Ala Ala
        35

<210> SEQ ID NO 328
<211> LENGTH: 39
<212> TYPE: PRT
<213> ORGANISM: Artificial Sequence
<220> FEATURE:
<223> OTHER INFORMATION: FW sequence

<400> SEQUENCE: 328

Tyr Ala Asp Ser Val Lys Gly Arg Phe Thr Ile Ser Arg Asp Val Thr
1               5                   10                  15

Lys Asn Thr Ile Tyr Leu Gln Met Asn Ser Leu Lys Pro Glu Asp Thr
            20                  25                  30

Ala Ile Tyr Tyr Cys Ala Glu
        35

<210> SEQ ID NO 329
<211> LENGTH: 39
<212> TYPE: PRT
<213> ORGANISM: Artificial Sequence
<220> FEATURE:
<223> OTHER INFORMATION: FW sequence

<400> SEQUENCE: 329

Tyr Ala Glu Ser Val Lys Gly Arg Phe Thr Ile Ser Arg Asp Asn Ala
1               5                   10                  15

Lys Asn Thr Met Tyr Leu Gln Met Asn Asn Leu Lys Pro Glu Asp Thr
            20                  25                  30

Ala Val Tyr Tyr Cys Ala Ala
        35

<210> SEQ ID NO 330
<211> LENGTH: 39
<212> TYPE: PRT
```

```
<213> ORGANISM: Artificial Sequence
<220> FEATURE:
<223> OTHER INFORMATION: FW sequence
<220> FEATURE:
<221> NAME/KEY: SITE
<222> LOCATION: (12)..(12)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa can be any naturally occurring amino acid
<220> FEATURE:
<221> NAME/KEY: SITE
<222> LOCATION: (31)..(31)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 330

His Ser Asn Ser Val Lys Gly Arg Phe Thr Met Xaa Ser Asp Asp Xaa
1               5                   10                  15

Lys Asn Thr Val Tyr Leu Gln Leu Asp Ser Leu Lys Pro Asp Xaa Thr
                20                  25                  30

Ala Val Xaa Tyr Cys Ala Ala
            35

<210> SEQ ID NO 331
<211> LENGTH: 39
<212> TYPE: PRT
<213> ORGANISM: Artificial Sequence
<220> FEATURE:
<223> OTHER INFORMATION: FW sequence

<400> SEQUENCE: 331

His Ser Asn Ser Val Lys Gly Arg Phe Thr Met Ser Ser Asp Asp Asn
1               5                   10                  15

Lys Asn Thr Val Tyr Leu Gln Leu Asp Ser Leu Lys Pro Asp Asp Thr
                20                  25                  30

Ala Val Tyr Tyr Cys Ala Ala
            35

<210> SEQ ID NO 332
<211> LENGTH: 39
<212> TYPE: PRT
<213> ORGANISM: Artificial Sequence
<220> FEATURE:
<223> OTHER INFORMATION: FW sequence

<400> SEQUENCE: 332

Tyr Gly Asp Ser Val Lys Gly Arg Phe Thr Ile Ser Arg Asp Asn Ala
1               5                   10                  15

Lys Asn Thr Val Tyr Leu Gln Met Asn Asn Leu Lys Pro Glu Asp Thr
                20                  25                  30

Ala Val Tyr Tyr Cys Ala Ala
            35

<210> SEQ ID NO 333
<211> LENGTH: 39
<212> TYPE: PRT
<213> ORGANISM: Artificial Sequence
<220> FEATURE:
<223> OTHER INFORMATION: FW sequence

<400> SEQUENCE: 333
```

Tyr Ser Asp Ser Val Lys Gly Arg Phe Thr Ile Ser Arg Asp Asn Val
1               5                   10                  15

Lys Gln Met Met Tyr Leu Ala Met Asn Ser Leu Lys Pro Glu Asp Thr
            20                  25                  30

Ala Val Tyr Phe Cys Ala Glu
        35

<210> SEQ ID NO 334
<211> LENGTH: 39
<212> TYPE: PRT
<213> ORGANISM: Artificial Sequence
<220> FEATURE:
<223> OTHER INFORMATION: FW sequence

<400> SEQUENCE: 334

Tyr Ser Asp Ser Val Lys Gly Arg Phe Thr Ile Ser Arg Asp Asn Val
1               5                   10                  15

Lys Gln Met Met Tyr Leu Ala Met Asn Ser Leu Lys Pro Glu Asp Thr
            20                  25                  30

Ala Val Tyr Phe Cys Ala Glu
        35

<210> SEQ ID NO 335
<211> LENGTH: 39
<212> TYPE: PRT
<213> ORGANISM: Artificial Sequence
<220> FEATURE:
<223> OTHER INFORMATION: FW sequence

<400> SEQUENCE: 335

Tyr Ser Asp Ser Val Lys Gly Arg Phe Thr Ile Ser Arg Asp Asn Val
1               5                   10                  15

Lys Ser Thr Met Tyr Leu Val Met Asn Ser Leu Lys Pro Glu Asp Thr
            20                  25                  30

Ala Val Tyr Tyr Cys Ala Glu
        35

<210> SEQ ID NO 336
<211> LENGTH: 39
<212> TYPE: PRT
<213> ORGANISM: Artificial Sequence
<220> FEATURE:
<223> OTHER INFORMATION: FW sequence

<400> SEQUENCE: 336

Tyr Ser Asp Ser Val Lys Gly Arg Phe Thr Ile Ser Arg Asp Asn Val
1               5                   10                  15

Lys Ser Thr Met Tyr Leu Val Met Asn Ser Leu Lys Pro Glu Asp Thr
            20                  25                  30

Ala Val Tyr Tyr Cys Ala Glu
        35

<210> SEQ ID NO 337
<211> LENGTH: 39
<212> TYPE: PRT
<213> ORGANISM: Artificial Sequence
<220> FEATURE:
<223> OTHER INFORMATION: FW sequence

<400> SEQUENCE: 337

Tyr Ser Asp Ser Val Lys Gly Arg Phe Ala Ile Ser Arg Asp Asn Ala
1               5                   10                  15

```
Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 338
<211> LENGTH: 39
<212> TYPE: PRT
<213> ORGANISM: Artificial Sequence
<220> FEATURE:
<223> OTHER INFORMATION: FW sequence

<400> SEQUENCE: 338

Tyr Ser Asp Ser Val Lys Gly Arg Phe Thr Ile Ser Arg Asp Asn Asp
1               5                   10                  15

Lys Asn Thr Ala Tyr Leu Gln Met Asn Ser Leu Lys Pro Glu Asp Thr
            20                  25                  30

Ala Leu Tyr Tyr Cys Ala Ala
        35

<210> SEQ ID NO 339
<211> LENGTH: 39
<212> TYPE: PRT
<213> ORGANISM: Artificial Sequence
<220> FEATURE:
<223> OTHER INFORMATION: FW sequence

<400> SEQUENCE: 339

Tyr Leu Asp Thr Val Lys Gly Arg Phe Thr Ile Ser Arg Asp Asn Ala
1               5                   10                  15

Lys Ser Thr Val Tyr Leu Gln Met Asn Ser Leu Lys Pro Glu Asp Thr
            20                  25                  30

Ala Val Tyr Tyr Cys Ala Ala
        35

<210> SEQ ID NO 340
<211> LENGTH: 39
<212> TYPE: PRT
<213> ORGANISM: Artificial Sequence
<220> FEATURE:
<223> OTHER INFORMATION: FW sequence

<400> SEQUENCE: 340

Tyr Leu Asp Thr Val Lys Gly Arg Phe Thr Ile Ser Arg Asp Asn Ala
1               5                   10                  15

Lys Ser Thr Val Tyr Leu Gln Met Asn Ser Leu Lys Pro Glu Asp Thr
            20                  25                  30

Ala Val Tyr Tyr Cys Ala Ala
        35

<210> SEQ ID NO 341
<211> LENGTH: 39
<212> TYPE: PRT
<213> ORGANISM: Artificial Sequence
<220> FEATURE:
<223> OTHER INFORMATION: FW sequence

<400> SEQUENCE: 341

Tyr Ser Asp Ser Val Lys Gly Arg Phe Thr Ile Ser Arg Asp Ile Pro
1               5                   10                  15

Lys Asn Thr Val Tyr Leu Gln Met Asn Ser Leu Lys Pro Glu Asp Thr
            20                  25                  30
```

Ala Leu Tyr Tyr Cys Ala Ala
        35

<210> SEQ ID NO 342
<211> LENGTH: 39
<212> TYPE: PRT
<213> ORGANISM: Artificial Sequence
<220> FEATURE:
<223> OTHER INFORMATION: FW sequence

<400> SEQUENCE: 342

Tyr Ala Asp Ser Val Arg Gly Arg Phe Thr Met Ser Arg Asp Ile Ala
1               5                   10                  15

Lys Asn Thr Val Tyr Leu Gln Met Asn Ser Leu Lys Glu Glu Asp Thr
            20                  25                  30

Ala Leu Tyr Tyr Cys Ala Ala
        35

<210> SEQ ID NO 343
<211> LENGTH: 39
<212> TYPE: PRT
<213> ORGANISM: Artificial Sequence
<220> FEATURE:
<223> OTHER INFORMATION: FW sequence

<400> SEQUENCE: 343

Tyr Ala Asp Ser Val Lys Gly Arg Phe Thr Ile Ala Ser Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 344
<211> LENGTH: 39
<212> TYPE: PRT
<213> ORGANISM: Artificial Sequence
<220> FEATURE:
<223> OTHER INFORMATION: FW sequence

<400> SEQUENCE: 344

Tyr Ala Asp Ser Val Lys Gly Arg Phe Thr Ile Ala Ser Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 345
<211> LENGTH: 39
<212> TYPE: PRT
<213> ORGANISM: Artificial Sequence
<220> FEATURE:
<223> OTHER INFORMATION: FW sequence

<400> SEQUENCE: 345

Tyr Ala Asp Ser Val Lys Gly Arg Phe Thr Ile Ser Ser Asp Asn Ala
1               5                   10                  15

Lys Asn Thr Val Tyr Leu His Met Asn Ser Leu Lys Pro Glu Asp Thr
            20                  25                  30

Ala Val Tyr Tyr Cys Ala Ala
        35

<210> SEQ ID NO 346
<211> LENGTH: 39
<212> TYPE: PRT
<213> ORGANISM: Artificial Sequence
<220> FEATURE:
<223> OTHER INFORMATION: FW sequence

<400> SEQUENCE: 346

Tyr Ala Asp Ser Val Lys Gly Arg Phe Thr Ile Ser Ser Asp Asn Ala
1               5                   10                  15

Lys Asn Met Val Tyr Leu Gln Met Asp Asn Leu Lys Pro Glu Asp Thr
            20                  25                  30

Ala Val Tyr Tyr Cys Ala Ala
        35

<210> SEQ ID NO 347
<211> LENGTH: 39
<212> TYPE: PRT
<213> ORGANISM: Artificial Sequence
<220> FEATURE:
<223> OTHER INFORMATION: FW sequence

<400> SEQUENCE: 347

Tyr Ala Asp Ser Val Lys Gly Arg Phe Thr Ile Ser Ser Asp Asn Ala
1               5                   10                  15

Lys Asn Thr Val Tyr Leu Gln Met Asn Ser Leu Lys Pro Glu Asp Thr
            20                  25                  30

Ala Val Tyr Phe Cys Ala Ala
        35

<210> SEQ ID NO 348
<211> LENGTH: 39
<212> TYPE: PRT
<213> ORGANISM: Artificial Sequence
<220> FEATURE:
<223> OTHER INFORMATION: FW sequence

<400> SEQUENCE: 348

Tyr Ala Asp Ser Val Lys Gly Arg Phe Thr Ile Ser Ser Asp Asn Ala
1               5                   10                  15

Lys Asn Thr Val Tyr Leu Gln Met Asn Ser Leu Lys Pro Glu Asp Thr
            20                  25                  30

Ala Val Tyr Phe Cys Ala Ala
        35

<210> SEQ ID NO 349
<211> LENGTH: 8
<212> TYPE: PRT
<213> ORGANISM: Artificial Sequence
<220> FEATURE:
<223> OTHER INFORMATION: CDR sequence

<400> SEQUENCE: 349

Ala His Thr Phe Ser Gly Ser Phe
1               5

<210> SEQ ID NO 350
<211> LENGTH: 8
<212> TYPE: PRT
<213> ORGANISM: Artificial Sequence
<220> FEATURE:
<223> OTHER INFORMATION: CDR sequence

<400> SEQUENCE: 350

Ala His Thr Phe Ser Gly Ser Phe
1               5

<210> SEQ ID NO 351
<211> LENGTH: 8
<212> TYPE: PRT
<213> ORGANISM: Artificial Sequence
<220> FEATURE:
<223> OTHER INFORMATION: CDR sequence

<400> SEQUENCE: 351

Ala His Thr Phe Ser Gly Ser Phe
1               5

<210> SEQ ID NO 352
<211> LENGTH: 8
<212> TYPE: PRT
<213> ORGANISM: Artificial Sequence
<220> FEATURE:
<223> OTHER INFORMATION: CDR sequence

<400> SEQUENCE: 352

Asp His Thr Phe Ala Gly Val Tyr
1               5

<210> SEQ ID NO 353
<211> LENGTH: 8
<212> TYPE: PRT
<213> ORGANISM: Artificial Sequence
<220> FEATURE:
<223> OTHER INFORMATION: CDR sequence

<400> SEQUENCE: 353

Asp His Thr Phe Ala Gly Val Tyr
1               5

<210> SEQ ID NO 354
<211> LENGTH: 8
<212> TYPE: PRT
<213> ORGANISM: Artificial Sequence
<220> FEATURE:
<223> OTHER INFORMATION: CDR sequence

<400> SEQUENCE: 354

His His Thr Phe Ala Gly Ala Tyr
1               5

<210> SEQ ID NO 355
<211> LENGTH: 8
<212> TYPE: PRT
<213> ORGANISM: Artificial Sequence
<220> FEATURE:
<223> OTHER INFORMATION: CDR sequence

<400> SEQUENCE: 355

Asp His Thr Phe Ala Gly Val Tyr
1               5

<210> SEQ ID NO 356
<211> LENGTH: 8
<212> TYPE: PRT
<213> ORGANISM: Artificial Sequence
<220> FEATURE:
<223> OTHER INFORMATION: CDR sequence

<400> SEQUENCE: 356

```
Glu His Thr Phe Met Gly Ala Tyr
1               5

<210> SEQ ID NO 357
<211> LENGTH: 8
<212> TYPE: PRT
<213> ORGANISM: Artificial Sequence
<220> FEATURE:
<223> OTHER INFORMATION: CDR sequence

<400> SEQUENCE: 357

Trp His Val Phe Arg Gly Asn Tyr
1               5

<210> SEQ ID NO 358
<211> LENGTH: 8
<212> TYPE: PRT
<213> ORGANISM: Artificial Sequence
<220> FEATURE:
<223> OTHER INFORMATION: CDR sequence

<400> SEQUENCE: 358

Val Ile Arg Thr Tyr Ser Thr Tyr
1               5

<210> SEQ ID NO 359
<211> LENGTH: 9
<212> TYPE: PRT
<213> ORGANISM: Artificial Sequence
<220> FEATURE:
<223> OTHER INFORMATION: CDR sequence

<400> SEQUENCE: 359

Trp His Tyr Ala Ala Gly Arg Asp Tyr
1               5

<210> SEQ ID NO 360
<211> LENGTH: 9
<212> TYPE: PRT
<213> ORGANISM: Artificial Sequence
<220> FEATURE:
<223> OTHER INFORMATION: CDR sequence

<400> SEQUENCE: 360

Trp His Tyr Ala Ala Gly Arg Asp Tyr
1               5

<210> SEQ ID NO 361
<211> LENGTH: 9
<212> TYPE: PRT
<213> ORGANISM: Artificial Sequence
<220> FEATURE:
<223> OTHER INFORMATION: CDR sequence

<400> SEQUENCE: 361

Trp His Tyr Ala Ala Gly Arg Asp Tyr
1               5

<210> SEQ ID NO 362
<211> LENGTH: 9
<212> TYPE: PRT
<213> ORGANISM: Artificial Sequence
<220> FEATURE:
<223> OTHER INFORMATION: CDR sequence

<400> SEQUENCE: 362

Trp His Tyr Ala Ala Gly Arg Asp Tyr
```

```
<210> SEQ ID NO 363
<211> LENGTH: 9
<212> TYPE: PRT
<213> ORGANISM: Artificial Sequence
<220> FEATURE:
<223> OTHER INFORMATION: CDR sequence

<400> SEQUENCE: 363

Ala Ser Thr Ala Val Gly Ala Asp Thr
1               5

<210> SEQ ID NO 364
<211> LENGTH: 9
<212> TYPE: PRT
<213> ORGANISM: Artificial Sequence
<220> FEATURE:
<223> OTHER INFORMATION: CDR sequence

<400> SEQUENCE: 364

Ala Ser Pro Ala Val Gly Ala Asp Thr
1               5

<210> SEQ ID NO 365
<211> LENGTH: 9
<212> TYPE: PRT
<213> ORGANISM: Artificial Sequence
<220> FEATURE:
<223> OTHER INFORMATION: CDR sequence

<400> SEQUENCE: 365

Gly Asn Pro Gly Thr Ser Tyr His Tyr
1               5

<210> SEQ ID NO 366
<211> LENGTH: 9
<212> TYPE: PRT
<213> ORGANISM: Artificial Sequence
<220> FEATURE:
<223> OTHER INFORMATION: CDR sequence

<400> SEQUENCE: 366

Gly Asn Pro Gly Thr Arg Tyr Ile Tyr
1               5

<210> SEQ ID NO 367
<211> LENGTH: 12
<212> TYPE: PRT
<213> ORGANISM: Artificial Sequence
<220> FEATURE:
<223> OTHER INFORMATION: CDR sequence

<400> SEQUENCE: 367

Asp Arg Phe Ser Val Val Ala Val Glu Tyr Asp Tyr
1               5                   10

<210> SEQ ID NO 368
<211> LENGTH: 12
<212> TYPE: PRT
<213> ORGANISM: Artificial Sequence
<220> FEATURE:
<223> OTHER INFORMATION: CDR sequence

<400> SEQUENCE: 368

Asp Arg Phe Ser Val Val Ala Val Glu Tyr Asp Tyr
1               5                   10
```

```
<210> SEQ ID NO 369
<211> LENGTH: 13
<212> TYPE: PRT
<213> ORGANISM: Artificial Sequence
<220> FEATURE:
<223> OTHER INFORMATION: CDR sequence

<400> SEQUENCE: 369

Gly Leu Lys Arg Ile Gly Asp Gln Arg Glu Ala Asp Tyr
1               5                   10

<210> SEQ ID NO 370
<211> LENGTH: 13
<212> TYPE: PRT
<213> ORGANISM: Artificial Sequence
<220> FEATURE:
<223> OTHER INFORMATION: CDR sequence

<400> SEQUENCE: 370

Gly Leu Lys Arg Ile Gly Asp Gln Arg Glu Ala Asp Tyr
1               5                   10

<210> SEQ ID NO 371
<211> LENGTH: 13
<212> TYPE: PRT
<213> ORGANISM: Artificial Sequence
<220> FEATURE:
<223> OTHER INFORMATION: CDR sequence

<400> SEQUENCE: 371

Gly Leu Lys Arg Ile Gly Asp Gln Arg Glu Ala Asp Tyr
1               5                   10

<210> SEQ ID NO 372
<211> LENGTH: 14
<212> TYPE: PRT
<213> ORGANISM: Artificial Sequence
<220> FEATURE:
<223> OTHER INFORMATION: CDR sequence

<400> SEQUENCE: 372

Asp Arg Phe Val Val Ala Ala Gly Thr His Asp Leu Asp Tyr
1               5                   10

<210> SEQ ID NO 373
<211> LENGTH: 14
<212> TYPE: PRT
<213> ORGANISM: Artificial Sequence
<220> FEATURE:
<223> OTHER INFORMATION: CDR sequence

<400> SEQUENCE: 373

Asp Arg Phe Val Val Ala Ala Gly Thr His Asp Leu Asp Tyr
1               5                   10

<210> SEQ ID NO 374
<211> LENGTH: 14
<212> TYPE: PRT
<213> ORGANISM: Artificial Sequence
<220> FEATURE:
<223> OTHER INFORMATION: CDR sequence

<400> SEQUENCE: 374

Asp Arg Phe Ala Val Ala Ser Gly Thr His Asp Leu Asp Tyr
1               5                   10
```

```
<210> SEQ ID NO 375
<211> LENGTH: 14
<212> TYPE: PRT
<213> ORGANISM: Artificial Sequence
<220> FEATURE:
<223> OTHER INFORMATION: CDR sequence

<400> SEQUENCE: 375

Asp Arg Phe Ala Val Ala Ile Gly Thr His Asp Leu Asp Tyr
1               5                   10

<210> SEQ ID NO 376
<211> LENGTH: 14
<212> TYPE: PRT
<213> ORGANISM: Artificial Sequence
<220> FEATURE:
<223> OTHER INFORMATION: CDR sequence

<400> SEQUENCE: 376

Asp Arg Phe Thr Leu Val Pro Thr Thr Ser Asp Leu Asp Tyr
1               5                   10

<210> SEQ ID NO 377
<211> LENGTH: 14
<212> TYPE: PRT
<213> ORGANISM: Artificial Sequence
<220> FEATURE:
<223> OTHER INFORMATION: CDR sequence

<400> SEQUENCE: 377

Arg Phe Trp Ile Gly Val Arg Ala Pro Ala Glu Tyr Asn Tyr
1               5                   10

<210> SEQ ID NO 378
<211> LENGTH: 14
<212> TYPE: PRT
<213> ORGANISM: Artificial Sequence
<220> FEATURE:
<223> OTHER INFORMATION: CDR sequence

<400> SEQUENCE: 378

Arg Phe Trp Ile Gly Val Arg Ala Pro Ala Glu Tyr Asn Tyr
1               5                   10

<210> SEQ ID NO 379
<211> LENGTH: 14
<212> TYPE: PRT
<213> ORGANISM: Artificial Sequence
<220> FEATURE:
<223> OTHER INFORMATION: CDR sequence

<400> SEQUENCE: 379

Arg Trp Trp Ile Ala Val Arg Ala Pro Ala Glu Tyr Asn Tyr
1               5                   10

<210> SEQ ID NO 380
<211> LENGTH: 14
<212> TYPE: PRT
<213> ORGANISM: Artificial Sequence
<220> FEATURE:
<223> OTHER INFORMATION: CDR sequence

<400> SEQUENCE: 380

Arg Trp Trp Ile Ala Val Arg Ala Pro Ala Glu Tyr Asn Tyr
1               5                   10
```

```
<210> SEQ ID NO 381
<211> LENGTH: 15
<212> TYPE: PRT
<213> ORGANISM: Artificial Sequence
<220> FEATURE:
<223> OTHER INFORMATION: CDR sequence

<400> SEQUENCE: 381

Asp Arg Trp Gly Leu Phe Ser Leu Ser Ile Ala Thr Pro Thr His
1               5                   10                  15

<210> SEQ ID NO 382
<211> LENGTH: 15
<212> TYPE: PRT
<213> ORGANISM: Artificial Sequence
<220> FEATURE:
<223> OTHER INFORMATION: CDR sequence

<400> SEQUENCE: 382

Asp Arg Leu Val Leu Val Ala Leu Ser Ile Ala Asp Pro Gly Phe
1               5                   10                  15

<210> SEQ ID NO 383
<211> LENGTH: 15
<212> TYPE: PRT
<213> ORGANISM: Artificial Sequence
<220> FEATURE:
<223> OTHER INFORMATION: CDR sequence

<400> SEQUENCE: 383

Gly Phe Pro Val Leu Val Ala Leu Ser Ile Ala Asp Pro Asp Tyr
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: CDR sequence

<400> SEQUENCE: 384

Gly Phe Pro Val Leu Thr Ala Leu His Ile Ala Asp Pro Asp Tyr
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: CDR sequence

<400> SEQUENCE: 385

Gly Arg Gly Ile Val Ala Gly Arg Ile Pro Ala Glu Tyr Ala Asp
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: CDR sequence

<400> SEQUENCE: 386

Gly Arg Thr Ala Ser Ala Ser Thr Met Ile Arg Glu Tyr Asp Ser
1               5                   10                  15

<210> SEQ ID NO 387
```

```
<211> LENGTH: 15
<212> TYPE: PRT
<213> ORGANISM: Artificial Sequence
<220> FEATURE:
<223> OTHER INFORMATION: CDR sequence

<400> SEQUENCE: 387

Asp Arg Leu Val Ile Thr Lys Leu Ser Ile Ala Asp Pro Gly Tyr
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: CDR sequence

<400> SEQUENCE: 388

Cys Thr Ser Val Val Val Leu Leu Ala Pro Asn Trp Tyr Glu Tyr
1               5                   10                  15

<210> SEQ ID NO 389
<211> LENGTH: 15
<212> TYPE: PRT
<213> ORGANISM: Artificial Sequence
<220> FEATURE:
<223> OTHER INFORMATION: CDR sequence

<400> SEQUENCE: 389

Thr Thr Ser Val Val Val Leu Leu Ala Pro Asn Trp Tyr Glu Tyr
1               5                   10                  15

<210> SEQ ID NO 390
<211> LENGTH: 16
<212> TYPE: PRT
<213> ORGANISM: Artificial Sequence
<220> FEATURE:
<223> OTHER INFORMATION: CDR sequence

<400> SEQUENCE: 390

Arg Leu Arg Gly Trp Ile Thr Thr Arg Lys Pro Asn Glu Tyr Asp Tyr
1               5                   10                  15

<210> SEQ ID NO 391
<211> LENGTH: 17
<212> TYPE: PRT
<213> ORGANISM: Artificial Sequence
<220> FEATURE:
<223> OTHER INFORMATION: CDR sequence

<400> SEQUENCE: 391

Ala Arg Ser Ala Gly Leu Gly Ser Ser Arg Arg Ile Glu Gly Tyr Asp
1               5                   10                  15

Lys

<210> SEQ ID NO 392
<211> LENGTH: 17
<212> TYPE: PRT
<213> ORGANISM: Artificial Sequence
<220> FEATURE:
<223> OTHER INFORMATION: CDR sequence

<400> SEQUENCE: 392

Ala Arg Ser Ala Gly Leu Gly Ser Ser Arg Arg Ile Glu Gly Tyr Asp
1               5                   10                  15

Lys
```

<210> SEQ ID NO 393
<211> LENGTH: 17
<212> TYPE: PRT
<213> ORGANISM: Artificial Sequence
<220> FEATURE:
<223> OTHER INFORMATION: CDR sequence

<400> SEQUENCE: 393

Ala Arg Ser Ala Glu Leu Gly Ser Ser Arg Lys Ile Gln Gly Tyr Asp
1               5                   10                  15

Gln

<210> SEQ ID NO 394
<211> LENGTH: 17
<212> TYPE: PRT
<213> ORGANISM: Artificial Sequence
<220> FEATURE:
<223> OTHER INFORMATION: CDR sequence

<400> SEQUENCE: 394

Ala Arg Ser Ala Glu Leu Gly Ser Ser Arg Lys Ile Gln Gly Tyr Asp
1               5                   10                  15

Gln

<210> SEQ ID NO 395
<211> LENGTH: 19
<212> TYPE: PRT
<213> ORGANISM: Artificial Sequence
<220> FEATURE:
<223> OTHER INFORMATION: CDR sequence

<400> SEQUENCE: 395

Gln Tyr Gln Asp Arg Tyr Tyr Asp Glu Phe Thr Trp Lys Glu Lys Asp
1               5                   10                  15

Met Asp Tyr

<210> SEQ ID NO 396
<211> LENGTH: 19
<212> TYPE: PRT
<213> ORGANISM: Artificial Sequence
<220> FEATURE:
<223> OTHER INFORMATION: CDR sequence

<400> SEQUENCE: 396

Gln Tyr Gln Glu Arg Tyr Tyr Ser Asp Phe Ser Leu Lys Glu Lys Gly
1               5                   10                  15

Met Glu Tyr

<210> SEQ ID NO 397
<211> LENGTH: 19
<212> TYPE: PRT
<213> ORGANISM: Artificial Sequence
<220> FEATURE:
<223> OTHER INFORMATION: CDR sequence

<400> SEQUENCE: 397

Arg Tyr Gln Pro Arg Tyr Tyr Asp Ser Gly Asp Met Asp Gly Tyr Glu
1               5                   10                  15

Tyr Glu Phe

<210> SEQ ID NO 398
<211> LENGTH: 19

```
<212> TYPE: PRT
<213> ORGANISM: Artificial Sequence
<220> FEATURE:
<223> OTHER INFORMATION: CDR sequence

<400> SEQUENCE: 398

Arg Tyr Gln Pro Arg Tyr Tyr Asp Ser Gly Asp Met Asp Gly Tyr Glu
1               5                   10                  15

Tyr Asp Asn

<210> SEQ ID NO 399
<211> LENGTH: 19
<212> TYPE: PRT
<213> ORGANISM: Artificial Sequence
<220> FEATURE:
<223> OTHER INFORMATION: CDR sequence

<400> SEQUENCE: 399

Val Asp Arg Ser Thr Gly Trp Asp Ser Trp Arg Asp Asp Pro Asp Gln
1               5                   10                  15

Tyr Asp Tyr

<210> SEQ ID NO 400
<211> LENGTH: 19
<212> TYPE: PRT
<213> ORGANISM: Artificial Sequence
<220> FEATURE:
<223> OTHER INFORMATION: CDR sequence

<400> SEQUENCE: 400

Ala Asp Arg Phe Arg Gly Trp Ala Thr Trp Arg Asp Asp Pro Asp Gln
1               5                   10                  15

Tyr Asp Tyr

<210> SEQ ID NO 401
<211> LENGTH: 24
<212> TYPE: PRT
<213> ORGANISM: Artificial Sequence
<220> FEATURE:
<223> OTHER INFORMATION: CDR sequence

<400> SEQUENCE: 401

Asp Val Thr Leu Asn Pro Phe Thr Gly Trp Asn Thr Arg Ser Gly Pro
1               5                   10                  15

Met Tyr Arg Tyr Glu Tyr Asp Tyr
            20

<210> SEQ ID NO 402
<211> LENGTH: 24
<212> TYPE: PRT
<213> ORGANISM: Artificial Sequence
<220> FEATURE:
<223> OTHER INFORMATION: CDR sequence

<400> SEQUENCE: 402

Asp Val Thr Leu Asn Pro Phe Thr Gly Trp Asn Thr Arg Ser Gly Pro
1               5                   10                  15

Met Tyr Arg Tyr Glu Tyr Asp Tyr
            20

<210> SEQ ID NO 403
<211> LENGTH: 24
<212> TYPE: PRT
<213> ORGANISM: Artificial Sequence
```

<220> FEATURE:
<223> OTHER INFORMATION: CDR sequence

<400> SEQUENCE: 403

Asp Val Thr Leu Asn Pro Phe Thr Gly Trp Thr Arg Ser Gly Pro
1               5                   10                  15

Met Tyr Arg Tyr Glu Tyr Asp Tyr
            20

<210> SEQ ID NO 404
<211> LENGTH: 24
<212> TYPE: PRT
<213> ORGANISM: Artificial Sequence
<220> FEATURE:
<223> OTHER INFORMATION: CDR sequence

<400> SEQUENCE: 404

Asp Val Thr Leu Asn Pro Phe Thr Gly Trp Asp Thr Arg Ser Gly Pro
1               5                   10                  15

Met Tyr Arg Tyr Glu Tyr Asp Tyr
            20

<210> SEQ ID NO 405
<211> LENGTH: 24
<212> TYPE: PRT
<213> ORGANISM: Artificial Sequence
<220> FEATURE:
<223> OTHER INFORMATION: CDR sequence

<400> SEQUENCE: 405

Asp Val Thr Leu Asn Pro Phe Thr Gly Trp Asp Thr Arg Ser Gly Pro
1               5                   10                  15

Met Tyr Arg Tyr Glu Tyr Asp Tyr
            20

<210> SEQ ID NO 406
<211> LENGTH: 24
<212> TYPE: PRT
<213> ORGANISM: Artificial Sequence
<220> FEATURE:
<223> OTHER INFORMATION: CDR sequence

<400> SEQUENCE: 406

Asp Val Thr Leu Asn Pro Phe Thr Gly Trp Asp Thr Arg Ser Gly Pro
1               5                   10                  15

Met Tyr Arg Tyr Glu Tyr Asp Tyr
            20

<210> SEQ ID NO 407
<211> LENGTH: 11
<212> TYPE: PRT
<213> ORGANISM: Artificial Sequence
<220> FEATURE:
<223> OTHER INFORMATION: FW sequence

<400> SEQUENCE: 407

Trp Gly Gln Gly Thr Gln Val Thr Val Ser Ser
1               5                   10

<210> SEQ ID NO 408
<211> LENGTH: 11
<212> TYPE: PRT
<213> ORGANISM: Artificial Sequence
<220> FEATURE:
<223> OTHER INFORMATION: FW sequence

<400> SEQUENCE: 408

Trp Gly Gln Gly Thr Gln Val Thr Val Ser Ser
1               5                   10

<210> SEQ ID NO 409
<211> LENGTH: 11
<212> TYPE: PRT
<213> ORGANISM: Artificial Sequence
<220> FEATURE:
<223> OTHER INFORMATION: FW sequence

<400> SEQUENCE: 409

Trp Gly Gln Gly Thr Gln Val Thr Val Ser Ser
1               5                   10

<210> SEQ ID NO 410
<211> LENGTH: 11
<212> TYPE: PRT
<213> ORGANISM: Artificial Sequence
<220> FEATURE:
<223> OTHER INFORMATION: FW sequence

<400> SEQUENCE: 410

Trp Gly Gln Gly Thr Gln Val Thr Val Ser Ser
1               5                   10

<210> SEQ ID NO 411
<211> LENGTH: 11
<212> TYPE: PRT
<213> ORGANISM: Artificial Sequence
<220> FEATURE:
<223> OTHER INFORMATION: FW sequence

<400> SEQUENCE: 411

Trp Gly Gln Gly Thr Gln Val Thr Val Ser Ser
1               5                   10

<210> SEQ ID NO 412
<211> LENGTH: 11
<212> TYPE: PRT
<213> ORGANISM: Artificial Sequence
<220> FEATURE:
<223> OTHER INFORMATION: FW sequence

<400> SEQUENCE: 412

Trp Gly Gln Gly Thr Gln Val Thr Val Ser Ser
1               5                   10

<210> SEQ ID NO 413
<211> LENGTH: 11
<212> TYPE: PRT
<213> ORGANISM: Artificial Sequence
<220> FEATURE:
<223> OTHER INFORMATION: FW sequence

<400> SEQUENCE: 413

Trp Gly Gln Gly Thr Gln Val Thr Val Ser Ser
1               5                   10

<210> SEQ ID NO 414
<211> LENGTH: 11
<212> TYPE: PRT
<213> ORGANISM: Artificial Sequence
<220> FEATURE:
<223> OTHER INFORMATION: FW sequence

```
<400> SEQUENCE: 414

Trp Gly Gln Gly Thr Gln Val Thr Val Ser Ser
1               5                   10

<210> SEQ ID NO 415
<211> LENGTH: 11
<212> TYPE: PRT
<213> ORGANISM: Artificial Sequence
<220> FEATURE:
<223> OTHER INFORMATION: FW sequence

<400> SEQUENCE: 415

Trp Gly Gln Gly Thr Gln Val Thr Val Ser Ser
1               5                   10

<210> SEQ ID NO 416
<211> LENGTH: 11
<212> TYPE: PRT
<213> ORGANISM: Artificial Sequence
<220> FEATURE:
<223> OTHER INFORMATION: FW sequence

<400> SEQUENCE: 416

Trp Gly Gln Gly Thr Gln Val Thr Val Ser Ser
1               5                   10

<210> SEQ ID NO 417
<211> LENGTH: 11
<212> TYPE: PRT
<213> ORGANISM: Artificial Sequence
<220> FEATURE:
<223> OTHER INFORMATION: FW sequence

<400> SEQUENCE: 417

Trp Gly Gln Gly Thr Gln Val Thr Val Ser Ser
1               5                   10

<210> SEQ ID NO 418
<211> LENGTH: 11
<212> TYPE: PRT
<213> ORGANISM: Artificial Sequence
<220> FEATURE:
<223> OTHER INFORMATION: FW sequence

<400> SEQUENCE: 418

Trp Gly Gln Gly Thr Gln Val Thr Val Ser Ser
1               5                   10

<210> SEQ ID NO 419
<211> LENGTH: 11
<212> TYPE: PRT
<213> ORGANISM: Artificial Sequence
<220> FEATURE:
<223> OTHER INFORMATION: FW sequence

<400> SEQUENCE: 419

Trp Gly Gln Gly Thr Gln Val Thr Val Ser Ser
1               5                   10

<210> SEQ ID NO 420
<211> LENGTH: 11
<212> TYPE: PRT
<213> ORGANISM: Artificial Sequence
<220> FEATURE:
<223> OTHER INFORMATION: FW sequence

<400> SEQUENCE: 420
```

```
Trp Gly Gln Gly Thr Gln Val Thr Val Ser Ser
1               5                   10

<210> SEQ ID NO 421
<211> LENGTH: 11
<212> TYPE: PRT
<213> ORGANISM: Artificial Sequence
<220> FEATURE:
<223> OTHER INFORMATION: FW sequence

<400> SEQUENCE: 421

Trp Gly Gln Gly Thr Arg Val Thr Val Ser Ser
1               5                   10

<210> SEQ ID NO 422
<211> LENGTH: 11
<212> TYPE: PRT
<213> ORGANISM: Artificial Sequence
<220> FEATURE:
<223> OTHER INFORMATION: FW sequence

<400> SEQUENCE: 422

Trp Gly Gln Gly Thr Arg Val Thr Val Ser Ser
1               5                   10

<210> SEQ ID NO 423
<211> LENGTH: 11
<212> TYPE: PRT
<213> ORGANISM: Artificial Sequence
<220> FEATURE:
<223> OTHER INFORMATION: FW sequence

<400> SEQUENCE: 423

Trp Gly Gln Gly Thr Gln Val Thr Val Ser Ser
1               5                   10

<210> SEQ ID NO 424
<211> LENGTH: 11
<212> TYPE: PRT
<213> ORGANISM: Artificial Sequence
<220> FEATURE:
<223> OTHER INFORMATION: FW sequence

<400> SEQUENCE: 424

Trp Gly Gln Gly Thr Gln Val Thr Val Ser Ser
1               5                   10

<210> SEQ ID NO 425
<211> LENGTH: 11
<212> TYPE: PRT
<213> ORGANISM: Artificial Sequence
<220> FEATURE:
<223> OTHER INFORMATION: FW sequence

<400> SEQUENCE: 425

Trp Gly Gln Gly Thr Gln Val Thr Val Ser Ser
1               5                   10

<210> SEQ ID NO 426
<211> LENGTH: 11
<212> TYPE: PRT
<213> ORGANISM: Artificial Sequence
<220> FEATURE:
<223> OTHER INFORMATION: FW sequence

<400> SEQUENCE: 426
```

Trp Gly Gln Gly Thr Gln Val Thr Val Ser Ser
1               5                   10

<210> SEQ ID NO 427
<211> LENGTH: 11
<212> TYPE: PRT
<213> ORGANISM: Artificial Sequence
<220> FEATURE:
<223> OTHER INFORMATION: FW sequence

<400> SEQUENCE: 427

Trp Gly Gln Gly Thr Gln Val Thr Val Ser Ser
1               5                   10

<210> SEQ ID NO 428
<211> LENGTH: 11
<212> TYPE: PRT
<213> ORGANISM: Artificial Sequence
<220> FEATURE:
<223> OTHER INFORMATION: FW sequence

<400> SEQUENCE: 428

Trp Gly Gln Gly Thr Gln Val Thr Val Ala Ser
1               5                   10

<210> SEQ ID NO 429
<211> LENGTH: 11
<212> TYPE: PRT
<213> ORGANISM: Artificial Sequence
<220> FEATURE:
<223> OTHER INFORMATION: FW sequence

<400> SEQUENCE: 429

Trp Gly Gln Gly Thr Gln Val Thr Val Ser Ser
1               5                   10

<210> SEQ ID NO 430
<211> LENGTH: 11
<212> TYPE: PRT
<213> ORGANISM: Artificial Sequence
<220> FEATURE:
<223> OTHER INFORMATION: FW sequence

<400> SEQUENCE: 430

Trp Gly Gln Gly Thr Gln Val Thr Val Ser Ser
1               5                   10

<210> SEQ ID NO 431
<211> LENGTH: 11
<212> TYPE: PRT
<213> ORGANISM: Artificial Sequence
<220> FEATURE:
<223> OTHER INFORMATION: FW sequence

<400> SEQUENCE: 431

Trp Gly Gln Gly Thr Gln Val Thr Val Ser Ser
1               5                   10

<210> SEQ ID NO 432
<211> LENGTH: 11
<212> TYPE: PRT
<213> ORGANISM: Artificial Sequence
<220> FEATURE:
<223> OTHER INFORMATION: FW sequence

<400> SEQUENCE: 432

Trp Gly Gln Gly Thr Gln Val Thr Val Ser Ser

```
1               5                   10
```

<210> SEQ ID NO 433
<211> LENGTH: 11
<212> TYPE: PRT
<213> ORGANISM: Artificial Sequence
<220> FEATURE:
<223> OTHER INFORMATION: FW sequence

<400> SEQUENCE: 433

```
Trp Gly Gln Gly Thr Gln Val Thr Val Ser Ser
1               5                   10
```

<210> SEQ ID NO 434
<211> LENGTH: 11
<212> TYPE: PRT
<213> ORGANISM: Artificial Sequence
<220> FEATURE:
<223> OTHER INFORMATION: FW sequence

<400> SEQUENCE: 434

```
Trp Gly Gln Gly Thr Gln Val Thr Val Ser Ser
1               5                   10
```

<210> SEQ ID NO 435
<211> LENGTH: 11
<212> TYPE: PRT
<213> ORGANISM: Artificial Sequence
<220> FEATURE:
<223> OTHER INFORMATION: FW sequence

<400> SEQUENCE: 435

```
Trp Gly Gln Gly Thr Gln Val Thr Val Ser Ser
1               5                   10
```

<210> SEQ ID NO 436
<211> LENGTH: 11
<212> TYPE: PRT
<213> ORGANISM: Artificial Sequence
<220> FEATURE:
<223> OTHER INFORMATION: FW sequence

<400> SEQUENCE: 436

```
Trp Gly Gln Gly Thr Gln Val Thr Val Ser Ser
1               5                   10
```

<210> SEQ ID NO 437
<211> LENGTH: 11
<212> TYPE: PRT
<213> ORGANISM: Artificial Sequence
<220> FEATURE:
<223> OTHER INFORMATION: FW sequence

<400> SEQUENCE: 437

```
Trp Gly Gln Gly Thr Gln Val Thr Val Ser Ser
1               5                   10
```

<210> SEQ ID NO 438
<211> LENGTH: 11
<212> TYPE: PRT
<213> ORGANISM: Artificial Sequence
<220> FEATURE:
<223> OTHER INFORMATION: FW sequence

<400> SEQUENCE: 438

```
Trp Gly Gln Gly Thr Gln Val Thr Val Ser Ser
1               5                   10
```

<210> SEQ ID NO 439
<211> LENGTH: 11
<212> TYPE: PRT
<213> ORGANISM: Artificial Sequence
<220> FEATURE:
<223> OTHER INFORMATION: FW sequence

<400> SEQUENCE: 439

Trp Gly Gln Gly Thr Gln Val Thr Val Ser Ser
1               5                   10

<210> SEQ ID NO 440
<211> LENGTH: 11
<212> TYPE: PRT
<213> ORGANISM: Artificial Sequence
<220> FEATURE:
<223> OTHER INFORMATION: FW sequence

<400> SEQUENCE: 440

Trp Gly Gln Gly Thr Arg Val Thr Val Ser Ser
1               5                   10

<210> SEQ ID NO 441
<211> LENGTH: 11
<212> TYPE: PRT
<213> ORGANISM: Artificial Sequence
<220> FEATURE:
<223> OTHER INFORMATION: FW sequence

<400> SEQUENCE: 441

Trp Gly Gln Gly Thr Gln Val Thr Val Ser Thr
1               5                   10

<210> SEQ ID NO 442
<211> LENGTH: 11
<212> TYPE: PRT
<213> ORGANISM: Artificial Sequence
<220> FEATURE:
<223> OTHER INFORMATION: FW sequence

<400> SEQUENCE: 442

Trp Gly Gln Gly Thr Gln Val Thr Val Ser Pro
1               5                   10

<210> SEQ ID NO 443
<211> LENGTH: 11
<212> TYPE: PRT
<213> ORGANISM: Artificial Sequence
<220> FEATURE:
<223> OTHER INFORMATION: FW sequence

<400> SEQUENCE: 443

Trp Gly Gln Gly Thr Gln Val Thr Val Ser Ser
1               5                   10

<210> SEQ ID NO 444
<211> LENGTH: 11
<212> TYPE: PRT
<213> ORGANISM: Artificial Sequence
<220> FEATURE:
<223> OTHER INFORMATION: FW sequence

<400> SEQUENCE: 444

Trp Gly Gln Gly Thr Gln Val Thr Val Ser Glu
1               5                   10

<210> SEQ ID NO 445
<211> LENGTH: 11
<212> TYPE: PRT
<213> ORGANISM: Artificial Sequence
<220> FEATURE:
<223> OTHER INFORMATION: FW sequence

<400> SEQUENCE: 445

Trp Gly Gln Gly Thr Gln Val Thr Val Ser Ser
1               5                   10

<210> SEQ ID NO 446
<211> LENGTH: 11
<212> TYPE: PRT
<213> ORGANISM: Artificial Sequence
<220> FEATURE:
<223> OTHER INFORMATION: FW sequence

<400> SEQUENCE: 446

Trp Gly Gln Gly Thr Gln Val Thr Val Ser Ser
1               5                   10

<210> SEQ ID NO 447
<211> LENGTH: 11
<212> TYPE: PRT
<213> ORGANISM: Artificial Sequence
<220> FEATURE:
<223> OTHER INFORMATION: FW sequence

<400> SEQUENCE: 447

Trp Gly Gln Gly Thr Gln Val Thr Val Ser Ser
1               5                   10

<210> SEQ ID NO 448
<211> LENGTH: 11
<212> TYPE: PRT
<213> ORGANISM: Artificial Sequence
<220> FEATURE:
<223> OTHER INFORMATION: FW sequence

<400> SEQUENCE: 448

Trp Gly Gln Gly Thr Gln Val Thr Val Ala Ser
1               5                   10

<210> SEQ ID NO 449
<211> LENGTH: 11
<212> TYPE: PRT
<213> ORGANISM: Artificial Sequence
<220> FEATURE:
<223> OTHER INFORMATION: FW sequence

<400> SEQUENCE: 449

Trp Gly Arg Gly Thr Gln Val Thr Val Ser Ser
1               5                   10

<210> SEQ ID NO 450
<211> LENGTH: 11
<212> TYPE: PRT
<213> ORGANISM: Artificial Sequence
<220> FEATURE:
<223> OTHER INFORMATION: FW sequence

<400> SEQUENCE: 450

Trp Gly Arg Gly Thr Gln Val Thr Val Ser Ser
1               5                   10

```
<210> SEQ ID NO 451
<211> LENGTH: 11
<212> TYPE: PRT
<213> ORGANISM: Artificial Sequence
<220> FEATURE:
<223> OTHER INFORMATION: FW sequence

<400> SEQUENCE: 451

Trp Gly Arg Gly Thr Gln Val Thr Val Ser Ser
1               5                   10

<210> SEQ ID NO 452
<211> LENGTH: 11
<212> TYPE: PRT
<213> ORGANISM: Artificial Sequence
<220> FEATURE:
<223> OTHER INFORMATION: FW sequence

<400> SEQUENCE: 452

Trp Gly Arg Gly Thr Arg Val Thr Val Ser Ser
1               5                   10

<210> SEQ ID NO 453
<211> LENGTH: 11
<212> TYPE: PRT
<213> ORGANISM: Artificial Sequence
<220> FEATURE:
<223> OTHER INFORMATION: FW sequence

<400> SEQUENCE: 453

Trp Gly Lys Gly Thr Leu Val Thr Val Ser Ser
1               5                   10

<210> SEQ ID NO 454
<211> LENGTH: 11
<212> TYPE: PRT
<213> ORGANISM: Artificial Sequence
<220> FEATURE:
<223> OTHER INFORMATION: FW sequence

<400> SEQUENCE: 454

Trp Gly Lys Gly Thr Leu Val Thr Val Ser Ser
1               5                   10

<210> SEQ ID NO 455
<211> LENGTH: 11
<212> TYPE: PRT
<213> ORGANISM: Artificial Sequence
<220> FEATURE:
<223> OTHER INFORMATION: FW sequence

<400> SEQUENCE: 455

Trp Gly Gln Gly Thr Gln Val Thr Val Ser Ser
1               5                   10

<210> SEQ ID NO 456
<211> LENGTH: 11
<212> TYPE: PRT
<213> ORGANISM: Artificial Sequence
<220> FEATURE:
<223> OTHER INFORMATION: FW sequence

<400> SEQUENCE: 456

Trp Gly Gln Gly Thr Gln Val Thr Val Ser Ser
1               5                   10

<210> SEQ ID NO 457
```

```
<210> SEQ ID NO 457
<211> LENGTH: 11
<212> TYPE: PRT
<213> ORGANISM: Artificial Sequence
<220> FEATURE:
<223> OTHER INFORMATION: FW sequence

<400> SEQUENCE: 457

Trp Asp Gln Gly Thr Gln Val Thr Val Ser Ser
1               5                   10

<210> SEQ ID NO 458
<211> LENGTH: 11
<212> TYPE: PRT
<213> ORGANISM: Artificial Sequence
<220> FEATURE:
<223> OTHER INFORMATION: FW sequence

<400> SEQUENCE: 458

Trp Asp Gln Gly Thr Gln Val Thr Val Ser Ser
1               5                   10

<210> SEQ ID NO 459
<211> LENGTH: 11
<212> TYPE: PRT
<213> ORGANISM: Artificial Sequence
<220> FEATURE:
<223> OTHER INFORMATION: FW sequence

<400> SEQUENCE: 459

Trp Gly Gln Gly Thr Gln Val Thr Val Ser Ser
1               5                   10

<210> SEQ ID NO 460
<211> LENGTH: 11
<212> TYPE: PRT
<213> ORGANISM: Artificial Sequence
<220> FEATURE:
<223> OTHER INFORMATION: FW sequence

<400> SEQUENCE: 460

Trp Gly Gln Gly Thr Gln Val Thr Val Ser Ser
1               5                   10

<210> SEQ ID NO 461
<211> LENGTH: 11
<212> TYPE: PRT
<213> ORGANISM: Artificial Sequence
<220> FEATURE:
<223> OTHER INFORMATION: FW sequence

<400> SEQUENCE: 461

Trp Gly Gln Gly Thr Gln Val Thr Val Ser Ser
1               5                   10

<210> SEQ ID NO 462
<211> LENGTH: 11
<212> TYPE: PRT
<213> ORGANISM: Artificial Sequence
<220> FEATURE:
<223> OTHER INFORMATION: FW sequence

<400> SEQUENCE: 462

Trp Gly Gln Gly Thr Gln Val Thr Val Ser Ser
1               5                   10

<210> SEQ ID NO 463
<211> LENGTH: 11
```

```
<212> TYPE: PRT
<213> ORGANISM: Artificial Sequence
<220> FEATURE:
<223> OTHER INFORMATION: FW sequence

<400> SEQUENCE: 463

Trp Gly Gln Gly Thr Gln Val Thr Val Ser Ser
1               5                   10

<210> SEQ ID NO 464
<211> LENGTH: 11
<212> TYPE: PRT
<213> ORGANISM: Artificial Sequence
<220> FEATURE:
<223> OTHER INFORMATION: FW sequence

<400> SEQUENCE: 464

Trp Gly Gln Gly Thr Gln Val Thr Val Ser Ser
1               5                   10

<210> SEQ ID NO 465
<211> LENGTH: 300
<212> TYPE: PRT
<213> ORGANISM: Artificial Sequence
<220> FEATURE:
<223> OTHER INFORMATION: human CD38

<400> SEQUENCE: 465

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
```

```
                    245                 250                 255
Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300

<210> SEQ ID NO 466
<211> LENGTH: 231
<212> TYPE: PRT
<213> ORGANISM: Artificial Sequence
<220> FEATURE:
<223> OTHER INFORMATION: human IgG1

<400> SEQUENCE: 466

Ala Ala Ala Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Val Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 467
<211> LENGTH: 223
<212> TYPE: PRT
<213> ORGANISM: Artificial Sequence
<220> FEATURE:
<223> OTHER INFORMATION: mouse IgG2c

<400> SEQUENCE: 467

Ala Ala Ala Pro Cys Pro Pro Leu Lys Glu Cys Pro Pro Cys Ala Ala
1               5                   10                  15
```

```
Pro Asp Leu Leu Gly Gly Pro Ser Val Phe Ile Phe Pro Lys Ile
            20                  25                  30

Lys Asp Val Leu Met Ile Ser Leu Ser Pro Met Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Arg Ala
            100                 105                 110

Leu Pro Ser Pro Ile Glu Lys Thr Ile Ser Lys Pro Arg Gly Pro Val
        115                 120                 125

Arg Ala Pro Gln Val Tyr Val Leu Pro Pro Ala Glu Glu Met Thr
    130                 135                 140

Lys Lys Glu Phe Ser Leu Thr Cys Met Ile Thr Gly Phe Leu Pro Ala
145                 150                 155                 160

Glu Ile Ala Val Asp Trp Thr Ser Asn Gly Arg Thr Glu Gln Asn Tyr
                165                 170                 175

Lys Asn Thr Ala Thr Val Leu Asp Ser Asp Gly Ser Tyr Phe Met Tyr
            180                 185                 190

Ser Lys Leu Lys Val Gln Lys Ser Thr Trp Glu Arg Arg Asn Leu Phe
        195                 200                 205

Ala Cys Ser Met Gly His Glu Gly Ser Ala Gln Ser Pro Tyr Asp
    210                 215                 220

<210> SEQ ID NO 468
<211> LENGTH: 115
<212> TYPE: PRT
<213> ORGANISM: Artificial Sequence
<220> FEATURE:
<223> OTHER INFORMATION: CDR sequence

<400> SEQUENCE: 468

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 469
<211> LENGTH: 115
<212> TYPE: PRT
<213> ORGANISM: Artificial Sequence
<220> FEATURE:
```

<223> OTHER INFORMATION: CDR sequence

<400> SEQUENCE: 469

Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 470
<211> LENGTH: 116
<212> TYPE: PRT
<213> ORGANISM: Artificial Sequence
<220> FEATURE:
<223> OTHER INFORMATION: CDR sequence

<400> SEQUENCE: 470

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 471
<211> LENGTH: 116
<212> TYPE: PRT
<213> ORGANISM: Artificial Sequence
<220> FEATURE:
<223> OTHER INFORMATION: CDR sequence

<400> SEQUENCE: 471

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val

```
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 472
<211> LENGTH: 115
<212> TYPE: PRT
<213> ORGANISM: Artificial Sequence
<220> FEATURE:
<223> OTHER INFORMATION: CDR sequence

<400> SEQUENCE: 472

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 473
<211> LENGTH: 116
<212> TYPE: PRT
<213> ORGANISM: Artificial Sequence
<220> FEATURE:
<223> OTHER INFORMATION: CDR sequence

<400> SEQUENCE: 473

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95
```

-continued

Thr Ile Gly Gly Ser Leu Ser Arg Ser Ser Gln Gly Thr Leu Val Lys
                100                 105                 110

Val Ser Ser Ala
        115

<210> SEQ ID NO 474
<211> LENGTH: 115
<212> TYPE: PRT
<213> ORGANISM: Artificial Sequence
<220> FEATURE:
<223> OTHER INFORMATION: CDR sequence

<400> SEQUENCE: 474

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 475
<211> LENGTH: 116
<212> TYPE: PRT
<213> ORGANISM: Artificial Sequence
<220> FEATURE:
<223> OTHER INFORMATION: CDR sequence

<400> SEQUENCE: 475

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser Ala
        115

<210> SEQ ID NO 476
<211> LENGTH: 117
<212> TYPE: PRT
<213> ORGANISM: Artificial Sequence

```
<220> FEATURE:
<223> OTHER INFORMATION: CDR sequence

<400> SEQUENCE: 476

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 477
<211> LENGTH: 17
<212> TYPE: PRT
<213> ORGANISM: Artificial Sequence
<220> FEATURE:
<223> OTHER INFORMATION: Tag

<400> SEQUENCE: 477

Ala Ala Ala Glu Gln Lys Leu Ile Ser Glu Glu Asp Leu Asn Gly Ala
1               5                   10                  15

Ala

<210> SEQ ID NO 478
<211> LENGTH: 118
<212> TYPE: PRT
<213> ORGANISM: Artificial Sequence
<220> FEATURE:
<223> OTHER INFORMATION: CDR sequence

<400> SEQUENCE: 478

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115
```

<210> SEQ ID NO 479
<211> LENGTH: 116
<212> TYPE: PRT
<213> ORGANISM: Artificial Sequence
<220> FEATURE:
<223> OTHER INFORMATION: CDR sequence

<400> SEQUENCE: 479

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 480
<211> LENGTH: 117
<212> TYPE: PRT
<213> ORGANISM: Artificial Sequence
<220> FEATURE:
<223> OTHER INFORMATION: CDR sequence

<400> SEQUENCE: 480

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 481
<211> LENGTH: 118
<212> TYPE: PRT
<213> ORGANISM: Artificial Sequence
<220> FEATURE:
<223> OTHER INFORMATION: CDR sequence

<400> SEQUENCE: 481

Glu Val Gln Leu Val Glu Ser Gly Gly Gly Val Val Gln Pro Gly Asn
1               5                   10                  15

-continued

```
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 482
<211> LENGTH: 3
<212> TYPE: PRT
<213> ORGANISM: Artificial Sequence
<220> FEATURE:
<223> OTHER INFORMATION: linker

<400> SEQUENCE: 482

Ala Ala Ala
1

<210> SEQ ID NO 483
<211> LENGTH: 5
<212> TYPE: PRT
<213> ORGANISM: Artificial Sequence
<220> FEATURE:
<223> OTHER INFORMATION: linker

<400> SEQUENCE: 483

Gly Gly Gly Gly Ser
1               5

<210> SEQ ID NO 484
<211> LENGTH: 7
<212> TYPE: PRT
<213> ORGANISM: Artificial Sequence
<220> FEATURE:
<223> OTHER INFORMATION: linker

<400> SEQUENCE: 484

Ser Gly Gly Ser Gly Gly Ser
1               5

<210> SEQ ID NO 485
<211> LENGTH: 9
<212> TYPE: PRT
<213> ORGANISM: Artificial Sequence
<220> FEATURE:
<223> OTHER INFORMATION: linker

<400> SEQUENCE: 485

Gly Gly Gly Gly Cys Gly Gly Gly Ser
1               5

<210> SEQ ID NO 486
<211> LENGTH: 9
<212> TYPE: PRT
<213> ORGANISM: Artificial Sequence
```

```
<220> FEATURE:
<223> OTHER INFORMATION: linker

<400> SEQUENCE: 486

Gly Gly Gly Gly Ser Gly Gly Gly Ser
1               5

<210> SEQ ID NO 487
<211> LENGTH: 10
<212> TYPE: PRT
<213> ORGANISM: Artificial Sequence
<220> FEATURE:
<223> OTHER INFORMATION: linker

<400> SEQUENCE: 487

Gly Gly Gly Gly Ser Gly Gly Gly Gly Ser
1               5                   10

<210> SEQ ID NO 488
<211> LENGTH: 15
<212> TYPE: PRT
<213> ORGANISM: Artificial Sequence
<220> FEATURE:
<223> OTHER INFORMATION: linker

<400> SEQUENCE: 488

Gly Gly Gly Gly Ser Gly Gly Gly Gly Ser Gly Gly Gly Gly Ser
1               5                   10                  15

<210> SEQ ID NO 489
<211> LENGTH: 18
<212> TYPE: PRT
<213> ORGANISM: Artificial Sequence
<220> FEATURE:
<223> OTHER INFORMATION: linker

<400> SEQUENCE: 489

Gly Gly Gly Gly Ser Gly Gly Gly Gly Ser Gly Gly Gly Gly Gly
1               5                   10                  15

Gly Ser

<210> SEQ ID NO 490
<211> LENGTH: 20
<212> TYPE: PRT
<213> ORGANISM: Artificial Sequence
<220> FEATURE:
<223> OTHER INFORMATION: linker

<400> SEQUENCE: 490

Gly Gly Gly Gly Ser Gly Gly Gly Gly Ser Gly Gly Gly Gly Ser Gly
1               5                   10                  15

Gly Gly Gly Ser
            20

<210> SEQ ID NO 491
<211> LENGTH: 25
<212> TYPE: PRT
<213> ORGANISM: Artificial Sequence
<220> FEATURE:
<223> OTHER INFORMATION: linker

<400> SEQUENCE: 491

Gly Gly Gly Gly Ser Gly Gly Gly Gly Ser Gly Gly Gly Gly Ser Gly
1               5                   10                  15

Gly Gly Gly Ser Gly Gly Gly Gly Ser
```

```
<210> SEQ ID NO 492
<211> LENGTH: 30
<212> TYPE: PRT
<213> ORGANISM: Artificial Sequence
<220> FEATURE:
<223> OTHER INFORMATION: linker

<400> SEQUENCE: 492

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 493
<211> LENGTH: 35
<212> TYPE: PRT
<213> ORGANISM: Artificial Sequence
<220> FEATURE:
<223> OTHER INFORMATION: linker

<400> SEQUENCE: 493

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser
        35

<210> SEQ ID NO 494
<211> LENGTH: 40
<212> TYPE: PRT
<213> ORGANISM: Artificial Sequence
<220> FEATURE:
<223> OTHER INFORMATION: linker

<400> SEQUENCE: 494

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser
        35                  40
```

ANTIGEN-BINDING POLYPEPTIDES DIRECTED AGAINST CD38

RELATED APPLICATIONS

This application is a national stage filing under 35 U.S.C. § 371 of International Patent Application Serial No. PCT/EP2016/077361, filed Nov. 10, 2016, which claims the benefit under 35 U.S.C. § 119(e) of U.S. Provisional Application Ser. No. 62/253,318, filed Nov. 10, 2015, the contents of each of which is incorporated by reference herein in its entirety for all purposes.

The invention relates to antigen-binding polypeptides comprising the CDR1, CDR2, and CDR3 region of a VHH domain of a camelid heavy chain antibody. The polypeptides specifically bind to CD38 and are therefore suitable for the diagnosis and for the therapeutic and prophylactic treatment of diseases which are characterized by increased CD38 expression. Conjugates and pharmaceutical compositions comprising the antigen-binding polypeptides are also disclosed. In addition, the invention relates to the use of such antigen-binding polypeptides in methods for the detection of CD38 and/or CD38-expressing cells in a biological sample. A process for the purification and concentration of CD38 and/or CD38-expressing cells in which the antigen-binding polypeptides are used are also described.

BACKGROUND OF THE INVENTION

The cell surface marker CD38 is an approximately 42 kDa transmembrane glycoprotein of type II, which is expressed on the surface of cells of the immune system, but also on other cells (1). CD38 consists of a short intracellular N-terminal domain, a transmembrane helix and a longer extracellular domain located at the C-terminus of the protein (2).

CD38 is a multifunctional enzyme, the important steps in the synthesis of the second messenger ADP-ribose (ADPR), nicotinic acid adenine dinucleotide phosphate (NAADP) and cyclic ADP-ribose (cADPR) catalyzed. These signal molecules are involved in the modulation of intracellular $Ca^{2+}$-levels (3-5). It is further suggested that CD38, when in interaction with ADP-ribosyl transferases, is able to modulate the immune response (6). Binding of its ligand CD31 induces CD38 to further increase cytokines (7).

It has been recognized that CD38 is upregulated in many hematopoietic disorders. For example, it is found that CD38 is expressed at high levels on the surface of cells of multiple myeloma, malignant lymphoma and in different cells that are found in the course of leukemia. Clinically, the presence of CD38 is already routinely used as a marker for chronic lymphocytic leukemia (CLL) (8). In CLL, there is a strong expansion of B-lymphocytes (9). High levels of CD38 are a marker for CLL patients with a poor prognosis. It is believed that CD38 influences the proliferation and expansion of B lymphocytes (8).

Also for the HIV-I infection, CD38 is a prognostic marker. Increased expression of CD38 on T-cells is an indicator of the progression of the disease, whereas a decreased expression is seen as an indicator of an effective HAART (highly active antiretroviral therapy) therapy (10). Monoclonal antibodies against CD38, which can be used in diagnosis and therapy, are well known in the prior art (8). Human anti-CD38 antibodies are currently being tested in clinical trials of phase I and phase II in the treatment of multiple myeloma. References (11-13) disclose the use of CD38-specific antibodies which eliminate CD38-expressing cells by apoptosis or by cytotoxic mechanisms, in the treatment of cancer or autoimmune diseases.

Disadvantages in the use of polyclonal and/or monoclonal antibodies in the field of human medicine result from their often insufficient stability after administration. In addition, the costs incurred in the production of monoclonal antibodies are very high. In particular, the preparation of humanised antibodies, which should have a low immunogenicity in order to be suitable for use in humans, is labor and cost intensive. Additionally, whole antibodies have limited tissue penetration because of their size. A significant improvement of these adverse characteristics for therapy is therefore necessary for an efficient and financially viable therapy.

In the prior art, several strategies have been developed to solve the problems associated with the administration of antibodies problems. These strategies are predominantly based on the use of fragments of full IgG antibodies. For instance, Fv, Fab, F(ab') and F(ab')$_2$ have been used for therapeutic purposes. However, these fragments have often a reduced specificity and/or affinity for the antigen compared to the complete antibody to. Furthermore, these fragments often show only a low solubility in aqueous solutions.

Accordingly, there is a need for improved medicaments that are soluble, easy to manufacture and which easily penetrate tissues and bind the target.

Complement dependent cytotoxicity (CDC) is, next to antibody-dependent cellular cytotoxicity (ADCC) a very important mechanism for optimal therapeutic monoclonal antibodies (mAb) function against cancer (Beum et al. 2008 J. Immunology 181:822-832), and this effector function is totally conserved even after a chemotherapy treatment. CDC activity is mediated via the Fc portion of antibodies. However, this activity is generated by some antibodies (Manches et al. 2003 Blood 101:949-954), but not all of them (Cardarelli et al. 2002 Cancer Immunology, Immunotherapy 51:15-24; Wang et al. 2004 Angiogenesis 7:335-345). In general, antibody fragments lacking the Fc portion are not mediating CDC activity.

Constructs comprising immunoglobulin single variable domains that are linked to an Fc portion are known. For example, as described in EP 0 698 097 and in Hamers-Casterman et al. (Nature 1993, June 3; 363 (6428): 446-8), the naturally occurring "heavy chain antibodies" from Camelidae comprise naturally occurring single variable domains (called "$V_{HH}$ domains") that are linked via a hinge region to an Fc portion. Interestingly, as further described in these references, these heavy chain antibodies lack the $C_H1$ domain that is present in conventional 4-chain antibodies, with the $V_{HH}$ being directly linked—via the hinge—to the $C_H2$ domain of the Fc portion. WO2009/068630 in the name of Ablynx NV describes multiple ISVDs that can be linked to a human Fc portion, with improved binding characteristics.

CD38 specific Nanobodies derived from heavy chain only antibodies from camelids as well as CD38-Fc fusion proteins have been described by Fumey et al. (Poster PEGS Europe November 2014). The authors show that these Nanobodies detect CD38 expressing tumors in vivo. Moreover, the Nanobody-Fc fusion proteins show potent complement dependent cytotoxicity.

Efficacious immunotherapies should specifically bind to the target and simultaneously activate the CDC. However, while the results obtained to date establish anti-CD38 Nanobody-Fc fusion proteins as useful in immunotherapy, it remains unclear which epitopes on CD38 targeted by particular Nanobodies are especially advantageous for therapeutic purposes. As such, there is a need in the art for further insight into the specific functional properties that make anti-CD38 ISVDs therapeutically effective, as well as for improved therapeutic CD38 binders which are more effective in treating various types of cancer and other conditions, such as inflammatory diseases. Moreover, there is a need for improved diagnostics.

SUMMARY OF THE INVENTION

The present invention provides for the first time ISVDs that are capable of specifically binding to different epitopes of CD38. Epitope binning experiments revealed that the epitopes recognized by the ISVDs, i.e. Epitope 1 ("E1"), Epitope 2 ("E2"), and Epitope 3 ("E3"), did not overlap. A combination of ISVDs binding to Epitope 1 and Epitope 3 displayed a synergistic effect over the individual ISVDs. Moreover, this combination outperformed the benchmark. Despite conformational restraints, biparatopic constructs comprising ISVDs binding to Epitope 1 and Epitope 3 showed a similar effect as the corresponding combination of individual ISVDs. It was also demonstrated that the biparatopic Fc constructs were efficacious in range of different CD38-expressing tumor cell lines as well as tumor cells derived from human patients. Unexpectedly, it was discovered that a combination of ISVDs in which at least one ISVDs binds to Epitope 2 (e.g. the combination of E2 and E1 or the combination of E2 and E3) outperformed the combination in which such an ISVD was lacking (e.g. the combination E1+E3).

The ISVDs of the present invention are particularly suitable for use in the diagnosis and/or in the therapeutic treatment of disorders which are characterized by an increased expression of CD38.

Accordingly, the present invention relates to a polypeptide comprising at least one immunoglobulin single variable domain (ISVD) that specifically binds to CD38 with an $EC_{50}$ value of less than 200 pM, preferably said ISVD inhibits tumor cell growth. Even more preferably, said CD38 is human CD38 (SEQ ID NO: 465).

Accordingly, the present invention relates to a polypeptide as described herein, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 117-174; and
    (b) amino acid sequences that have 4, 3, 2, or 1 amino acid(s) difference with the amino acid sequences of SEQ ID NOs: 117-174; and/or
  (ii) CDR2 is chosen from the group consisting of:
    (c) SEQ ID NOs: 233-290; and
    (d) amino acid sequences that have 4, 3, 2, or 1 amino acid(s) difference with the amino acid sequences of SEQ ID NOs: 233-290; and/or
  (iii) CDR3 is chosen from the group consisting of:
    (e) SEQ ID NOs: 349-406; and
    (f) amino acid sequences that have 4, 3, 2, or 1 amino acid(s) difference with the amino acid sequences of SEQ ID NOs: 349-406.

Accordingly, the present invention relates to a polypeptide as described herein, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 131, 132, 134, 140, 144, 146, 150, 151, 152, 153, 155, 158; and
    (b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
  (ii) CDR2 is chosen from the group consisting of:
    (c) SEQ ID NOs: 247, 248, 250, 256, 260, 262, 266, 267, 268, 269, 271, 274; and
    (d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
  (iii) CDR3 is chosen from the group consisting of:
    (e) SEQ ID NOs: 363, 364, 366, 372, 376, 378, 382, 383, 384, 385, 387, 390; and
    (f) amino acid sequences that have 4, 3, 2, or 1 amino acid(s) difference with the amino acid sequences of SEQ ID NOs: 363, 364, 366, 372, 376, 378, 382, 383, 384, 385, 387, 390.

Accordingly, the present invention relates to a polypeptide as described herein, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 129, 163, 164, 165, 166; and
    (b) amino acid sequences that have 4, 3, 2, or 1 amino acid(s) difference with the amino acid sequences of SEQ ID NOs: 129, 163, 164, 165, 166; and/or
  (ii) CDR2 is chosen from the group consisting of:
    (c) SEQ ID NOs: 245, 279, 280, 281, 282; and
    (d) amino acid sequences that have 4, 3, 2, or 1 amino acid(s) difference with the amino acid sequences of SEQ ID NOs: 245, 279, 280, 281, 282; and/or
  (iii) CDR3 is chosen from the group consisting of:
    (e) SEQ ID NOs: 361, 395, 396, 397, 398; and
    (f) amino acid sequences that have 4, 3, 2, or 1 amino acid(s) difference with the amino acid sequences of SEQ ID NOs: 361, 395, 396, 397, 398.

Accordingly, the present invention relates to a polypeptide as described herein, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 1, 3, 4, 9, 10, 20, 43, 44, 45, 46, 51, 52, 53, 54, 55, 56, 57, 58; and
    (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
  (ii) CDR2 is chosen from the group consisting of:
    (c) SEQ ID NOs: 233, 235, 236, 241, 242, 252, 275, 276, 277, 278, 283, 284, 285, 286, 287, 288, 289, 290; and
    (d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or (iii) CDR3 is chosen from the group consisting of:
(e) SEQ ID NOs: 349, 351, 352, 357, 358, 368, 391, 392, 393, 394, 399, 400, 401, 402, 403, 404, 405, 406; and
(f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

Accordingly, the present invention relates to a polypeptide as described herein, wherein said ISVD is chosen from the group consisting of
- ISVDs in which CDR1 is represented by SEQ ID NOs: 117-174, CDR2 is represented by SEQ ID NOs: 233-290, and CDR3 is represented by SEQ ID NOs: 349-406;
- ISVD represented by SEQ ID NOs: 1 to 58; and,
- ISVD represented by at least 80% or more sequence identity to any one of SEQ ID NOs: 1 to 58.

Accordingly, the present invention relates to a polypeptide as described herein, wherein said CDRs are chosen from the group consisting of:
CDR1 is SEQ ID NO: 117, CDR2 is SEQ ID NO: 233 and CDR3 is SEQ ID NO: 349;
CDR1 is SEQ ID NO: 118, CDR2 is SEQ ID NO: 234 and CDR3 is SEQ ID NO: 350;
CDR1 is SEQ ID NO: 119, CDR2 is SEQ ID NO: 235 and CDR3 is SEQ ID NO: 351;
CDR1 is SEQ ID NO: 120, CDR2 is SEQ ID NO: 236 and CDR3 is SEQ ID NO: 352;
CDR1 is SEQ ID NO: 121, CDR2 is SEQ ID NO: 237 and CDR3 is SEQ ID NO: 353;
CDR1 is SEQ ID NO: 122, CDR2 is SEQ ID NO: 238 and CDR3 is SEQ ID NO: 354;
CDR1 is SEQ ID NO: 123, CDR2 is SEQ ID NO: 239 and CDR3 is SEQ ID NO: 355;
CDR1 is SEQ ID NO: 124, CDR2 is SEQ ID NO: 240 and CDR3 is SEQ ID NO: 356;
CDR1 is SEQ ID NO: 125, CDR2 is SEQ ID NO: 241 and CDR3 is SEQ ID NO: 357;
CDR1 is SEQ ID NO: 126, CDR2 is SEQ ID NO: 242 and CDR3 is SEQ ID NO: 358;
CDR1 is SEQ ID NO: 127, CDR2 is SEQ ID NO: 243 and CDR3 is SEQ ID NO: 359;
CDR1 is SEQ ID NO: 128, CDR2 is SEQ ID NO: 244 and CDR3 is SEQ ID NO: 360;
CDR1 is SEQ ID NO: 129, CDR2 is SEQ ID NO: 245 and CDR3 is SEQ ID NO: 361;
CDR1 is SEQ ID NO: 130, CDR2 is SEQ ID NO: 246 and CDR3 is SEQ ID NO: 362;
CDR1 is SEQ ID NO: 131, CDR2 is SEQ ID NO: 247 and CDR3 is SEQ ID NO: 363;
CDR1 is SEQ ID NO: 132, CDR2 is SEQ ID NO: 248 and CDR3 is SEQ ID NO: 364;
CDR1 is SEQ ID NO: 133, CDR2 is SEQ ID NO: 249 and CDR3 is SEQ ID NO: 365;
CDR1 is SEQ ID NO: 134, CDR2 is SEQ ID NO: 250 and CDR3 is SEQ ID NO: 366;
CDR1 is SEQ ID NO: 135, CDR2 is SEQ ID NO: 251 and CDR3 is SEQ ID NO: 367;
CDR1 is SEQ ID NO: 136, CDR2 is SEQ ID NO: 252 and CDR3 is SEQ ID NO: 368;
CDR1 is SEQ ID NO: 137, CDR2 is SEQ ID NO: 253 and CDR3 is SEQ ID NO: 369;
CDR1 is SEQ ID NO: 138, CDR2 is SEQ ID NO: 254 and CDR3 is SEQ ID NO: 370;
CDR1 is SEQ ID NO: 139, CDR2 is SEQ ID NO: 255 and CDR3 is SEQ ID NO: 371;
CDR1 is SEQ ID NO: 140, CDR2 is SEQ ID NO: 256 and CDR3 is SEQ ID NO: 372;
CDR1 is SEQ ID NO: 141, CDR2 is SEQ ID NO: 257 and CDR3 is SEQ ID NO: 373;
CDR1 is SEQ ID NO: 142, CDR2 is SEQ ID NO: 258 and CDR3 is SEQ ID NO: 374;
CDR1 is SEQ ID NO: 143, CDR2 is SEQ ID NO: 259 and CDR3 is SEQ ID NO: 375;
CDR1 is SEQ ID NO: 144, CDR2 is SEQ ID NO: 260 and CDR3 is SEQ ID NO: 376;
CDR1 is SEQ ID NO: 145, CDR2 is SEQ ID NO: 261 and CDR3 is SEQ ID NO: 377;
CDR1 is SEQ ID NO: 146, CDR2 is SEQ ID NO: 262 and CDR3 is SEQ ID NO: 378;
CDR1 is SEQ ID NO: 147, CDR2 is SEQ ID NO: 263 and CDR3 is SEQ ID NO: 379;
CDR1 is SEQ ID NO: 148, CDR2 is SEQ ID NO: 264 and CDR3 is SEQ ID NO: 380;
CDR1 is SEQ ID NO: 149, CDR2 is SEQ ID NO: 265 and CDR3 is SEQ ID NO: 381;
CDR1 is SEQ ID NO: 150, CDR2 is SEQ ID NO: 266 and CDR3 is SEQ ID NO: 382;
CDR1 is SEQ ID NO: 151, CDR2 is SEQ ID NO: 267 and CDR3 is SEQ ID NO: 383;
CDR1 is SEQ ID NO: 152, CDR2 is SEQ ID NO: 268 and CDR3 is SEQ ID NO: 384;
CDR1 is SEQ ID NO: 153, CDR2 is SEQ ID NO: 269 and CDR3 is SEQ ID NO: 385;
CDR1 is SEQ ID NO: 154, CDR2 is SEQ ID NO: 270 and CDR3 is SEQ ID NO: 386;
CDR1 is SEQ ID NO: 155, CDR2 is SEQ ID NO: 271 and CDR3 is SEQ ID NO: 387;
CDR1 is SEQ ID NO: 156, CDR2 is SEQ ID NO: 272 and CDR3 is SEQ ID NO: 388;
CDR1 is SEQ ID NO: 157, CDR2 is SEQ ID NO: 273 and CDR3 is SEQ ID NO: 389;
CDR1 is SEQ ID NO: 158, CDR2 is SEQ ID NO: 274 and CDR3 is SEQ ID NO: 390;
CDR1 is SEQ ID NO: 159, CDR2 is SEQ ID NO: 275 and CDR3 is SEQ ID NO: 391;
CDR1 is SEQ ID NO: 160, CDR2 is SEQ ID NO: 276 and CDR3 is SEQ ID NO: 392;
CDR1 is SEQ ID NO: 161, CDR2 is SEQ ID NO: 277 and CDR3 is SEQ ID NO: 393;
CDR1 is SEQ ID NO: 162, CDR2 is SEQ ID NO: 278 and CDR3 is SEQ ID NO: 394;
CDR1 is SEQ ID NO: 163, CDR2 is SEQ ID NO: 279 and CDR3 is SEQ ID NO: 395;
CDR1 is SEQ ID NO: 164, CDR2 is SEQ ID NO: 280 and CDR3 is SEQ ID NO: 396;
CDR1 is SEQ ID NO: 165, CDR2 is SEQ ID NO: 281 and CDR3 is SEQ ID NO: 397;
CDR1 is SEQ ID NO: 166, CDR2 is SEQ ID NO: 282 and CDR3 is SEQ ID NO: 398;
CDR1 is SEQ ID NO: 167, CDR2 is SEQ ID NO: 283 and CDR3 is SEQ ID NO: 399;
CDR1 is SEQ ID NO: 168, CDR2 is SEQ ID NO: 284 and CDR3 is SEQ ID NO: 400;
CDR1 is SEQ ID NO: 169, CDR2 is SEQ ID NO: 285 and CDR3 is SEQ ID NO: 401;
CDR1 is SEQ ID NO: 170, CDR2 is SEQ ID NO: 286 and CDR3 is SEQ ID NO: 402;
CDR1 is SEQ ID NO: 171, CDR2 is SEQ ID NO: 287 and CDR3 is SEQ ID NO: 403;

CDR1 is SEQ ID NO: 172, CDR2 is SEQ ID NO: 288 and CDR3 is SEQ ID NO: 404;

CDR1 is SEQ ID NO: 173, CDR2 is SEQ ID NO: 289 and CDR3 is SEQ ID NO: 405; and

CDR1 is SEQ ID NO: 174, CDR2 is SEQ ID NO: 290 and CDR3 is SEQ ID NO: 406.

Accordingly, the present invention relates to a polypeptide as described herein, comprising a first ISVD and a second ISVD that each specifically binds to CD38 with an $EC_{50}$ value of less than 200 pM.

Accordingly, the present invention relates to a polypeptide as described herein, wherein said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 129, 163, 164, 165, 166; and
(b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
(c) SEQ ID NOs: 245, 279, 280, 281, 282; and
(d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
(e) SEQ ID NOs: 361, 395, 396, 397, 398; and
(f) amino acid sequences that have 4, 3, 2, or 1 amino acid(s) difference with the amino acid sequences of SEQ ID NOs: 361, 395, 396, 397, 398.

Accordingly, the present invention relates to a polypeptide as described herein, wherein said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 1, 3, 4, 9, 10, 20, 43, 44, 45, 46, 51, 52, 53, 54, 55, 56, 57, 58; and
(b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
(c) SEQ ID NOs: 233, 235, 236, 241, 242, 252, 275, 276, 277, 278, 283, 284, 285, 286, 287, 288, 289, 290; and
(d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
(e) SEQ ID NOs: 349, 351, 352, 357, 358, 368, 391, 392, 393, 394, 399, 400, 401, 402, 403, 404, 405, 406; and
(f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

Accordingly, the present invention relates to a polypeptide as described herein, wherein said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 129, 163, 164, 165, 166; and
(b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
(c) SEQ ID NOs: 245, 279, 280, 281, 282; and
(d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
(e) SEQ ID NOs: 361, 395, 396, 397, 398; and
(f) amino acid sequences that have 4, 3, 2, or 1 amino acid(s) difference with the amino acid sequences of SEQ ID NOs: 361, 395, 396, 397, 398; and said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 1, 3, 4, 9, 10, 20, 43, 44, 45, 46, 51, 52, 53, 54, 55, 56, 57, 58; and (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
(c) SEQ ID NOs: 233, 235, 236, 241, 242, 252, 275, 276, 277, 278, 283, 284, 285, 286, 287, 288, 289, 290; and
(d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
(e) SEQ ID NOs: 349, 351, 352, 357, 358, 368, 391, 392, 393, 394, 399, 400, 401, 402, 403, 404, 405, 406; and
(f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

Accordingly, the present invention relates to a polypeptide as described herein,
wherein the $EC_{50}$ in a FACS assay is 190 pM or less, such as less than 180, 170, 160, 150, 140, 130, 120, 110, 100 or even less, such as less than 90, 80, 70, 60, 50, 40, 35, 30, 25, 20, or even less, such as less than 16 pM; and/or
wherein said polypeptide binds to CD38 with an $IC_{50}$ of at most 100 nM, such as 50 nM, 20 nM, 10 nM, 9 nM, 8 nM, 7 nM, 6 nM, 5 nM, 4 nM, 3 nM, preferably even at most 2 nM, such as 1 nM, as determined by a competition FACS; and/or
wherein said polypeptide binds to CD38 with an $IC_{50}$ which is at least 10%, such as 20%, 30%, 50%, 80%, 90%, or even 100% better than the $IC_{50}$ of a benchmark, preferably as determined by a competition FACS.

Accordingly, the present invention relates to a polypeptide as described herein, comprising at least two ISVDs that can bind CD38, wherein said ISVDs are different.

Accordingly, the present invention relates to a polypeptide as described herein, comprising at least two ISVDs that can bind CD38, wherein said ISVDs bind different epitopes on CD38.

Accordingly, the present invention relates to a polypeptide as described herein, wherein said at least two ISVDs are directly linked to each other or linked to each other via a linker.

Accordingly, the present invention relates to a polypeptide as described herein, in which the linker is selected from the group of linkers with SEQ ID NOs: 482-494.

Accordingly, the present invention relates to a polypeptide as described herein, further comprising one or more other groups, residues, moieties or binding units, optionally linked via one or more peptidic linkers.

Accordingly, the present invention relates to a polypeptide as described herein, in which said one or more other groups, residues, moieties or binding units provide the polypeptide with increased half-life, compared to the corresponding polypeptide without such groups, residues, moieties or binding units.

Accordingly, the present invention relates to a polypeptide as described herein, in which said one or more other groups, residues, moieties or binding units that provide the polypeptide with increased half-life is chosen from the group consisting of polyethylene glycol, serum proteins or fragments thereof, binding units that can bind to serum proteins, an Fc portion, an antibody constant region, and small proteins or peptides that can bind to serum proteins.

Accordingly, the present invention relates to a polypeptide as described herein, further comprising a drug, such as a toxin or toxin moiety, or an imaging agent.

Accordingly, the present invention relates to a polypeptide as described herein, wherein said ISVD is chosen from the group consisting of single domain antibodies, domain antibodies, amino acid sequences suitable for use as single domain antibody, amino acid sequences suitable for use as domain antibody, dAbs, amino acid sequences suitable for use as dAb, Nanobodies, VHHs, humanized VHHs, and camelized VHs.

Accordingly, the present invention relates to a polypeptide as described herein, further comprising a CH2 and a CH3 constant domain.

Accordingly, the present invention relates to a polypeptide as described herein, wherein said CH2 and said CH3 domain are directly linked or linked via a linker.

In a further especially preferred aspect, the present invention relates to an immunoglobulin construct comprising a first polypeptide as described herein, and a second polypeptide as described herein, wherein said CH2 domains and said CH3 domains of said polypeptides form an Fc portion.

Also, the present invention relates to an immunoglobulin construct as described herein, wherein said first polypeptide and said second polypeptide are the same.

The present invention relates also to an immunoglobulin construct as described herein, wherein said CH2 domain of said first polypeptide pairs with said CH2 domain of said second polypeptide, and/or said CH3 domain of said first polypeptide pairs with said CH3 domain of said second polypeptide.

The present invention relates also to an immunoglobulin construct as described herein, wherein said first polypeptide comprises a first ISVD and second ISVD, and said second polypeptide comprises a first ISVD and a second ISVD.

The present invention relates also to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or (iii) CDR3 is chosen from the group consisting of:
  (e) SEQ ID NOs: 363, 364, 366, 372, 376, 378, 382, 383, 384, 385, 387, 390; and
  (f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and said second ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 129, 163, 164, 165, 166; and
  (b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
  (c) SEQ ID NOs: 245, 279, 280, 281, 282; and
  (d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
  (e) SEQ ID NOs: 361, 395, 396, 397, 398; and
  (f) amino acid sequences that have 4, 3, 2, or 1 amino acid(s) difference with the amino acid sequences of SEQ ID NOs: 361, 395, 396, 397, 398.

The present invention relates also to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 131, 132, 134, 140, 144, 146, 150, 151, 152, 153, 155, 158; and
  (b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
  (c) SEQ ID NOs: 247, 248, 250, 256, 260, 262, 266, 267, 268, 269, 271, 274; and
  (d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
  (e) SEQ ID NOs: 363, 364, 366, 372, 376, 378, 382, 383, 384, 385, 387, 390; and
  (f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and said second ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 1, 3, 4, 9, 10, 20, 43, 44, 45, 46, 51, 52, 53, 54, 55, 56, 57, 58; and
  (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
  (c) SEQ ID NOs: 233, 235, 236, 241, 242, 252, 275, 276, 277, 278, 283, 284, 285, 286, 287, 288, 289, 290; and
  (d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
  (e) SEQ ID NOs: 349, 351, 352, 357, 358, 368, 391, 392, 393, 394, 399, 400, 401, 402, 403, 404, 405, 406; and
  (f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

The present invention relates also to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 129, 163, 164, 165, 166; and
  (b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
  (c) SEQ ID NOs: 245, 279, 280, 281, 282; and
  (d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
  (e) SEQ ID NOs: 361, 395, 396, 397, 398; and
  (f) amino acid sequences that have 4, 3, 2, or 1 amino acid(s) difference with the amino acid sequences of SEQ ID NOs: 361, 395, 396, 397, 398; and said second ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 1, 3, 4, 9, 10, 20, 43, 44, 45, 46, 51, 52, 53, 54, 55, 56, 57, 58; and
  (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
  (c) SEQ ID NOs: 233, 235, 236, 241, 242, 252, 275, 276, 277, 278, 283, 284, 285, 286, 287, 288, 289, 290; and
  (d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
  (e) SEQ ID NOs: 349, 351, 352, 357, 358, 368, 391, 392, 393, 394, 399, 400, 401, 402, 403, 404, 405, 406; and
  (f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

The present invention relates also to an immunoglobulin construct as described herein, wherein said first polypeptide and said second polypeptide are the same.

The present invention relates also to an immunoglobulin construct as described herein, wherein said first ISVD binds a first epitope of CD38 and said second ISVD binds a second epitope on CD38, wherein said first epitope is different from said second epitope, preferably said first epitope does not overlap with said second epitope.

The present invention relates also to an immunoglobulin construct as described herein, further comprising a drug, such as a toxin or toxin moiety, or an imaging agent.

In addition, the present invention relates to a pharmaceutical composition comprising a polypeptide as described herein, or an immunoglobulin construct as described herein.

The present invention relates to a polypeptide as described herein, the immunoglobulin construct as described herein or the pharmaceutical composition as described herein for use in a method of therapeutic treatment of a disease which is characterized by increased CD38 expression.

The present invention relates to a polypeptide as described herein, the immunoglobulin construct as described herein or the pharmaceutical composition as described herein for use in a method of therapeutic treatment of a hyperproliferative disease or an autoimmune disease.

The present invention relates to a polypeptide as described herein, the immunoglobulin construct as described herein or the pharmaceutical composition as described herein for use in a method of therapeutic treatment of Burkitt's lymphoma, T-cell lymphoma, hairy cell leukemia, chronic lymphocytic leukemia (CLL), multiple myeloma, chronic myelogenous leukemia (CML), acute myeloid leukemia (AML), acute lymphoblastic leukemia (ALL), CD38-expressing solid tumor, systemic lupus erythematosus (SLE), rheumatoid arthritis, Crohn's disease, ulcerative colitis, Hashimoto's thyroiditis, ankylosing spondylitis, multiple sclerosis, Graves' disease, Sjögren's syndrome, polymyositis, bullous pemphigoid, glomerulonephritis, vasculitis or asthma, Barraquer-Simons Syndrome, autoimmune heart disease, inflammatory bowel disease, paroxysmal nocturnal hemoglobinuria, atypical hemolytic uremic syndrome and ischemia-reperfusion injuries and rejection of transplanted organs.

The present invention also relates to a nucleic acid molecule that encodes a polypeptide as described herein.

The present invention also relates to an expression vector comprising a nucleic acid molecule as described herein.

The present invention also relates to a host cell comprising a nucleic acid molecule as described herein or an expression vector as described herein.

The present invention also relates to a method for the recombinant production of a polypeptide as described herein, comprising (a) culturing the host cell as described herein under conditions which allow the expression of a nucleic acid molecule as described herein; and (b) isolating the polypeptide from the culture.

The present invention also relates to a method for determining competitor polypeptides competing with a polypeptide represented by SEQ ID NOs: 1-58, comprising
determining binding of said competitor polypeptide in the presence of polypeptide represented by SEQ ID NOs: 1-58 to CD38;
detecting a competitor polypeptide when the binding to CD38 of said competitor polypeptide is reduced by at least 10%, such as 20%, 30%, 40%, 50% or even more, such as 80%, 90% or even 100% in the presence of a polypeptide represented by SEQ ID NOs: 1-58, compared to the binding to CD38 of the competitor in the absence of the polypeptide represented by SEQ ID NOs: 1-58.

BRIEF DESCRIPTION OF THE FIGURES

FIG. 2 (A) CD38-specific Nanobodies show dissociation rates in the lower nM range. 50 µl samples of human blood were incubated with serially titrated, purified monovalent Nanobodies for 30 min at RT. Cells were washed twice and bound Nbs were detected with FITC-conjugated anti-c-myc (9E10). T cells were stained with APC-conjugated anti-CD3. Erythrocytes were lysed and cells were analyzed by flow cytometry. Gating was performed on lymphocytes and CD3-negative cells.

(B) FACS analyses confirm binding of VHHs to CD38 on blood leukocytes (CD16+ NK cells and a subset of CD19 int B cells)

FIG. 3 LP-1 myeloma cells were incubated with 2 µg Fc-fusion proteins as indicated in FIG. 3 in the presence of 20% pooled human serum as a source for complement for 1 h at 37° C. Cell death was determined by the uptake of propidium iodide (PI).

FIG. 4 Titration of the combination versus individual constructs. LP-1 myeloma cells were incubated with different concentrations of immunoglobulin constructs in the presence of pooled human serum as a source of complement for 2 h at 37° C. Cell death was determined by propidium iodide staining.

Figure 5:
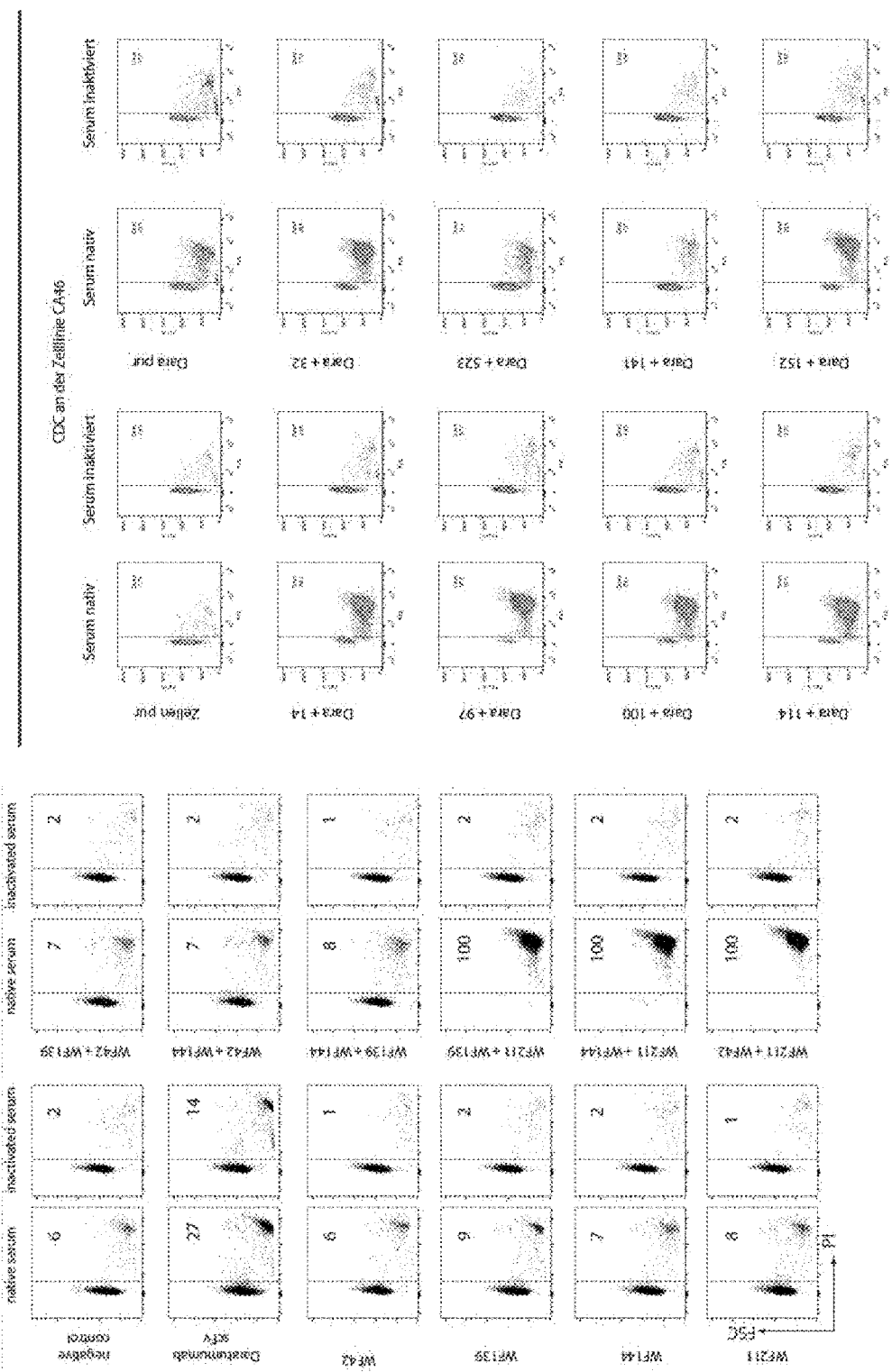

FIG. 5 Combinations of Nb-Fc fusion proteins recognizing distinct epitopes show potent cytotoxicity to CA46 lymphoma cells: KSV037 (A) KSV064 (B). CA46 lymphoma cells were incubated for 20 min at 4° C. with Daratumumab scFv-Fc, individual Nb-Fc (2 µg/120 µl) or with combinations of two Nb-Fc fusion proteins (1 µg each) (A), or combinations of a Nb-Fc fusion protein and Daratumumab scFv-Fc (1 µg each) (B) before addition of 20 µl of either native human serum of inactivated human serum (incubated for 30 min at 56° C. to inactivate complement components). Cells were incubated further for 60 min at 37° C., washed, resuspended in PBS/BSA/propidium iodide, and analyzed by flow cytometry.

Figure 6:
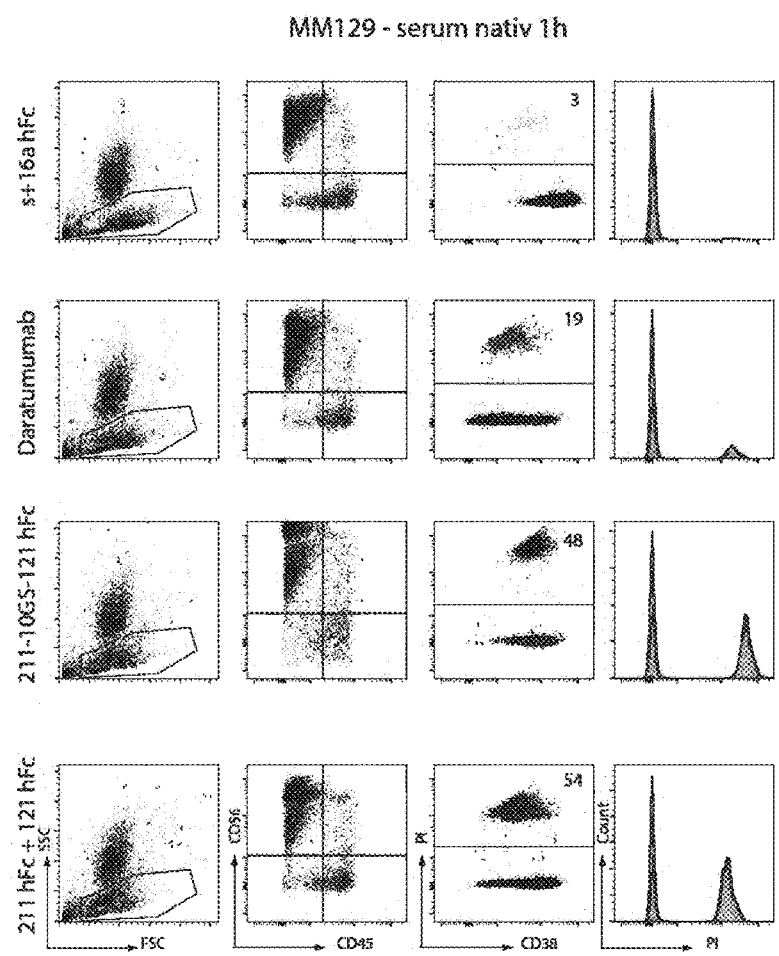
Figure 6:
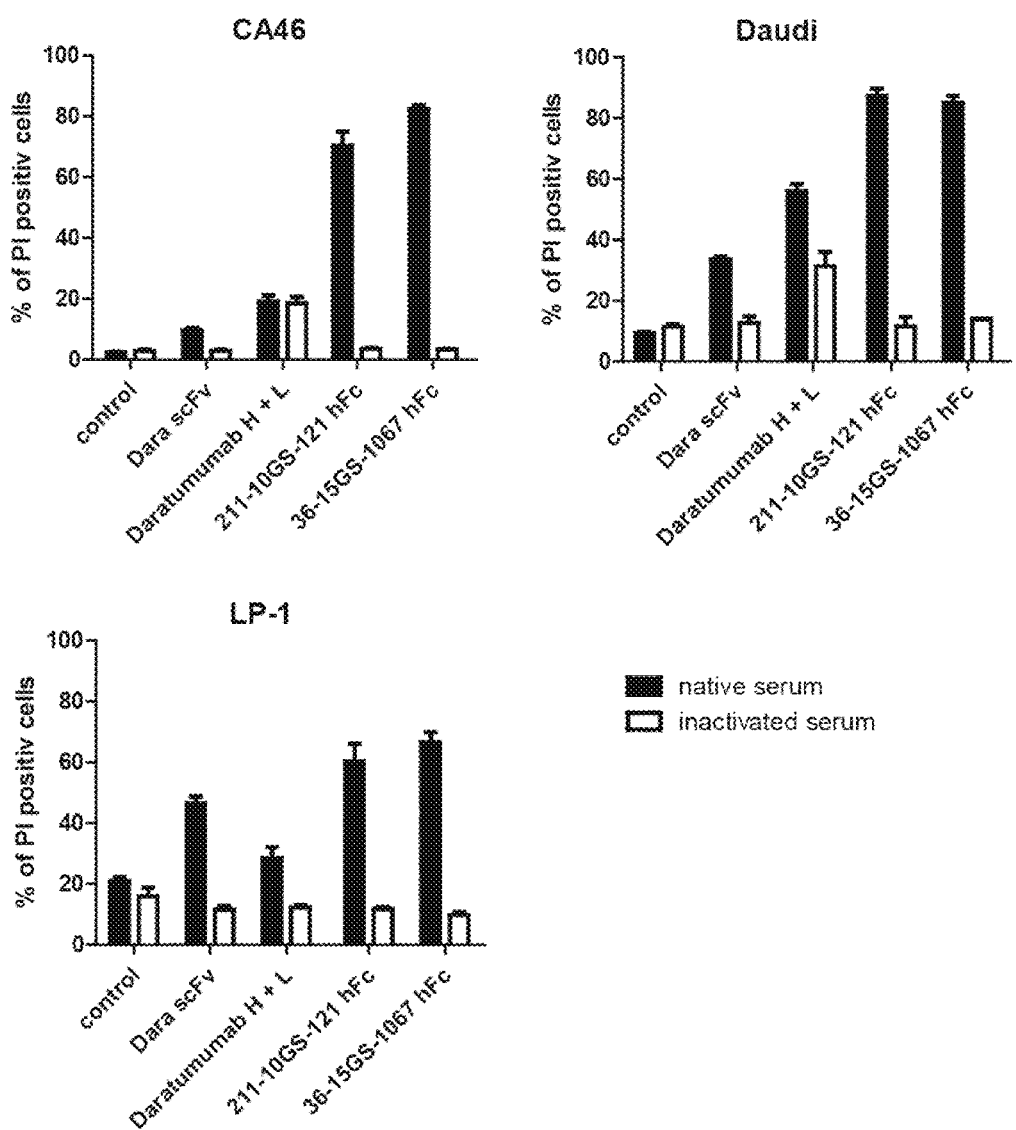

FIG. 6 (A) Biparatopic immunoglobulin constructs show potent cytotoxicity to primary myeloma cells (KSV123). Primary bone marrow cells from a myeloma patient were purified by Ficoll density gradient centrifugation, washed, and incubated for 10 min at 4° with Daratumumab scFv, biparatopic Nb-Nb 211-10GS-121 Fc fusion protein, or an irrelevant control Nb-Fc fusion protein (each at 2 µg/124 µl) or with a combination of 211 Nb-Fc and 121 Nb-Fc fusion proteins (1 µg each/120 µl) before addition of 10 µl of human serum. Cells were incubated further for 60 min at 37° C., washed, and counterstained with fluorochrome conjugated mAbs against CD56, CD45 or appropriated CD38-specific Nbs (binding to an independent distinct from those in the Nb Fc fusions) for 60 min at 4°. Cells were washed, resuspended in PBS/BSA/propidium iodide, and analyzed by flow cytometry. PI staining of myeloma cells was assessed by gating on CD56+/CD45lo cells.

(B) CDC of biparatopic anti-CD38 VHH-Fc constructs in comparison to Daratumumab in the scFv-Fc (Dara scFv) and full IgG (Daratumumab H+L) formats. Numbers indicate % of PI-positive cells.

Figure 7:
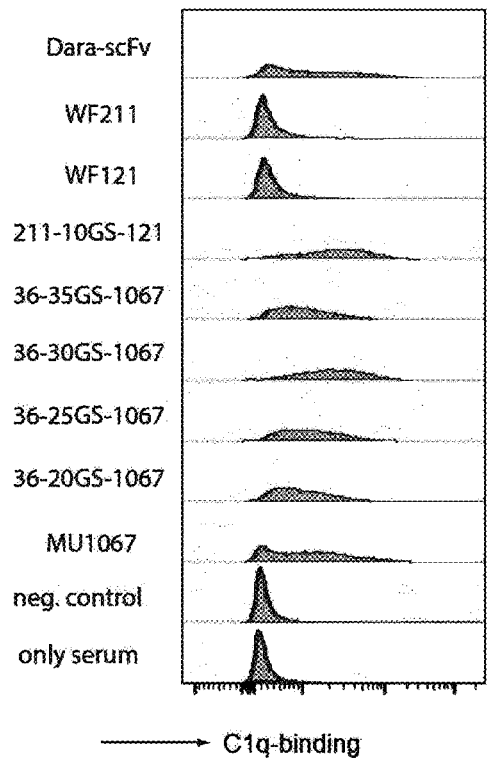

FIG. 7 Biparatopic immunoglobulin constucts show high capacity to bind complement factor C1q.

Figure 8:
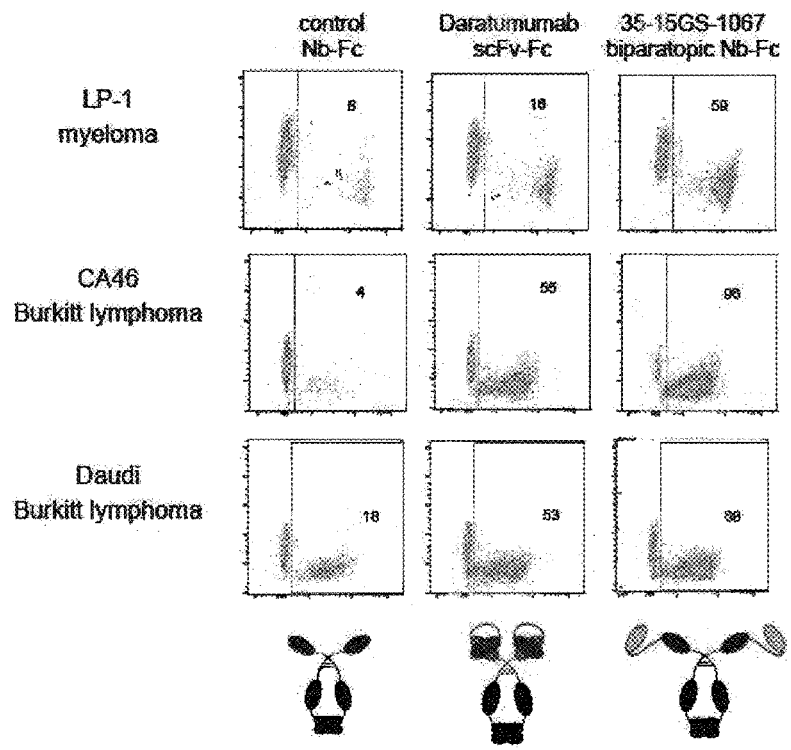

FIG. 8 Biparatopic immunoglobulin constucts are cytotoxic in a range of cancers.

Figure 9:
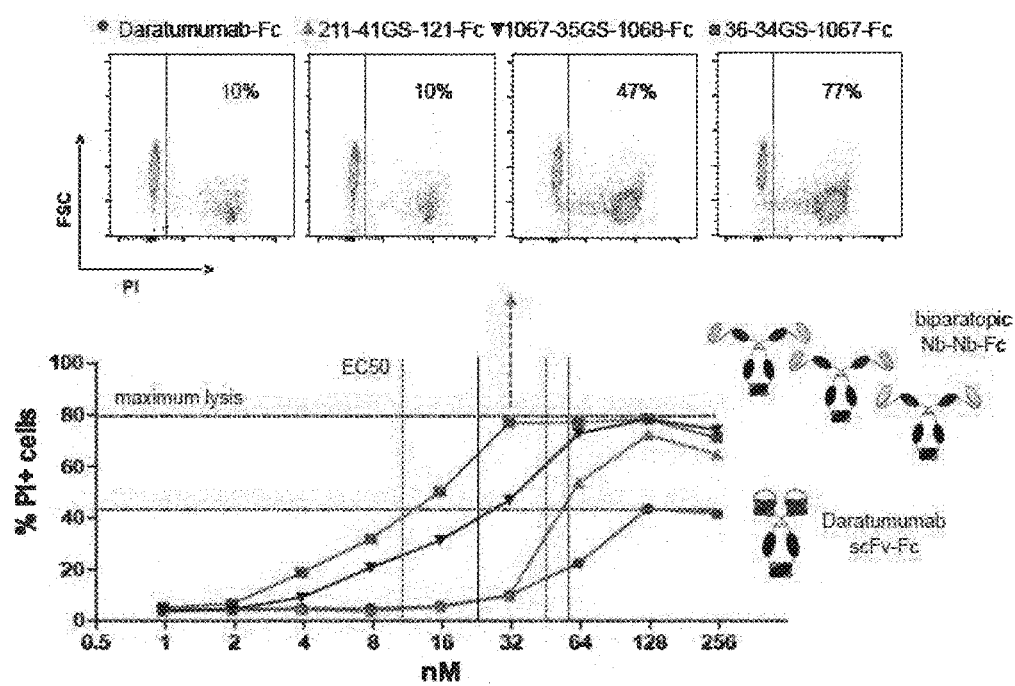

FIG. 9 Biparatopic immunoglobulin constucts binding different epitopes are more cytotoxic than the benchmark.

Figure 10:
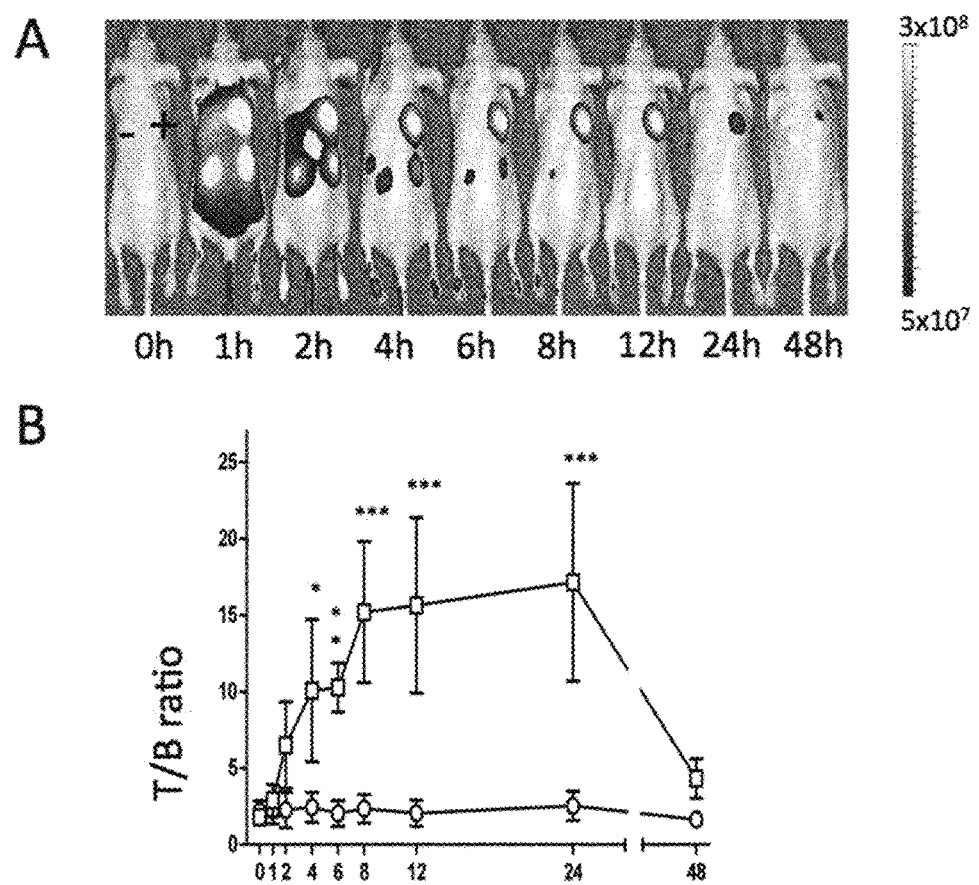

FIG. 10 Alexa680-conjugated Nanobodies provide excellent discrimination of CD38+ tumors in vivo. A) Optical molecular Imaging was performed before and 1 h, 2 h, 4 h, 6 h, 8 h, 12 h, 24 h and 48 h after Nb injection. Signal intensities of identical doses are all equally leveled to allow fair visual comparison. Signals below the tumors correspond to the kidneys. Signals on the tail and feet likely reflect contact with urine containing labeled Nbs. B) T/B ratios of CD38-positive and CD38-negative tumors were determined from regions of interests (ROIs). ROIs were drawn around tumors and normal tissue (hind leg) for semi-quantitative analyses. T/B ratios of CD38-positive and CD38-negative tumors were calculated by subtracting background signals from radiant efficiencies of ROIs around tumors. T/B ratios are plotted as a function of time.

Figure 11:
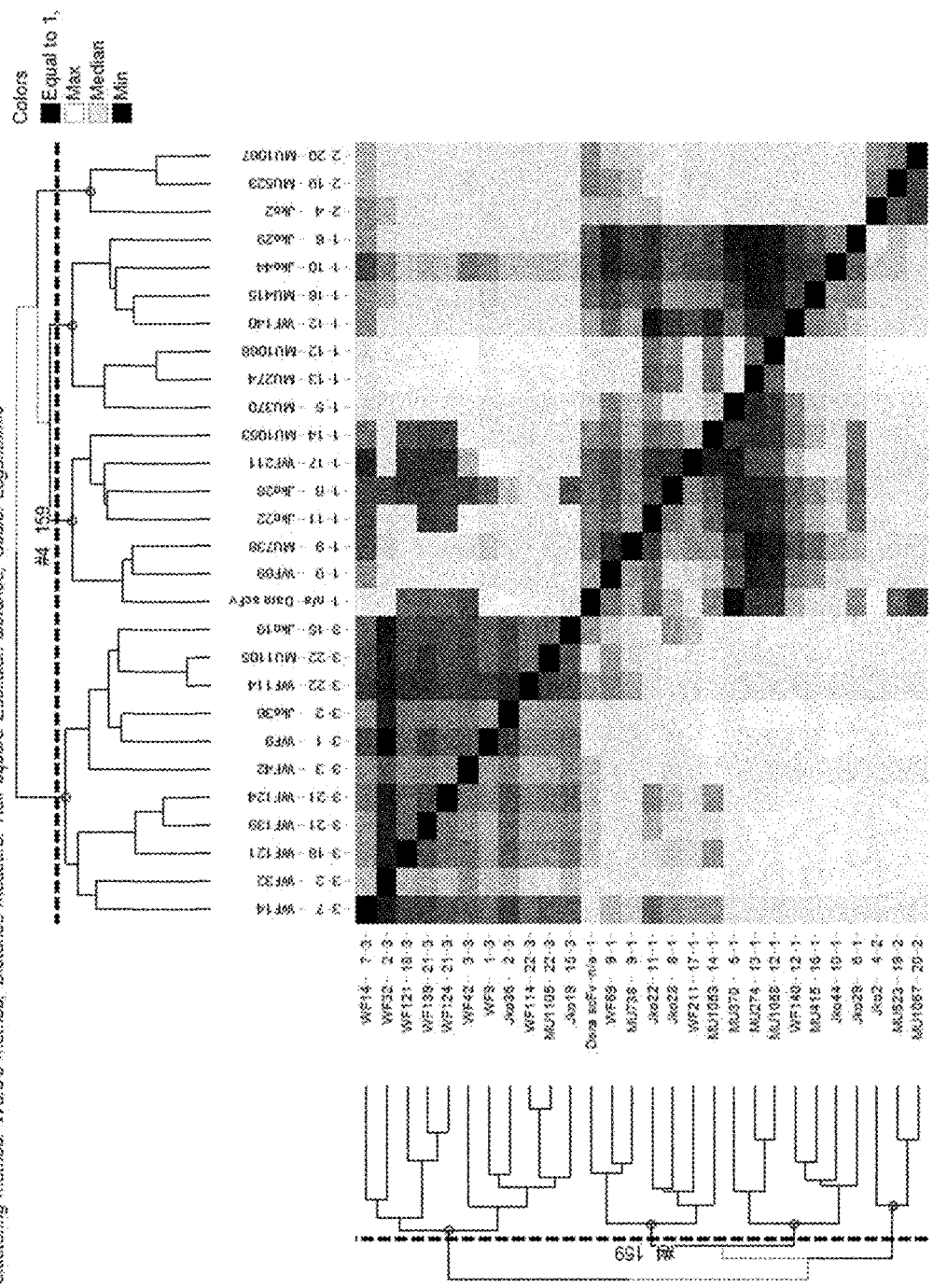
Figure 11:
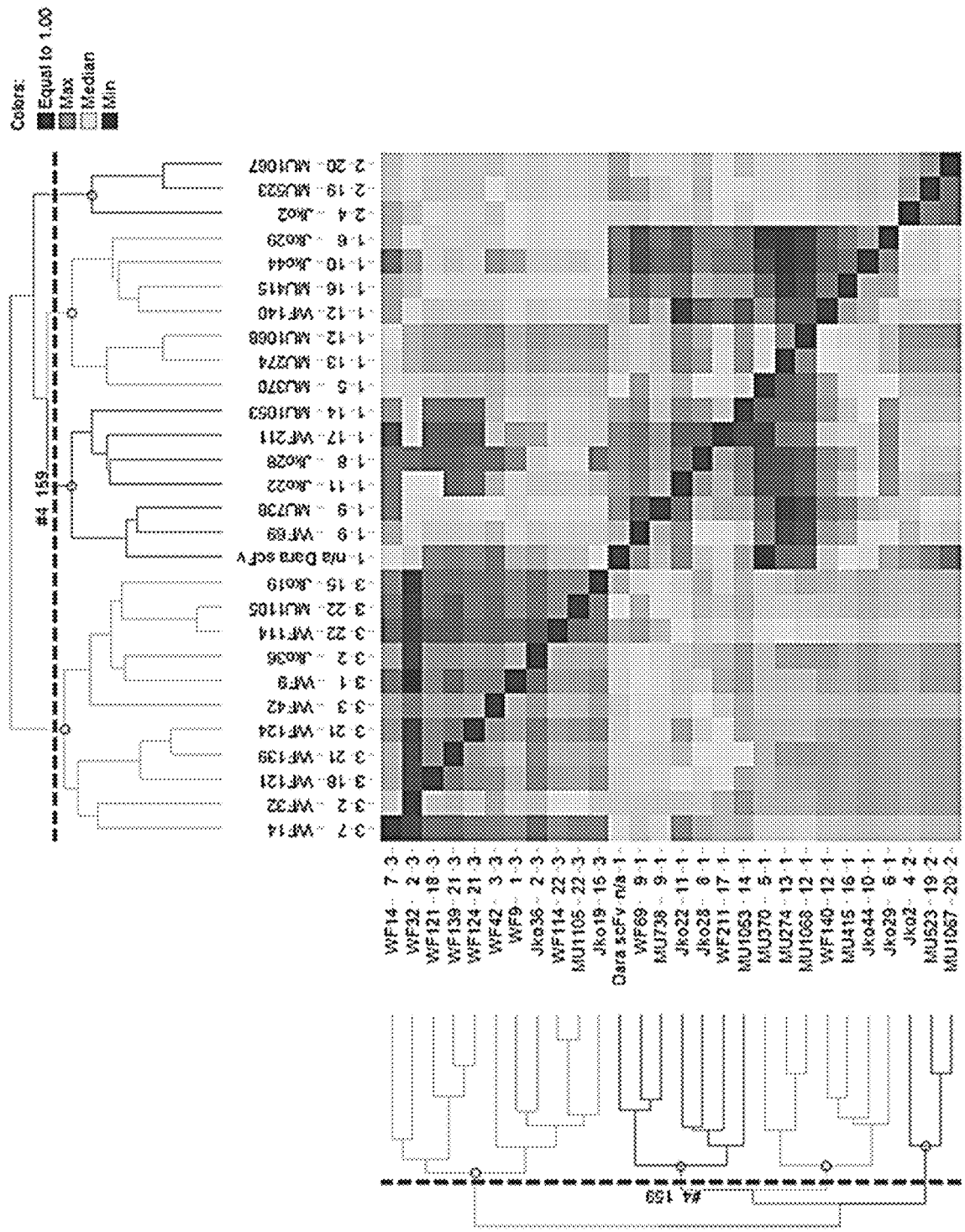

FIG. 11 Sensorgram of in-tandem epitope binning analysis with 28 monovalent purified anti-CD38 VHHs and Daratumumab scFv as benchmark by bioluminescence analysis on Octet RED384 (ForteBio). Sensorgrams of the association and dissociation of the second analyte were recorded. Binding capture levels were assessed at timeframe of 10 seconds at the end of the loading. Non-hierarchical clustering was done with Ward's method.

Figure 12:
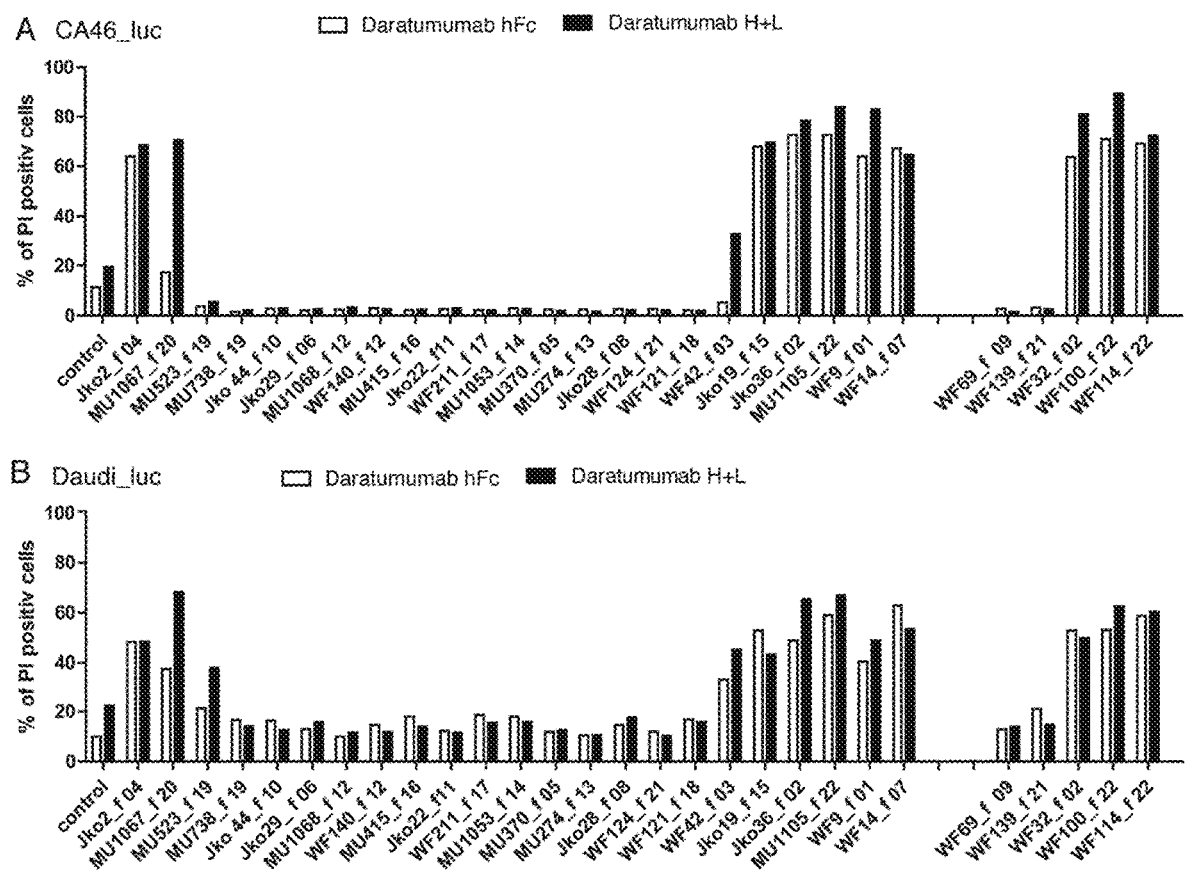

FIG. 12 CDC measured by combinations of anti-CD38 VHH-Fc with Daratumumab scFv-Fc (Daratumumab hc) and full IgG formats (Daratumumab H+L). VHH-Fc that recognize a distinct epitope than Daratumamab enhance the CDC of both Daratumumab hc and Daratumumab H+L, irrespective of the format. Family numbers are indicated by "f".

Figure 13:
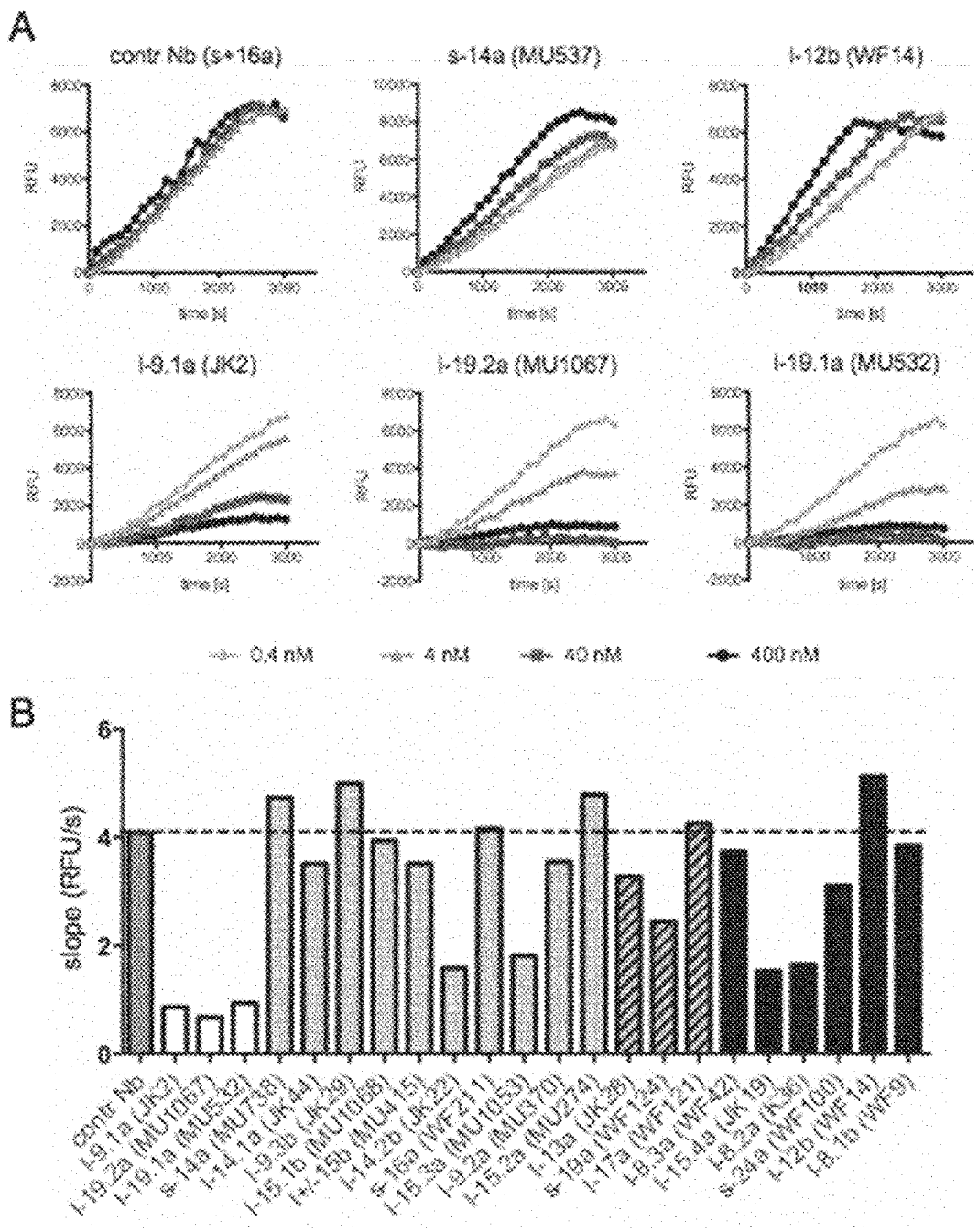

FIG. 13 Effect of anti-CD38 VHH on GDPR cyclase activity of CD38. A) Fluorescence traces of different concentrations of VHHs that either inhibit or potentiate the GDPR cyclase activity of CD38. Faster conversion of substrate indicates CD38 enzyme sensitisation and a higher slope (RFU/s), whereas slower conversion and a lower slope indicates inhibition of enzyme activity. B) Inhibition or potentiation of CD38 enzymatic activity by a single dose of 400 nM VHH. White bars indicate epitope 2 VHHs, in grey epitope 1, black bars epitope 3.

Figure 14:
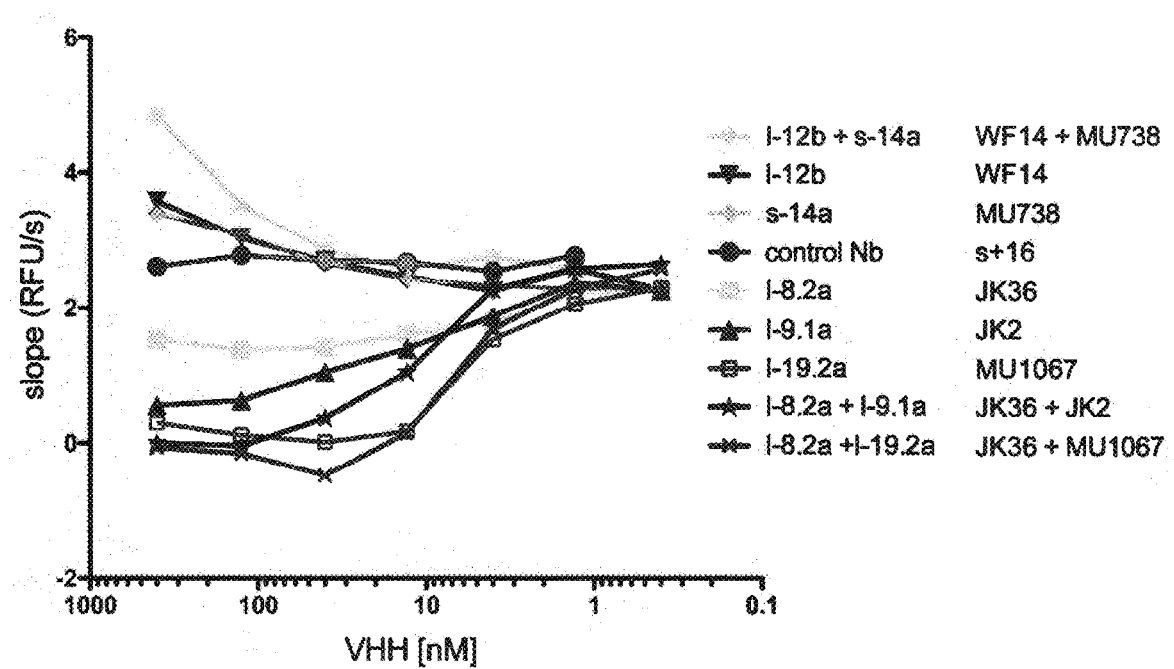

FIG. 14 Synergic effects of combinations of anti-CD38 VHH on potentiation or inhibition of the cGDPR cyclase activity of CD38.

Figure 15:
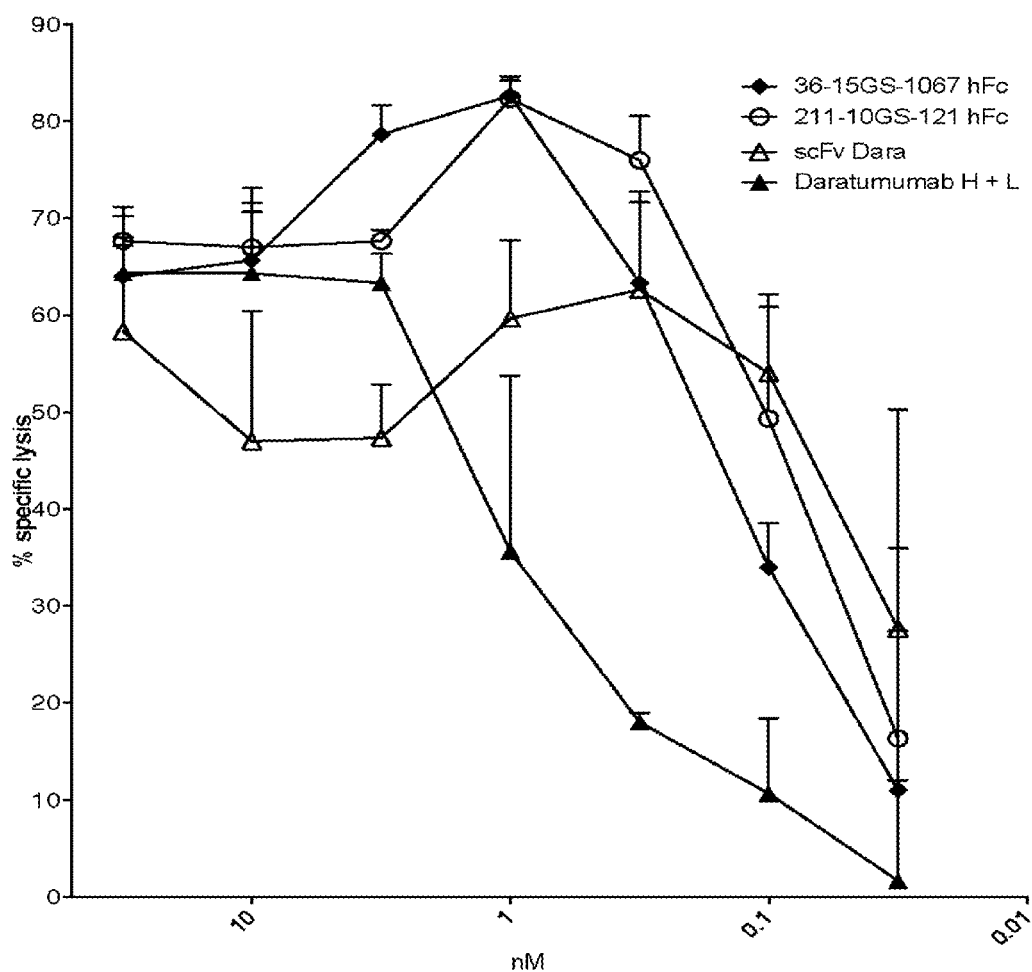

FIG. 15 ADCC activity of biparatopic anti-CD38 VHH in comparison to Daratumumab (Daratumumab H+L). CD38+ CA46 cells were used as target cells. CD16-transfected NK92 effector cells were added at an effector to target cell ratio of 3:1. Cell killing was assessed after 3 hours.

FIG. 16 Effect of biparatopic CD38 VHH-Fc WF211-10GS-WF121-Fc on tumor growth and survival in an orthotopic CD38+ CA46 Xenograft model.

Figure 17:
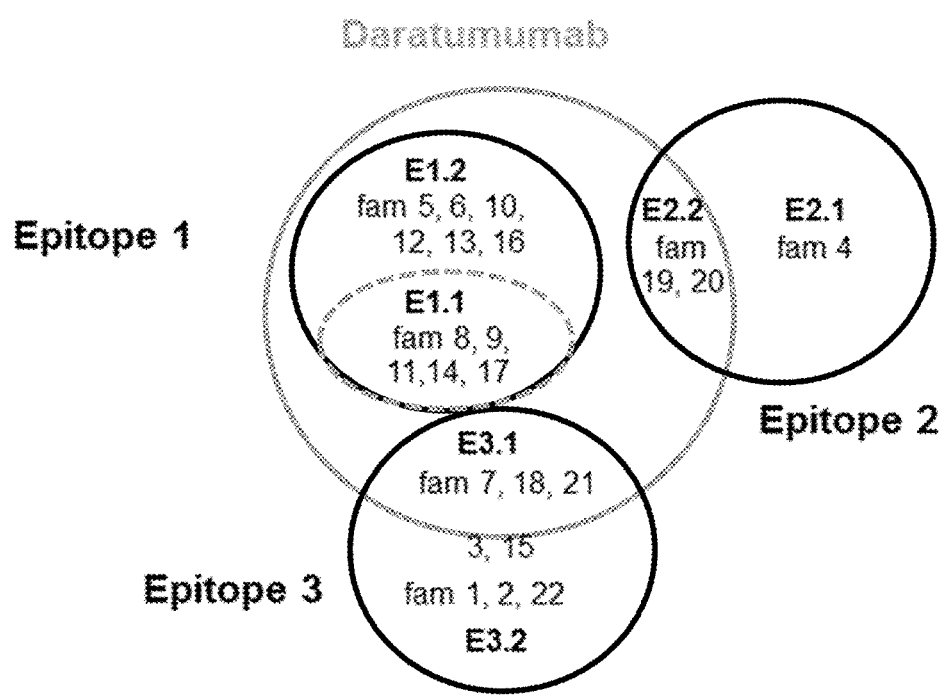

FIG. 17 Venn diagram of the VHH epitopes on CD38 as defined by hierarchical clusturing of epitope binning results and crossblockade analysis.

DESCRIPTION OF THE INVENTION

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd.Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, Calif., 1981); Roitt et al. (Immunology (6th. Ed.) Mosby/Elsevier, Edinburgh, 2001), Roitt et al. (Roitt's Essential Immunology ($10^{th}$ Ed.) Blackwell Publishing, UK, 2001), and Janeway et al. (Immunobiology (6th Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 2357768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al.

("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

The "amino acid difference" can be any one, two, three or maximal four substitutions, deletions or insertions, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind CD38 with the same, about the same, or a higher affinity compared to the polypeptide comprising the one or more CDR sequences without the one, two, three or maximal four substitutions, deletions or insertions, said affinity as e.g. measured by surface plasmon resonance (SPR).

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

A "Nanobody family", "VHH family" or "family" as used in the present specification refers to a group of Nanobodies and/or VHH sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"—CD38).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. Preferably, a monovalent polypeptide of the invention will bind to the desired antigen with an affinity less than 500 nM, preferably less than 200 nM, more preferably less than 10 nM, such as e.g., between 10 and 5 nM or less. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays, such as for instance by screening purified ISVDs against ISVDs displayed on phage in a competition ELISA. If an ISVD binding to CD38 competes with another ISVD binding to CD38 (e.g. the purified ISVD in the competition ELISA), said ISVDs belong to the same epitope bin, e.g. bind the same or similar epitope on CD38. If an ISVD binding to CD38 does not compete or only partially competes with another ISVD binding to CD38 (e.g. the purified ISVD in the competition ELISA), said ISVDs belong to a different epitope bin, e.g. do not bind the same or similar epitope on CD38. Particularly suitable quantitative cross-blocking assays include e.g. a fluorescence-activated cell sorting (FACS) binding assay with CD38 expressed on cells. The extent of (cross)-blocking can be measured by e.g. (reduced) channel fluorescence.

Epitopes and epitope bins can also be identified (as well as assigning ISVDs to epitope bins) by solving the crystal structure of complexes of ISVDs with CD38, such as by X-ray crystallography (reference is made to e.g. Li et al. 2016 Nature Sci. Rep. 6:27055/D01:10.1038/srep27055). In general, ISVDs belonging to different epitope bins will complex with different amino acid residues on CD38. However, it will be appreciated that ISVDs can be assigned to different epitope bins if the different ISVDs do not compete with each other for instance as determined by the assays as described herein although the complexes of these ISVDs with CD38 has some, but not all, amino acid residues in common.

In the present invention it was found that CD38-specific ISVDs essentially bind to three different non-overlapping epitopes, which were tentatively designated "Epitope 1", "Epitope 2" and "Epitope 3", and the respective ISVDs are also indicated herein "Epitope 1 ISVDs or VHHs", "Epitope 2 ISVDs or VHHs" and "Epitope 3 ISVDs or VHHs". The Daratumumab epitope overlaps with Epitope 1 ISVDs, and part of Epitope 2 ISVDs and Epitope 3 ISVDs as shown in FIG. 17.

ISVD families such as the VHH families I-9.2a, I-9.2b, I-9.3b, S-14a, I-14.1a, I-14.2b, I-15.1b, I-15.2a, I-15.2b, I-15.3a, s-15a, and s-16a recognize and bind Epitope 1. These families do not compete with representative epitope 2 ISVDs or VHHs (e.g. MU1067, MU523, JK2), or epitope 3 ISVDs or VHHS (e.g. WF36, WF152, WF100).

ISVD families such as the VHH families I-9.1c, I-19.1a, I-19.1b, I-19.2a, and I-19.2b recognize and bind Epitope 2. These families do not compete with representative epitope 1 ISVDs or VHHs (e.g. MU1068, MU274, MU211), or epitope 3 ISVDs or VHHs (e.g. WF36, WF152, WF100).

ISVD families such as the VHH families I-8.1a, I-8.1b, I-8.2a, I-8.2f, I-8.3a, I-12b, I-17a, I-17a, I-17b, I-17c, s-19a, s-19b, s-24a, s+/−24b, s-24c, s+/−24d and I-24a recognize and bind Epitope 3. These families do not compete with representative epitope 1 ISVDs or VHHs (e.g. MU1068, MU274, MU211), or epitope 2 ISVDs or VHHs (e.g. MU1067, MU523, JK2).

The polypeptide according to any one of the preceding claims, comprising at least two ISVDs, e.g. a first ISVD that can bind CD38 and a second ISVD that can bind CD38, wherein said first ISVD does not compete with said second ISVD in a competition assay as defined herein, such as e.g. a competition ELISA or a fluorescence-activated cell sorting (FACS) binding assay with CD38 expressed on cells, e.g. said first ISVD and said second ISVD bind different epitopes on CD38, and belong to different epitope bins.

The following generally describes a suitable FACS assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The FACS instrument (e.g. FACS Canto; Becton Dickinson) is operated in line with the manufacturer's recommendations.

To evaluate the "(cross)-blocking" or "(cross)-competition" between two binding agents (such as e.g. two immunoglobulin single variable domains and/or Nanobodies) for binding CD38, a FACS competition experiment can be performed using cells (such as e.g. Flp-In™-293 cells) overexpressing human CD38 and the parental cells as background cell line. Different detection reagents can be used including e.g. monoclonal ANT-FLAG® M2 antibody (Sigma-Aldrich, cat # F1804), monoclonal anti-C-myc antibody (Sigma-Aldrich, cat # WH0004609M2), monoclonal ANTI-HIS TAG antibody (Sigma-Aldrich, cat # SAB1305538), each labeled differently. A wide range of fluorophores can be used as labels in flow cytometry such as described at: http://www.thefcn.org/flow-fluorochromes). Fluorophores, or simply "fluors", are typically attached to the antibody (e.g. the immunoglobulin single variable domains, such as Nanobodies) that recognizes CD38 or to the antibody that is used as detection reagent. Various conjugated antibodies are available, such as (without being limiting) for example antibodies conjugated to Alexa Fluor®, DyLight®, Rhodamine, PE, FITC, and Cy3. Each fluorophore has a characteristic peak excitation and emission wavelength. The combination of labels which can be used will depend on the wavelength of the lamp(s) or laser(s) used to excite the fluorophore and on the detectors available.

To evaluate the competition between two test binding agents (termed A and B) for binding to CD38, a dilution series of cold (without any label) binding agent A is added to (e.g. 200 000) cells together with the labeled binding agent B*. The concentration of binding agent B* in the test mix should be high enough to readily saturate the binding sites on CD38 expressed on the cells. The concentration of binding agent B* that saturates the binding sites for that binding agent on CD38 expressed on the cells can be determined with a titration series of binding agent B* on the CD38 cells and determination of the $EC_{50}$ value for binding. In order to work at saturating concentration, binding agent B* can be used at 100× the $EC_{50}$ concentration.

After incubation of the cells with the mixture of binding agent A and binding agent B* and cells wash, read out can be performed on a FACS. First a gate is set on the intact cells as determined from the scatter profile and the total amount of channel fluorescence is recorded.

A separate solution of binding agent B* is also prepared. Binding agent B* in this solutions should be in the same buffer and at the same concentration as in the test mix (with binding agent A and B*). This separate solution is also added to the cells. After incubation and cells wash, read out can be performed on a FACS. First a gate is set on the intact cells as determined from the scatter profile and the total amount of channel fluorescence is recorded.

A reduction of fluorescence for the cells incubated with the mixture of binding agent A and B* compared to the fluorescence for the cells incubated with the separate solution of binding agent B* indicates that binding agent A (cross)-blocks binding by binding agent B* for binding to CD38 expressed on the cells.

A cross-blocking immunoglobulin, antibody, immunoglobulin single variable domain, polypeptide or other binding agent according to the invention is one which will bind to the CD38 in the above FACS cross-blocking assay such that during the assay and in the presence of a second immunoglobulin, antibody, immunoglobulin single variable domain, polypeptide or other binding agent the recorded fluorescence is between 80% and 0.1% (e.g. 80% to 4%) of the maximum fluorescence (measured for the separate labelled immunoglobulin, antibody, immunoglobulin single variable domain, polypeptide or other binding agent), specifically between 75% and 0.1% (e.g. 75% to 4%) of the maximum fluorescence, and more specifically between 70% and 0.1% (e.g. 70% to 4%) of maximum fluorescence (as just defined above).

The competition between two test binding agents (termed A* and B*) for binding to CD38 can also be evaluated by adding both binding agents, each labeled with a different fluorophore, to the CD38 expressing cells. After incubation and cells wash, read out can be performed on a FACS. A gate is set for each fluorophore and the total amount of channel fluorescence is recorded. Reduction and/or absence of fluorescence of one of the fluorophore indicate (cross)-blocking by the binding agents for binding to CD38 expressed on the cells.

Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein.

The terms "enhancing an immune response" and "inducing an immune response" are used interchangeably herein and refer to a process that results in the activation, stimulation or proliferation of one or more response(s) of the complement system, T cells, B cells, macrophages, and/or natural killer (NK) cells. The polypeptides and immunoglobulin constructs of the invention are capable of inducing an immune response, such as the activation of complement system, proliferation or activation of T cells, B cells or natural killer cells. Suitable assays to measure complement activity, T cell, B cell and natural killer cell activation are known in the art described herein, for instance as described in Buillard et al. 2013, J. Exp. Med. Vol. 210, 9: 1685-1693; Zhou et al. October 2010, J. Immunother. Vol. 33, No 8; and Hanabuchi 2006, Blood, Vol. 107, No 9: 3617-3623, respectively. The term "immune response" includes "antibody-dependent cell-mediated cytotoxicity" ("ADCC"), "complement-dependent cytotoxicity" ("CDC"), "antibody-dependent cellular phagocytosis" ("ADCP") and "complement-dependent cellular cytotoxicity" ("CDCC"). The complement system triggers a cascade of effects that results in opsonization, chemotaxis, inflammation, lysis and apoptosis. The fragment crystallizable portion (Fc portion) is the tail region of an antibody that interacts with cell surface receptors called Fc receptors and some proteins of the complement system. This property allows antibodies to activate the immune system further.

Immune responses can be determined by a variety of assays, including but not limited to FACS, proliferation assays, cytotoxicity assays, cell killing assays, phagocytosis assays, reporter gene assays (e.g. NF-κB luciferase reporter assay), T cell activation assay, cell surface receptor binding assays and assays to measure expression of known markers of activation or cytokine secretion, which are all well known in the art.

The term "complement-dependent cytotoxicity" ("CDC"), as used herein, is intended to refer to the process of antibody-mediated complement activation leading to lysis of the antibody bound to its target on a cell or virion as a result of pores in the membrane that are created by MAC (membrane attack complex) assembly. CDC can be evaluated by in vitro assay such as a CDC assay in which normal human serum is used as a complement source, as described in the Examples section or in a C1q efficacy assay, all well known to the person skilled in the art.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. ADCC can be determined using well known methods.

The term "antibody-dependent cellular phagocytosis" ("ADCP") as used herein is intended to refer to a mechanism of elimination of antibody-coated target cells or virions by internalization by phagocytes. The internalized antibody-coated target cells or virions are contained in a vesicle called a phagosome, which then fuses with one or more lysosomes to form a phagolysosome. ADCP may be evaluated by using an in vitro cytotoxicity assay with macrophages as effector cells and video microscopy as described by van Bij et al. in Journal of Hepatology Volume 53, Issue 4, October 2010, Pages 677-685.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC.

As used herein, the term "inhibits tumor cell growth" is intended to include any measurable decrease in the proliferation of tumor cells in vitro or tumor growth in vivo, e.g., decrease by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%.

As used herein, the term "potency" is a measure of an agent, such as a immunoglobulin construct, benchmark, polypeptide, ISVD or Nanobody, its biological activity. Potency of an agent can be determined by any suitable method known in the art, such as for instance as described in the examples section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays (e.g. NF-κB luciferase reporter assay), T cell activation assay, cell surface receptor binding assays and assays to measure induction/inhibition of functionally essential protein or other signal molecule (such as phosphorylated proteins, enzymes, cytokines, cAMP and the like), and assays to measure expression of known markers of activation or cytokine secretion, all well known in the art. Results from cell based potency assays can be expressed as "relative potency" as determined by comparison of the immunoglobulin construct of the invention to the response obtained for the corresponding benchmark (cf. examples section).

A compound, e.g. the immunoglobulin construct of the invention, is said to be more potent than a benchmark, e.g. the reference compound, when the response obtained for the compound, e.g. the immunoglobulin construct of the invention, is at least 1.5 times, such as 2 times, but preferably at least 3 times, such as at least 4 times, at least 5 times, at least 6 times, at least 7 times, at least 8 times, at least 9 times, or even at least 10 times better (e.g. functionally better) than the response by the reference compound, e.g. the corresponding benchmark in a given assay.

The "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect. The efficacy of a polypeptide of the invention can be evaluated using in vivo models.

The efficacy or potency of the immunoglobulin constructs, immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (e.g. Burgess et al., Cancer Res 2006 66:1721-9), immunoglobulin constructization assays (e.g. WO2009/007427A2, Goetsch, 2009), signaling assays (e.g. Burgess et al., Mol Cancer Ther 9:400-9), proliferation/survival assays (e.g. Pacchiana et al., J Biol Chem 2010 September M110.134031), cell adhesion assays (e.g. Holt et al., Haematologica 2005 90:479-88) and migration assays (e.g. Kong-Beltran et al., Cancer Cell 6:75-84), endothelial cell sprouting assays (e.g. Wang et al., J Immunol. 2009; 183:3204-11), and in vivo xenograft models (e.g. Jin et al., Cancer Res. 2008 68:4360-8), as well as the assays and animal models used in the experimental part below and in the prior art cited herein. A means to express the inhibition of said first target in-vitro is by $IC_{50}$.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the standard handbooks, such as Kenneth et al (Chemical Stability of Pharmaceuticals: A Handbook for Pharmacists, John Wiley & Sons Inc., 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t1/2-beta, either with or without an increase in the t1/2-alpha and/or the AUC or both.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeably) for the preparation of a polypeptide, which may optionally contain one or more further immunoglobulin single variable domains that can serve as a binding unit (i.e., against the same or another epitope on CD38 and/or against one or more other antigens, proteins or targets than CD38).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., CD38) and at least one binding unit is directed against a second antigen (i.e., different from CD38) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., CD38) and at least one further immunoglobulin single variable domain directed against a second antigen (i.e., different from CD38), whereas a "trispecific" polypeptide of the invention is a polypeptide that comprises at least one immunoglobulin single variable domain directed against a first antigen (i.e., CD38), at least one further immunoglobulin single variable domain directed against a second antigen (i.e., different from CD38) and at least one further immunoglobulin single variable domain directed against a third antigen (i.e., different from both CD38 and the second antigen); etc.

"Multiparatopic polypeptides", such as e.g., "biparatopic polypeptides" or "triparatopic polypeptides", comprise or essentially consist of two or more binding units that each have a different paratope (as will be further described herein).

CD38 Binders

Based on extensive immunization, screening, characterization and combinatory strategies, the present inventors surprisingly observed that polypeptides comprising immunoglobulin single variable domains bound to different epitopes of CD38, and showed favourable properties for modulating CD38 mediated immune responses compared to the CD38 antagonizing molecules described in the prior art.

The present invention provides polypeptides (also referred to herein as "polypeptides of the invention") that have specificity for and/or that bind CD38, preferably human CD38. CD38 (cluster of differentiation 38), also known as cyclic ADP ribose hydrolase is a glycoprotein found on the surface of many immune cells, including CD4+, CD8+, B lymphocytes and natural killer cells. CD38 also functions in cell adhesion, signal transduction and calcium signaling. In a preferred embodiment, the protein, binds to the polypeptide of the invention to human CD38 (GenBank Accession No. BAA18966.1 (SEQ ID NO.: 465) In a particularly preferred embodiment, the polypeptide of the invention binds specifically to the C-terminal localized extracellular domain of CD38. The extracellular domain of CD38 in human CD38 extends from amino acid 42 to 300.

```
                                          SEQ ID NO: 465
       MANCEFSPVS GDKPCCRLSR RAQLCLGVSI

LVLILVVVLA VVVPRWRQQW SGPGTTKRFP

ETVLARCVKY TEIHPEMRHV DCQSVWDAFK

GAFISKHPCN ITEEDYQPLM KLGTQTVPCN

KILLWSRIKD LAHQFTQVQR DMFTLEDTLL

GYLADDLTWC GEFNTSKINY QSCPDWRKDC

SNNPVSVFWK TVSRRFAEAA CDVVHVMLNG

SRSKIFDKNS TFGSVEVHNL QPEKVQTLEA

WVIHGGREDS RDLCQDPTIK ELESIISKRN

IQFSCKNIYR PDKFLQCVKN PEDSSCTSEI
```

The polypeptides and immunoglobulin constructs provided by the present invention can be used in a variety of immunotherapeutic applications, such as in the treatment of a variety of cancers, immune disorders and infectious diseases, as will be further defined herein.

Accordingly, the present invention provides polypeptides and immunoglobulin constructs binding CD38 with particular functional properties which are linked with improved and desirable therapeutic and/or pharmacological properties, in addition to other advantageous properties (such as, for example, improved ease of preparation, good stability, and/or reduced costs of goods), compared to the prior art amino acid sequences and antibodies.

The present invention provides stretches of amino acid residues (SEQ ID NOs: 117-174, SEQ ID NOs: 233-290, and SEQ ID NOs: 349-406; Table A-1) that are particularly suited for binding CD38. In particular, the invention provides stretches of amino acid residues which bind CD38 and wherein the binding of said stretches to said CD38 enhances an immune response (as described herein). These stretches of amino acid residues may be present in, and/or may be incorporated into, a polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against CD38. These stretches of amino acid residues are also referred to herein as "CDR sequence(s) of the invention" (i.e., as "CDR1 sequence(s) of the invention", "CDR2 sequence(s) of the invention" and "CDR3 sequence(s) of the invention", respectively).

In an embodiment, the present invention relates to a polypeptide as described herein, that comprises at least one immunoglobulin single variable domain (ISVD) that specifically binds to CD38 with an $EC_{50}$ value of less than 200 pM, preferably said CD38 is human CD38 (SEQ ID NO: 465).

In an embodiment, the present invention relates to a polypeptide as described herein, wherein said ISVD inhibits tumor cell growth.

It should however be noted that the invention in its broadest sense is not limited to a specific structural role or function that these stretches of amino acid residues may have in a polypeptide of the invention, as long as these stretches of amino acid residues allow the polypeptide of the invention to bind to CD38 with a certain affinity and potency (as defined herein). Thus, generally, the invention in its broadest sense provides monovalent polypeptides (also referred to herein as "monovalent polypeptide(s) of the invention") that are capable of binding to CD38 with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to CD38. It should however also be noted that the presence of only one such CDR sequence in a monovalent polypeptide of the invention may by itself already be sufficient to provide the monovalent polypeptide of the invention the capacity of binding to CD38; reference is for example made to the so-called "Expedite fragments" described in WO 03/050531.

Epitope binning experiments revealed that the ISVDs bound to three different non-overlapping epitopes: Epitope 1, Epitope 2 and Epitope 3. The ISVDs can be classified accordingly.

In a specific, but non-limiting aspect, the monovalent polypeptide of the invention, may comprise at least one stretch of amino acid residues that is chosen from the group consisting of:
(i) CDR1 sequences:
    (a) SEQ ID NOs: 131, 132, 134, 140, 144, 146, 150, 151, 152, 153, 155, 158; and
    (b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 sequences:
    (c) SEQ ID NOs: 247, 248, 250, 256, 260, 262, 266, 267, 268, 269, 271, 274; and
    (d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 sequences:
    (e) SEQ ID NOs: 363, 364, 366, 372, 376, 378, 382, 383, 384, 385, 387, 390; and
    (f) amino acid sequences that have 4, 3, 2, or 1 amino acid(s) difference with the amino acid sequences of SEQ ID NOs: 363, 364, 366, 372, 376, 378, 382, 383, 384, 385, 387, 390.

In a further specific, but non-limiting aspect, the monovalent polypeptide of the invention, may comprise at least one stretch of amino acid residues that is chosen from the group consisting of:
(i) CDR1 sequences:
    (a) SEQ ID NOs: 129, 163, 164, 165, 166; and
    (b) amino acid sequences that have 4, 3, 2, or 1 amino acid(s) difference with the amino acid sequences of SEQ ID NOs: 129, 163, 164, 165, 166; and/or
(ii) CDR2 sequences:
    (c) SEQ ID NOs: 245, 279, 280, 281, 282; and
    (d) amino acid sequences that have 4, 3, 2, or 1 amino acid(s) difference with the amino acid sequences of SEQ ID NOs: 245, 279, 280, 281, 282; and/or
(iii) CDR3 sequences:
    (e) SEQ ID NOs: 361, 395, 396, 397, 398; and
    (f) amino acid sequences that have 4, 3, 2, or 1 amino acid(s) difference with the amino acid sequences of SEQ ID NOs: 361, 395, 396, 397, 398.

In a specific, but non-limiting aspect, the monovalent polypeptide of the invention, may comprise at least one stretch of amino acid residues that is chosen from the group consisting of:
(i) CDR1 sequences:
    (a) SEQ ID NOs: 1, 3, 4, 9, 10, 20, 43, 44, 45, 46, 51, 52, 53, 54, 55, 56, 57, 58; and
    (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 sequences:
    (c) SEQ ID NOs: 233, 235, 236, 241, 242, 252, 275, 276, 277, 278, 283, 284, 285, 286, 287, 288, 289, 290; and
    (d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 sequences:
    (e) SEQ ID NOs: 349, 351, 352, 357, 358, 368, 391, 392, 393, 394, 399, 400, 401, 402, 403, 404, 405, 406; and
    (f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

In particular, a monovalent polypeptide of the invention may be a monovalent polypeptide that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the monovalent polypeptide of the invention comprises more than one, such as two or more stretches of amino acid residues chosen from the group consisting of the CDR1 sequences of the invention, the CDR2 sequences of the invention and/or the CDR3 sequences of the invention. Preferably, the monovalent polypeptide of the invention comprises three stretches of amino acid residues chosen from the group consisting of the CDR1 sequences of the invention, the CDR2 sequences of the invention and the CDR3 sequences of the invention, respectively. The combinations of CDRs that are mentioned herein as being preferred for the monovalent polypeptides of the invention are listed in Table A-1.

It should be further noted that the invention is not limited as to the origin of the monovalent polypeptide of the invention (or of the nucleic acid of the invention used to express it), nor as to the way that the monovalent polypeptide or nucleic acid of the invention is (or has been) generated or obtained. Thus, the monovalent polypeptides of the invention may be naturally occurring monovalent polypeptides (from any suitable species) or synthetic or semi-synthetic monovalent polypeptides.

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDRs onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In said monovalent polypeptides of the invention, the CDRs may be linked to further amino acid sequences and/or may be linked to each other via amino acid sequences, in which said amino acid sequences are preferably framework sequences or are amino acid sequences that act as framework sequences, or together form a scaffold for presenting the CDRs.

According to a preferred, but non-limiting embodiment, the monovalent polypeptides of the invention comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. In such a monovalent polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, a monovalent polypeptide of the present invention essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 117-174; and
  (b) amino acid sequences that have 4, 3, 2, or 1 amino acid(s) difference with the amino acid sequences of SEQ ID NOs: 117-174; and/or (ii) CDR2 is chosen from the group consisting of:
  (c) SEQ ID NOs: 233-290; and
  (d) amino acid sequences that have 4, 3, 2, or 1 amino acid(s) difference with the amino acid sequences of SEQ ID NOs: 233-290; and/or
(iii) CDR3 is chosen from the group consisting of:
  (e) SEQ ID NOs: 349-406; and
  (f) amino acid sequences that have 4, 3, 2, or 1 amino acid(s) difference with the amino acid sequences of SEQ ID NOs: 349-406.

Further preferred CDR sequences are depicted in Table A-1.

Sequence analysis of the resulting binders resulted also in the identification of distinct families. A corresponding alignment is provided in Table A-2. Classification into different families was based on sequence similarities and differences in the CDRs. Representatives of all families were isolated based on affinity binding to CD38 and CDC activity (cf. Examples).

In one specific, but non-limiting aspect, the monovalent polypeptide of the invention may be a monovalent polypeptide that comprises an immunoglobulin fold or a monovalent polypeptide that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding CD38. Accordingly, in a preferred aspect the monovalent polypeptide of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the monovalent polypeptide of the invention is an immunoglobulin single variable domain such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

In particular, the framework sequences present in the monovalent polypeptides of the invention may contain one or more of Hallmark residues (as defined in Tables A-3 to A-8 of WO 08/020079), such that the monovalent polypeptide of the invention is a Nanobody. Some preferred, but non-limiting examples of (suitable combinations of) such framework sequences will become clear from the further disclosure herein (see e.g., Table A-1). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, the invention provides polypeptides comprising at least one immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:
i) have at least 80%, more preferably 90%, even more preferably 95% amino acid identity with at least one of the amino acid sequences of SEQ ID NOs: 1-58 (see Table A-3), in which for the purposes of determining the degree of amino acid identity, the amino acid residues that form the CDR sequences are disregarded. In this respect, reference is also made to Table A-1, which lists the framework 1 sequences (SEQ ID NOs: 59-116), framework 2 sequences (SEQ ID NOs: 175-232), framework 3 sequences (SEQ ID NOs: 291-348) and framework 4 sequences (SEQ ID NOs: 407-464) of the immunoglobulin single variable domains of SEQ ID NOs: 1-58 (see Table A-2); or combinations of framework sequences as depicted in Table A-1; and in which:
iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

In an embodiment, the present invention provides a polypeptide as described herein, wherein said ISVD is chosen from the group consisting of
  ISVDs in which CDR1 is represented by SEQ ID NOs: 117-174, CDR2 is represented by SEQ ID NOs: 233-290, and CDR3 is represented by SEQ ID NOs: 349-406;
  ISVD represented by SEQ ID NO:s 1 to 58; and,
  ISVD represented by at least 80% or more sequence identity to any one of SEQ ID NO:s 1 to 58.

In an embodiment, the present invention provides a polypeptide as described herein, wherein said CDRs are chosen from the group consisting of:
CDR1 is SEQ ID NO: 117, CDR2 is SEQ ID NO: 233 and CDR3 is SEQ ID NO: 349;
CDR1 is SEQ ID NO: 118, CDR2 is SEQ ID NO: 234 and CDR3 is SEQ ID NO: 350;
CDR1 is SEQ ID NO: 119, CDR2 is SEQ ID NO: 235 and CDR3 is SEQ ID NO: 351;
CDR1 is SEQ ID NO: 120, CDR2 is SEQ ID NO: 236 and CDR3 is SEQ ID NO: 352;
CDR1 is SEQ ID NO: 121, CDR2 is SEQ ID NO: 237 and CDR3 is SEQ ID NO: 353;
CDR1 is SEQ ID NO: 122, CDR2 is SEQ ID NO: 238 and CDR3 is SEQ ID NO: 354;
CDR1 is SEQ ID NO: 123, CDR2 is SEQ ID NO: 239 and CDR3 is SEQ ID NO: 355;
CDR1 is SEQ ID NO: 124, CDR2 is SEQ ID NO: 240 and CDR3 is SEQ ID NO: 356;
CDR1 is SEQ ID NO: 125, CDR2 is SEQ ID NO: 241 and CDR3 is SEQ ID NO: 357;
CDR1 is SEQ ID NO: 126, CDR2 is SEQ ID NO: 242 and CDR3 is SEQ ID NO: 358;
CDR1 is SEQ ID NO: 127, CDR2 is SEQ ID NO: 243 and CDR3 is SEQ ID NO: 359;
CDR1 is SEQ ID NO: 128, CDR2 is SEQ ID NO: 244 and CDR3 is SEQ ID NO: 360;
CDR1 is SEQ ID NO: 129, CDR2 is SEQ ID NO: 245 and CDR3 is SEQ ID NO: 361;
CDR1 is SEQ ID NO: 130, CDR2 is SEQ ID NO: 246 and CDR3 is SEQ ID NO: 362;
CDR1 is SEQ ID NO: 131, CDR2 is SEQ ID NO: 247 and CDR3 is SEQ ID NO: 363;
CDR1 is SEQ ID NO: 132, CDR2 is SEQ ID NO: 248 and CDR3 is SEQ ID NO: 364;
CDR1 is SEQ ID NO: 133, CDR2 is SEQ ID NO: 249 and CDR3 is SEQ ID NO: 365;
CDR1 is SEQ ID NO: 134, CDR2 is SEQ ID NO: 250 and CDR3 is SEQ ID NO: 366;
CDR1 is SEQ ID NO: 135, CDR2 is SEQ ID NO: 251 and CDR3 is SEQ ID NO: 367;
CDR1 is SEQ ID NO: 136, CDR2 is SEQ ID NO: 252 and CDR3 is SEQ ID NO: 368;
CDR1 is SEQ ID NO: 137, CDR2 is SEQ ID NO: 253 and CDR3 is SEQ ID NO: 369;
CDR1 is SEQ ID NO: 138, CDR2 is SEQ ID NO: 254 and CDR3 is SEQ ID NO: 370;
CDR1 is SEQ ID NO: 139, CDR2 is SEQ ID NO: 255 and CDR3 is SEQ ID NO: 371;
CDR1 is SEQ ID NO: 140, CDR2 is SEQ ID NO: 256 and CDR3 is SEQ ID NO: 372;
CDR1 is SEQ ID NO: 141, CDR2 is SEQ ID NO: 257 and CDR3 is SEQ ID NO: 373;
CDR1 is SEQ ID NO: 142, CDR2 is SEQ ID NO: 258 and CDR3 is SEQ ID NO: 374;
CDR1 is SEQ ID NO: 143, CDR2 is SEQ ID NO: 259 and CDR3 is SEQ ID NO: 375;
CDR1 is SEQ ID NO: 144, CDR2 is SEQ ID NO: 260 and CDR3 is SEQ ID NO: 376;
CDR1 is SEQ ID NO: 145, CDR2 is SEQ ID NO: 261 and CDR3 is SEQ ID NO: 377;
CDR1 is SEQ ID NO: 146, CDR2 is SEQ ID NO: 262 and CDR3 is SEQ ID NO: 378;
CDR1 is SEQ ID NO: 147, CDR2 is SEQ ID NO: 263 and CDR3 is SEQ ID NO: 379;
CDR1 is SEQ ID NO: 148, CDR2 is SEQ ID NO: 264 and CDR3 is SEQ ID NO: 380;
CDR1 is SEQ ID NO: 149, CDR2 is SEQ ID NO: 265 and CDR3 is SEQ ID NO: 381;
CDR1 is SEQ ID NO: 150, CDR2 is SEQ ID NO: 266 and CDR3 is SEQ ID NO: 382;
CDR1 is SEQ ID NO: 151, CDR2 is SEQ ID NO: 267 and CDR3 is SEQ ID NO: 383;
CDR1 is SEQ ID NO: 152, CDR2 is SEQ ID NO: 268 and CDR3 is SEQ ID NO: 384;
CDR1 is SEQ ID NO: 153, CDR2 is SEQ ID NO: 269 and CDR3 is SEQ ID NO: 385;
CDR1 is SEQ ID NO: 154, CDR2 is SEQ ID NO: 270 and CDR3 is SEQ ID NO: 386;
CDR1 is SEQ ID NO: 155, CDR2 is SEQ ID NO: 271 and CDR3 is SEQ ID NO: 387;
CDR1 is SEQ ID NO: 156, CDR2 is SEQ ID NO: 272 and CDR3 is SEQ ID NO: 388;
CDR1 is SEQ ID NO: 157, CDR2 is SEQ ID NO: 273 and CDR3 is SEQ ID NO: 389;
CDR1 is SEQ ID NO: 158, CDR2 is SEQ ID NO: 274 and CDR3 is SEQ ID NO: 390;

CDR1 is SEQ ID NO: 159, CDR2 is SEQ ID NO: 275 and CDR3 is SEQ ID NO: 391;
CDR1 is SEQ ID NO: 160, CDR2 is SEQ ID NO: 276 and CDR3 is SEQ ID NO: 392;
CDR1 is SEQ ID NO: 161, CDR2 is SEQ ID NO: 277 and CDR3 is SEQ ID NO: 393;
CDR1 is SEQ ID NO: 162, CDR2 is SEQ ID NO: 278 and CDR3 is SEQ ID NO: 394;
CDR1 is SEQ ID NO: 163, CDR2 is SEQ ID NO: 279 and CDR3 is SEQ ID NO: 395;
CDR1 is SEQ ID NO: 164, CDR2 is SEQ ID NO: 280 and CDR3 is SEQ ID NO: 396;
CDR1 is SEQ ID NO: 165, CDR2 is SEQ ID NO: 281 and CDR3 is SEQ ID NO: 397;
CDR1 is SEQ ID NO: 166, CDR2 is SEQ ID NO: 282 and CDR3 is SEQ ID NO: 398;
CDR1 is SEQ ID NO: 167, CDR2 is SEQ ID NO: 283 and CDR3 is SEQ ID NO: 399;
CDR1 is SEQ ID NO: 168, CDR2 is SEQ ID NO: 284 and CDR3 is SEQ ID NO: 400;
CDR1 is SEQ ID NO: 169, CDR2 is SEQ ID NO: 285 and CDR3 is SEQ ID NO: 401;
CDR1 is SEQ ID NO: 170, CDR2 is SEQ ID NO: 286 and CDR3 is SEQ ID NO: 402;
CDR1 is SEQ ID NO: 171, CDR2 is SEQ ID NO: 287 and CDR3 is SEQ ID NO: 403;
CDR1 is SEQ ID NO: 172, CDR2 is SEQ ID NO: 288 and CDR3 is SEQ ID NO: 404;
CDR1 is SEQ ID NO: 173, CDR2 is SEQ ID NO: 289 and CDR3 is SEQ ID NO: 405; and
CDR1 is SEQ ID NO: 174, CDR2 is SEQ ID NO: 290 and CDR3 is SEQ ID NO: 406.

The immunoglobulins (and in particular immunoglobulin single variable domains) of the invention may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the immunoglobulins (and in particular immunoglobulin single variable domains) of the invention may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the immunoglobulins of the invention contain the mutations according to one of (i) to (v) above (or a suitable combination thereof):
the amino acid residue at position 11 is preferably chosen from L, V or K (and is most preferably V); and
the amino acid residue at position 14 is preferably suitably chosen from A or P; and
the amino acid residue at position 41 is preferably suitably chosen from A or P; and
the amino acid residue at position 89 is preferably suitably chosen from T, V or L; and
the amino acid residue at position 108 is preferably suitably chosen from Q or L; and
the amino acid residue at position 110 is preferably suitably chosen from T, K or Q; and
the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the immunoglobulins of the invention may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, an immunoglobulin of the invention may contain such a C-terminal extension when it forms the C-terminal end of a protein, polypeptide or other compound or construct comprising the same (again, as further described in said US provisional applications as well as WO 12/175741).

The present invention relates to a method for determining competitors, such as polypeptides, competing with a polypeptide as described herein, such as SEQ ID NO:s 1-58, wherein the polypeptide as described herein competes with or cross blocks the competitor polypeptide for binding to CD38, such as, for instance hCD38 (SEQ ID NO: 465), wherein the binding to CD38 of the competitor is reduced by at least 5%, such as 10%, 20%, 30%, 40%, 50% or even more, such as 80%, 90% or even 100% (i.e. virtually undetectable in a given assay) in the presence of a polypeptide of the invention, compared to the binding to CD38 of the competitor in the absence of the polypeptide of the invention. Competition and cross blocking can be determined by any means known in the art, such as, for instance, competition ELISA or FACS assay.

The present invention also relates to competitors competing with a polypeptide as described herein, such as SEQ ID NO:s 1-58, wherein the competitor competes with or cross blocks the polypeptide as described herein for binding to CD38, wherein the binding to CD38 of the polypeptide of the invention is reduced by at least 5%, such as 10%, 20%, 30%, 40%, 50% or even more, such as 80%, or even more such as at least 90% or even 100% (i.e. virtually undetectable in a given assay) in the presence of said competitor, compared to the binding to CD38 by the polypeptide of the invention in the absence of said competitor. In an aspect the present invention relates to a polypeptide cross-blocking binding to CD38 by a polypeptide of the invention such as one of SEQ ID NO:s 1-58 and/or is cross-blocked from binding to CD38 by at least one of SEQ ID NO:s 1-38, wherein said polypeptide comprises at least one VH, VL, dAb, immunoglobulin single variable domain (ISVD) specifically binding to CD38, wherein binding to CD38 preferably modulates an activity of CD38.

Suitable FACS assay for determining whether an immunoglobulin, antibody, immunoglobulin single variable domain, polypeptide or other binding agent cross-blocks or is capable of cross-blocking according to the invention is described below. It will be appreciated that the assay can be used with any of the immunoglobulins, antibodies, immunoglobulin single variable domains, polypeptides or other binding agents described herein. The FACS instrument (e.g. FACS Canto; Becton Dickinson) is operated in line with the manufacturer's recommendations.

Hence, in a further preferred aspect, the present invention relates to a method for determining competitor polypeptides competing with a polypeptide represented by SEQ ID NO:s 1-58, comprising determining binding of said competitor polypeptide in the presence of polypeptide represented by SEQ ID NO:s 1-58 to CD38;

detecting a competitor polypeptide when the binding to CD38 of said competitor polypeptide is reduced by at least 10%, such as 20%, 30%, 40%, 50% or even more, such as 80%, 90% or even 100% in the presence of a polypeptide represented by SEQ ID NO:s 1-58, compared to the binding to CD38 of the competitor in the absence of the polypeptide represented by SEQ ID NO:s 1-58.

There are advantages from a regulatory point as well as thermodynamically in bivalent binding. However, it is also known that there is a considerable conformational constraint in binding epitopes simultaneously when there is a limited degree of conformational freedom. Although bivalent binding may result in an increased avidity, e.g. conventional antibodies when both paratopes are identical, this is less evident in case of different paratopes. In particular, when an epitope is bound by a first paratope, this obstructs binding by the second paratope to the second epitope. This is especially true in case of different affinities. The inventors uncovered that multivalent polypeptides displayed in essence the same activities and efficiencies in immune responses as the combination of the corresponding monovalent polypeptides, despite these conformational constraints of the multivalent format or the differences in affinity for the target. The inventors also discovered that the multivalent polypeptides comprising ISVDs directed against different epitopes of CD38 displayed even enhanced immune responses compared to the benchmark molecules, which were based on conventional antibodies.

Hence, the invention further relates to a multivalent polypeptide (also referred to herein as a "multivalent polypeptide(s) of the invention") that comprises or (essentially) consists of at least one immunoglobulin single variable domain (or suitable fragments thereof) directed against CD38 and one additional immunoglobulin single variable domain, which is preferably also directed against CD38.

In a preferred aspect, the multivalent polypeptide of the invention comprises or essentially consists of two or more immunoglobulin single variable domains directed against human CD38. The two or more immunoglobulin single variable domains may optionally be linked via one or more peptidic linkers.

In the multivalent polypeptide of the invention, the two or more immunoglobulin single variable domains, such as Nanobodies, may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical immunoglobulin single variable domains, e.g. Nanobodies; (b) a first immunoglobulin single variable domain, such as a Nanobody, directed against a first antigenic determinant of a protein or antigen and a second immunoglobulin single variable domain, such as a Nanobody, directed against the same antigenic determinant of said protein or antigen, wherein said first immunoglobulin single variable domain is different from said second ISVD; (c) a first immunoglobulin single variable domain, such as a Nanobody, directed against a first antigenic determinant of a protein or antigen and a second immunoglobulin single variable domain, such as a Nanobody, directed against another antigenic determinant of said protein or antigen, different from said first antigenic determinant; or (d) a first immunoglobulin single variable domain, such as a Nanobody, directed against a first protein or antigen and a second immunoglobulin single variable domain, such as a Nanobody, directed against a second protein or antigen (i.e. different from said first protein or antigen). Similarly, a trivalent polypeptide of the invention may, for example and without being limited thereto comprise (a) three identical immunoglobulin single variable domains such as Nanobodies; (b) two identical immunoglobulin single variable domains such as Nanobodies against a first antigenic determinant of a protein or antigen and a third immunoglobulin single variable domain, such as a Nanobody, directed against a different antigenic determinant of the same protein or antigen; (c) two identical immunoglobulin single variable domains such as Nanobodies against a first antigenic determinant of a protein or antigen and a third immunoglobulin single variable domain, such as a Nanobody, directed against a second protein or antigen different from said first protein or antigen; (d) a first immunoglobulin single variable domain, such as a Nanobody, directed against a first antigenic determinant of a first protein or antigen, a second immunoglobulin single variable domain, such as a Nanobody, directed against a second antigenic determinant of said first protein or antigen, different from said first antigenic determinant and a third immunoglobulin single variable domain, such as a Nanobody, directed against a second protein or antigen different from said first protein or antigen; or (e) a first immunoglobulin single variable domain, such as a Nanobody, directed against a first protein or antigen, a second immunoglobulin single variable domain, such as a Nanobody, directed against a second protein or antigen different from said first protein or antigen, and a third immunoglobulin single variable domain, such as a Nanobody, directed against a third protein or antigen different from said first and second protein or antigen.

Polypeptides of the invention that contain at least two immunoglobulin single variable domains, e.g. Nanobodies, in which at least one immunoglobulin single variable domain, such as a Nanobody, is directed against a first antigen (i.e. against CD38) and at least one immunoglobulin single variable domain, e.g. a Nanobody, is directed against a second antigen (i.e. different from CD38), will also be referred to as "multispecific" polypeptides of the invention, and the immunoglobulin single variable domains, such as Nanobodies, present in such polypeptides will also be referred to herein as being in a "multispecific format". Thus, for example, a "bispecific" polypeptide of the invention is a polypeptide that comprises at least one immunoglobulin single variable domain, such as a Nanobody, directed against a first antigen (i.e. CD38) and at least one further immunoglobulin single variable domain, such as a Nanobody, directed against a second antigen (i.e. different from CD38), whereas a "trispecific" polypeptide of the invention is a polypeptide that comprises at least one immunoglobulin single variable domain, such as a Nanobody, directed against a first antigen (i.e. CD38), at least one further immunoglobulin single variable domain, such as a Nanobody, directed against a second antigen (i.e. different from CD38) and at least one further immunoglobulin single variable domain, such as a Nanobody, directed against a third antigen (i.e. different from both CD38, and the second antigen); etc.

Accordingly, in one aspect, in its simplest form, the multivalent polypeptide of the invention is a bivalent polypeptide of the invention comprising a first immunoglobulin single variable domain, such as a Nanobody, directed against CD38, and an identical second immunoglobulin single variable domain, such as a Nanobody, directed against CD38, wherein said first and second immunoglobulin single variable domain, such as a Nanobody, may optionally be linked via a linker sequence (as defined herein); in its simplest form a trivalent polypeptide of the invention comprises a first immunoglobulin single variable domain, such as a Nanobody, directed against CD38, an identical second immunoglobulin single variable domain, such as a Nanobody, directed against CD38 and an identical third immunoglobulin single variable domain, such as a Nanobody, directed against CD38, in which said first, second and third immunoglobulin single variable domain, such as a Nanobody, may optionally be linked via one or more, and in particular two, linker sequences.

In another aspect, the multivalent polypeptide of the invention may be a bispecific polypeptide of the invention, comprising a first immunoglobulin single variable domain, such as a Nanobody, directed against CD38, and a second immunoglobulin single variable domain, such as a Nanobody, directed against a second antigen, in which said first and second immunoglobulin single variable domain, such as a Nanobody, may optionally be linked via a linker sequence (as defined herein); whereas a multivalent polypeptide of the invention may also be a trispecific polypeptide of the invention, comprising a first immunoglobulin single variable domain, such as a Nanobody, directed against CD38, a second immunoglobulin single variable domain, such as a Nanobody, directed against a second antigen and a third immunoglobulin single variable domain, such as a Nanobody, directed against a third antigen, in which said first, second and third immunoglobulin single variable domain, such as a Nanobody, may optionally be linked via one or more, and in particular two, linker sequences.

In another aspect, the polypeptide of the invention is a trivalent, bispecific polypeptide. A trivalent, bispecific polypeptide of the invention in its simplest form may be a trivalent polypeptide of the invention (as defined herein), comprising two identical immunoglobulin single variable domains such as Nanobodies against CD38 and a third immunoglobulin single variable domain, such as a Nanobody, directed against another antigen (e.g. serum albumin), in which said first, second and third immunoglobulin single variable domain, such as a Nanobody, may optionally be linked via one or more, and in particular two, linker sequences.

In a further aspect, the polypeptide of the invention is a multiparatopic polypeptide (also referred to herein as "multiparatopic polypeptide(s) of the invention"), such as e.g., (a) "biparatopic polypeptide(s) of the invention" or "triparatopic polypeptide(s) of the invention". The term "multiparatopic" (antigen-) binding molecule or "multiparatopic" polypeptide as used herein shall mean a polypeptide comprising at least two (i.e. two or more) immunoglobulin single variable domains, wherein a "first" immunoglobulin single variable domain is directed against CD38 and a "second" immunoglobulin single variable domain is directed against CD38, and wherein these "first" and "second" immunoglobulin single variable domains have a different paratope. Accordingly, the multiparatopic polypeptide comprises or consists of two or more immunoglobulin single variable domains that are directed against CD38, wherein at least one "first" immunoglobulin single variable domain is directed against a first epitope on CD38 and at least one "second" immunoglobulin single variable domain is directed against a second epitope on CD38 different from the first epitope on CD38.

In a further especially preferred aspect, the polypeptide of the invention is a biparatopic polypeptide. The term "biparatopic" (antigen-)binding molecule or "biparatopic" polypeptide as used herein shall mean a polypeptide comprising a "first" immunoglobulin single variable domain directed against CD38 and a "second" immunoglobulin single variable domain directed against CD38, wherein the "first" and "second" immunoglobulin single variable domains have a different paratope. Accordingly, the biparatopic polypeptide comprises or consists of two or more immunoglobulin single variable domains that are directed against CD38, wherein a "first" immunoglobulin single variable domain is directed against a first epitope on CD38 and a "second" immunoglobulin single variable domain is directed against a second epitope on CD38 different from the first epitope on CD38.

In another aspect, the polypeptide of the invention is a triparatopic polypeptide. The term "triparatopic" (antigen-) binding molecule or "triparatopic" polypeptide as used herein shall mean a polypeptide comprising a "first" immunoglobulin single variable domain directed against CD38, a "second" immunoglobulin single variable domain directed against CD38 and a "third" immunoglobulin single variable domain directed against CD38, wherein these "first", "second" and "third" immunoglobulin single variable domains have a different paratope. Accordingly, the triparatopic polypeptide comprises or consists of three or more immunoglobulin single variable domains that are directed against CD38, wherein a "first" immunoglobulin single variable domain is directed against a first epitope on CD38, a "second" immunoglobulin single variable domain is directed against a second epitope on CD38 different from the first epitope on CD38, and a "third" immunoglobulin single variable domain is directed against a third epitope on CD38 different from the first and second epitope on CD38.

The two or more immunoglobulin single variable domains present in the multivalent polypeptide of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody or a partially or fully humanized VHH. In a preferred aspect of the invention, the immunoglobulin single variable domains encompassed in the multivalent polypeptide of the invention are one or more monovalent polypeptides of the invention, as defined herein.

In an embodiment, the present invention provides a polypeptide as described herein, comprising a first ISVD and a second ISVD that each specifically binds to CD38 with an $EC_{50}$ value of less than 200 nM.

In an embodiment, the present invention provides a polypeptide as described herein, comprising at least two ISVDs that can bind CD38, wherein said ISVDs are different.

In an embodiment, the present invention provides a polypeptide as described herein, comprising at least two ISVDs that can bind CD38, wherein said ISVDs bind different epitopes on CD38.

In an embodiment, the present invention provides a polypeptide as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and
said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 129, 163, 164, 165, 166; and
(b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
(c) SEQ ID NOs: 245, 279, 280, 281, 282; and
(d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
(e) SEQ ID NOs: 361, 395, 396, 397, 398; and
(f) amino acid sequences that have 4, 3, 2, or 1 amino acid(s) difference with the amino acid sequences of SEQ ID NOs: 361, 395, 396, 397, 398.

In an embodiment, the present invention provides a polypeptide as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and
said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 1, 3, 4, 9, 10, 20, 43, 44, 45, 46, 51, 52, 53, 54, 55, 56, 57, 58; and
(b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
(c) SEQ ID NOs: 233, 235, 236, 241, 242, 252, 275, 276, 277, 278, 283, 284, 285, 286, 287, 288, 289, 290; and
(d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
(e) SEQ ID NOs: 349, 351, 352, 357, 358, 368, 391, 392, 393, 394, 399, 400, 401, 402, 403, 404, 405, 406; and
(f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

In an embodiment, the present invention provides a polypeptide as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 129, 163, 164, 165, 166; and
(b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
(c) SEQ ID NOs: 245, 279, 280, 281, 282; and
(d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
(e) SEQ ID NOs: 361, 395, 396, 397, 398; and
(f) amino acid sequences that have 4, 3, 2, or 1 amino acid(s) difference with the amino acid sequences of SEQ ID NOs: 361, 395, 396, 397, 398; and
said second ISVD essentially consists of 4 framework regions (FR1 to FR4, respectively) and 3 complementarity determining regions (CDR1 to CDR3, respectively), in which:

(i) CDR1 is chosen from the group consisting of:
(a) SEQ ID NOs: 1, 3, 4, 9, 10, 20, 43, 44, 45, 46, 51, 52, 53, 54, 55, 56, 57, 58; and
(b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
(c) SEQ ID NOs: 233, 235, 236, 241, 242, 252, 275, 276, 277, 278, 283, 284, 285, 286, 287, 288, 289, 290; and
(d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
(e) SEQ ID NOs: 349, 351, 352, 357, 358, 368, 391, 392, 393, 394, 399, 400, 401, 402, 403, 404, 405, 406; and
(f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

Binding of the multivalent polypeptides of the invention to CD38 can be measured in binding assays. Typical assays include (without being limiting) assays in which CD38 is exposed on a cell surface (cf. Examples). A preferred assay for measuring binding of the multivalent polypeptides of the invention to CD38 is a FACS assay, such as e.g. the FACS assay as described in the examples, wherein binding of the multivalent polypeptides of the invention to CD38 expressed on cells. Some preferred $EC_{50}$ and/or KD values for binding of the polypeptides of the invention to CD38 will become clear from the further description and examples herein.

In such FACS binding assay, the multivalent polypeptides of the present invention may have $EC_{50}$ values in binding human CD38 of $10^{-8}$ M or lower, more preferably of $10^{-9}$ M or lower, or even of $10^{-10}$ M or lower, such as $10^{-11}$ M. For example, in such FACS binding assay, the multivalent polypeptides of the present invention may have $EC_{50}$ values in binding human CD38 between $10^{-11}$ M and $10^{-8}$ M, such as between $10^{-11}$ M and $10^{-10}$ M, between $10^{-10}$ M and $10^{-9}$ M or between $10^{-11}$ M and $10^{-10}$ M.

In an embodiment, the present invention provides a polypeptide as described herein,
wherein the $EC_{50}$ in a FACS assay is 190 pM or less, such as less than 180, 170, 160, 150, 140, 130, 120, 110, 100 or even less, such as less than 90, 80, 70, 60, 50, 40, 35, 30, 25, 20, or even less, such as less than 16 pM; and/or
wherein said polypeptide binds to CD38 with an $IC_{50}$ of at most 100 nM, such as 50 nM, 20 nM, 10 nM, 9 nM, 8 nM, 7 nM, 6 nM, 5 nM, 4 nM, 3 nM, preferably even at most 2 nM, such as 1 nM, as determined by a competition FACS; and/or
wherein said polypeptide binds to CD38 with an $IC_{50}$ which is at least 10%, such as 20%, 30%, 50%, 80%, 90%, or even 100% better than the $IC_{50}$ of a benchmark, preferably as determined by a competition FACS.

The multivalent polypeptides of the invention bind CD38 and can modulate (i.e. increase, enhance, stimulate or potentiate) the immune response. More particularly, the polypeptides of the present invention may enhance an immune response, such as enhance CDC activity.

The inventors surprisingly observed that the polypeptides of the invention when bound to an Fc portion efficiently induced an immune response, such as a CDC. Moreover, a combination of two, monovalent Fc constructs, each directed to a different epitope on CD38, displayed a far better potency, e.g. an immune response than the corresponding benchmark. Also, when bivalent polypeptides comprising ISVDs directed against different epitopes on CD38 were formatted in an Fc construct, this Fc construct also displayed a far better potency, e.g. an immune response than the corresponding benchmark.

As used herein, a "benchmark" is used as a point of reference for evaluating performance, such as one or more functional characteristics of a molecule, such as, for instance, affinity, efficacy, and potency as described herein. The particular immunoglobulin construct will determine the appropriateness of a certain benchmark, which can readily be assessed by a person skilled in the art.

Hence, in an especially preferred aspect, the present invention provides immunoglobulin constructs that comprise two polypeptides (each, a "polypeptide of the invention"), in which each polypeptide comprises one or more ISVDs that are linked, usually via a suitable hinge region or linker, to one or more constant domains (e.g. a CH2 and/or a CH3 domain) that, in the final construct, together form an Fc portion.

Thus, the "immunoglobulin constructs of the invention" generally comprise an Fc portion (as defined herein) in which each of the two polypeptides that form the Fc portion is linked, optionally via a suitable linker or hinge region, to two or more single variable domains (also as defined herein). Such constructs may for example be as described in EP 1 621 554, WO 02/056910 or WO2009/068630.

The polypeptides of the invention, and their use in forming the constructs of the invention, are further aspects of the invention. Also, in a specific aspect of the invention, as further described herein, these polypeptides of the invention may also be used as such (i.e. without interaction with another polypeptide chain and/or not as part of an immunoglobulin construct of the invention).

Preferably, in the constructs of the invention, each polypeptide of the invention comprises at least one, such as one, two or three ISVDs, and more preferably only two ISVDs. In other words, the immunoglobulin constructs of the invention preferably comprise a total of 4 ISVDs (i.e. 2 in each polypeptide).

Also, each polypeptide of the invention will usually comprise either two constant domains (for example, in case of an Fc portion that is derived from IgG, IgA or IgD) or three constant domains (for example, in case of an Fc portion that is derived from IgM or IgE), such that, in the final construct, the constant domains of the two polypeptide chains form an Fc portion, for example an Fc portion that is derived from IgG (e.g. IgG1, IgG2, IgG3 or IgG4), IgA, IgD, IgE or IgM, or a variant, analog, mutant, part or fragment thereof (including chimeric Fc portions), that may or may not have effector functions, as further described herein.

Figure 1:
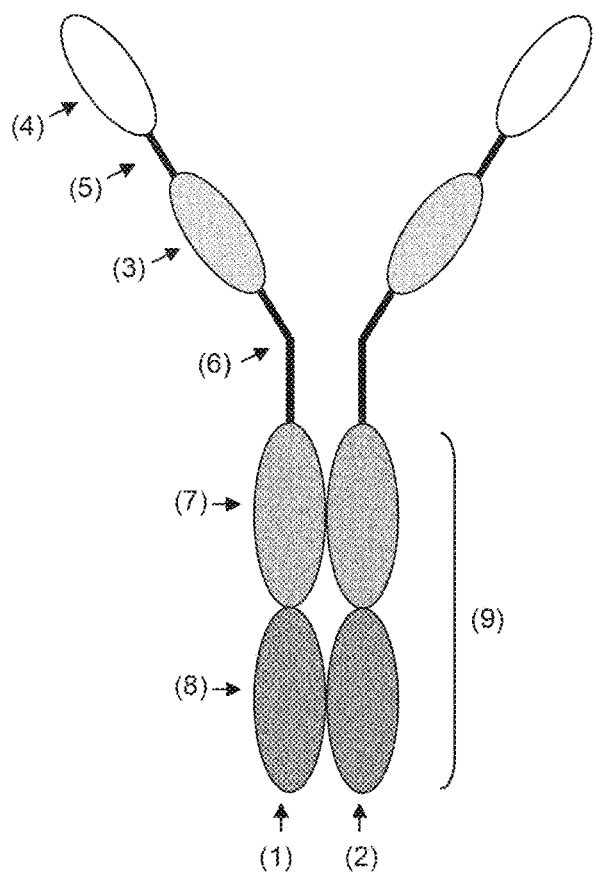
FIG. 1 Schematic depiction of an exemplary immunoglobulin construct. In this case, the construct comprises two polypeptides (1) and (2), which each comprise two constant domains (7) and (8), a "first" ISVD (3) and a "second" ISVD (4). The first ISVD (3) is linked, optionally via a suitable linker (5), to the second ISVD (4), and is also linked to the constant domains, optionally (and usually) via a suitable linker or hinge region (6). The constant domains (7) and (8) of the polypeptide (1) and the corresponding constant domains (7) and (8) of the polypeptide chain (2) together form the Fc portion (9).

Constructs of the invention with 4 single variable domains and 4 constant domains (for example forming an Fc portion derived from an IgG or IgA, or an analog, mutant or variant thereof) are schematically shown in the non-limiting FIG. 1. The constructs comprise two polypeptides (1) and (2), which each comprise two constant domains (7) and (8), a "first" ISVD (3) and a "second" ISVD (4). The first ISVD (3) is linked, optionally via a suitable linker (5), to the second ISVD (4), and is also linked to the constant domains, optionally (and usually) via a suitable linker or hinge region (6). The constant domains (7) and (8) of the polypeptide (1) and the corresponding constant domains (7) and (8) of the polypeptide chain (2) together form the Fc portion (9). The corresponding constant domains on the two polypeptides pair, e.g. bind covalently, with each other, for instance the CH2 domain on polypeptide 1 pairs with the CH2 domain on polypeptide 2, and the CH3 domain on polypeptide 1 pairs with the CH3 domain on polypeptide 2, etc.

Accordingly, in an aspect of the invention in the immunoglobulin construct of the invention said CH2 domain of said first polypeptide pairs with said CH2 domain of said second polypeptide, and/or said CH3 domain of said first polypeptide pairs with said CH3 domain of said second polypeptide. The Fc-portion of an immunoglobulin is defined as the fragment of an antibody which would be typically generated after digestion of an antibody with papain (which is known for someone skilled in the art) which includes the two CH2-CH3 regions of an immunoglobulin and a connecting region, e.g. a hinge region. The constant domain of an antibody heavy chain defines the antibody isotype, e.g. IgGI, IgG2, IgG3, IgG4, IgAI, IgA2, IgM, IgD, or IgE.

The Fc-portion mediates the effector functions of antibodies with cell surface receptors called Fc receptors and proteins of the complement system, such as antibody dependent cell-mediated cytotoxicity (ADCC) or complement dependent cytotoxicity (CDC).

The term "CH2 region" or "CH2 domain" as used herein is intended to refer the CH2 region of an immunoglobulin. Thus, for example the CH2 region of a human IgGI antibody corresponds to amino acids 228-340 according to the EU numbering system. However, the CH2 region may also be any of the other subtypes as described herein.

The term "CH3 region" or "CH3 domain" as used herein is intended to refer the CH3 region of an immunoglobulin. Thus, for example the CH3 region of a human IgGI antibody corresponds to amino acids 341-447 according to the EU numbering system. However, the CH3 region may also be any of the other subtypes as described herein.

A preferred region comprising a CH2 domain, a hinge and a CH3 domain is represented by SEQ ID NO: 466 and 467.

```
human IgG1
                                       SEQ ID NO: 466
AAASDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSREEVTKNQVSLT

CLVKGFYPSDIAVEWESNGQPENNYKTTPPVLDSDGSFFLYSKLTVDKSR

WQQGNVFSCSVMHEALHNHYTQKSLSLSPGK mouse IgG2c
                                       SEQ ID NO: 467
AAAPCPPLKECPPCAAPDLLGGPSVFIFPPKIKDVLMISLSPMVTCVVVD

VSEDDPDVQISWFVNNVEVHTAQTQTHREDYNSTLRVVSALPIQHQDWMS

GKEFKCKVNNRALPSPIEKTISKPRGPVRAPQVYVLPPPAEEMTKKEFSL

TCMITGFLPAEIAVDWTSNGRTEQNYKNTATVLDSDGSYFMYSKLKVQKS

TWERRNLFACSMGHEGSAQSPYD
```

The polypeptides of the invention comprising Fc portions can be generated by any suitable method known by the person skilled in the art, such as e.g. described by Scheuplein et al. 2010). For instance, individual ISVDs can be recloned as fusion proteins to the Fc portion of mouse IgG1 or human IgG1 by PCR amplification with primers flanked by suitable restriction sites, followed by digestion and ligation into the expression vector pME.

In an aspect of the invention, the polypeptide according to the invention further comprises a CH2 and a CH3 constant domain, preferably said CH2 and said CH3 domain are directly linked or linked via a linker.

In a preferred but non-limiting aspect of the invention, the immunoglobulin constructs of the invention comprise an Fc portion that is linked (optionally via a suitable linker or hinge region) to a pair of first ISVDs (i.e. one linked to each polypeptide that forms the Fc portion, as further described herein), which are linked (optionally via a suitable linker) to a pair of second ISVDs, wherein the constructs and the ISVDs present therein are such that:
 both of the first ISVDs are directed against a first target, antigen epitope, antigenic determinant, part, domain or subunit of CD38; and
 both of the second ISVDs are directed against a second target, antigen, epitope, antigenic determinant, part, domain or subunit of CD38;
wherein the first target, antigen epitope, antigenic determinant, part, domain or subunit of CD38 is different from the second target, antigen, epitope, antigenic determinant, part, domain or subunit of CD38.

According to another aspect, one or more polypeptides of the invention may be linked (optionally via a suitable linker or hinge region) to one or more constant domains (for example, 2 or 3 constant domains that can be used as part of/to form an Fc portion), to an Fc portion, to an antibody constant region of an IgG type and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) a Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains.

In particular, the immunoglobulin constructs of the invention bind to a target with an affinity (suitably measured and/or expressed as a $K_D$-value (actual or apparent), a $K_A$-value (actual or apparent), a $k_{on}$-rate and/or a $k_{off}$-rate better than the benchmark.

In an embodiment, the present invention relates to a immunoglobulin construct comprising polypeptides as described herein, wherein said immunoglobulin construct binds to a target with an $IC_{50}$ which is at least 10%, such as 20%, 30%, 50%, 80%, 90%, or even 100% better or more than the $IC_{50}$ of a benchmark, for instance as determined in a ligand competition assay, competition FACS, a functional cellular assay, such as inhibition of ligand-induced chemotaxis, an Alphascreen assay, etc., preferably by a competition FACS.

In an embodiment, the present invention relates to a immunoglobulin construct comprising polypeptides as described herein, wherein said immunoglobulin construct binds to a target with an $IC_{50}$ which is at least 1.5 times, such as 2 times, 3 times or 4 times, and even 5 times or 10 times better than the $IC_{50}$ of a benchmark, for instance as determined in a ligand competition assay, competition FACS, a functional cellular assay, such as inhibition of ligand-induced chemotaxis, an Alphascreen assay, etc., preferably by a competition FACS.

In an embodiment, the present invention relates to a immunoglobulin construct comprising polypeptides as described herein, having an $IC_{50}$ of between 200 nM and 0.01 nM, such as 0.01, 0.05, 0.1, 0.15, 2, 3, 4, 5, 6, 7, 8, 9, 10, 15, 20, 30, 40, 50, 60, 70, 80, 90, 100, 110, 120, 130, 140, 150, 160, 170, 180, 190 or 200 nM, for instance determined in a ligand competition assay, competition FACS, a functional cellular assay, such as inhibition of ligand-induced chemotaxis, an Alphascreen assay, etc.

Accordingly, the present invention relates to an immunoglobulin construct comprising a first polypeptide according to the invention further comprising a CH2 and a CH3 domain, preferably said CH2 and a CH3 domain are directly linked or linked via a linker and a second polypeptide according to the invention further comprising a CH2 and a CH3 domain, preferably said CH2 and a CH3 domain are directly linked or linked via a linker, wherein said CH2 domains and said CH3 domains of said polypeptides form an Fc portion.

In a further preferred embodiment of the invention, said first polypeptide and said second polypeptide are the same in the immunoglobulin construct.

In an embodiment, the present invention relates to an immunoglobulin construct as described herein, wherein said first polypeptide comprises a first ISVD and second ISVD, and said second polypeptide comprises a first ISVD and a second ISVD.

In an embodiment, the present invention relates to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and
said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 129, 163, 164, 165, 166; and
(b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
(c) SEQ ID NOs: 245, 279, 280, 281, 282; and
(d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
(e) SEQ ID NOs: 361, 395, 396, 397, 398; and
(f) amino acid sequences that have 4, 3, 2, or 1 amino acid(s) difference with the amino acid sequences of SEQ ID NOs: 361, 395, 396, 397, 398.

In an embodiment, the present invention relates to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 131, 132, 134, 140, 144, 146, 150, 151, 152, 153, 155, 158; and
(b) amino acid sequences that have 4, 3, 2, or 1 amino acid(s) difference with the amino acid sequences of SEQ ID NOs: 131, 132, 134, 140, 144, 146, 150, 151, 152, 153, 155, 158; and/or
(ii) CDR2 is chosen from the group consisting of:
(c) SEQ ID NOs: 247, 248, 250, 256, 260, 262, 266, 267, 268, 269, 271, 274; and
(d) amino acid sequences that have 4, 3, 2, or 1 amino acid(s) difference with the amino acid sequences of SEQ ID NOs: 247, 248, 250, 256, 260, 262, 266, 267, 268, 269, 271, 274; and/or
(iii) CDR3 is chosen from the group consisting of:
(e) SEQ ID NOs: 363, 364, 366, 372, 376, 378, 382, 383, 384, 385, 387, 390; and
(f) amino acid sequences that have 4, 3, 2, or 1 amino acid(s) difference with the amino acid sequences of SEQ ID NOs: 363, 364, 366, 372, 376, 378, 382, 383, 384, 385, 387, 390; and
said second ISVD essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 1, 3, 4, 9, 10, 20, 43, 44, 45, 46, 51, 52, 53, 54, 55, 56, 57, 58; and
(b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
(c) SEQ ID NOs: 233, 235, 236, 241, 242, 252, 275, 276, 277, 278, 283, 284, 285, 286, 287, 288, 289, 290; and
(d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or (iii) CDR3 is chosen from the group consisting of:
  (e) SEQ ID NOs: 349, 351, 352, 357, 358, 368, 391, 392, 393, 394, 399, 400, 401, 402, 403, 404, 405, 406; and
  (f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

In an embodiment, the present invention relates to an immunoglobulin construct as described herein, wherein
said first ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 129, 163, 164, 165, 166; and
  (b) amino acid sequences that have 4, 3, 2, or 1 amino acid(s) difference with the amino acid sequences of SEQ ID NOs: 129, 163, 164, 165, 166; and/or
(ii) CDR2 is chosen from the group consisting of:
  (c) SEQ ID NOs: 245, 279, 280, 281, 282; and
  (d) amino acid sequences that have 4, 3, 2, or 1 amino acid(s) difference with the amino acid sequences of SEQ ID NOs: 245, 279, 280, 281, 282; and/or
(iii) CDR3 is chosen from the group consisting of:
  (e) SEQ ID NOs: 361, 395, 396, 397, 398; and
  (f) amino acid sequences that have 4, 3, 2, or 1 amino acid(s) difference with the amino acid sequences of SEQ ID NOs: 361, 395, 396, 397, 398; and
said second ISVD essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 1, 3, 4, 9, 10, 20, 43, 44, 45, 46, 51, 52, 53, 54, 55, 56, 57, 58; and
  (b) amino acid sequences that have 4, 3, 2, or 1 amino acid(s) difference with the amino acid sequences of SEQ ID NOs: 1, 3, 4, 9, 10, 20, 43, 44, 45, 46, 51, 52, 53, 54, 55, 56, 57, 58; and/or
(ii) CDR2 is chosen from the group consisting of:
  (c) SEQ ID NOs: 233, 235, 236, 241, 242, 252, 275, 276, 277, 278, 283, 284, 285, 286, 287, 288, 289, 290; and
  (d) amino acid sequences that have 4, 3, 2, or 1 amino acid(s) difference with the amino acid sequences of SEQ ID NOs: 233, 235, 236, 241, 242, 252, 275, 276, 277, 278, 283, 284, 285, 286, 287, 288, 289, 290; and/or
(iii) CDR3 is chosen from the group consisting of:
  (e) SEQ ID NOs: 349, 351, 352, 357, 358, 368, 391, 392, 393, 394, 399, 400, 401, 402, 403, 404, 405, 406; and
  (f) amino acid sequences that have 4, 3, 2, or 1 amino acid(s) difference with the amino acid sequences of SEQ ID NOs: 349, 351, 352, 357, 358, 368, 391, 392, 393, 394, 399, 400, 401, 402, 403, 404, 405, 406.

In an embodiment, the present invention relates to an immunoglobulin construct as described herein, wherein said first polypeptide and said second polypeptide are the same.

In an embodiment, the present invention relates to an immunoglobulin construct as described herein, wherein said first ISVD binds a first epitope of CD38 and said second ISVD binds a second epitope on CD38, wherein said first epitope is different from said second epitope, preferably said first epitope does not overlap with said second epitope.

The monovalent polypeptide of the invention and the multivalent polypeptide of the invention (whether or not comprised in the immunoglobulin constructs of the invention) may or may not further comprise one or more other groups, residues, moieties or binding units. These monovalent polypeptides as well as multivalent polypeptides (with or without additional groups, residues, moieties or binding units) are all referred to as "compound(s) of the invention", "construct(s) of the invention" and/or "polypeptide(s) of the invention".

For example, such further groups, residues, moieties or binding units may be one or more additional amino acid sequences, such that the polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are immunoglobulin single variable domains chosen from the group consisting of Domain antibodies, amino acids that are suitable for use as a domain antibody, single domain antibodies, amino acids that are suitable for use as a single domain antibody, "dAb"'s, amino acids that are suitable for use as a dAb, Nanobodies (such as e.g. VHH, humanized VHH or camelized VH sequences).

As described above, additional binding units, such as immunoglobulin single variable domains having different antigen specificity can be linked to form multispecific polypeptides. By combining immunoglobulin single variable domains of two or more specificities, bispecific, trispecific etc. constructs can be formed. For example, a polypeptide according to the invention may comprise one, two, three or more immunoglobulin single variable domains directed against CD38 and one immunoglobulin single variable domain against another target. Such constructs and modifications thereof, which the skilled person can readily envisage, are all encompassed by the term "compound of the invention, construct of the invention and/or polypeptide of the invention" as used herein.

In the compounds, constructs and/or polypeptides described above, the one, two, three or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Examples of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may or may not be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compound, construct and/or polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

Also encompassed in the present invention are compounds, constructs and/or polypeptides that comprise an immunoglobulin or polypeptide of the invention and further comprising tags or other functional moieties, e.g., toxins, labels, radiochemicals, etc.

Alternatively, the additional groups, residues, moieties or binding units may for example be chemical groups, residues, moieties, which may or may not by themselves be biologically and/or pharmacologically active. For example, and without limitation, such groups may be linked to the one or more immunoglobulin single variable domains or monovalent polypeptides of the invention so as to provide a "derivative" of the polypeptide of the invention.

Accordingly, the invention in its broadest sense also comprises compounds, constructs and/or polypeptides that are derivatives of the polypeptides of the invention. Such derivatives can generally be obtained by modification, and in particular by chemical and/or biological (e.g., enzymatical) modification, of the polypeptides of the invention and/or of one or more of the amino acid residues that form polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more functional groups, residues or moieties into or onto the polypeptide of the invention, and in particular of one or more functional groups, residues or moieties that confer one or more desired properties or functionalities to the polypeptide of the invention. Examples of such functional groups will be clear to the skilled person.

For example, such modification may comprise the introduction (e.g., by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, Pa., 1980). Such functional groups may for example be linked directly (for example covalently) to a polypeptide of the invention, or optionally via a suitable linker or spacer, as will again be clear to the skilled person.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or preproform of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatic cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 206);

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

In an embodiment, the present invention relates to polypeptide as described herein, further comprising one or more other groups, residues, moieties or binding units, optionally linked via one or more peptidic linkers.

In a specific aspect of the invention, a compound or construct is prepared that has an increased half-life, compared to the corresponding polypeptide of the invention. Examples of polypeptides of the invention that comprise such half-life extending moieties for example include, without limitation, polypeptides in which the immunoglobulin single variable domains are suitable linked to one or more serum proteins or fragments thereof (such as (human) serum albumin or suitable fragments thereof) or to one or more binding units that can bind to serum proteins (such as, for example, Domain antibodies, amino acids that are suitable for use as a domain antibody, single domain antibodies, amino acids that are suitable for use as a single domain antibody, "dAb"'s, amino acids that are suitable for use as a dAb, Nanobodies, VHH sequences, humanized VHH sequences or camelized VH sequences) that can bind to serum proteins (such as serum albumin (such as human serum albumin)), serum immunoglobulins (such as IgG), transferrin or one of the other serum proteins listed in WO 04/003019; polypeptides in which the immunoglobulin single variable domain is linked to an Fc domain (such as a human Fc), an antibody constant region (such as an antibody constant region from an IgG) or a suitable part or fragment thereof; or polypeptides in which the one or more immunoglobulin single variable domains are suitably linked to one or more small proteins or peptides that can bind to serum proteins (such as, without limitation, the proteins and peptides described in WO 91/01743, WO 01/45746 or WO 02/076489). Reference is also made to the dAb's described in WO 03/002609 and WO 04/003019 and to Harmsen et al. (Vaccine 23: 4926-42, 2005); to EP 0368684, as well as to WO 08/028977, WO 08/043821, WO 08/043822 by Ablynx N.V. and WO 08/068280.

According to a specific, but non-limiting aspect of the invention, the polypeptides of the invention may contain, besides the one or more immunoglobulin single variable domains and/or monovalent polypeptides of the invention against CD38, at least one immunoglobulin single variable domain against human serum albumin. These immunoglobulin single variable domains against human serum albumin may be as generally described in the applications by Ablynx N.V. cited above (see for example WO 04/062551). Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred, as well as the Nanobodies disclosed in WO 2012/175400 (SEQ ID NOs: 1-11 of WO 2012/175400) and the Nanobody with SEQ ID NO: 109 disclosed in the U.S. provisional application No. 62/047,560 entitled "Improved immunoglobulin single variable domains" (date of filing: Sep. 8, 2014; assignee: Ablynx N.V.).

In a particularly preferred but non-limiting aspect of the invention, the invention provides a polypeptide of the invention comprising at least one immunoglobulin single variable domain (ISVD); and further comprising one or more (preferably one) serum albumin binding immunoglobulin single variable domain as described herein, e.g. the serum albumin binding immunoglobulin single variable domain of Alb11, Alb23, Alb129, Alb132, Alb8, Alb11 (S112K)-A, Alb82, Alb82-A, Alb82-AA, Alb82-AAA, Alb82-G, Alb82-GG, Alb82-GGG (see Table A-4).

TABLE A-4

Serum albumin binding ISVD sequences ("ID" refers to the SEQ ID NO as used herein)

| Name | ID | Amino acid sequence |
|---|---|---|
| Alb8 | 468 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb23 | 469 | EVQLLESGGGLVQPGGSLRLSCAASGFTFRSFGMSWVRQAPGKGPEWVSSISGSGSDTLYADS VKGRFTISRDNSKNTLYLQMNSLRPEDTAVYYCTIGGSLSRSSQGTLVTVSS |
| Alb129 | 470 | EVQLVESGGGVVQPGNSLRLSCAASGFTFSSFGMSWVRQAPGKGLEWVSSISGSGSDTLYADS VKGRFTISRDNAKTTLYLQMNSLRPEDTATYYCTIGGSLSRSSQGTLVTVSSA |
| Alb132 | 471 | EVQLVESGGGVVQPGGSLRLSCAASGFTFRSFGMSWVRQAPGKGPEWVSSISGSGSDTLYAD SVKGRFTISRDNSKNTLYLQMNSLRPEDTATYYCTIGGSLSRSSQGTLVTVSSA |
| Alb11 | 472 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb11 (S112K)-A | 473 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVKVSSA |
| Alb82 | 474 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSS |
| Alb82-A | 475 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSA |
| Alb82-AA | 476 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSAA |
| Alb82-AAA | 478 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSAAA |
| Alb82-G | 479 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSG |
| Alb82-GG | 480 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSGG |
| Alb82-GGG | 481 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSGGG |

Accordingly, the polypeptide of the invention may, for example, be a trivalent, bispecific polypeptide, comprising two immunoglobulin single variable domains, preferably monovalent polypeptides of the invention against CD38 and a third immunoglobulin single variable domain directed against (human) serum albumin, in which said first, second and third immunoglobulin single variable domain may optionally be linked via one or more, and in particular three, linker sequences.

Other amino acid sequences that can be suitably linked to the polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068628. Coupling of a polypeptide of the invention to an Fc portion or an antibody constant region may also lead to an increased half-life, compared to the corresponding polypeptide of the invention.

Other suitable constructs comprising one or more polypeptides of the invention and one or more constant domains with increased half-life in vivo will be clear to the skilled person. Generally, any fusion protein or derivatives with increased half-life will preferably have a molecular weight of more than 50 kD, the cut-off value for renal absorption.

In another specific, but non-limiting, aspect, the polypeptides of the invention may be linked (optionally via a suitable linker or hinge region) to naturally occurring, synthetic or semi-synthetic constant domains (or analogs, variants, mutants, parts or fragments thereof) that have a reduced (or essentially no) tendency to self-associate into immunoglobulin constructs (i.e. compared to constant domains that naturally occur in conventional 4-chain antibodies). Such monomeric (i.e. not self-associating) Fc chain variants, or fragments thereof, will be clear to the skilled person. For example, Helm et al. (J. Biol. Chem. 271: 7494, 1996), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

Generally, the polypeptides of the invention with increased half-life preferably have a half-life that is increased with more than 1 hour, preferably more than 2 hours, more preferably more than 6 hours, such as more than 12 hours, or even more than 24, 48 or 72 hours, compared to the half-life of the corresponding immunoglobulin single variable domain or polypeptide of the invention per se.

In another preferred, but non-limiting aspect, such polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In an embodiment, the invention relates to a polypeptide as described herein, in which said one or more other groups, residues, moieties or binding units provide the polypeptide with increased half-life, compared to the corresponding polypeptide without such groups, residues, moieties or binding units.

In an embodiment, the invention relates to a polypeptide as described herein, in which said one or more other groups, residues, moieties or binding units that provide the polypeptide with increased half-life is chosen from the group consisting of polyethylene glycol, serum proteins or fragments thereof, binding units that can bind to serum proteins, an Fc portion, an antibody constant region, and small proteins or peptides that can bind to serum proteins.

A specific example is a derivative polypeptide of the invention (see below) wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000 Dalton, such as more than 10,000 and less than 200,000, such as less than 100,000; for example in the range of 20,000-80,000 Dalton.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radioisotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example is the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the compounds, constructs, polypeptides and/or derivatives are such that they bind to CD38, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention). Such derivatives will usually also have a CD38 efficacy and/or potency as defined herein.

In view of the specificity, the polypeptides of the invention are also very suitable for conjugation to imaging agents. Suitable imaging agents for conjugating to antibodies are well known in the art, and similarly useful for conjugating to the polypeptides of the present invention. Suitable imaging agents include but are not limited to molecules preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Accordingly, the present invention relates to a polypeptide according to the invention, further comprising an imaging agent, including, but not limited to a molecule preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Such compounds, constructs and/or polypeptides of the invention and derivatives thereof may also be in essentially isolated form (as defined herein).

The invention further relates to methods for preparing the compounds, constructs, polypeptides, nucleic acids, host cells, and compositions described herein, including a host cell comprising a nucleic acid molecule as described herein or an expression vector as described herein.

In some embodiments, the polypeptides of the invention are conjugated with drugs to form polypeptide-drug conjugates (PDCs). Contemporaneous antibody-drug conjugates (ADCs) are used in oncology applications, where the use of antibody-drug conjugates for the local delivery of drugs, such as cytotoxic or cytostatic agents, toxin or toxin, moieties, allows for the targeted delivery of the drug moiety to tumors, which can allow higher efficacy, lower toxicity, etc. These ADCs have three components: (1) a monoclonal antibody conjugated through a (2) linker to a (3) toxin moiety or toxin. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety. The PDCs also have three components: (1) a polypeptide conjugated through a (2) linker to a (3) drug, such as a toxin moiety or toxin. The person skilled in the art will appreciate that the technology, methods, means, etc. of ADCs are equally applicable to PDCs.

The invention provides polypeptides of the invention (whether or not comprised in the immunoglobulin construct of the invention) comprising a drug, such as a toxin or toxin moiety.

The drug, e.g. toxin moiety or toxin can be linked or conjugated to the polypeptide using any suitable method. Generally, conjugation is done by covalent attachment to the polypeptide, as known in the art, and generally relies on a linker, often a peptide linkage. For example, the drug, such as toxin moiety or toxin can be covalently bonded to the polypeptide directly or through a suitable linker. Suitable linkers can include non-cleavable or cleavable linkers, for example, pH cleavable linkers that comprise a cleavage site for a cellular enzyme (e.g., cellular esterases, cellular proteases such as cathepsin B, see e.g. examples section). Such cleavable linkers can be used to prepare a ligand that can release a drug, such as a toxin moiety or toxin after the polypeptide is internalized. A variety of methods for linking or conjugating a drug, such as a toxin moiety or toxin to a polypeptide can be used. The particular method selected will depend on the drug, such as a toxin moiety or toxin and polypeptide to be linked or conjugated. If desired, linkers that contain terminal functional groups can be used to link the polypeptide and drug, e.g. a toxin moiety or toxin. Generally, conjugation is accomplished by reacting the drug, e.g. a toxin moiety or toxin that contains a reactive functional group (or is modified to contain a reactive functional group) with a linker or directly with a polypeptide. Covalent bonds formed by reacting a drug, e.g. a toxin moiety or toxin that contains (or is modified to contain) a chemical moiety or functional group that can, under appropriate conditions, react with a second chemical group thereby forming a covalent bond. If desired, a suitable reactive chemical group can be added to polypeptide or to a linker using any suitable method. (See, e.g., Hermanson, G. T., Bioconjugate Techniques, Academic Press: San Diego, Calif. (1996).) Many suitable reactive chemical group combinations are known in the art, for example an amine group can react with an electrophilic group such as tosylate, mesylate, halo (chloro, bromo, fluoro, iodo), N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)).

As described below, the drug of the PDC can be any number of agents, including but not limited to cytostatic agents, cytotoxic agents such as chemotherapeutic agents, growth inhibitory agents, toxins (for example, an enzymatically active toxin of bacterial, fungal, plant, or animal origin, or fragments thereof), toxin moieties, or a radioactive isotope (that is, a radioconjugate) are provided. In other embodiments, the invention further provides methods of using the PDCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Drugs, such as toxins may be used as polypeptides-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of a polypeptide of the invention and one or more small molecule toxins, such as a maytansinoids, dolastatins, auristatins, a trichothecene, calicheamicin, and CC1065, and the derivatives of these toxins that have toxin activity, are contemplated.

Other drugs, such as antitumor agents that can be conjugated to the polypeptides of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Drugs, such as enzymatically active toxins and fragments thereof which can be used include diphtheria A chain, nonbinding active fragments of diphtheria toxin, exotoxin A chain (from *Pseudomonas aeruginosa*), bacterial *Pseudomonas* exotoxin PE38, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates a PDC formed between a polypeptide of the invention and a compound with nucleolytic activity (e.g., a ribonuclease or a DNA endonuclease such as a deoxyribonuclease; DNase).

For selective destruction of the tumor, the polypeptide of the invention may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or 1123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

The generation of polypeptide-drug conjugate compounds can be accomplished by any technique known to the skilled artisan in the field of ADCs. Briefly, the polypeptide-drug conjugate compounds can include polypeptide of the invention as the Antibody unit, a drug, and optionally a linker that joins the drug and the binding agent.

Methods of determining whether a drug or an antibody-drug conjugate exerts an effect, e.g. a cytostatic and/or cytotoxic effect on a cell are known. Generally, the effect, e.g. a cytotoxic or cytostatic activity of an Antibody Drug Conjugate can be measured by: exposing mammalian cells expressing a target protein of the Antibody Drug Conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug Conjugate. These methods are equally applicable to PDCs.

Accordingly the invention relates to a polypeptide of the invention (whether or not comprised in the immunoglobulin construct of the invention) further comprising a drug, such as a toxin or toxin moiety, or an imaging agent. For the sake of clarity, the invention also relates to an immunoglobulin construct (comprising polypeptides of the invention) further comprising a drug, such as a toxin or toxin moiety, or an imaging agent.

The multivalent polypeptides of the invention can generally be prepared by a method which comprises at least the step of suitably linking the immunoglobulin single variable domain and/or monovalent polypeptide of the invention to one or more further immunoglobulin single variable domains and/or monovalent polypeptides of the invention, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more immunoglobulin single variable domains and/or monovalent polypeptides of the invention and for example one or more linkers together in a suitable manner. The immunoglobulin single variable domains and/or monovalent polypeptides of the invention (and linkers) can be coupled by any method known in the art and as further described herein. Preferred techniques include the linking of the nucleic acid sequences that encode the immunoglobulin single variable domains and/or monovalent polypeptides of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

The present invention also relates to the use of an immunoglobulin single variable domain and/or monovalent polypeptide of the invention in preparing a multivalent polypeptide of the invention. The method for the preparation of a multivalent polypeptide will comprise the linking of an immunoglobulin single variable domain and/or monovalent polypeptide of the invention to at least one further immunoglobulin single variable domain and/or monovalent polypeptide of the invention, optionally via one or more linkers. The immunoglobulin single variable domain and/or monovalent polypeptide of the invention is then used as a binding domain or binding unit in providing and/or preparing the multivalent polypeptide comprising two (e.g., in a bivalent polypeptide), three (e.g., in a trivalent polypeptide), four (e.g., in a tetravalent) or more (e.g., in a multivalent polypeptide) binding units. In this respect, the immunoglobulin singe variable domain and/or the monovalent polypeptide of the invention may be used as a binding domain or binding unit in providing and/or preparing a multivalent, such as bivalent, trivalent or tetravalent polypeptide of the invention comprising two, three, four or more binding units.

The present invention also relates to the use of an immunoglobulin single variable domain and/or particularly, a monovalent polypeptide of the invention (as described herein) in preparing a multivalent polypeptide. The method for the preparation of the multivalent polypeptide will comprise the linking of the immunoglobulin single variable domain and/or monovalent polypeptide of the invention to at least one further immunoglobulin single variable domain and/or monovalent polypeptide of the invention, optionally via one or more linkers.

Suitable spacers or linkers for use in multivalent polypeptides of the invention will be clear to the skilled person, and may generally be any linker or spacer used in the art to link amino acid sequences.

Preferably, said linker or spacer is suitable for use in constructing polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_xser_y)_z$, such as (for example $(gly_4ser)_3$ or $(gly_3ser_2)_3$, as described in WO 99/42077, hinge-like regions such as the hinge regions of naturally occurring heavy chain antibodies or similar sequences (such as described in WO 94/04678).

Some other particularly preferred linkers are mentioned in Table A-5.

TABLE A-5

| Linker sequences ("ID" refers to the SEQ ID NO as used herein) | | |
| --- | --- | --- |
| Name | ID | Amino acid sequence |
| 3A linker | 482 | AAA |
| 5GS linker | 483 | GGGGS |

TABLE A-5-continued

Linker sequences ("ID" refers to the SEQ ID NO as used herein)

| Name | ID | Amino acid sequence |
|---|---|---|
| 7GS linker | 484 | SGGSGGS |
| 8GS linker | 485 | GGGGCGGGS |
| 9GS linker | 486 | GGGGSGGGS |
| 10GS linker | 487 | GGGGSGGGGS |
| 15GS linker | 488 | GGGGSGGGGSGGGGS |
| 18GS linker | 489 | GGGGSGGGGSGGGGGGS |
| 20GS linker | 490 | GGGGSGGGGSGGGGSGGGGS |
| 25GS linker | 491 | GGGGSGGGGSGGGGSGGGGSGGGGS |
| 30GS linker | 492 | GGGGSGGGGSGGGGSGGGGSGGGGSGGGGS |
| 35GS linker | 493 | GGGGSGGGGSGGGGSGGGGSGGGGSGGGGSGGGGS |
| 40GS linker | 494 | GGGGSGGGGSGGGGSGGGGSGGGGSGGGGSGGGGSGGGGS |

In an embodiment, the present invention provides a polypeptide as described herein, wherein said at least two ISVDs are directly linked to each other or linked to each other via a linker, preferably the linker is selected from the group of linkers with SEQ ID NOs: 482-494.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is also within the scope of the invention that the linker(s) used confer one or more other favourable properties or functionality to the polypeptides of the invention, and/or provide one or more sites for the formation of derivatives and/or for the attachment of functional groups (e.g., as described herein for the derivatives of the polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:

the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:

isolating and/or purifying the polypeptide of the invention thus obtained.

In particular, such a method may comprise the steps of:

cultivating and/or maintaining a host of the invention under conditions that are such that said host of the invention expresses and/or produces at least one polypeptide of the invention;

optionally followed by:

isolating and/or purifying the polypeptide of the invention thus obtained.

The present invention also relates to a method for the recombinant production of a polypeptide as described herein, comprising (a) culturing the host cell of the invention under conditions which allow the expression of a nucleic acid molecule of the invention; and (b) isolating the polypeptide from the culture.

Accordingly, the present invention also relates to a nucleic acid or nucleotide sequence that encodes a polypeptide of the invention (also referred to as "nucleic acid of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated form, as defined herein. The nucleic acid of the invention may also be in the form of, be present in and/or be part of a vector, such as for example a plasmid, cosmid or YAC, which again may be in essentially isolated form.

In an embodiment, the present invention relates to an expression vector comprising a nucleic acid molecule as described herein.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding an immunoglobulin single variable domain or a monovalent polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

Generally, for pharmaceutical use, the polypeptides, compounds, and/or (immunoglobulin) constructs of the invention may be formulated as a pharmaceutical preparation or composition comprising at least one polypeptide, compound, and/or (immunoglobulin) construct of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc., wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one polypeptide of the invention, at least one compound of the invention, at least one (immunoglobulin) construct of the invention or at least one nucleic acid of the invention and at least one suitable carrier, diluent or excipient (i.e., suitable for pharmaceutical use), and optionally one or more further active substances. In a particular aspect, the invention relates to a pharmaceutical composition that contains at least one of SEQ ID NOs: 1-58, or the CDRs comprised in said SEQ ID NO:s 1-58, or an ISVD comprising at least one of SEQ ID NO:s 117-174, 233-290 or 349-406 (cf. Table A-1) and at least one suitable carrier, diluent or excipient (i.e., suitable for pharmaceutical use), and optionally one or more further active substances.

Generally, the polypeptides, compounds and/or (immunoglobulin) constructs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides, compounds and/or (immunoglobulin) constructs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

Thus, the polypeptides, compounds and/or (immunoglobulin) constructs of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides, compounds and/or (immunoglobulin) constructs of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide, compound and/or (immunoglobulin) construct of the invention. Their percentage in the compositions and preparations may, of course, be varied and may conveniently be between about 2 to about 60% of the weight of a given unit dosage form. The amount of the polypeptide, compound and/or (immunoglobulin) construct of the invention in such therapeutically useful compositions is such that an effective dosage level will be obtained.

The tablets, troches, pills, capsules, and the like may also contain binders, excipients, disintegrating agents, lubricants and sweetening or flavoring agents, for example those mentioned on pages 143-144 of WO08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides, compounds and/or constructs of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides, compounds and/or (immunoglobulin) constructs of the invention may be incorporated into sustained-release preparations and devices.

Preparations and formulations for oral administration may also be provided with an enteric coating that will allow the (immunoglobulin) constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides, compounds and/or (immunoglobulin) constructs of the invention may also be administered intravenously or intraperitoneally by infusion or injection. Particular examples are as further described on pages 144 and 145 of WO 08/020079 or in PCT/EP2010/062975 (entire document).

For topical administration, the polypeptides, compounds and/or constructs of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Useful dosages of the polypeptides, compounds and/or (immunoglobulin) constructs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the polypeptides, compounds and/or (immunoglobulin) constructs of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides, compounds and/or (immunoglobulin) constructs of the invention required for use in treatment will vary not only with the particular polypeptide, compound and/or (immunoglobulin) construct selected but also with the route of administration, the nature of the condition being treated and the age and condition of the patient and will be ultimately at the discretion of the attendant physician or clinician. Also the dosage of the polypeptides, compounds and/or (immunoglobulin) constructs of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration.

Necessary modifications in this dosage range may be determined by one of ordinary skill in the art using only routine experimentation given the teachings herein. The dosage can also be adjusted by the individual physician in the event of any complication.

In an embodiment, the present invention relates to a pharmaceutical composition comprising a polypeptide as described herein or a immunoglobulin construct as described herein.

The invention further relates to applications and uses of the polypeptides, compounds and/or immunoglobulin constructs, nucleic acids, host cells and compositions described herein, as well as to methods for the prevention and/or treatment of CD38 associated diseases, disorders or conditions, such as various cancers and inflammatory diseases. Some preferred but non-limiting applications and uses will become clear from the further description herein.

The polypeptide, compound and/or construct of the invention can generally be used to enhance an immune response. In particular, the polypeptide, compound and/or (immunoglobulin) construct of the invention can enhance CDC activity by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100% compared to the status of CDC activity in the absence of the polypeptide, compound and/or (immunoglobulin) construct of the invention, as determined by a suitable assay, such as those described herein.

In another aspect, the polypeptide, compound and/or (immunoglobulin) construct of the invention can inhibit tumor growth, induce tumor regression, increase progression-free survival and/or extend overall survival in an individual that has a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100% compared to the tumor, progression-free survival and/or overall survival in that individual in the absence of the polypeptide, compound and/or (immunoglobulin) construct of the invention, as determined by a suitable assay, such as those described herein.

In a further aspect, the invention relates to a method for the prevention and/or treatment of at least one CD38 associated disease, disorder or condition, said method comprising administering, to a subject in need thereof, a pharmaceutically active amount of a polypeptide of the invention, of a compound of the invention, of an (immunoglobulin) construct of the invention and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases, disorders and conditions mentioned herein.

The invention relates to a method for the prevention and/or treatment of at least one disease, disorder or condition that is associated with CD38, with its biological or pharmacological activity, and/or with the biological pathways or signaling in which CD38 is involved, said method comprising administering, to a subject in need thereof, a pharmaceutically active amount of a polypeptide of the invention, of a compound of the invention, of a construct of the invention and/or of a pharmaceutical composition comprising the same. In particular, said pharmaceutically effective amount may be an amount that is sufficient to stimulate, enhance or agonize CD38, its biological or pharmacological activity, and/or the biological pathways or signaling in which CD38 is involved; and/or an amount that provides a level of the polypeptide of the invention, of the compound of the invention, and/or of the (immunoglobulin) construct of the invention in the circulation that is sufficient to stimulate, enhance or agonize CD38, its biological or pharmacological activity, and/or the biological pathways or signaling in which CD38 is involved, in particular a CD38 mediated immune response.

The invention also relates to a method for the prevention and/or treatment of at least one disease, disorder and/or condition that can be prevented and/or treated by administering of a polypeptide of the invention, of a compound of the invention and/or of an (immunoglobulin) construct of the invention to a patient, said method comprising administering, to a subject in need thereof, a pharmaceutically active amount of a polypeptide of the invention, of a compound of the invention, of an (immunoglobulin) construct of the invention and/or of a pharmaceutical composition comprising the same.

More in particular, the invention relates to a method for the prevention and/or treatment of at least one disease, disorder and/or condition chosen from the group consisting of the diseases, disorders and conditions listed herein, said method comprising administering, to a subject in need thereof, a pharmaceutically active amount of a polypeptide of the invention, of a compound of the invention, of an (immunoglobulin) construct of the invention and/or of a pharmaceutical composition comprising the same.

The invention also relates to a method for enhancing an immune response, e.g. CDC activity.

The invention also relates to a method for enhancing proliferation or activation of T cells, B cells or natural killer cells.

The invention also relates to a method for inhibiting tumor growth.

The invention also relates to a method for prevention and/or treatment of CD38 mediated diseases, said method comprising administering, to a subject in need thereof, a pharmaceutically active amount of a polypeptide of the invention, of a compound of the invention, of an (immunoglobulin) construct of the invention and/or of a pharmaceutical composition comprising the same.

More in particular, the invention also relates to a method for enhancing an immune response, such as, CDC-activity, ADCC-activity, ADCP-activity, CDCC-activity, proliferation or activation of T cells, B cells or natural killer cells, said method comprising administering, to a subject in need thereof, a pharmaceutically active amount of a polypeptide of the invention, of a compound of the invention, of an (immunoglobulin) construct of the invention and/or of a pharmaceutical composition comprising the same.

The invention also relates to a method for inhibiting tumor growth, said method comprising administering, to a subject in need thereof, a pharmaceutically active amount of a polypeptide of the invention, of a compound of the invention, of an (immunoglobulin) construct of the invention and/or of a pharmaceutical composition comprising the same.

The invention also relates to a method for prevention and/or treatment of cancer, said method comprising administering, to a subject in need thereof, a pharmaceutically active amount of a polypeptide of the invention, of a compound of the invention, of an (immunoglobulin) construct of the invention and/or of a pharmaceutical composition comprising the same.

More in particular, the invention also relates to a method for enhancing proliferation or activation of an immune response, said method comprising administering a pharmaceutically active amount of at least one of SEQ ID NOs: 1-58, or the CDRs comprised in said SEQ ID NO:s 1-58, or an ISVD comprising at least one of SEQ ID NO:s 117-174, 233-290 or 349-406, an (immunoglobulin) construct comprising the same and/or of a pharmaceutical composition comprising the same.

The invention also relates to a method for inhibiting tumor growth, said method comprising administering a pharmaceutically active amount of at least one of SEQ ID NOs: 1-58, or the CDRs comprised in said SEQ ID NO:s 1-58, or an ISVD comprising at least one of SEQ ID NO:s 117-174, 233-290 or 349-406, an (immunoglobulin) construct comprising the same, and/or of a pharmaceutical composition comprising the same.

In an embodiment, the present invention relates to a polypeptide as described herein, an immunoglobulin construct as described herein, and/or the pharmaceutical composition as described herein, for use in a method of therapeutic treatment of a disease which is characterized by increased CD38 expression.

In an embodiment, the present invention relates to a polypeptide as described herein, an immunoglobulin construct as described herein, and/or the pharmaceutical composition as described herein, for use in a method of therapeutic treatment of a hyperproliferative disease or an autoimmune disease.

In an embodiment, the present invention relates to a polypeptide as described herein, an immunoglobulin construct as described herein, and/or the pharmaceutical composition as described herein, for use in a method of therapeutic treatment of Burkitt's lymphoma, T-cell lymphoma, hairy cell leukemia, chronic lymphocytic leukemia (CLL), multiple myeloma, chronic myelogenous leukemia (CML), acute myeloid leukemia (AML), acute lymphoblastic leukemia (ALL), CD38-expressing solid tumor, systemic lupus erythematosus (SLE), rheumatoid arthritis, Crohn's disease, ulcerative colitis, Hashimoto's thyroiditis, ankylosing spondylitis, multiple sclerosis, Graves' disease, Sjögren's syndrome, polymyositis, bullous pemphigoid, glomerulonephritis, vasculitis or asthma, Barraquer-Simons Syndrome, autoimmune heart disease, inflammatory bowel disease, paroxysmal nocturnal hemoglobinuria, atypical hemolytic uremic syndrome and ischemia-reperfusion injuries and rejection of transplanted organs.

In a further embodiment, the invention relates to a method for inhibiting and/or killing of a CD38-expressing cell.

The polypeptides of the present invention are particularly suitable for use in a method for diagnosing a disease that is characterized by an increased expression of CD38. The diagnosis based on the detection of cells or tissues that express amplified CD38. These cells and tissues can be detected by means of suitable markers after binding of the polypeptides of the invention.

Numerous diseases have been described that are associated with an increased expression of CD38. For instance, an increased CD38 expression is demonstrated in certain hyperproliferative diseases, such as in some malignant tumors such as prostate tumors, and in particular also at hematological cancers, such as Non-Hodgkin's lymphoma. Lymphomas, which show increased expression of CD38 on B lymphocytes, may be diagnosed on the basis of this increased expression such as, for example, chronic lymphocytic leukemia (CLL), multiple myeloma, chronic myelogenous leukemia (CML), acute myeloid leukemia (AML) and acute lymphoblastic leukemia (ALL).

In addition to neoplastic diseases, autoimmune diseases and inflammatory diseases are known in which specific cells show increased expression of CD38. These diseases, such as, for instance systemic lupus erythematosus (SLE), rheumatoid arthritis, multiple sclerosis and asthma, can be diagnosed using the antigen-binding polypeptides of the present invention.

Thus, the present invention also relates to a method for diagnosing a disease that is characterized by an increased cellular expression of CD38, which comprises:
(a) contacting a polypeptide of the invention with a biological sample from a patient, under conditions that allow the formation of complexes of the polypeptide and CD38 present in the sample of the patient; and
(b) detecting complexes of the polypeptide and CD38-expressing cells present in the sample of the patient;
wherein the presence of the complexes in step (b) indicates that the patient is suffering from a disease that is characterized by increased CD38 expression.

The disease to be diagnosed is preferably a hyperproliferative disease or an autoimmune disease. It is particularly preferred that the disease is selected from the group consisting of is: Burkitt's lymphoma, T-cell lymphoma, hairy cell leukemia, chronic lymphocytic leukemia (CLL), multiple myeloma, chronic myelogenous leukemia (CML), acute myeloid leukemia (AML), acute lymphoblastic leukemia (ALL), CD38-expressing solid tumor, systemic lupus erythematosus (SLE), rheumatoid arthritis, Crohn's disease, ulcerative colitis, Hashimoto's thyroiditis, ankylosing spondylitis, multiple sclerosis, Graves' disease, Sjögren's syndrome, polymyositis, bullous pemphigoid, glomerulonephritis, vasculitis or asthma, Barraquer-Simons Syndrome, autoimmune heart disease, inflammatory bowel disease, paroxysmal nocturnal hemoglobinuria, atypical hemolytic uremic syndrome and ischemia-reperfusion injuries and rejection of transplanted organs.

In a preferred embodiment of the invention, the method of diagnosis of malignant non-Hodgkin's lymphoma is, preferably multiple myeloma, CLL, CML, AML or ALL.

The biological sample may be a tissue sample from a patient, for example, a tissue specimen from a tumor. It may further also be a sample of body fluid, such as to blood or lymph. The sample can be a blood sample containing B lymphocytes and/or T-lymphocytes. Depending on the disease to be diagnosed it may also be a certain fraction of a body fluid. For instance, the fraction of the patient's blood to be analyzed in a method in diagnosing CLL, CML, AML or ALL, which contains B-lymphocytes.

The number of complexes which can be detected in step (b) in the course of diagnosis is compared with a reference sample, which was analyzed under identical conditions. The reference sample may be derived from a patient, wherein the disease to be detected has been diagnosed, eg Multiple myeloma, CLL, CML, AML or ALL. In this case, a measurement showing an approximately identical number of complexes in the patient sample and the reference sample indicates a high probability that the patient is also diagnosed with the respective disease. Alternatively, the reference sample may be derived from a healthy individual. In this case, when the measured number of the complexes in the patient sample is significantly different, for example, is increased, compared to the reference sample then this measurement indicates a high probability that the patient is also diagnosed with the respective disease.

EXAMPLES

Materials & Methods
Protein Production and Llama Immunizations.

The extracellular domain of a variant of CD38 in which the three potential N-linked glycosylation sites were inactivated was produced as a secretory protein in yeast cells was kindly provided by Hon Cheung Lee, Hong-Kong. Eukaryotic expression vectors for CD38 were kindly provided by Fabio Malavasi, Torino. Two llamas (Lama glama) (designated 10, 25) were immunized subcutaneously with purified recombinant protein emulsified with Specol adjuvant (50 µg in 400 µl total volume) {Boersma, 1992 #85; Koch-Nolte, 2007 #2; Alzogaray, 2011 #1}. Two llamas (designated 538 and 539) were immunized by ballistic cDNA immunization. The humoral immune response was monitored in serially diluted serum by ELISA on microtiter plates (Nunc MaxiSorp, Thermo Fisher Scientific, Waltham, Mass.) coated with recombinant CD38, using monoclonal antibodies directed against llama IgG2 and IgG3 kindly provided by Dr. Judyith Appelton, Cornell University, NY {Daley, 2005 #99}. Animals were bled 10-14 d after the 3rd or 4th boost.

Construction of Phage Display Library and Selection of CD38-Specific Nanobodies.

Mononuclear cells were isolated from 120 ml of blood by Ficoll-Paque™ (GE Healthcare, Chalfont St Giles, UK) gradient centrifugation. RNA purified from these cells by TRIZOL reagent (Invitrogen, Carlsbad, Calif.) was subjected to cDNA synthesis with random hexamer primers. The Nanobody coding region was amplified by PCR with degenerate Nanobody-specific primers. PCR products were purified from agarose gels, digested sequentially with SfiI and NotI (NEB, Ipswich, Mass.) and cloned into the pHEN2 phagemid vector downstream of the PeIB-leader peptide and upstream of the chimeric His6×-Myc epitope tag {Zarebski, 2005 #86; Alzogaray, 2011 #1}. Transformation into XL1-Blue E. coli (Stratagene, La Jolla, Calif.) yielded libraries with sizes of $4.0 \times 10^5$-$10^7$ clones. Phage particles were precipitated with polyethylene glycol from culture supernatants of transformants infected with a 10-fold excess of M13K07 helper phage (GE Healthcare, Chalfont St Giles, UK). Panning of specific phage was performed using either CD38 immobilized on microtiter plates (Nunc MaxiSorp, Thermo Fisher Scientific, Waltham, Mass.) or in solution with CD38-transfected Yac-1 cells. Phage particles ($1.6 \times 10^{14}$) were incubated with CD38 or CD38 transfected cells for 60 min with agitation at room temperature in PBS, 10% Carnation non fat dry milk powder (Nestle, Glendale, Calif.). Following extensive washing, bound phages were eluted from ELISA plates with 50 mM diethylamine and neutralized with 1M Tris-HCl pH 8. Phages were eluted from transfected cells by trypsinization. Eluted phages were titrated and subjected to one or two more rounds of panning, following the same procedure. Phage titres were determined at all steps by infection of TG1 E. coli cells (Stratagene, La Jolla, Calif.). Plasmid DNA was isolated from single colonies and subjected to sequence analyses using pHEN2-specific forward and reverse primers.

Production and Reformatting of Nanobodies

Monomeric Nanobodies were expressed in HB2151 E. coli cells (GE Healthcare, Chalfont St Giles, UK). Protein expression was induced with IPTG (Roche, Rotkreuz, Switzerland) when bacterial cultures had reached an $OD_{600}$ of 0.5 and cells were harvested after further cultivation for 3-4 h at 37° C. Periplasmic lysates were generated by osmotic shock and removal of bacterial debris by high speed centrifugation. Nanobodies were readily purified from E. coli periplasmic lysates by immobilized metal affinity chromatography (IMAC).

The coding region of selected Nanobodies was subcloned using NcoI and NotI into the pCSE2.5 vector {Schirrmann, 2010 #58} (kindly provided by Thomas Schirrmann, Braunschweig). Biparatopic Nanobodies were constructed by PCR using a (G4S)n linker to fuse the two Nanobodies. The Nanobody Fc-fusion format was generated by sub-cloning the coding sequence of one or two Nanobodies joined by a GS-linker upstream of the hinge and Fc-domains of mouse IgG2c or human IgG1 in the pCSE2.5 vector. The Daratumumab scFv-Fc fusion protein was generated by gene synthesis using the published sequence (WO 2011/154453) by fusing the VH domain and the VL domain via a 15G5 linker flanked by NcoI and NotI sites and cloned upstream of the hinge and Fc-domains of mouse IgG2c or human IgG1 in the pCSE2.5 vector.

Recombinant myc-his tagged Nanobodies, Nanobody-Fc fusion proteins, and scFv-Fc fusion proteins were expressed in transiently transfected HEK-6E cells cultivated in serum-free medium. Six days post transfection, supernatants were harvested and cleared by centrifugation. Nanobodies in cell supernatants were quantified by SDS-PAGE and Coomassie staining relative to marker proteins of known quantities: 10 µl samples of the supernatant were size fractionated side by side with standard proteins (albumin 4 µg, IgH 2 µg, IgL 1 µg, lysozyme 0.4 µg; albumin 1 µg, IgH 0.5 µg, IgL 0.25 µg, lysozyme 0.1 µg). Yields of recombinant Nbs typically ranged from 0.5-3 µg/10 µl.

Myc-His tagged Nanobodies were purified by immobilized metal affinity chromatography using Ni-NTA agarose (Sigma, St Louis, Mo.).

Fc-fusion proteins were purified by affinity chromatography using protein G-sepharose (GE-Healthcare).

ELISA

Recombinant CD38 (100 ng/100 µl PBS/well) was adsorbed to 96-well Nunc MaxiSorp plates (Thermo Fisher Scientific, Waltham, Mass.) at 4° C. overnight. Wells were washed twice with PBS and blocked for 2 hours with PBS containing 5% nonfat powdered milk at room temperature. Wells were incubated for 30 min with Nanobody-containing periplasma lysates (diluted 1:10 in PBS). Following washing with PBS/0.05% Tween 20, bound Nanobodies were detected with peroxidase-conjugated anti-c-Myc mAb 9E10 (Sigma, St Louis, Mo.) and (TMB) (Sigma, St Louis, Mo.) as substrate. The absorbance at 450 nm was measured using a Victor3 ELISA-reader (Perkin-Elmer, Waltham, Mass.).

For affinity analyses, wells were incubated for 60 min with serial dilutions of monovalent nanobodies in PBS containing 10 µg/ml BSA. Wells were washed three times with PBS/0.05% Tween 20. Bound antibodies were detected with peroxidase-conjugated anti-c-Myc mAb 9E10 and TMB as substrate.

For epitope analyses, wells were preincubated with excess monovalent nanobodies or nanobody-Fc fusion proteins (500 ng/100 µl PBS, 1% BSA) for 30 min at RT before addition of preconjugated VHH-anti-c-myc and further incubation for 20 min at RT. The absorbance at 450 nm was measured using a Victor3 ELISA-reader (Perkin-Elmer, Waltham, Mass.).

FACS

Untransfected Yac-1 cells and Yac-1 cells stably transfected with human CD38 were incubated for 30 min with Nanobody-containing periplasma lysates (diluted 1:10 in PBS). Following washing with PBS/0.1% BSA, bound Nanobodies were detected with FITC-conjugated anti-c-Myc mAb 9E10 (Sigma, St Louis, Mo.).

For affinity analyses, CD38-transfected cells were incubated for 60 min with serial dilutions of monovalent Nanobodies in PBS/0.1% BSA. Cells were washed three times with PBS/0.1% BSA. Bound antibodies were detected with FITC-conjugated anti-c-Myc mAb 9E10.

For Nb dissociation analyses, two separate aliquots of CD38-transfected cells were incubated either with Cell Proliferation Dye eFluor 450 (eBioscience) or with Alexa648-conjugated Nbs for 20 min at 4° C. Cells were washed four times, mixed at a 1:1 ratio and further incubated at 4° C. for 0, 20, 60, or 180 min before FACS analyses. In some experiments cells were analyzed at 0, 0.5 and 16 h after mixing. The dissociation of Nbs from the target cells and association with the eFluor 450 labeled cells was analyzed using the FlowJo software (Treestar).

For epitope analyses, cells were preincubated with excess monovalent Nanobodies or monoclonal antibodies (2 µg/100 µl PBS/0.1% BSA) for 30 min at RT before addition of fluorochrome-conjugated Nanobodies (500 ng in 0.5 µl PBS) and further incubation for 20 min at RT. Cells were washed and analyzed by flow cytometry on a BD-FACS Canto. Data were analyzed using the FlowJo software (Treestar).

Complement Dependent Cytotoxicity Assays

Myeloma (LP-1) or Burkitt Lymphoma (Daudi, CA46, JijoyeM13) cell lines were preincubated for 10 min at 4° C. with Nb-Fc fusion proteins before addition of human serum (15%) and further incubation for 1 h at 37° C. Cells were washed and resuspended in PBS/0.2% BSA/propidium iodide before FACS analysis.

Bone marrow cells from a myeloma patient were purified by Ficoll density gradient centrifugation and preincubated for 10 min at 4° C. with Nb-Fc fusion proteins before addition of human serum (15%) and further incubation for 1 h at 37° C. Cells were washed and stained for 30 min at 4° C. with fluorochrome-conjugated mAbs against CD45 and CD56 as well as with an appropriate fluorochrome conjugated CD38-specific Nb (for cells treated with Daratumumab-scFv-Fc Nb JK36, for biparatopic 211-10GS-121 Nb-Fc Nb MU523). Cells were then washed and resuspended in PBS/0.2% BSA/propidium iodide before FACS analysis.

Example 1: Induction of CD38-Specific Heavy Chain Antibodies by Immunization

Four llamas were immunized with CD38 for the induction of heavy chain antibodies. In particular, llamas 10 and 25 were immunized and boosted according to various protocols with recombinant human non-glycosylated extracellular domain of CD38 (SEQ ID NO: 465), while other llamas 538, 539 were immunized with a CD38 expression vector (expressing complete sequence), essentially as described previously (Koch-Nolte et al 2007 FASEB J. 21:3490-3498). Each llama received four antigen doses with administration intervals of two weeks. Each dose consisted of 12 shots of plasmid-conjugated gold particles (1 µg of DNA conjugated onto 0.5 mg gold particles per shot) applied with a pressure setting at 600 psi into the skin. Three weeks after the final genetic immunization, a single boost with $2 \times 10^7$ CD38-transfected Hek293 cells was given. At regular intervals, blood samples were collected to monitor the induction of the humoral immune response over time. For the isolation of B-cell tissues, blood was collected from these animals 3 and 9 days after the fourth DNA immunization (PBL1 and PBL2), and 4 and 8 days after the cell boost (PBL3 and PBL4). Peripheral blood mononuclear cells were prepared from blood samples using Ficoll-Hypaque according to the manufacturer's instructions. Immunoglobulin subclasses were purified from the sera of the llamas via protein G and protein A affinity chromatography. First, the immune sera were applied to a protein G-Sepharose column. For the elution of bound IgG protein, the pH values of the buffers were chosen so that fractionation was carried out according to sub-types (25). The heavy chain IgG2c subtype antibodies were eluted at pH 3.5, while the IgG1 antibodies were eluted at pH 2.7 from the column. The fraction, which was not bound to the protein G column, was applied to a protein A column. At pH 4.5 and 2.7 heavy-chain IgG2b subtype antibodies were eluted. The purification of IgG subclasses was checked by SDS-PAGE gel electrophoresis.

The successful induction of humoral immune response and reactivity of the immune sera, as well as the purified IgG subclasses were confirmed by ELISA. Compared to the control antigen EDIN (Enzyme-Toxin from *Staphylococcus aureus*) both immune sera and purified IgG subclasses showed specific reactivity against recombinant human CD38 (data not shown).

Example 2: Selection and Sequence Analysis of CD38-Specific VHHs from Phage Display Libraries of the Immunized Llamas To create a phage display library RNA was isolated from the peripheral blood lymphocytes of llamas after the last injection with the help of the RNeasy Midi Kit (Qiagen GmbH Hilden) and converted into cDNA by reverse transcription. For reverse transcription random hexamers were used, which bind to different positions of the RNA. The cDNA coding for the VHH was amplified by PCR. In short, the PCR-amplified VHH repertoire was cloned via specific restriction sites into a phagemid vector designed to facilitate phage display of the VHH library (pHEN2, including a C-terminal 6HIS and a myc-tag). The ligation products were then transformed into *E. coli* to create a phage library expressing VHH fragments. Phages were prepared according to standard protocols (see for example WO 04/041865, WO 04/041863, WO 04/062551, WO 05/044858 and other prior art and applications filed by Ablynx N.V. cited herein).

DNA sequence analysis from each of 12 randomly selected clones confirmed the successful cloning of a wide VHH repertoire.

Selection of CD38-specific VHH from the immune phage libraries was done using whole cell selections. Non-specific VHHs were removed via negative selection by incubation with $1 \times 10^7$ non-transfected NIH-3T3 cells (ATCC, embryonic connective tissue of *M. musculus*). Two or three rounds of selection were carried out on CD38-transfected NIH-3T3 cells. After each selection round, an enrichment of specific clones was detected by sequencing.

Clones that were found more than once, or where a plurality of clones were found with just a few amino acid substitutions in the CDR regions have been defined as a family.

Example 3: Recombinant Expression of VHH in *E. coli* Cells

Representing VHHs of the above identified families were expressed in *E. coli*. Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein). In essence, the transformed bacterial cells were resuspended in 100 ml 2×YT (BD Difco, Heidelberg) containing 100 µg/ml carbenicillin until the optical density reached 0.5. Protein expression was induced by isopropyl-β-D-thiogalactopyranoside (IPTG), and ended after 3 h by centrifugation of the cells. By osmotic shock the outer cell wall was broken to collect the periplasmatic fraction containing the VHH. The VHHs were purified via the HIS tag by metal ion affinity chromatography. The VHHs were subsequently dialyzed against PBS and after determination of the protein concentration stored at 4° C. SDS-PAGE analysis confirmed the purity, integrity and concentration of the purified VHHs (not shown). The monomeric VHHs were purified with a yield between 0.1 and 10 mg per liter of culture.

Example 4: Analysis of the Binding Specificity of the Selected VHHs by Flow Cytometry 4.1 Binding to CD38-Transfected NIH-3T3 and LP-1 Myeloma Cells The binding specificities of the purified monovalent anti-CD38 VHHs representing the various families were determined by binding to CD38-transfected NIH-3T3 cells and parental cells via flow cytometry. In order to increase the binding strength, the VHHs were pre-incubated with fluorescently labelled antibody directed to the C-terminal c-myc tag at a molar ratio of 1:7 to mimic a bivalent format (anti-c-Myc-FITC, 9E10 AbD Serotec). 1×10⁶ cells were incubated with 1 µg of the fluorochrome-conjugated antibody for 30 min at 4° C. After washing twice, the cells were resuspended in PBS and analysed by flow cytometry on FACS Calibur or FACS Canto (BD Biosciences, Heidelberg). The data evaluation was conducted using the software FlowJo (Treestar, Stanford, US).

28 VHH families showed specific binding to human CD38 with transfected NIH-3T3 mouse fibroblasts, but not to non-transfected cells (data not shown). Dose-dependent binding of selected anti-CD38 VHHs to CD38 was further confirmed by binding to the CD38-expressing LP-1 myeloma cell line (data not shown).

4.2 Binding to Native CD38 on Blood Leukocytes and Human Tumor Cell Lines

Next, purified monovalent anti-CD38 VHH were analysed for binding to native CD38 on the cell surface of peripheral blood leukocytes (PBMCs) by flow cytometry. To this end 50 µl of human blood was incubated for 30 min at RT with serial dilutions of VHHs (ranging 50 ng to 16 pg) with an excess of FITC-labelled anti-c-Myc antibody. To distinguish between NK cells and B lymphocytes that express CD38 strongly, and T lymphocytes which express CD38 weakly, an APC-labelled anti-CD3 antibody was used. After washing the cells and lysis of erythrocytes by lysis buffer, binding was examined by flow cytometry. A VHH specific for toxin B of *Clostridium difficile* (VHH L-14) was used as a negative control. As positive control, a FITC-labelled monoclonal antibody against CD38 (anti-human CD38-FITC, IA10, BD Biosciences) was used. The lymphocytes were defined on forward and side scattered light. Using the FlowJo software the mean fluorescence intensity (MFI) of the CD3-negative cell population was calculated. Background binding of VHH did not exceed the level of CD38 antibody control. The negative control VHH L-14 showed no binding. A titration curve allowed a semi-quantitative statement on the binding affinity of the investigated VHHs (FIG. 2A), where a high MFI indicates a slow dissociation rate and high binding affinity.

Binding of the VHH to B lymphocytes and NK cell subsets within the PBMC pool was further deciphered in multi-colour FACS analysis on freshly isolated PBMCs. A subset of VHHs were conjugated to fluorochrome Alexa-647 using the Alexa Fluor 647 Protein Labeling Kits (Molecular Probes, Eugene, USA) and allowed to bind to 1×10⁶ PBMCs in 0.1 mL PBS supplemented with 0.1% BSA for 30 minutes at 4° C. To distinguish NK cells and plasma cells that express CD38 strongly, cells were counterstained with APC-Cy7-labeled monoclonal antibody against CD16 (3G8) and FITC-labeled monoclonal antibody against CD19 (H1B19). The directly labelled anti-CD38 1A10 antibody served as reference.

Binding results are depicted in FIG. 2B.

The results show staining of CD38 on NK cells and on plasma cells.

4.3 Binding to Soluble CD38

The binding affinities of a selection of purified monovalent anti-CD38 VHHs to soluble, non-glycosylated, recombinant human CD38 were analyzed by micro-scale thermophoresis. The method is based on the principle of thermophoresis, i.e. the directed movement of molecules along a temperature gradient. This is generated by an infrared laser and tracks the movement of the molecules within the gradient by means of fluorescence microscopy and measured. When there is an interaction, the thermophoretic movement of the molecules in solution changes. For the measurements, serial dilutions of the monomeric unlabelled VHHs were incubated with a constant concentration of Alexa 647-conjugated CD38 (12.5 nM and 5 nM) in MST-buffer (25 mM Tris/HCl pH 8, 100 mM NaCl, 0.1% BSA, 0.1% Tween-20, 0.5 mM DTT) for 10 minutes. The batches were analyzed in NanoTemper Monolith NT.115. Changes in the fluorescence values were measured as a percentage change in normalized fluorescence and considered in relation to the VHH concentrations. The dissociation constant $K_D$ was calculated using the GraphPad Prism software from measurement results of two independent tests carried out.

Various VHHs, including MU397 (SEQ ID NO: 33), MU1068 (SEQ ID NO: 34), MU1067 (SEQ ID NO: 49), MU523 (SEQ ID NO: 47), MU274 (SEQ ID NO: 35) showed high affinity binding to CD38 with $K_D$ values in the low nanomolar range (1-6 nM) as shown in Table 4.3A).

TABLE 4.3A

KD values for binding of selected VHHs to CD38, n = 2.

| VHH | Family | Clone | $K_D$ [nM] |
|---|---|---|---|
| MU397 | 12 | L-15.1a | 1 |
| MU1068 | 13 | L-15.1b | 138 |
| MU274 | 13 | L-15.2a | 3 |
| MU523 | 19 | L-19.1a | 3 |
| MU1067 | 20 | L-19.2a | 4.5 |
| MU1053 | 14 | L-15.3 | 6 |
| MU54 | 22 | S-24a | 16 |
| MU415 | 16 | L+15 | 23 |
| MU370 | 5 | L-9.1a | 225 |

In addition, the binding off-rate constants of a large panel of monovalent purified VHH to human CD38 protein were determined by bioluminescence kinetic analysis on Octet RED384 (ForteBio). Direct immobilisation of human CD38 on the AR2G biosensor surface was done in acetate buffer pH 6, and regeneration of analytes was done with 100 nM HCL. Analytes were initially tested at a saturating dose of 1 µM, and for those VHH with very fast on-rates also at 100 nM. As references served the scFv of Daratumamab (Dara scFv), and an irrelevant cAblys3 VHH as negative control. Sensorgrams were fitted using kinetic 1:1 Langmuirian model. Non-specific binding was corrected for in the off-rate analysis by parallel reference sensor subtraction.

Off-rates are depicted in Table 4.3B. Off-rates ranged from $2.2E^3$ to $7.8 E^{-5}$ 1/s, with Daratumumab scFv having an off-rate of 4.4E-03 1/s.

TABLE 4.3B

Off-rates for binding of VHH to immobilised human CD38 protein assessed on Octet BLI.

| VHH | Family | FAMILY | $K_{dis}$ (s-1) |
|---|---|---|---|
| WF9 | 1 | I-8.1b | 2.2E-03 |
| WF32 | 2 | I-8.2f | 2.6E-04 |
| Jk36 | 2 | I-8.2a | 2.0E-04 |
| WF42 | 3 | I-8.3a | 3.8E-04 |
| Jk2 | 4 | I-9.1c | 1.1E-03 |
| MU370 | 5 | I-9.2a | 5.1E-04 |
| Jk29 | 6 | I-9.3b | 1.8E-04 |
| WF14 | 7 | I-12b | 6.3E-03 |
| JK28 | 8 | I-13a | 6.3E-04 |
| WF69 | 9 | S-14b | 2.0E-03 |
| MU738 | 9 | S-14a | 2.9E-03 |
| Jk44 | 10 | I-14.1a | 2.4E-04 |
| Jk22 | 11 | I-14.2b | 3.2E-03 |
| MU1068 | 13 | I-15.1b | 2.1E-04 |
| WF140 | 13 | s-15a | 5.4E-04 |
| MU274 | 13 | I-15.2a | 1.1E-04 |
| MU1053 | 14 | I-15.3a | 9.0E-04 |
| Jk19 | 15 | I-15.4a | 1.1E-04 |
| MU415 | 16 | I+15b | 1.1E-03 |
| WF211 | 17 | s-16a | 4.5E-03 |
| WF121 | 18 | I-17a | <2.3E-04# |
| MU523 | 19 | I-19.1a | 7.8E-05 |
| MU1067 | 20 | I-19.2a | 1.2E-04 |
| WF139 | 21 | s-19b | <2.2E-04# |
| WF124 | 21 | s-19a | <2.5E-04# |
| MU1105 | 22 | I-24a | <3.0E-04# |
| WF114 | 22 | s+/-24b | <1.4E-04# |
| WF100 | 22 | s+/-24d | 5.1E-04 |
| Dara scFv | | | 4.4E-03 | no accurate off-rates could be determined due to sensitivity limits were reached.

4.4 Sequence Analysis

Representative clones that were confirmed for CD38 specific binding were sequenced. The sequences are provided in Table A-3.

Example 5: Different VHH Families Recognize Diverse Epitopes

To evaluate the epitopes on the CD38 protein recognised by the different VHH families, representative purified VHHs of different families were binned against a smaller set of fluorescently labelled VHHs. In particular, a subset of VHHs were conjugated to fluorochrome Alexa-647 using the Alexa Fluor 647 Protein Labeling Kits (Molecular Probes, Eugene, USA), and subsequently used for epitope mapping. In addition, the scFv of Daratumumab was also Alexa-647 labelled and included in the same panel.

5×E5 LP-1 myeloma cells in 100 µl PBS/0.5% BSA were pre-incubated with 5 µg of non-conjugated VHHs for 10 min at RT and further incubated for 30 min at RT with 500 ng of Alexa-647-conjugated VHHs before FACS analyses. A reduction in the FACS signal indicates a competitive binding of the unconjugated VHHs. ART2 specific VHHs served as a negative control, which showed no binding to CD38. Non-conjugated variants of the respective fluorochrome-conjugated VHHs served as positive controls.

The results of the FACS experiments are summarized in Table 5A.

TABLE 5A

Competition of binding of VHHs to CD38+ LP-1 myeloma cells. Cross-blockade analyses with Alexa647-conjugated VHHs for binding to CD38-expressing LP-1 myeloma cells. Numbers indicate % inhibition of fluorochrome binding compared to the competition with an irrelevant VHH.

| EPI-TOPE | VHH | Fam | Clone | % Binding of Alexa467-labelled VHH ||||||||| Dara scFv |
|---|---|---|---|---|---|---|---|---|---|---|---|---|---|
| | | | | WF211 | MU1068 | MU274 | JK2 | MU1067 | MU523 | JK19 | JK36 | WF100 | |
| 1 | MU738 | 9 | S-14a | 64 | 74 | 53 | 8 | 6 | −15 | −8 | 39 | 33 | 87 |
| 1 | Jk22 | 11 | I-14.2b | 97 | 97 | 96 | 23 | 0 | −8 | 29 | 27 | 5 | 99 |
| 1 | JK28 | 8 | I-13a | 94 | 95 | 94 | −10 | 8 | −9 | 96 | 74 | 60 | 99 |
| 1 | WF211 | 17 | s-16a | 97 | 97 | 96 | 12 | 8 | −9 | 52 | 18 | 4 | |
| 1 | MU1053 | 14 | I-15.3a | 94 | 95 | 93 | −11 | 6 | −10 | 38 | 10 | 12 | 98 |
| 1 | MU370 | 5 | I-9.2a | 89 | 86 | 80 | −8 | 5 | −5 | 31 | 24 | 26 | 97 |
| 1 | MU274 | 13 | I-15.2a | 98 | 99 | 99 | −32 | 7 | −7 | 14 | 36 | 45 | 99 |
| 1 | MU1068 | 13 | I-15.1b | 86 | 90 | 81 | 0 | 5 | −7 | 36 | 46 | 35 | 97 |
| 1 | MU415 | 16 | I+15b | 98 | 98 | 98 | 36 | 7 | −11 | 18 | 37 | 47 | 98 |
| 1 | Jk44 | 10 | I-14.1a | 87 | 90 | 83 | 10 | 3 | −13 | −6 | 45 | 28 | 95 |
| 1 | Jk29 | 6 | I-9.3b | 97 | 98 | 98 | 9 | 4 | −4 | 1 | 33 | 36 | 99 |
| 2 | Jk2 | 4 | I-9.1c | −2 | 15 | 3 | 56 | 17 | 16 | 9 | 9 | 20 | −1 |
| 2 | MU523 | 19 | I-19.1a | 30 | 71 | 20 | 99 | 98 | 99 | 8 | 43 | 40 | 99 |
| 2 | MU1067 | 20 | I-19.2a | 31 | 79 | 8 | 99 | 99 | 98 | 34 | 26 | 48 | 99 |
| 3 | WF14 | 7 | I-12b | 16 | 25 | 6 | 26 | 2 | −12 | 69 | 62 | 69 | 32 |
| 3 | WF121 | 18 | I-17a | 71 | 59 | 10 | 16 | 5 | −13 | 99 | 99 | 99 | 99 |
| 3 | WF124 | 21 | s-19a | 88 | 64 | 15 | 22 | 3 | −9 | 97 | 100 | 99 | 99 |
| 3 | WF42 | 3 | I-8.3a | 3 | 23 | 7 | 14 | 4 | −2 | 99 | 99 | 97 | 97 |
| 3 | WF9 | 1 | I-8.1b | −16 | 18 | 5 | 22 | 3 | −13 | 65 | 49 | 66 | −23 |
| 3 | Jk36 | 2 | I-8.2a | −13 | 22 | 16 | 18 | 4 | −13 | 97 | 97 | 96 | −9 |
| 3 | WF100 | 22 | s+/−24d | 9 | 27 | 0 | 52 | 6 | −7 | 88 | 90 | 80 | 46 |
| 3 | Jk19 | 15 | I-15.4a | 12 | 39 | 8 | −35 | 1 | −17 | 97 | 99 | 98 | 86 |

Notably, VHHs with the prefix "Jk" are also indicated by the prefix "jk", "Jko" or "jko" in the present invention.

CD38-specific VHHs essentially bind to three different non-overlapping epitopes, which were tentatively designated "Epitope 1", "Epitope 2" and "Epitope 3". The Daratumumab epitope overlaps with VHH clones of Epitope 1, and part of Epitope 2, and Epitope 3.

VHH families I-9.2a, I-9.2b, I-9.3b, S-14a, I-14.1a, I-14.2b, I-15.1b, I-15.2a, I-15.2b, I-15.3a, s-15a, and s-16a recognize and bind Epitope 1. These families do not compete with representative VHHs of epitope 2 (MU1067, MU523, JK2), or epitope 3 (WF36, WF152, WF100).

VHH families I-9.1c, I-19.1a, I-19.1b, I-19.2a, and I-19.2b) recognize and bind Epitope 2. These families do not compete with representative VHHs of epitope 1 (MU1068, MU274, MU211), nor epitope 3 (WF36, WF152, WF100).

VHH families I-8.1a, I-8.1b, I-8.2a, I-8.2f, I-8.3a, I-12b, I-17a, I-17a, I-17b, I-17c, s-19a, s-19b, s-24a, s+/−24b, s-24c, s+/−24d and I-24a recognize and bind Epitope 3. These families do not compete with representative VHHs of epitope 1 (MU1068, MU274, MU211), nor epitope 2 (MU1067, MU523, JK2).

Table 5B summarizes the epitope binning results.

TABLE 5B

| Epitope 1 | | | | Epitope 2 | | | Epitope 3 | | | |
|---|---|---|---|---|---|---|---|---|---|---|
| VHH | clone ID | Family | Cluster | VHH | clone ID | Family | VHH | clone ID | Family | Cluster |
| WF69 | s-14.1b | 9 | 1.1 | jk12 | I-9.1a | 4 | jk46 | I-12.1 | 7 | 3.1 |
| MU737 | s-14.1c | | | jk14 | I-9.1b | | WF14 | I-12.1 | | |
| MU738 | s-14.1a | | | jk49 | I-9.1a | | WF121 | I-17.1a | 18 | |
| MU727 | s-14.1d | | | jk2 | I-9.1c | | WF127 | I-17.1a | | |
| MU1053 | I-15.3a | 14 | | jk42 | I-9.1d | | WF144 | I-17.1a | | |
| WF211 | s-16.1a | 17 | | MU523 | I-19.1a | 19 | WF129 | I-17.1b | | |
| jk20 | I-13.1a | 8 | | MU1065 | I-19.1b | | WF141 | I-17.1c | | |
| jk28 | I-13.1a | | | MU1067 | I-19.2a | 20 | WF124 | s-19.1a | 21 | |
| jk26 | I-13.1b | | | MU551 | I-19.2b | | WF139 | s-19.1b | | |
| jk27 | s-13.1a | | | | | | WF42 | I-8.3a | 3 | 3.2 |
| jk22 | I-14.2b | 11 | | | | | jk19 | I-15.4 | 15 | |
| jk33 | I-14.2a | | | | | | WF9 | I-8.1b | 1 | |
| jk34 | I-14.2c | | | | | | WF152 | I-8.1a | | |
| jk35 | I-14.2d | | | | | | jk54 | I-8.1a | | |
| MU370 | I-9.2a | 5 | 1.2 | | | | jk30 | I-8.2b | 2 | |
| MU375 | I-9.2b | | | | | | jk31 | I-8.2d | | |
| Jk25 | I-9.3a | 6 | | | | | jk36 | I-8.2a | | |
| jk29 | I-9.3b | | | | | | jk32 | I-8.2e | | |
| MU397 | I-15.1a | 12 | | | | | jk24 | I-8.2c | | |
| WF140 | s-15.1a | 13 | | | | | WF32 | I-8.2f | | |
| MU1068 | I-15.1b | | | | | | MU1103 | s-24.1c | 22 | |
| MU274 | I-15.2a | | | | | | MU725 | s-14.1a | | |
| MU413 | I-15.2b | | | | | | WF100 | s-24.1d | | |
| Jk44 | I-14.1a | 10 | | | | | WF114 | s-24.1b | | |

TABLE 5B-continued

| | Epitope 1 | | | | Epitope 2 | | | Epitope 3 | | |
|---|---|---|---|---|---|---|---|---|---|---|
| VHH | clone ID | Family | Cluster | VHH | clone ID | Family | VHH | clone ID | Family | Cluster |
| MU535 | s+15.1a | 16 | | | | | WF97 | I-24.1a | | |
| MU415 | I-15.1b | | | | | | MU110 | I-24.1a | | |

While VHH can be grouped into three non-overlapping epitope groups based on binding competition on cells, there are competitors and non-competitors of Daratumamab within the groups. This cross-blockade can indicate sterical hindrance due to overlapping epitopes, or due to stabilisation of different conformation of CD38. To further assess simultaneous binding of VHH to CD38, an in-tandem epitope binning analysis was done with 28 monovalent purified anti-CD38 VHHs and Daratumumab scFv as benchmark by bioluminescence analysis on Octet RED384 (ForteBio). Direct immobilisation of human CD38 at 10 μg/mL on the AR2G biosensor surface was done (in acetate buffer pH 6). Regeneration of the CD38 biosensors was performed using 5 regeneration pulses of 5 seconds with 100 nM HCL. VHH were allowed to bind to CD38 at a saturating concentration of 100 nM, while Daratumumab scFv was assessed at 1 μM. Sensorgrams of the association and dissociation of the second analyte were recorded. Binding capture levels were assessed at timeframe of 10 seconds at the end of the loading. Non-hierarchical clustering was done with Ward's method.

Results are summarized in FIG. 11.

The previous identified 3 epitope bins via cross-blockade FACS were confirmed by in-tandem epitope binning. In general, bi-directional blocking was observed within each epitope group. Sub-clusters within each group can be assigned. Within epitope 3, a subgroup was identified comprising of families 3, 7, 18 and 21 that competed with Daratumumab (cluster 3.1). Within epitope group 1, a subgroup comprising of (8, 11, 14 and 17, respectively) competed also a subset of families within cluster 3.1, but not with cluster 3.2 families. Within epitope group 2, family 4 can simultaneously bind with Daratumumab to CD38, whereas the two other families 19 and 20 compete for binding.

While Family 9 is binned within epitope 1, it is also competing with epitope 2 and some epitope 3 families, suggesting that it binds a different conformation of CD38 than the other epitope 1 families. Displacement-like behaviour was observed for VHHs of family 7 and family 9, showing dissociation during the association of the second VHH. Without being bound by any theory, this may indicate that these VHH bind to a different conformation of CD38 than the other VHH families.

The epitopes of different VHHs within epitope 1 and epitope 2 have been determined by co-crystallisation with CD38 protein. Structural information for CD38-MU375 (fam 5, I-9.2, epitope 1), CD38-MU551 (fam 20, I-19.2, epitope 2) and CD38-MU1053 (fam 14, I-15.3, epitope 1), respectively, is available in PDB code 5F21, 5F10 and 5F1K (Li et al. 2016, Scientific reports). All three VHHs are competing with Daratumumab for binding to cells and recombinant protein, suggesting overlapping epitopes. In line with this, Ser274 of CD38, which is described to be important for Daratumumab binding, is part of the footprint on CD38 in each of the two epitope 1 VHHs. Families 5 and 14 are separated in two sub-clusters within epitope 1. This is in line with a partial overlapping footprint.

Example 6: Different Combinations of Nb-Fc Show Potent Complement-Dependent Cytotoxicity (CDC)

Antibody therapy has been proven to be highly powerful for cancer treatment. Two important mechanisms used by antibody drugs to kill targeted tumor cells are Antibody-Dependent Cell-Mediated Cytotoxicity (ADCC), and Complement Dependent Cytotoxicity (CDC). In order to assess the potential CDC activity of the anti-CD38 VHHs, various selected VHHs were generated as genetic fusions with a human Fc-tail (hFc, IgG1) essentially as described in WO2009068630.

6.1 CDC Towards CD38-Expressing Human Tumor Cell Lines

WF211-hFc is based on WF211 (SEQ ID NO: 42; Family s-16a) binding Epitope 1; WF121-hFc is based on WF121 (SEQ ID NO: 43; Family I-17a) binding Epitope 3. As positive control scFv Dara hFc was used. scFv Dara hFc is based on the single chain Fv region of Daratumumab, but in which said Fv region is conjugated similarly to hFc, in order to facilitate a direct comparison with the VHHs of the invention.

For negative controls, comparable Nb-Fc fusion proteins directed against mouse ART2.2 (s+16a hFc) or Toxin B (601) were used.

LP-1 myeloma cells were incubated with 2 μg Fc-fusion proteins in the presence of 20% pooled human serum as a source for complement for 1 h at 37° C. Cell death was determined by the uptake of propidium iodide (PI).

The results are depicted in FIG. 3.

WF121-hFc and WF211-hFc have about the same cytotoxicity as the negative control (s+16a hFc). In contrast, Daratumumab scFv hFc demonstrates an increased CDC-mediated cytotoxicity with about 34% PI positive cells. Unexpectedly, the combination of WF121-hFc and WF211-hFc ("combination"), binding to both Epitope 1 and Epitope 3 demonstrates a clear synergistic cytotoxic activity with about 92% PI positive cells.

6.2 Titration of the Combination Versus the Individual Constructs.

In order to further evaluate the cytotoxic effect of the combination versus the individual Nb-hFc fusion proteins, a titration with different amounts was performed under essentially the same conditions as set out in Example 6.1.

The results are depicted in FIG. 4.

The results corroborate the superior effect of the combination binding to both Epitope 1 and Epitope 3 simultaneously over binding with only one of the individual moieties.

6.3 Combination with Daratumumab in CA46 Human Burkitt's Lymphoma

In order to assess the significance of the different epitopes in relation to the used moieties, the experiment of Example 6.1 was repeated but now with a combination (WF139hFc; SEQ ID NO: 52+WF42hFc; SEQ ID NO: 10), in which both Nanobodies bound to Epitope 3 compared to a combination (WF211hFc; SEQ ID NO: 42+WF42hFc; SEQ ID NO: 10), in which the Nanobodies bound to Epitope 1 and 3, respectively. As controls toxB (601) and Daratumumab hFc (binding to Epitope 1) were used. The cytotoxic effect was tested in CA46 human Burkitt's lymphoma cells.

The results are depicted in FIG. 5.

These results corroborate the finding that a combination, now binders to both Epitope 1 and Epitope 3 of CD38, has a synergistic effect. Moreover, the results demonstrate the general applicability of the cytotoxic effect when binding to two different epitopes in various cancers.

In order to assess whether the finding of binding to two different epitopes on CD38 is more generally applicable, i.e. not limited to the specific format of the binders, the experiment was repeated with different VHHs and Daratumumab hFc.

It was demonstrated that (1) VHHs not competing with Daratumumab, combined with (2) Daratumumab displayed synergy. This combination resulted in a vastly increased cell death for the combination (from 16% of Daratumumab hFc alone to 87% in the combination). In contrast, (1) VHHs competing with Daratumumab, combined with (2) Daratumumab did not display synergy (Table 6.4).

Again, the results demonstrate the general applicability of the cytotoxic effect when binding to two different epitopes in various cancers.

6.4 Combination of Anti-CD38 VHH-Fc with Daratumumab in Daudi Human Burkitt's Lymphoma, Comparison of Daratumumab hFc and Daratumumab H+L.

The combination of Daratumumab scFv-Fc (Daratumumab hFc) with a non-competing VHH-Fc binding to a different epitope showed vastly increased CDC-mediated cell killing. In the next step the inventors set out to test whether VHH-Fc could also synergize with the conventional Daratumumab format, hence the full IgG composed of 2 light chains and two heavy chains (Daratumumab H+L). To this end, the conventional antibody format of Daratumumab was produced by co-transfection of HEK-6E with expression vectors encoding the full length light and heavy chains of Daratumumab. The CDC cytotoxic effects of Daratumumab hFc and Daratumumab H+L alone and in combination with different anti-CD38 VHH-Fc were tested in two different cell lines expressing CD38, CA46 and Daudi human Burkitt lymphoma cells.

The results are depicted in FIG. 12.

Results indicate that anti-CD38 VHH-Fc that recognize a distinct epitope than Daratumumab enhance the CDC of both Daratumumab hFc and Daratumumab H+L, irrespective of the format.

A more extensive analysis of CDC induced by combinations of VHH-Fc was performed using representative VHH-Fc members of epitope 1 (WF211, MU274), epitope 2 (JK2, MU1067), and epitope 3 (JK36, WF100).

The results are depicted in Table 6.4.

The results show that the CDC of both WF211-Fc and MU274-Fc, i.e. two different VHH-Fc members binding to epitope 1, is dramatically enhanced by VHH-Fc binding to either epitope 2 or to epitope 3, but not by other VHH-Fc members binding to epitope 1. In contrast, the CDC of JK2-Fc and MU1067-Fc, i.e. VHH-Fc members binding to epitope 2, is dramatically enhanced by VHH-Fc members binding to epitope 1 or to epitope 3 but not by other VHH-Fc members binding to epitope 2. Further, the CDC of JK36-Fc and of WF100-Fc, i.e. VHH-Fc members binding to epitope 3, is dramatically enhanced by VHH-Fc members binding to epitope 1 or to epitope 2 but not by other VHH-Fc members binding to epitope 3. Finally, the CDC of Daratumumab hFc is dramatically enhanced by a subset of VHH-Fc members (b) binding to epitope 2 or to epitope 3 but not by any VHH-Fc member binding to epitope 1. Together, the results demonstrate the general applicability of the cytotoxic effect when binding to two different epitopes in various cancers.

TABLE 6.4

Combinations of VHH-Fc that bind to non-overlapping epitopes on CD38 dramaticall enhance the CDC of other VHH-Fc and of Daratumumab hFc. Numbers indicate percentages of PI positive CA46 lymphoma cells following 90 minutes incubation in the presence of the indicated combinations of VHH-Fc or Daratumumab-hFc (Dara-Fc) and 20% human serum.

| | | | | Combination with | | | | | | |
|---|---|---|---|---|---|---|---|---|---|---|
| Epitope | ID | Family | Clone | Jk2-Fc | MU1067-Fc | MU211-Fc | WF274-Fc | Jk36-Fc | WF100-Fc | Dara-Fc |
| E2 | Jk2-Fc | 4 | I-9.1c | 5 | 4 | 99 | 100 | 100 | 96 | 68 |
| E2 | MU1067-Fc | 20 | I-19.2a | 4 | 5 | 100 | 99 | 100 | 96 | 71 |
| E2 | MU523-Fc | 19 | I-19.1a | 4 | 5 | 100 | 100 | 100 | 96 | 6 |
| E1 | MU370-Fc | 5 | I-9.2a | 100 | 100 | 1 | 2 | 100 | 97 | 2 |
| E1 | Jk29-Fc | 6 | I-9.3b | 99 | 100 | 1 | 2 | 100 | 97 | 3 |
| E1 | JK28-Fc | 8 | I-13a | 100 | 100 | 2 | 1 | 100 | 53 | 2 |
| E1 | MU738-Fc | 9 | s-14a | 100 | 100 | 2 | 3 | 100 | 97 | 2 |
| E1 | WF69 | 9 | s-14b | 100 | 100 | 1 | 3 | 100 | 97 | 2 |
| E1 | Jk44-Fc | 10 | I-14.1a | 100 | 100 | 3 | 4 | 100 | 98 | 3 |
| E1 | Jk22-Fc | 11 | I-14.2b | 99 | 100 | 2 | 4 | 100 | 90 | 3 |
| E1 | MU1068-Fc | 12 | I-15.1b | 100 | 100 | 1 | 1 | 100 | 96 | 3 |
| E1 | WF140 | 12 | s-15.1c | 100 | 100 | 1 | 1 | 100 | 96 | 3 |
| E1 | MU274-Fc | 13 | I-15.2a | 100 | 100 | 2 | 2 | 100 | 95 | 2 |
| E1 | MU1053-Fc | 14 | I-15.3a | 100 | 100 | 2 | 1 | 100 | 54 | 3 |
| E1 | MU415-Fc | 16 | I+/−5b | 100 | 100 | 2 | 3 | 100 | 96 | 3 |
| E1 | WF211-Fc | 17 | s-16a | 100 | 100 | 3 | 3 | 100 | 37 | 2 |
| E3 | WF9-Fc | 1 | I-8.1b | 100 | 100 | 100 | 100 | 4 | 2 | 83.0 |
| E3 | Jk36-Fc | 2 | I-8.2a | 100 | 100 | 98 | 100 | 4 | 2 | 78.4 |
| E3 | WF32 | 2 | I-8.2f | 100 | 100 | 97 | 100 | 5 | 2 | 81 |
| E3 | WF14-Fc | 7 | I-12b | 81 | 97 | 2 | 100 | 4 | 2 | 64.5 |
| E3 | Jk19-Fc | 15 | I-15.4a | 100 | 100 | 100 | 100 | 5 | 2 | 70.0 |
| E3 | MU1105 | 22 | s-24a | 100 | 100 | 100 | 100 | 4 | 2 | 83.9 |
| E3 | WF100-Fc | 22 | s+/−24d | 100 | 100 | 99 | 100 | 5 | 2 | 89.2 |

TABLE 6.4-continued

Combinations of VHH-Fc that bind to non-overlapping epitopes on CD38 dramaticall
enhance the CDC of other VHH-Fc and of Daratumumab hFc. Numbers indicate percentages of PI
positive CA46 lymphoma cells following 90 minutes incubation in the presence of the indicated
combinations of VHH-Fc or Daratumumab-hFc (Dara-Fc) and 20% human serum.

| | | | | Combination with | | | | | | |
|---|---|---|---|---|---|---|---|---|---|---|
| Epitope | ID | Family | Clone | Jk2-Fc | MU1067-Fc | MU211-Fc | WF274-Fc | Jk36-Fc | WF100-Fc | Dara-Fc |
| E3 | WF114 | 22 | s+/−24b | 100 | 100 | 99 | 100 | 4 | 2 | 72.4 |
| E3 | WF42-Fc | 3 | I-8.3a | 95 | 98 | 99 | 100 | 8 | 2 | 33 |
| E3 | WF124-Fc | 21 | s-19a | 96 | 100 | 50 | 100 | 4 | 2 | 2 |
| E3 | WF121-Fc | 18 | I-17a | 99 | 99 | 99 | 100 | 4 | 2 | 2 |
| E3 | WF139 | 21 | s-19b | 99 | 99 | 100 | 100 | 5 | 2 | 3 |

Example 7: Biparatopic Immunoglobulin Constructs

In view of the surprising results with the combination of binders to Epitope 1 and Epitope 3, the present inventors set out to test biparatopic constructs. Biparatopic constructs have various advantages over the combination of individual moieties, including manufacturability and approval. For instance, obtaining marketing approval for therapeutic use of combinations by authorities necessitates approval and medical dossiers of each individual moiety. On the other hand, biparatopic constructs have the inherent disadvantages that the ratio as well as position of both components is fixed. For instance, in the biparatopic construct the position of an individual binding moiety may influence the binding capacities of the other moiety.

7.1 Biparatopic Constructs have Cytotoxic Activity Towards Myeloma Cells in Primary Bone Marrow Samples.

Similar to Example 6.1, various constructs including a biparatopic immunoglobulin constructs, were tested in cancer cells, but now in primary bone marrow cells derived from myeloma patients.

The construct 211-10GS-121-hFc is based on the same moieties as the combination, i.e. WF211 (SEQ ID NO: 42) and WF121 (SEQ ID NO: 43). These binding moieties were linked via a 10GS linker, followed by the hFc. As positive control, scFv Dara hFc was used. The construct s+16a-hFc was used as negative control.

Fresh bone marrow cells of myeloma patients were incubated with 2 µg Fc-fusion proteins in the presence of 20% pooled human serum as a source for complement for 2 h at 37° C. Cells were then stained with different mAbs at 4° C. and cell death was determined by the uptake of PI staining.

The results are depicted in FIG. 6A.

From the results it can be seen that the biparatopic immunoglobulin construct has slightly less cytotoxic activity than the combination of the two binders against Epitope 1 and Epitope 3. This implies—unexpectedly—that the conformational constraints in the construct, including the position of the individual moieties in the construct, have a limited impact on the cytotoxic activity.

Moreover, the biparatopic immunoglobulin construct is at least 2.5 times more cytotoxic than the benchmark.

In addition, the cytotoxic activities of the biparatopic immunoglobulin constructs were directly compared to Daratumumab in the conventional IgG format. To this end, LP-1 myeloma cells, CA46 Burkitt lymphoma cells and Daudi Burkit lymphoma cells were incubated with 2 µg Fc-fusion proteins or 4 µg Daratumumab H+L in the presence of 20% pooled human serum as a source for complement for 2 h at 37° C., essentially as described above. Cell death was determined by the uptake of PI staining.

The results are depicted in FIG. 6B.

The results confirm the superior cytotoxic activities of the biparatopic immunoglobulin constructs compared to Daratumumab in a range of different cancers.

7.2 Biparatopic Constructs Show High Capacity to Bind Complement Factor C1q.

As set out before, the complement system has a primary function in host defense and clears the body of foreign cells, microorganisms, and cell debris, either by direct lysis or by recruitment of leukocytes that promote phagocytosis and cytotoxicity. It consists of more than 40 plasma and cellular proteins (receptors and regulators). The classical pathway is triggered by the formation of antigen-antibody complexes (immune complexes), which bind the C1 complex, consisting inter alia of C1q.

In order to evaluate the binding of biparatopic immunoglobulin constructs to complement factor C1q LP1 myeloma cells were incubated for 20 min at 4° C. with saturating amounts (2 µg/120 µl) of the indicated Nb-Fc or Nb—Nb-Fc fusion proteins. Cells were washed twice and incubated further with FITC-conjugated C1q for 30 min at 4° C. Cells were washed twice and analyzed by flow cytometry.

The results are depicted in FIG. 7.

It can be seen that Biparatopic immunoglobulin constructs show high capacity to bind complement factor C1q.

7.3 Biparatopic Constructs are More Cytotoxic in Various Different Cancers than Daratumumab In order to evaluate the broad versatility of the concept, the biparatopic immunoglobulin constructs were tested in various cell lines, essentially as set out in Example 7.1.

In this case the immunoglobulin construct 36-35GS-1067-hFc was used, which was based on JK36 (SEQ ID NO: 31), binding to epitope 3, and MU1067 (SEQ ID NO: 49), binding to epitope 2.

These binding moieties were linked via a 35GS linker linker, followed by the hFc. As positive control scFv Dara hFc was used. The construct s+16a-hFc was used as negative control.

LP-1 myeloma cells, CA46 Burkitt lymphoma cells and Daudi Burkit lymphoma cells were incubated with 2 µg Fc-fusion proteins in the presence of 20% pooled human serum as a source for complement for 2 h at 37° C., essentially as described above. Cells were then stained with different mAbs at 4° C. and cell death was determined by the uptake of PI staining.

The results are depicted in FIG. 8.

From the results it can be seen that the biparatopic immunoglobulin construct is cytotoxic in a range of different cancers. Moreover, the immunoglobulin biparatopic construct is in all cases more efficacious, i.e. displays a higher cytotoxic activity, than the benchmark.

7.4 Biparatopic Constructs with Epitope 2 Binders are Superior Over Other Combinations As noted in Example 5, the binding to CD38 of the different Nb families could be assigned to three different non-overlapping epitopes, i.e. Epitope 1, Epitope 2 and Epitope 3. In order to assess whether the combination of the different epitopes has an effect on efficacy, an experiment was set up to evaluate all combinations in comparison to Daratumumab hFc. Biparatopic immunoglobulin constructs were generated from VHHs representative for a specific Epitope. The VHHs were linked by GS linkers and C-terminally conjugated to a human Fc tail:

Biparatopic Combinations:

| Combination name | | based on SEQ ID NO: s |
|---|---|---|
| E1 + E3 | [WF211]-41GS-[WF121]-hFc | [42] + [43] |
| E2 + E1 | [MU1067]-35GS-[MU1068]-hFc | [49] + [34] |
| E3 + E2 | [JK36]-34GS-[MU1067]-hFc | [4] + [49] |

The different biparatopic immunoglobulin constructs were tested for cytotoxic activity in a CA46 Burkitt lymphoma cell line, essentially as described in Example 6.3.

The results are depicted in FIG. 9.

From the results it can be seen that any biparatopic combination of anti-CD38 VHH having different epitopes is more cytotoxic than the benchmark. Surprisingly, a combination comprising binders to Epitope 2 are more efficacious than a combination without these binders.

Example 8: ISVDs Discriminate Excellently of CD38-Positive Tumors In Vivo

In view of the binding results it was set out whether the specific CD38 ISVDs could bind to CD38 in an in vivo setting, and could be used as imaging agents to detect CD38-positive tumors in vivo.

A two-sided tumor model was used in which stable CD38-transfected DC27.10 mouse lymphoma cells and non-transfected DC27.10 cells were injected subcutaneously in the left and right flanks of Nude mice. Seven days after tumor implantation, mice received 50 µg of monovalent VHH conjugated to the near-infrared fluorescent Alexa-680 dye, AF680-MU1067 (family 20, I-19.2a, epitope 2) injected into the tail vein. Real-life tissue distribution in mice and in tissues was monitored by an intravital imaging system (IVIS200) up to 48 hours. Total radiant efficiency was determined with Living Image 4.2 software (Caliper Life Sciences). Tumor-to-background ratio was calculated by dividing the tumor uptake value by the back-ground value determined from the hind limb.

The results are depicted in FIG. 10.

AF680-labelled VHH detect CD38-expressing tumors in vivo, while no signals are seen in CD38-negative tumors or normal tissues. It can be seen that the anti-CD38 ISVDs provide excellent discrimination of CD38-expressing tumors in vivo.

Example 9: Anti-CD38 VHH Modulate the GDPR Cyclase Activity of CD38

Next the inventors examined whether monovalent purified anti-CD38 VHH could interfere with the enzymatic activity of CD38. CD38 catalyzes the synthesis of cyclic GDP-ribose (cGDPR) from nicotinamide guanine dinucleotide (NGD). Synthesis of cGDPR can be monitored conveniently by fluorimetry (Deckert et al. 2014 Clin. Canc. Res. 20:4574-83).

Briefly, CD38-catalyzed conversion of NGD to cyclic GDP-ribose was monitored over time by fluorimetry (with excitation and emission wavelengths of 300 nm and 410 nm, respectively). Recombinant extracellular domain of CD38 (aa 44-300, 5 nM) was preincubated for 15 minutes with monovalent VHH at a concentration between 0.4-400 nM for 15 minutes at RT in reaction buffer in black 96 well plates before addition of NGD (Sigma) to a final concentration of 80 µM. Independent assays were performed with triplicate wells. Readings from wells without CD38 were used as background and substracted from all readings. EX300/EX410 readings were plotted in relative fluorescence units (RFU) vs. time. Percent GDPR production was calculated relative to control samples in the absence of Nb (RFU of sample/RFU of control sample×100).

Results are shown in FIG. 13 (panel A and B).

VHHs of all three families recognising epitope 2, i.e. families 4, 19, and 20 (I-9.1, I-19.1a, I-19.2a) inhibited the conversion of NGD to cGDPR by CD38 in a dose dependent manner (FIG. 13A), with MU1067 being the most potent VHH (FIG. 13B). Several other VHHs also antagonised enzyme activity in part, i.e. family 14 (MU1053) and 11 (JK22) from epitope 1 and family 2 (JK36) and 15 (JK19) from epitope 3. Epitope 2 VHHs were the most potent antagonists of the GDPR cyclase activity of CD38. In contrast, two VHHs of family 9 (MU537, s-14, epitope 1) and family 7 (WF14, I-12b, epitope 3) potentiated the CD38-catalyzed synthesis of cGDPR (FIG. 13A).

Next the inventors set out to determine the effects of combinations of anti-CD38 VHHs with non-overlapping epitopes on the GDPR cyclase activity of CD38. VHHs were mixed at 1:1 ratio and serial dilutions were subsequently analysed in the same enzymatic activity assay. exhibit synergistic inhibitory or potentiating effects The results are depicted in FIG. 14.

The results indicate that the combination of two non-overlapping inhibiting VHH, family 4 (JK2, I-9.1a, epitope 2) together with family 2 (JK36, I-8.2a, epitope 3) synergize to inhibit the enzyme activity of CD38, hence showing cooperativity. The inhibition of the most potent epitope 2 VHH MU1067 (family 20, I-19.2a) was not further improved by addition of JK36, suggesting that maximum inhibition was already reached by this VHH alone.

Synergy was also observed when combining two different potentiating VHH, family 9 (MU738, s-14a) and family 7 (WF14, I-12b) in enhancement of the enzyme activity of CD38, indicating cooperativity. Interestingly, displacement behaviour (dissociation during the association) was observed for family 7 WF14 when family 9 VHH WF69 or MU738 were already bound to CD38, suggesting that these VHH bind to distinct conformations of CD38.

Together these results indicate that targeting of two non-overlapping epitopes on CD38 also has an synergy effect on GDPR cyclase activity of CD38 until maximum inhibition.

Example 10: ADCC of Anti-CD38 VHH-Fc

To assess the capacity of anti-CD38 VHH-Fc constructs to mediate antibody-dependent cell-mediated cytotoxicity (ADCC), a microplate assay was used up to measure loss of luciferase activity from luciferase-transfected target cells as an indicator of cell death. Hereto $5 \times 10^4$ luciferase-transfected CA46 Burkitt lymphoma cells that express CD38 were incubated with serial dilutions of VHH-Fc constructs or Daratumumab full IgG (H+L) for 10 minutes at 4° C. As effector cells, CD16-transfected NK92 cells were added at an effector to target cell ratio of 3:1 and cells were further incubated for 3 hours at 37° C. Cells were pelleted by centrifugation and resuspended in 0.1 mL PBS before addition of luciferin at a final concentration of 750 µg/ml and further incubation for 10 minutes at RT. Luciferase activity was measured on a microplate reader (Victor).

The results are depicted in FIG. 15

The results show that the biparatopic VVH-Fc JK36-15GS-MU1067-Fc (E3-E2) and WF211-10GS-WF121-Fc mediate ADCC of CA46 cells more effectively than Daratumumab in the scFv-Fc (hc) and full IgG (H+L) formats, reaching a maximal lysis of 85% for 35-15GS-1067-Fc and 211-10GS-121-Fc vs. 60% for Daratumumab hc and 65% for Daratumumab H+L.

Example 11: In Vivo Efficacy of VHH-Fc in Comparison to Daratumumab in Human CD38+ CA-46 Tumor Xenograft Model A systemic human xenograft model in C.B-17 SCID mice was used to test the therapeutic efficacy of biparatopic VHH-Fc in comparison to Daratumumab. One week after intravenous injection of luciferase-transfected CA46 cells, growth of tumors was detected 15 minutes after intravenous injection of luciferin by an intravital imaging system (IVIS200). Animals (n=5 per group) then received weekly intraperitoneal injections of biparatopic WF211-10GS-WF121-Fc (E1-E3), an irrelevant VHH-Fc, or Daratumumab scFv-Fc (Daratumumab hc) at a dose of 2 mg/kg (50 µg total/mouse) starting on day 7, i.e. after engraftment of tumors had been verified by IVIS. Injections were continued until d49 for a total of 6 injections (total 300 µg/mouse). Tumor growth was monitored every 7 days by imaging analysis after injection of luciferin.

The tumor growth and the overall survival results are depicted in FIG. 16.

The results show that the biparatopic CD38 VHH-Fc WF211-10GS-WF121-Fc inhibits the tumor growth to a similar extent as Daratumumab hc. In addition, treatment extended the survival, with 50% of the mice in the control group surviving up to 50 days, while 50% of the mice treated with Daratumumab hc survived until day 85 and 50% of the mice treated with 211-10GS-121-Fc survived until day 105.

This data indicate that biparatopic VHH-Fc constructs have therapeutic efficacy towards CD38-positive tumors and improve survival.

Example 12: Epitope Bins

In view of the above results of the ISVDs, the present inventors were able to refine the epitope bins. Each of the epitope 1 bin, epitope 2 bin and epitope 3 bin can be divided into two main subclusters:
(i) epitope 1.1 (E1.1) and epitope 1.2 (E1.2): both epitope 1.1 ISVDs and epitope 1.2 ISVDs compete with Daratumumab.
(ii) epitope 2.1 (E2.1) and epitope 2.2 (E2.2): epitope 2.1 ISVDs do not compete with Daratumumab, while epitope 2.2 ISVDs do compete with Daratumumab.
(ii) epitope 3.1 (E3.1) and epitope 3.2 (E3.2): epitope 3.2 ISVDs do not compete with Daratumumab, while epitope 3.1 ISVDs do compete with Daratumumab.

A venn-diagram summarizing the results is provided as FIG. 17.

These binning suggest that families in E3.2 can more broadly used as partner than E3.1 families as they combine with all epitope 1 ISVDs and epitope 2 ISVDs as well as Daratumumab.

BIBLIOGRAPHY (1) Liu et al. (2006), J Biol Chem 281(43):32861-9
(2) Liu et al. (2005), Structure, 13(9):1331-9
(3) Perraud et al. (2001), Nature, 411(6837):595-9
(4) Young et al. (2006), Biochem Biophys Res Commun, 346(1): 188-92
(5) Howard et al. (1993), Science, 262(5136):1056-9
(6) Koch-Nolte et al. (2006), Ann Med, 38(3):188-99
(7) Deaglio et al. (2000), Chem Immunol, 75:99-120
(8) Deaglio et al. (2008), Trends Mol Med, 14(5):210-18
(9) Mallone et al. (1998), J Clin Invest, 101(12):2821-30
(10) Roussanov et al. (2000), AIDS, 14(17):2715-22
(11) US 2009/0304710 A1
(12) US 2002/0164788 A1
(13) U.S. Pat. No. 8,088,896
(25) Hamers-Casterman, et al. (1993), Nature, 363(6428): 446-448
(27) Wienken, et al. (2010), Nat Commun 1:100
(28) Jerabek-Willemsen, et al. (2011), Assay Drug Dev Technol, 9(4):342-353

TABLE A-1

| Seq | fw1 | Seq | cdr1 | Seq | fw2 | Seq | cdr2 | Seq | fw3 | Seq | cdr3 | Seq | fw4 |
|---|---|---|---|---|---|---|---|---|---|---|---|---|---|
| 59 | QVQLQESGGGLVQPG GSLRLRLSCGAT | 177 | GIFSIN DMG | 175 | WYRQAPGK QRELVA | 233 | EITRGGS TN | 291 | YADSVKGRFTISRDNAKNTVLQMNSL NPEDTAVYYCNA | 349 | AHTFSGSF | 407 | WGQGTQ VTVSS |
| 60 | QVQLQESGGGLVQPG GSLRLSCGAT | 178 | GIIFSIN DMG | 176 | WYRQAPGK QRELVA | 234 | EITRGGS TN | 292 | YADSVKGRFTISRDNAKNTVLQMNSL NPEDTAVYYCNA | 350 | AHTFSGSF | 408 | WGQGTQ VTVSS |
| 61 | QVKLQESGGGLVQPG GSLRLSCGAT | 179 | GIIFSIN DMG | 177 | WYRQAPGK QRELVA | 235 | EITRGGS TN | 293 | YADSVKGRFTISRDNAKNTVVLQMNSL NPEDTAVYYCNA | 351 | AHTFSGSF | 409 | WGQGTQ VTVSS |
| 62 | QVQLQESGGGLVQPG GSLRLSCAAS | 180 | GIILRIY DMG | 178 | WYRQAPGK QRELVA | 236 | AITSRGS TN | 294 | YADSVKGRFTISRDNAENTVSLQMNSL KPGDTAVYYCNA | 352 | DHTFAGVY | 410 | WGQGTQ VTVSS |
| 63 | QVQLQESGGGLVQPG GSLRLSCAAS | 181 | GIILRIY DMG | 179 | WYRQAPGK QRELVA | 237 | AITSGGR TN | 295 | YADSVKGRFTISRDNAENTVSLQMNSL KSGDTAVYYCNA | 353 | DHTFAGVY | 411 | WGQGTQ VTVSS |
| 64 | QVQLQESGGGLVQPG GSLRLSCAAS | 182 | GIILRIY DMG | 180 | WYRQAPGK QRELVA | 238 | EITSGGS TN | 296 | YADSVKGRFTISRDNAENTVSLQMNSL KPGDTAVYYCNA | 354 | HHTFAGAY | 412 | WGQGTQ VTVSS |
| 65 | QVQLQESGGGLVQPG GSLRLSCAAS | 183 | GIILRLY DMG | 181 | WYRQTPGK QRELVA | 239 | EITSGGS TN | 297 | YADSVKGRFTISRDNAENTVSLQMNSL KSGDTAVYYCNA | 355 | DHTFAGVY | 413 | WGQGTQ VTVSS |
| 66 | QVQLQESGGGLVQPG GSLRLSCAAS | 184 | GSTLRLY DMG | 182 | WYRQADGK QRELVA | 240 | EITSGGS TN | 298 | YANSVKGRFTISRDNAENTVSLQMNSL KPEDTAVYYCNA | 356 | EHTFMGAY | 414 | WGQGTQ VTVSS |
| 67 | QVQLQESGGGLVQAG GSLRLSCAAS | 185 | GIILRIY DMG | 183 | WYRQAPGK QRELVA | 241 | AITSGGS TN | 299 | YASVKGRFTISRDNAKSMVLQMNSL KPEDTAVYYCNA | 357 | WHVFRGNY | 415 | WGQGTQ VTVSS |
| 68 | QVQLQESGGGLVQAG GSLTLSCAAS | 186 | RNTDSIE IMG | 184 | WYRQAPGK QREWVA | 242 | TINTGGN TG | 300 | YADSVKGRFAISRDNAKNTVYYCTA | 358 | VIRTYSTY | 416 | WGQGTQ VTVSS |
| 69 | QVQLQESGGGLVQPG GSLRLSCVAS | 187 | ERIFSRN TMG | 185 | WYRQAPGK QRELVA | 243 | RIASLGI TN | 301 | YADSVKGRFTISSDNAKNTVLQMNNL KPEDTAVYYCNY | 359 | WHYAAGRDY | 417 | WGQGTQ VTVSS |
| 70 | EVQLVESGGGLVQAG GSLRLSCVAS | 188 | ERIFSRN TMG | 186 | WYRQAPGK QRELVA | 244 | RIASLGI TN | 302 | YADSVKGRFTISSDNAKNTVVLQMNNL KPEDTAVYYCNY | 360 | WHYAAGRDY | 418 | WGQGTQ VTVSS |
| 71 | QVQLQESGGGLVQPG GSLRLSCVGS | 189 | ERIFSRN TMG | 187 | WYRQAPGK QRELVG | 245 | YVGSMGI TN | 303 | YADSVKGRFTISSDNAKNTVLQMNNL KPEDTAVYYCNY | 361 | WHYAAGRDY | 419 | WGQGTQ VTVSS |

TABLE A-1-continued

| Seq | fw1 | Seq | cdr1 | Seq | fw2 | Seq | cdr2 | Seq | fw3 | Seq | cdr3 | Seq | fw4 |
|---|---|---|---|---|---|---|---|---|---|---|---|---|---|
| 72 | QVKLQESGGGLVQPG GSLRLSCVAS | 130 | ERIFSRN TMG | 188 | WYRQAPGK QRELVA | 246 | YITSLGI AN | 304 | YADSVKGRFTISSDNAKNTVYLQMNNL KSEDTAVYNCNY | 362 | WHYAAGRDY | 420 | WGQGTQ VTVSS |
| 73 | DVQLQASGGGSVQAG GSLTLSCRYS | 131 | GGFVFRV SSMG | 189 | WYRQAPGN QRELIA | 247 | TITVGGK TN | 305 | YKDSVQGRFIISRNDTTVTLQMNRLQP EDTAVYYCNL | 363 | ASTAVGADT | 421 | WGQGTR VTVSS |
| 74 | DVQLQESGGGSVQAG GSLTLSCTAS | 132 | GLLFRLA SMG | 190 | WYRQAPGK ERELIA | 248 | TITVGGK TN | 306 | YKDSVQGRFIITRDNTGDNTKSTVTLQ MNRLKPEDTAVYYCNT | 364 | ASPAVGADT | 422 | WGQGTR VTVSS |
| 75 | QVKLQESGGGLVQPG GSLRLSCVAS | 133 | GSISSII TMG | 191 | WYRQAPGK QREFVA | 249 | RVIIGGS TG | 307 | YADSVKGRFTISRDNTKNTVVLEMNSL KPEDTAVYYCNA | 365 | GNPGTSYHY | 423 | WGQGTQ VTVSS |
| 76 | QVQLQESGGGLVQAG GSLRLSCAAS | 134 | GSISNII TMG | 192 | WYRQAPGK QREFVA | 250 | RIIIGGS TG | 308 | YSDSVKGRFTISRDNTGNTWYLQMNSL KPEDTAVYYCNA | 366 | GNPGTRYIY | 424 | WGQGTQ VTVSS |
| 77 | QVQLQESGGGLVQAG GSLRLSCAAS | 135 | GRTFSSV AMG | 193 | WFRQAPGK EREFVA | 251 | TINWSGG RTT | 309 | YADSVKGRFTISRDSAKNTVVLQMNSL KPEDTAVYYCAA | 367 | DRFSVVAVEYDY | 425 | WGQGTQ VTVSS |
| 78 | EVQLVESGGGLVQAG GSLRLSCAAS | 136 | GRTFSSV AMG | 194 | WFRQAPGR EREFVA | 252 | TINWSGG RTT | 310 | YADSVKGRFTISRDSAKNTVVLQMNSL KPEDTAVYYCAA | 368 | DRFSVVAVEYDY | 426 | WGQGTQ VTVSS |
| 79 | QVQLQESGGGLVQAG GSLRLSCAIS | 137 | GRTFIAD MG | 195 | WFRQAPGK EREFQA | 253 | GITWFGG STY | 311 | YADSVKGRFTISRDNTKNTLYLQMNSL KPEDTAIYYCAA | 369 | GLKRIGDQREADY | 427 | WGQGTQ VTVSS |
| 80 | EVQLVESGGGLVQAG GSLRLSCAIS | 138 | GRTF MG | 196 | WFRQAPGK EREFQA | 254 | GITWFGG STY | 312 | YADSVKGRFTISRDNTKNTLYLQMNSL KPEDTAIYYCAA | 370 | GLKRIGDQREADY | 428 | WGQGTQ VTVAS |
| 81 | QVQLQESGGGLVQAG GSVRLSCAIS | 139 | GRTFTNY MG | 197 | WFRQAPGK EREFQA | 255 | GITWFGG STY | 313 | YADSVKGRFTISRDNTKNTLYLQMNSL KPEDTAIYYCAA | 371 | GLKRIGDQREADY | 429 | WGQGTQ VTVSS |
| 82 | DVQLQASGGGLVQAG GSLRLSCAGS | 140 | GRTFTNY DMG | 198 | WFRQAPGK ERRFVA | 256 | AISGSGG SAR | 314 | YAVPVKGRFTITRDNAKNTVYLQMSSL KPEDTAVYYCAA | 372 | DRFVVAAGTHDLDY | 430 | WGQGTQ VTVSS |
| 83 | DVQLQESGGGLVQAG GSLRLSCAGS | 141 | GRTFTNY DMG | 199 | WFRQAPGK ERRFVA | 257 | AISGSGG SAR | 315 | YAVPVKGRFTITRDNAKNTVYLQMSSL KPEDTAVYYCAA | 373 | DRFVVAAGTHDLDY | 431 | WGQGTQ VTVSS |

TABLE A-1-continued

| Seq | fw1 | Seq | cdr1 | Seq | fw2 | Seq | cdr2 | Seq | fw3 | Seq | cdr3 | Seq | fw4 |
|---|---|---|---|---|---|---|---|---|---|---|---|---|---|
| 84 | DVQLQASGGGLVQAG GSLRLSCAGS | 142 | GRSFSSY AMG | 200 | WFRQAPGK AREIVA | 258 | TITRSGG STN | 316 | YAVPVKGRFTISRDNAKNTVLQMSSL KPEDTAVYYCAA | 374 | DRPAVASGTHDLDY | 432 | WGQGTQ VTVSS |
| 85 | DVQLQASGGGLVQAG GSLRLSCAGS | 143 | GRTFSSY AMG | 201 | WFRQAPGK EREFVA | 259 | SISWSGS RTN | 317 | YGVPVKGRFTISRDNAKNTVLQMSSL KPEDTAVYYCAA | 375 | DRPAVAIGTHDLDY | 433 | WGQGTQ VTVSS |
| 86 | QVQLQESGGGLVQAG GSLRLSCAAS | 144 | GRTDTRY TMG | 202 | WFRQAPGK EREFVS | 260 | GITWNGG TS | 318 | YADSVKGRFTISRDNGKNSVVLQMNSL KPEDTAVYYCAA | 376 | DRFTLVPTTSDLDY | 434 | WGQGTQ VTVSS |
| 87 | QVQLQESGGRLVQPG GSLRLSCAAS | 145 | GRTLSNY AMA | 203 | WFRQGPGK EREFVA | 261 | SISASDS TL | 319 | YADFVKGRFTISRDNAKNTVVLQMDSL KPEDTAVYYCAA | 377 | RFWIGVRAPAEYNY | 435 | WGQGTQ VTVSS |
| 88 | QVKLQESGGRLVQPG GSLRLSCAAS | 146 | GRTLSNY AMA | 204 | WFRQGPGK EREFVA | 262 | SISASDS TL | 320 | YADFVKGRFTISRDNAKNTVVLQMDSL KPEDTTVYYCAA | 378 | RFWIGVRAPAEYNY | 436 | WGQGTQ VTVSS |
| 89 | QVKLQESGGRLVQPG GSLRLSCAAS | 147 | GRTFSNY AMA | 205 | WFRQGPGK EREFVA | 263 | AISAADS TL | 321 | YADFVKGRFTISRDNAKNTVVLQMNSL KPEDTTVYYCAA | 379 | RWWIAVRAPAEYNY | 437 | WGQGTQ VTVSS |
| 90 | QVQLQESGGGLVQPG GSLRLSCAAS | 148 | GRTFSNY AMA | 206 | WFRQGPGK EREFVA | 264 | AISAADS TL | 322 | YADFVKGRFTISRDNAKNTVVLQMNSL KPEDTAVYYCAA | 380 | RWWIAVRAPAEYNY | 438 | WGQGTQ VTVSS |
| 91 | DVQLQASGGGLVQAG GSLRLSCAPS | 149 | GGTFDAY DMG | 207 | WYREAPGK KRQFVA | 265 | AVRSGGG TTR | 323 | YADSVKGRFTISRDDAKDTVFLQMNSL KPEDTALYYCAA | 381 | DRWGLFSLSIATPTH | 439 | WGQGTQ VTVSS |
| 92 | DVQLQASGGGSVQEG ESLKLSCVGS | 150 | GRTFSDW AMG | 208 | WYRQAPGK DREFVA | 266 | AVSGAGR GGKPS | 324 | YANSVKGRFTVSRDNAKNTVLQMDNL KPEDTAVYYCA | 382 | DRLVLIVALSIADPGF | 440 | WGQGTR VTVSS |
| 93 | DVQLQESGGGLVQAG GSLRLSCAAS | 151 | GVSFSRY TMG | 209 | WYREVPGK ERREFV | 267 | AAVRPSG DSTY | 325 | YGNSVKGRFSISRDDKNIVVLQMNSL KPEDTAVYYCAA | 383 | GFPVLIVALSIADPDY | 441 | WGQGTQ VTVST |
| 94 | DVQLQASGGGLVQTG DSLITVSCAAS | 152 | GLSFTRY TMG | 210 | WYREVPGK ERREFV | 268 | AAVKPAG DSAY | 326 | YGASVKGRFTASRDNAKNTVTLQMNSL KPEDTAIYYCAA | 384 | GFPVLTALHIADPPY | 442 | WGQGTQ VTVSP |
| 95 | DVQLQESGGGLVQAG GSLRLSCTGS | 153 | GRTFRNY PMA | 211 | WFRQAPGK EREFVA | 269 | GITWVGA STL | 327 | YADFAKGRFTISRDNAKNTVYSCAA KPEDTAVYSCAA | 385 | GRGIVAGRIPAEYAD | 443 | WGQGTQ VTVSS |

TABLE A-1-continued

| Seq | fw1 | Seq | cdr1 | Seq | fw2 | Seq | cdr2 | Seq | fw3 | Seq | cdr3 | Seq | fw4 |
|---|---|---|---|---|---|---|---|---|---|---|---|---|---|
| 96 | QVQLQESGGGLVQAGGSLRLSCAAS | 154 | GRTFVSFGMG | 212 | WFRQAPGKEREFVA | 270 | AINWRGSTTA | 328 | YADSVKGRFTISRDVTKNTIYLQMNSLKPEDTAIYYCAE | 386 | GRTASASTMIREYDS | 444 | WGQGTQVTVSE |
| 97 | DVQLQASGGGSVQAGGSLRLSCAAS | 155 | GLSFSDYAMG | 213 | WFRQBPGKERRFVA | 271 | SIRSSGGTT | 329 | YAESVKGRFTISRDNAKNTMYLQMNSLKPEDTAVYYCAA | 387 | DRLVITKLSIADPGY | 445 | WGQGTQVTVSS |
| 98 | VQLQASGGGLVQAGSLRLSCTVS | 156 | GFTSDDYTVG | 214 | WFRQAPGLKREGLS | 272 | CLSRRDGRFY | 330 | HSNSVKGRFTMXSDDXKNTVVLQLDSLKPDXTAVXYYCAA | 388 | CTSVVVLLAPNWYEY | 446 | WGQGTQVTVSS |
| 99 | VQLQASGGGLVQAGSLRLSCTVS | 157 | GFTSDDYTVG | 215 | WFRQAPGLKREGLS | 273 | CLSRRDGRFY | 331 | HSNSVKGRFTMSSDDNKNTVVLQLDSLKPDDTAVYYCAA | 389 | TTSVVVLLAPNWYEY | 447 | WGQGTQVTVSS |
| 100 | EVQLVESGGGLVQAGESLRLSCAAS | 158 | GRTFTNLGMG | 216 | WFRQAPGKEREFVA | 274 | ADTWSGTSTW | 332 | YGDSVKGRFTISRDNAKNTVVLQMNNLKPEDTAVYYCAA | 390 | RLRGWITRKPNEYDY | 448 | WGQGTQVTVAS |
| 101 | DVQLQESGGGLVQAGDSLRLSCEFS | 159 | GRTFSGFAMG | 217 | WFRQPPGKEREFVA | 275 | AINWSGSDTD | 333 | YSDSVKGRFTISRDNVKQMMYLAMNSLKPEDTAVYFCAA | 391 | ARSAGLGSSRRIEGYDK | 449 | WGRGTQVTVSS |
| 102 | DVQLQASGGGLVQAGDSLRLSCEFS | 160 | GRTFSGFAMG | 218 | WFRQPPGKEREFVA | 276 | AINWSGSDTD | 334 | YSDSVKGRFTISRDNVKQMMYLAMNSLKPEDTAVYFCAA | 392 | ARSAGLGSSRRIEGYDK | 450 | WGRGTQVTVSS |
| 103 | DVQLQASGGGLVQAGGSLRLSCAAS | 161 | GRTFSGFAMG | 219 | WFRQPPGKEREFVA | 277 | AINWSGSSVD | 335 | YSDSVKGRFTISRDNVKSTMYLVMNSLKPEDTAVYYCAE | 393 | ARSAELGSSRKIQGYDQ | 451 | WGRGTQVTVSS |
| 104 | DVQLQASGGGLVQAGGSLRLSCEFS | 162 | GRTFSGFAMG | 220 | WFRQPPGKEREFVA | 278 | AINWSGSSVD | 336 | YSDSVKGRFTISRDNVKSTMLVMNSLKPEDTAVYYCAE | 394 | ARSAELGSSRKIQGYDQ | 452 | WGRGTRVTVSS |
| 105 | DVQLQESGGGLVQAGSSLRISCAVS | 163 | GVRLDNYAMG | 221 | WFRQAPGKERESVA | 279 | GISWSSGTLL | 337 | YSDSVKGRFAISRDNAKNTVLQMNSLKPEDTAVYYCAA | 395 | QYQDRYYDEFTWKEKDMDY | 453 | WGKGTLVTVSS |
| 106 | DVQLQESGGGLVQAGDSLRLSCAAS | 164 | GPHFNNYAIG | 222 | WFRQAPGKEREFVA | 280 | GISWSSGSLL | 338 | YSDSVKGRFTISRDNDKNTAYLQMNSLKPEDTALYYCAA | 396 | QYQERYYSDFSLKEKGMEY | 454 | WGKGTLVTVSS |
| 107 | DVQLQESGGGLVQGSDSLRLSCVGS | 165 | GRRFDNYAMA | 223 | WFRQAPGKERTFVA | 281 | AISWSSSTTR | 339 | YLDTVKGRFTISRDNAKSTVVLQMNSLKPEDTAVYYCAA | 397 | RYQPRYDSGDMDGYEYEF | 455 | WGQGTQVTVSS |

TABLE A-1-continued

| Seq | fw1 | Seq | cdr1 | Seq | fw2 | Seq | cdr2 | Seq | fw3 | Seq | cdr3 | Seq | fw4 |
|---|---|---|---|---|---|---|---|---|---|---|---|---|---|
| 108 | DVQLQESGGGLVQAG HSLRLSCVGS | 166 | GSRFDNY AMG | 224 | WFRQAPGK EREFVA | 282 | AISWSSG TTR | 340 | YLDTVKGRFTISRDNAKSTVVLQMNSL KPEDTAVYYCAA | 398 | RYQPRYDSGDMDGY EYDN | 456 | WGQGTQ VTVSS |
| 109 | DVQLQASGGGLVQAG GSQRLSCAAS | 167 | GHTFSSY SMA | 225 | WFRQAPGK EREFVA | 283 | ANSMSGT KTA | 341 | YSDSVKGRFTISRDIPKNTVLQMNSL KPEDTALYYCAA | 399 | VDRSTGWDSWRDDPD QYDY | 457 | WDQGTQ VTVSS |
| 110 | SGGGLVQAGGSQRLS CAAS | 168 | GHTFSSY SMA | 226 | WFRQAPGK EREFVA | 284 | ANIMSGT NTY | 342 | YADSVRGRFTMSRDIAKNTVVLQMNSL KEEDTALYYCAA | 400 | ADRPRGWATWRDDPD QYDY | 458 | WDQGTQ VTVSS |
| 111 | DVQLQESGGGLVQAG GSLRLSCAAS | 169 | GFTFDDY VIG | 227 | WFRQAPGK EREGVS | 285 | SISNNNS TY | 343 | YADSVKGRFTIASDNAKNTVVLQMNSL KPEDTAVYYCAA | 401 | DVTLNPFTGWNTRSG PMYRYEYDY | 459 | WGQGTQ VTVSS |
| 112 | VQLQESGGGLVQAGG SLRLSCAAS | 170 | GFTFDDY VIG | 228 | WFRQAPGK ECEGVS | 286 | SISNNNS TY | 344 | YADSVKGRFTIASDNAKNTVVLQMNSL KPEDTAVYYCAA | 402 | DVTLNPFTGWNTRSG PMYRYEYDY | 460 | WGQGTQ VTVSS |
| 113 | DVQLQASGGGLVQAG GSLRLSCAAS | 171 | EFTFDDY VIG | 229 | WFRQAPGK EREGVS | 287 | SISSDGS TY | 345 | YADSVKGRFTISSDNAKNTVVLHMNSL KPEDTAVYYCAA | 403 | DVTLNPFTGWTTRSG PMYRYEYDY | 461 | WGQGTQ VTVSS |
| 114 | VQLQASGGGLVQAGG SLRLSCAAS | 172 | GFTFDDY VIG | 230 | WFRQSPGK EREGVS | 288 | CISSAGS TY | 346 | YADSVKGRFTISSDNAKNMVVLQMDNL KPEDTAVYYCAA | 404 | DVTLNPFTGWDTRSG PMYRYEYDY | 462 | WGQGTQ VTVSS |
| 115 | DVQLQASGGGLVQAG GSLRLSCAAS | 173 | GFTFDDY VIG | 231 | WFRQAPGK EREGVS | 289 | SISSSGS IY | 347 | YADSVKGRFTISSDNAKNTVVLQMNSL KPEDTAVYYCAA | 405 | DVTLNPFTGWDTRSG PMYRYEYDY | 463 | WGQGTQ VTVSS |
| 116 | DVQLQASGGGLVQAG GSLRLSCAAS | 174 | GFTFDDY VIG | 232 | WFRQAPGK EREGVS | 290 | SISSSGS IY | 348 | YADSVKGRFTISSDNAKNTVVLQMNSL KPEDTAVYFCAA | 406 | DVTLNPFTGWDTRSG PMYRYEYDY | 464 | WGQGTQ VTVSS |

Seq: SEQ ID NO
fw: Framework
cdr: Complementary Determining Region

TABLE A-2

```
              10         20         30         40         50         60         70         80         90        100        110        120        130
              |          |          |          |          |          |          |          |          |          |          |          |          |
Jk25    QVKLQESGGGLVQPGGSLRLSCVAS-GSISSIITMGWVRQAPGKQREFVA-RVIIGGSTG--YADSVKGRPTISRDNTKN---TVYLEMNSLKPEDTAVYYCNA----------GNPGTSYHY-
Jk29    ..Q...........................N.............................................G----N.W..Q..............................R.I---
MU725   D.Q.................A..........FTFDDVI..F.........E..G.S-SISNNN..Y-------................AS..A.............Q..A.DVTLNPFTGWNTRSG.MYR.E.DY
WF114   -.Q.................A..........FTFDDVI..F.........EC.G.S-SISNNN..Y-------................AS..A.............Q..A.DVTLNPFTGWNTRSG.MYR.E.DY
MU1103  D.Q..A..............A.........-EFTFDDVI..F.........E..G.S-SISSD...Y-------................S..A.............Q..A.DVTLNPFTGWTTRSG.MYR.E.DY
WF100   -.Q..A..............A...........FTFDDVI..F.S.......E..G.S-CISSA...Y-------................S..A.............H..A.DVTLNPFTGWDTRSG.MYR.E.DY
MU1105  D.Q.................A...........FTFDDVI..F.........E..G.S-SISSS..IY-------................S..A-----M--Q.DN....A.DVTLNPFTGWDTRSG.MYR.E.DY
WF97    ....................A...........FTFDDVI..F.........E..G.S-SISSS..IY-------................S..A.............Q...F.A.DVTLNPFTGWDTRSG.MYR.E.DY
Jk33    ..Q.................A..........R................RTL.NYA.A.F.G.....E............SISASD..L..........F.........Q.D......A.------RFWIGVRAPAE.N.---
Jk22    ....................A..........R................RTL.NYA.A.F.G.....E............SISASD..L..........F.........Q.D...T..A.------RFWIGVRAPAE.N.---
Jk35    ..Q.................A..........R................RTF.NYA.A.F.G.....E............AISAAD..L..........F.........Q......T..A.------RWWIAVRAPAE.N.---
Jk34    ....................A..........R................RTF.NYA.A.F.G.....E............AISAAD..L..........F.........Q.........A.------RWWIAVRAPAE.N.---
WF124   D.Q.................A..........HTF.SYS.A.F........E............ANSMS.TKTA...S.......IP......Q.........A.---------VDRSTGWDSWRDDPDQ.D.--
WF139   -...................A..Q.......HTF.SYS.A.F........E.............AN.MS.TNTY---.R..M..IA.............Q......E..L..A.------ADRFRGWATWRDDPDQ.D.--
WF211   E.Q.V...............AE..........RTFTNLG..F........E............ADTWS.TSTW---G.......A...............Q.N.........A.------RLRGWITTRK-PNE.D.---
MU535   -.Q..A...............A.........TV..FT.DDY.V..F.....LK..GLS-CLSRRDGRFY--HSN.........MXS.DX.........QLD...DX..X..A.---------CTSVVLLAPNW.E.---
MU415   -.Q..A...............A.........TV..FT.DDY.V..F.....LK..GLS-CLSRRDGRFY--HSN.........M.S.DN..........QLD.....D.......A.------TTSVVLLAPNW.E.---
WF152   ..Q.................A...........G.T-.I.F.ND........L.--EITR....N.........................A...........Q..N..........A.--------------AHTFSGSF-
Jk54    ..Q.................A...........G.T-.I.F.ND........L.--EITR....N.........................A...........Q..N..........A.--------------AHTFSGSF-
WF9     ..Q.................A...........G.T-.I.F.ND........L.--EITR....N.........................A...........Q..N..........A.--------------AHTFSGSF-
Jk36    ..Q.................A...........A....I.LR.YD.......L.--AITSR...N........................AE...........S.Q......G....A.--------------DHTFAGVY-
Jk30    ....................A...........A....I.LR.YD.......L.--AITS.R.N........................AE...........S.Q.....SG....A.--------------DHTFAGVY-
Jk31    ..Q.................A...........A....I.LRLYD.......L.--AITS...N........................AE...........S.Q.....SG....A.--------------DHTFAGVY-
Jk24    ..Q.................A...........A....I.LR.YD.T.....L.--EITS...N........................AE...........S.Q......G....A.--------------HHTFAGAY-
Jk32    ....................A..........TLRLYD...D..........L.--EITS...N........................AE...........S.Q...........A.--------------EHTFMGAY-
WF32    ..Q.................A...........A....I.LR.YD.......L.--AITS...N.............N.............A.S---M...Q...........A.--------------WHVFRGNY-
```

TABLE A-2-continued

```
JK12    .Q.............................-ER.F.RN........L...-IASL.I.N---.....S.A..............Q.N.------Y----------WHYAAGRD.--
JK14    E.Q.V..........A...............-ER.F.RN........L...-IASL.I.N---.....S.A..............Q.N.------Y----------WHYAAGRD.--
Jk2     .Q.............................G.-ER.F.RN......L.G-Y.GSM.I.N---...S.A..............Q.N.------Y----------WHYAAGRD.--
JK42    ..........................T.RY.G.FVFRVSS.......L...-YITSL.IAN---...S.A..............Q.N.S----N.Y----------WHYAAGRD.--
MU370   D.Q..A......S..A....T..........N..LI.-TITV.K.N---K..Q..I..ND...........T.Q.R.Q.---L----------ASTAVGADT---
MU375   D.Q..A......S..A....T..T..-.LLFRLAS...........E..LI.-TITV.K.N---K..Q..I.T........T.Q..R.-----T----------AS.AVGADT---
MU1053  D.Q..A.............TG..-.RTFRNYP.A.F..........E.....-GITWV.ASTL..-FA...........GDNTKS.T.Q..R.----S.A.---------GRGIVAGRI.AEYAD---
WF42    .Q.............A.....T..A..-.RNTD..EI.........W...-TINT.N.....................A........Q.H.-----T-----------VIRT.STY.-
JK19    .Q.............A...............A..-.RTFVSPG...F......E...-AINWR...TA............V.......-I..Q.-----I..AE------GRTASASTMIRE.DS--
WF121   D.Q..A.D...........EF.-.RTF.GPA....F.F.........E...-AINWS.DTD--S...V.Q---MM..A.........F.AE------ARSAGLGSSRRIEG.DK--
WF144   D.Q..A.D...........EF.-.RTF.GPA....F.F.........E...-AINWS.DTD--S...V.Q---MM..A.........F.AE------ARSAGLGSSRRIEG.DK--
WF129   D.Q..A.............EF.-.RTF.GFA....F.F.........E...-AINWS..SVD--S...V.S-----M..V........AE------ARSAELGSSRKIQG.DQ--
WF141   D.Q..A.............EF.-.RTF.GFA....F.F.........E...-AINWS..SVD--S...V.S-----M..V........AE------ARSAELGSSRKIQG.DQ--
MU523   D.Q..A.S...I.AV.-.VRLDNYA.....F.........E.S..-GISWSSG.LL--S.........A...........A------QYQDRYDEFTWKEKDMDY
MU1065  D.Q..A.D...........-.PHFNNYAI.....F.........E.....-GISWSGSLL---S..............D...........A.Q.----L..A------QYQERYYSDFSLKEKGMEY
MU1067  D.Q..A.D.........G..-.RRFDNYA.A.F...........E.T..-AISWSSG.TR--L.T.....A.S................Q.-------A------RYQPRYDSGDMDG.E.EF
MU551   D.Q..A.H............G..-.RFDNYA.....F...........E...-AISWSSG.TR--L.T.....A.S................Q.-------A------RYQPRYDSGDMDG.E.DN
Jk46    .Q.............A..................-.RTF.SVA.....F........E.....-TINWS.GRTT--.............SA................Q.-------A------DRFSVVAVEYD.---
WF14    E.Q.V..A..................-.RTF.SVA.....F..........RE.....-TINWS.GRTT--.............SA................Q.-------A------DRFSVVAVEYD.---
MU738   D.Q..A.............AG.-.RTFTNYD...F..........E.R..-AISGS.GSAR--.VP.........T..A................Q.S.-------A------DRFVVAAGTHDLD.---
WF69    D.Q..A.............AG.-.RTFTNYD...F..........E.R..-AISGS.GSAR--.VP.........T..A................Q.S.-------A------DRFVVAAGTHDLD.---
MU737   D.Q..A.............AG.-.RSF.SYA....F.........A..I.-TITRS.GSTN--.VPA...........A................Q.S.-------A------DRFAVASGTHDLD.---
MU727   D.Q..A.............AG.-.RTF.SYA....F.........E.....-SISWS..RTN--.GVP...........A................Q.S.-------A------DRFAVAIGTHDLD.---
Jk44    .Q.............A..................-.RTDTRY.....F.........E...-GITWN.G..S-...............G...........Q.-------A------DRFTLVPTTSDLL.---
MU1068  D.Q..A...S..E.E..K...G.-.RTF.DWA..................D.....-A.SGA.RG.KPS..N.........V.............Q.DN.-----A------DRLVLVALSTADPGF-
WF140   D.Q..A...S..A......A..-.LSF.DYA.....F..E...E.R...-SIRSS.G.T----E................A.......M..Q..Q.-------A------DRLVITKLSIADPGY-
```

TABLE A-2-continued

| | | | |
|---|---|---|---|
| MU274 | D.Q......A.......A..-VSF.RY......EV..E.REFVAAVRPS.D..Y---.GN.....S....DD.---I...Q.------GPPVLVALSTADPDY- |
| MU413 | D.Q..A....T.D.TV.A...LSFTRY......EV..E.REFVAAVKPA.D.AY---.GA....A...A......A.---T.Q.------GPPVLTALHIADPDY- |
| MU397 | D.Q..A.........AP..GTFDAYD....E...KQ.---A.RS.G.TR---........DA.D---...F.Q.------DRWGLFSLSIATPTH- |
| Jk20 | .Q..........A..--GRTF.AD....F......E..Q.--GITWF.GSTY-..................A.---L.Q.------GLKRIGDQREAD.-- |
| Jk27 | E.Q.V.......A..--GRTF.AD....F......E..Q.--GITWF.GSTY-..................A.---L.Q.------GLKRIGDQREAD.-- |
| Jk26 | .Q.........A..V.--GRTF.ND..F......E..Q.--GITWF.GSTY-..................A.---L.Q.------GLKRIGDQREAD.-- |

| | |
|---|---|
| | 140 |
| | ---:---:--- |
| Jk25 | -WGQGTQVTVSS |
| Jk29 | ............ |
| MU725 | ............ |
| WF114 | ............ |
| MU1103 | ............ |
| WF100 | ............ |
| MU1105 | ............ |
| WF97 | ............ |
| Jk33 | ............ |
| Jk22 | ............ |
| Jk35 | ............ |
| Jk34 | ............ |
| WF124 | .D.......... |
| WF139 | .D.......... |
| WF211 | ....A....... |
| MU535 | ............ |
| MU415 | ............ |
| WF152 | ............ |
| Jk54 | ............ |
| WF9 | ............ |

TABLE A-2-continued

| | |
|---|---|
| Jk36 | . . . . . . . . . . . . . . . |
| Jk30 | . . . . . . . . . . . . . . . |
| Jk31 | . . . . . . . . . . . . . . . |
| Jk24 | . . . . . . . . . . . . . . . |
| Jk32 | . . . . . . . . . . . . . . . |
| WF32 | . . . . . . . . . . . . . . . |
| JK12 | . . . . . . . . . . . . . . . |
| Jk14 | . . . . . . . . . . . . . . . |
| Jk2 | . . . . . . . . . . . . . . . |
| Jk42 | . . . . . . . . R . . . . . . |
| MU370 | . . . . . . R . . . . . . . . |
| MU375 | . . . . . . . . . . . . . . . |
| MU1053 | . . . . . . . . . . . . . . . |
| WF42 | . . . . . . . . . . . . . E . |
| Jk19 | . . . . . R . . . . . . . . . |
| WF121 | . . . . . R . . . . . . . . . |
| WF144 | . . . . . R . . . . . . . . . |
| WF129 | . . . . R . R . . . . . . . . |
| WF141 | . . . . K . L . . . . . . . . |
| MU523 | . . . . K . L . . . . . . . . |
| MU1065 | . . . . . . . . . . . . . . . |
| MU1067 | . . . . . . . . . . . . . . . |
| MU551 | . . . . . . . . . . . . . . . |
| Jk46 | . . . . . . . . . . . . . . . |
| WF14 | . . . . . . . . . . . . . . . |
| MU738 | . . . . . . . . . . . . . . . |

TABLE A-2-continued

| | |
|---|---|
| WF69 | . . . . . . . . . . . . . |
| MU737 | . . . . . . . . . . . . . |
| MU727 | . . . . . . . . . . . . . |
| Jk44 | . . . . . . . . . . . . . |
| MU1068 | . . . . . R . . . . . . |
| WF140 | . . . . . . . . . . . . . |
| MU274 | . . . . . . . . . . T |
| MU413 | . . . . . . . . . . P |
| MU397 | . . . . . . . . . . . . . |
| Jk20 | . . . . . . . . . . . . . |
| Jk27 | . . . . . . . . . A . |
| Jk26 | . . . . . . . . . . . . . |

TABLE A-3

| SEQ ID NO | NAME | AMINO ACID SEQUENCE |
|---|---|---|
| 1 | WF152 | QVQLQESGGGLVQPGGSLRLSCGATGIIFSINDMGWYRQAPGKQRELVAEITRGGSTNYADSVKGRFTISRDNAKNTVYLQMNSLNPEDTAVYYCNAAHTFSGSFWGQGTQVTVSS |
| 2 | Jk54 | QVQLQESGGGLVQPGGSLRLSCGATGIIFSINDMGWYRQAPGKQRELVAEITRGGSTNYADSVKGRFTISRDNAKNTVYLQMNSLNPEDTAVYYCNAAHTFSGSFWGQGTQVTVSS |
| 3 | WF9 | QVKLQESGGGLVQPGGSLRLSCGATGIIFSINDMGWYRQAPGKQRELVAEITRGGSTNYADSVKGRFTISRDNAKNTVYLQMNSLNPEDTAVYYCNAAHTFSGSFWGQGTQVTVSS |
| 4 | Jk36 | QVQLQESGGGLVQPGGSLRLSCAASGIILRIYDMGWYRQAPGKQRELVAAITSRGSTNYADSVKGRFTISRDNAENTVSLQMNSLKPGDTAVYYCNADHTFAGVYWGQGTQVTVSS |
| 5 | Jk30 | QVQLQESGGGLVQPGGSLRLSCAASGIILRIYDMGWYRQAPGKQRELVAAITSGGRTNYADSVKGRFTISRDNAENTVSLQMNSLKSGDTAVYYCNADHTFAGVYWGQGTQVTVSS |
| 6 | Jk24 | QVQLQESGGGLVQPGGSLRLSCAASGIILRIYDMGWYRQAPGKQRELVAEITSGGSTNYADSVKGRFTISRDNAENTVSLQMNSLKPGDTAVYYCNAHHTFAGAYWGQGTQVTVSS |
| 7 | Jk31 | QVQLQESGGGLVQPGGSLRLSCAASGIILRLYDMGWYRQTPGKQRELVAEITSGGSTNYADSVKGRFTISRDNAENTVSLQMNSLKSGDTAVYYCNADHTFAGVYWGQGTQVTVSS |
| 8 | Jk32 | QVQLQESGGGLVQPGGSLRLSCAASGSTLRLYDMGWYRQADGKQRELVAEITSGGSTNYANSVKGRFTISRDNAENTVSLQMNSLKPEDTAVYYCNAEHTFMGAYWGQGTQVTVSS |
| 9 | WF32 | QVQLQESGGGLVQAGGSLRLSCAASGIILRIYDMGWYRQAPGKQRELVAAITSGGSTNYADSVKGRFTISRDNAKSMVYLQMNSLKPEDTAVYYCNAWHVFRGNYWGQGTQVTVSS |
| 10 | WF42 | QVQLQESGGGLVQAGGSLTLSCAASRNTDSIEIMGWYRQAPGKQREWVATINTGGNTGYADSVKGRFAISRDNAKNTVYLQMHSLKPEDTAVYCTAVIRTYSTYWGQGTQVTVSS |
| 11 | JK12 | QVQLQESGGGLVQPGGSLRLSCVASERIFSRNTMGWYRQAPGKQRELVARIASLGITNYADSVKGRFTISSDNAKNTVYLQMNNLKPEDTAVYYCNYWHYAAGRDYWGQGTQVTVSS |
| 12 | Jk14 | EVQLVESGGGLVQAGGSLRLSCVASERIFSRNTMGWYRQAPGKQRELVARIASLGITNYADSVKGRFTISSDNAKNTVYLQMNNLKPEDTAVYYCNYWHYAAGRDYWGQGTQVTVSS |
| 13 | Jk2 | QVQLQESGGGLVQPGGSLRLSCVGSERIFSRNTMGWYRQAPGKQRELVGYVGSMGITNYADSVKGRFTISSDNAKNTVYLQMNNLKPEDTAVYYCNYWHYAAGRDYWGQGTQVTVSS |
| 14 | Jk42 | QVKLQESGGGLVQPGGSLRLSCVASERIFSRNTMGWYRQAPGKQRELVAYITSLGIANYADSVKGRFTISSDNAKNTVYLQMNNLKSEDTAVYNCNYWHYAAGRDYWGQGTQVTVSS |
| 15 | MU370 | DVQLQASGGGSVQAGGSLTLSCRYSGGFVFRVSSMGWYRQAPGNQRELIATITVGGKTNYKDSVQGRFIISRNDTTVTLQMNRLQPEDTAVYYCNLASTAVGADTWGQGTRVTVSS |
| 16 | MU375 | DVQLQESGGGSVQAGGSLTLSCTASGLLFRLASMGWYRQAPGKERELIATITVGGKTNYKDSVQGRFIITRDNTGDNTKSTVTLQMNRLKPEDTAVYYCNTASPAVGADTWGQGTRVTVSS |
| 17 | Jk25 | QVKLQESGGGLVQPGGSLRLSCVASGSISSIITMGWYRQAPGKQREFVARVIIGGSTGYADSVKGRFTISRDNTKNTVYLEMNSLKPEDTAVYYCNAGNPGTSYHYWGQGTQVTVSS |
| 18 | Jk29 | QVQLQESGGGLVQPGGSLRLSCVASGSISNIITMGWYRQAPGKQREFVARIIIGGSTGYSDSVKGRFTISRDNTGNTWYLQMNSLKPEDTAVYYCNAGNPGTRYIYWGQGTQVTVSS |
| 19 | Jk46 | QVQLQESGGGLVQAGGSLRLSCAASGRTFSSVAMGWFRQAPGKEREFVATINWSGGRTTYADSVKGRFTISRDSAKNTVYLQMNSLKPEDTAVYYCAADRFSVVAVEYDYWGQGTQVTVSS |
| 20 | WF14 | EVQLVESGGGLVQAGGSLRLSCAASGRTFSSVAMGWFRQAPGREREFVATINWSGGRTTYADSVKGRFTISRDSAKNTVYLQMNSLKPEDTAVYYCAADRFSVVAVEYDYWGQGTQVTVSS |
| 21 | Jk20 | QVQLQESGGGLVQAGGSLRLSCAISGRTFIADMGWFRQAPGKEREFQAGITWFGGSTYYADSVKGRFTISRDNTKNTLYLQMNSLKPEDTAIYYCAAGLKRIGDQREADYWGQGTQVTVSS |
| 22 | Jk27 | EVQLVESGGGLVQAGGSLRLSCAISGRTFIADMGWFRQAPGKEREFQAGITWFGGSTYYADSVKGRFTISRDNTKNTLYLQMNSLKPEDTAIYYCAAGLKRIGDQREADYWGQGTQVTVAS |
| 23 | Jk26 | QVQLQESGGGLVQAGGSVRLSCAISGRTFINDMGWFRQAPGKEREFQAGITWFGGSTYYADSVKGRFTISRDNTKNTLYLQMNSLKPEDTAIYYCAAGLKRIGDQREADYWGQGTQVTVSS |
| 24 | MU738 | DVQLQASGGGLVQAGGSLRLSCAGSGRTFTNYDMGWFRQAPGKERRFVAAISGSGGSARYAVPVKGRFTIRDNAKNTVYLQMSSLKPEDTAVYYCAADRFVVAAGTHDLDYWGQGTQVTVSS |
| 25 | WF69 | DVQLQESGGGLVQAGGSLRLSCAGSGRTFTNYDMGWFRQAPGKERRFVAAISGSGGSARYAVPVKGRFTIRDNAKNTVYLQMSSLKPEDTAVYYCAADRFVVAAGTHDLDYWGQGTQVTVSS |

TABLE A-3-continued

| SEQ ID NO | NAME | AMINO ACID SEQUENCE |
|---|---|---|
| 26 | MU737 | DVQLQASGGGLVQAGGSLRLSCAGSGRSFSSYAMGWFRQAPGKAREIVATITRSGGSTNYA VPVKGRFTISRDNAKNTVYLQMSSLKPEDTAVYYCAADRFAVASGTHDLDYWGQGTQVTVS S |
| 27 | MU727 | DVQLQASGGGLVQAGGSLRLSCAGSGRTFSSYAMGWFRQAPGKEREFVASISWSGSRTNY GVPVKGRFTISRDNAKNTVYLQMSSLKPEDTAVYYCAADRFAVAIGTHDLDYWGQGTQVTV SS |
| 28 | Jk44 | QVQLQESGGGLVQAGGSLRLSCAASGRTDTRYTMGWFRQAPGKEREFVSGITWNGGTSYA DSVKGRFTISRDNGKNSVYLQMNSLKPEDTAVYYCAADRFTLVPTTSDLDYWGQGTQVTVSS |
| 29 | Jk33 | QVQLQESGGRLVQPGGSLRLSCAASGRTLSNYAMAWFRQGPGKEREFVASISASDSTLYADF VKGRFTISRDNAKNTVYLQMDSLKPEDTTVYYCAARFWIGVRAPAEYNYWGQGTQVTVSS |
| 30 | Jk22 | QVKLQESGGRLVQPGGSLRLSCAASGRTLSNYAMAWFRQGPGKEREFVASISASDSTLYADF VKGRFTISRDNAKNTVYLQMDSLKPEDTTVYYCAARFWIGVRAPAEYNYWGQGTQVTVSS |
| 31 | Jk35 | QVKLQESGGRLVQPGGSLRLSCAASGRTFSNYAMAWFRQGPGKEREFVAAISAADSTLYADF VKGRFTISRDNAKNTVYLQMNSLKPEDTAVYYCAARWWIAVRAPAEYNYWGQGTQVTVSS |
| 32 | Jk34 | QVQLQESGGRLVQPGGSLRLSCAASGRTFSNYAMAWFRQGPGKEREFVAAISAADSTLYAD FVKGRFTISRDNAKNTVYLQMNSLKPEDTAVYYCAARWWIAVRAPAEYNYWGQGTQVTVS S |
| 33 | MU397 | DVQLQASGGGLVQAGGSLRLSCAPSGGTFDAYDMGWYREAPGKKRQFVAAVRSGGGTTRY ADSVKGRFTISRDDAKDTVFLQMNSLKPEDTALYYCAADRWGLFSLSIATPTHWGQGTQVTV SS |
| 34 | MU1068 | DVQLQASGGGSVQEGESLKLSCVGSGRTFSDWAMGWYRQAPGKDREFVAAVSGAGRGGK PSYANSVKGRFTVSRDNAKNTVYLQMDNLKPEDTAVYYCAADRLVLVALSIADPGFWGQGT RVTVSS |
| 35 | MU274 | DVQLQESGGGLVQAGGSLRLSCAASGVSFSRYTMGWYREVPGKERREFVAAVRPSGDSTYY GNSVKGRFSISRDDDKNIVYLQMNSLKPEDTAVYYCAAGFPVLVALSIADPDYWGQGTQVTV ST |
| 36 | MU413 | DVQLQASGGGLVQTGDSLTVSCAASGLSFTRYTMGWYREVPGKERREFVAAVKPAGDSAYY GASVKGRFTASRDNAKNTVTLQMNSLKPEDTAIYYCAAGFPVLTALHIADPDYWGQGTQVT VSP |
| 37 | MU1053 | DVQLQESGGGLVQAGGSLRLSCTGSGRTFRNYPMAWFRQAPGKEREFVAGITWVGASTLY ADFAKGRFTISRDNAKNTVYLQMNSLKPEDTAVYSCAAGRGIVAGRIPAEYADWGQGTQVT VSS |
| 38 | Jk19 | QVQLQESGGGLVQAGGSLRLSCAASGRTFVSFGMGWFRQAPGKEREFVAAINWRGSTTAY ADSVKGRFTISRDVTKNTIYLQMNSLKPEDTAIYYCAEGRTASASTMIREYDSWGQGTQVTVS E |
| 39 | WF140 | DVQLQASGGGSVQAGGSLRLSCAASGLSFSDYAMGWFRQEPGKERRFVASIRSSGGTTYAES VKGRFTISRDNAKNTMYLQMNNLKPEDTAVYYCAADRLVITKLSIADPGYWGQGTQVTVSS |
| 40 | MU535 | VQLQASGGGLVQAGGSLRLSCTVSGFTSDDYTVGWFRQAPGLKREGLSCLSRRDGRFYHSNS VKGRFTMXSDDXKNTVYLQLDSLKPDXTAVXYCAACTSVVVLLAPNWYEYWGQGTQVTVSS |
| 41 | MU415 | VQLQASGGGLVQAGGSLRLSCTVSGFTSDDYTVGWFRQAPGLKREGLSCLSRRDGRFYHSNS VKGRFTMSSDDNKNTVYLQLDSLKPDDTAVYYCAATTSVVVLLAPNWYEYWGQGTQVTVSS |
| 42 | WF211 | EVQLVESGGGLVQAGESLRLSCAAGRTFTNLGMGWFRQAPGKEREFVAADTWSGTSTWYG DSVKGRFTISRDNAKNTVYLQMNNLKPEDTAVYYCAARLRGWITTRKPNEYDYWGQGTQVT VAS |
| 43 | WF121 | DVQLQESGGGLVQAGDSLRLSCEFSGRTFSGFAMGWFRQFPGKEREFVAAINWSGSDTDYS DSVKGRFTISRDNVKQMMYLAMNSLKPEDTAVYFCAEARSAGLGSSRRIEGYDKWGRGTQV TVSS |
| 44 | WF144 | DVQLQESGGGLVQAGDSLRLSCEFSGRTFSGFAMGWFRQFPGKEREFVAAINWSGSDTDYS DSVKGRFTISRDNVKQMMYLAMNSLKPEDTAVYFCAEARSAGLGSSRRIEGYDKWGRGTQV TVSS |
| 45 | WF129 | DVQLQASGGGLVQAGGSLRLSCEFSGRTFSGFAMGWFRQFPGKEREFVAAINWSGSSVDYS DSVKGRFTISRDNVKSTMYLVMNSLKPEDTAVYYCAEARSAELGSSRKIQGYDQWGRGTQV TVSS |

TABLE A-3-continued

| SEQ ID NO | NAME | AMINO ACID SEQUENCE |
|---|---|---|
| 46 | WF141 | DVQLQASGGGLVQAGGSLRLSCEFSGRTFSGFAMGWFRQFPGKEREFVAAINWSGSSVDYS DSVKGRFTISRDNVKSTMYLVMNSLKPEDTAVYYCAEARSAELGSSRKIQGYDQWGRGTRVT VSS |
| 47 | MU523 | DVQLQESGGGLVQAGSSLRISCAVSGVRLDNYAMGWFRQAPGKERESVAGISWSSGTLLYS DSVKGRFAISRDNAKNTVYLQMNSLKPEDTAVYYCAAQYQDRYYDEFTWKEKDMDYWGKG TLVTVSS |
| 48 | MU1065 | DVQLQESGGGLVQAGDSLRLSCAASGPHFNNYAIGWFRQAPGKEREFVAGISWSSGSLLYSD SVKGRFTISRDNDKNTAYLQMNSLKPEDTALYYCAAQYQERYYSDFSLKEKGMEYWGKGTLV TVSS |
| 49 | MU1067 | DVQLQESGGGLVQAGDSLRLSCVGSGRRFDNYAMAWFRQAPGKERTFVAAISWSSGTTRYL DTVKGRFTISRDNAKSTVYLQMNSLKPEDTAVYYCAARYQPRYYDSGDMDGYEYEFWGQGT QVTVSS |
| 50 | MU551 | DVQLQESGGGLVQAGHSLRLSCVGSGSRFDNYAMGWFRQAPGKEREFVAAISWSSGTTRYL DTVKGRFTISRDNAKSTVYLQMNSLKPEDTAVYYCAARYQPRYYDSGDMDGYEYDNWGQG TQVTVSS |
| 51 | WF124 | DVQLQASGGGLVQAGGSQRLSCAASGHTFSSYSMAWFRQAPGKEREFVAANSMSGTKTAY SDSVKGRFTISRDIPKNTVYLQMNSLKPEDTALYYCAAVDRSTGWDSWRDDPDQYDYWDQ GTQVTVSS |
| 52 | WF139 | SGGGLVQAGGSQRLSCAASGHTFSSYSMAWFRQAPGKEREFVAANIMSGTNTYYADSVRG RFTMSRDIAKNTVYLQMNSLKEEDTALYYCAAADRFRGWATWRDDPDQYDYWDQGTQVT VSS |
| 53 | MU725 | DVQLQESGGGLVQAGGSLRLSCAASGFTFDDYVIGWFRQAPGKEREGVSSISNNNSTYYADS VKGRFTIASDNAKNTVYLQMNSLKPEDTAVYYCAADVTLNPFTGWNTRSGPMYRYEYDYW GQGTQVTVSS |
| 54 | WF114 | VQLQESGGGLVQAGGSLRLSCAASGFTFDDYVIGWFRQAPGKECEGVSSISNNNSTYYADSV KGRFTIASDNAKNTVYLQMNSLKPEDTAVYYCAADVTLNPFTGWNTRSGPMYRYEYDYWG QGTQVTVSS |
| 55 | MU1103 | DVQLQASGGGLVQAGGSLRLSCAASEFTFDDYVIGWFRQAPGKEREGVSSISSDGSTYYADS VKGRFTISSDNAKNTVYLHMNSLKPEDTAVYYCAADVTLNPFTGWTTRSGPMYRYEYDYWG QGTQVTVSS |
| 56 | WF100 | VQLQASGGGLVQAGGSLRLSCAASGFTFDDYVIGWFRQSPGKEREGVSCISSAGSTYYADSV KGRFTISSDNAKNMVYLQMDNLKPEDTAVYYCAADVTLNPFTGWDTRSGPMYRYEYDYWG QGTQVTVSS |
| 57 | MU1105 | DVQLQASGGGLVQAGGSLRLSCAASGFTFDDYVIGWFRQAPGKEREGVSSISSSGSIYYADSV KGRFTISSDNAKNTVYLQMNSLKPEDTAVYFCAADVTLNPFTGWDTRSGPMYRYEYDYWG QGTQVTVSS |
| 58 | WF97 | DVQLQASGGGLVQAGGSLRLSCAASGFTFDDYVIGWFRQAPGKEREGVSSISSSGSIYYADSV KGRFTISSDNAKNTVYLQMNSLKPEDTAVYFCAADVTLNPFTGWDTRSGPMYRYEYDYWG QGTQVTVSS |

The invention claimed is:

1. A polypeptide construct comprising:
a first immunoglobulin single variable domain (ISVD) that specifically binds to CD38 with an $EC_{50}$ value of less than 200 nM, and
a second ISVD that specifically binds to CD38 with an $EC_{50}$ value of less than 200 nM,
wherein said first ISVD binds a first epitope of CD38 and said second ISVD binds a second epitope of CD38, wherein said first epitope is different from said second epitope,
the polypeptide construct further comprising a CH2 and a CH3 constant domain and optionally the polypeptide construct comprises one or more other groups, residues, moieties or binding units, optionally linked via one or more peptidic linkers,
wherein said first ISVD and said second ISVD each comprises 3 complementarity determining regions (CDRs), in which:

(i) CDR1 is chosen from the group consisting of SEQ ID NOs: 117-174;
(ii) CDR2 is chosen from the group consisting of SEQ ID NOs: 233-290; and
(iii) CDR3 is chosen from the group consisting of SEQ ID NOs: 349-406.

2. The polypeptide construct according to claim 1, wherein said first or second ISVD is chosen from the group consisting of
ISVDs represented by SEQ ID NOs: 1 to 58.

3. The polypeptide construct according to claim 1, wherein each set of 3 CDRs of said first ISVD and said second ISVD is selected from the group consisting of:
CDR1 is SEQ ID NO: 117, CDR2 is SEQ ID NO: 233 and CDR3 is SEQ ID NO: 349;
CDR1 is SEQ ID NO: 118, CDR2 is SEQ ID NO: 234 and CDR3 is SEQ ID NO: 350;
CDR1 is SEQ ID NO: 119, CDR2 is SEQ ID NO: 235 and CDR3 is SEQ ID NO: 351;

CDR1 is SEQ ID NO: 120, CDR2 is SEQ ID NO: 236 and CDR3 is SEQ ID NO: 352;
CDR1 is SEQ ID NO: 121, CDR2 is SEQ ID NO: 237 and CDR3 is SEQ ID NO: 353;
CDR1 is SEQ ID NO: 122, CDR2 is SEQ ID NO: 238 and CDR3 is SEQ ID NO: 354;
CDR1 is SEQ ID NO: 123, CDR2 is SEQ ID NO: 239 and CDR3 is SEQ ID NO: 355;
CDR1 is SEQ ID NO: 124, CDR2 is SEQ ID NO: 240 and CDR3 is SEQ ID NO: 356;
CDR1 is SEQ ID NO: 125, CDR2 is SEQ ID NO: 241 and CDR3 is SEQ ID NO: 357;
CDR1 is SEQ ID NO: 126, CDR2 is SEQ ID NO: 242 and CDR3 is SEQ ID NO: 358;
CDR1 is SEQ ID NO: 127, CDR2 is SEQ ID NO: 243 and CDR3 is SEQ ID NO: 359;
CDR1 is SEQ ID NO: 128, CDR2 is SEQ ID NO: 244 and CDR3 is SEQ ID NO: 360;
CDR1 is SEQ ID NO: 129, CDR2 is SEQ ID NO: 245 and CDR3 is SEQ ID NO: 361;
CDR1 is SEQ ID NO: 130, CDR2 is SEQ ID NO: 246 and CDR3 is SEQ ID NO: 362;
CDR1 is SEQ ID NO: 131, CDR2 is SEQ ID NO: 247 and CDR3 is SEQ ID NO: 363;
CDR1 is SEQ ID NO: 132, CDR2 is SEQ ID NO: 248 and CDR3 is SEQ ID NO: 364;
CDR1 is SEQ ID NO: 133, CDR2 is SEQ ID NO: 249 and CDR3 is SEQ ID NO: 365;
CDR1 is SEQ ID NO: 134, CDR2 is SEQ ID NO: 250 and CDR3 is SEQ ID NO: 366;
CDR1 is SEQ ID NO: 135, CDR2 is SEQ ID NO: 251 and CDR3 is SEQ ID NO: 367;
CDR1 is SEQ ID NO: 136, CDR2 is SEQ ID NO: 252 and CDR3 is SEQ ID NO: 368;
CDR1 is SEQ ID NO: 137, CDR2 is SEQ ID NO: 253 and CDR3 is SEQ ID NO: 369;
CDR1 is SEQ ID NO: 138, CDR2 is SEQ ID NO: 254 and CDR3 is SEQ ID NO: 370;
CDR1 is SEQ ID NO: 139, CDR2 is SEQ ID NO: 255 and CDR3 is SEQ ID NO: 371;
CDR1 is SEQ ID NO: 140, CDR2 is SEQ ID NO: 256 and CDR3 is SEQ ID NO: 372;
CDR1 is SEQ ID NO: 141, CDR2 is SEQ ID NO: 257 and CDR3 is SEQ ID NO: 373;
CDR1 is SEQ ID NO: 142, CDR2 is SEQ ID NO: 258 and CDR3 is SEQ ID NO: 374;
CDR1 is SEQ ID NO: 143, CDR2 is SEQ ID NO: 259 and CDR3 is SEQ ID NO: 375;
CDR1 is SEQ ID NO: 144, CDR2 is SEQ ID NO: 260 and CDR3 is SEQ ID NO: 376;
CDR1 is SEQ ID NO: 145, CDR2 is SEQ ID NO: 261 and CDR3 is SEQ ID NO: 377;
CDR1 is SEQ ID NO: 146, CDR2 is SEQ ID NO: 262 and CDR3 is SEQ ID NO: 378;
CDR1 is SEQ ID NO: 147, CDR2 is SEQ ID NO: 263 and CDR3 is SEQ ID NO: 379;
CDR1 is SEQ ID NO: 148, CDR2 is SEQ ID NO: 264 and CDR3 is SEQ ID NO: 380;
CDR1 is SEQ ID NO: 149, CDR2 is SEQ ID NO: 265 and CDR3 is SEQ ID NO: 381;
CDR1 is SEQ ID NO: 150, CDR2 is SEQ ID NO: 266 and CDR3 is SEQ ID NO: 382;
CDR1 is SEQ ID NO: 151, CDR2 is SEQ ID NO: 267 and CDR3 is SEQ ID NO: 383;
CDR1 is SEQ ID NO: 152, CDR2 is SEQ ID NO: 268 and CDR3 is SEQ ID NO: 384;
CDR1 is SEQ ID NO: 153, CDR2 is SEQ ID NO: 269 and CDR3 is SEQ ID NO: 385;
CDR1 is SEQ ID NO: 154, CDR2 is SEQ ID NO: 270 and CDR3 is SEQ ID NO: 386;
CDR1 is SEQ ID NO: 155, CDR2 is SEQ ID NO: 271 and CDR3 is SEQ ID NO: 387;
CDR1 is SEQ ID NO: 156, CDR2 is SEQ ID NO: 272 and CDR3 is SEQ ID NO: 388;
CDR1 is SEQ ID NO: 157, CDR2 is SEQ ID NO: 273 and CDR3 is SEQ ID NO: 389;
CDR1 is SEQ ID NO: 158, CDR2 is SEQ ID NO: 274 and CDR3 is SEQ ID NO: 390;
CDR1 is SEQ ID NO: 159, CDR2 is SEQ ID NO: 275 and CDR3 is SEQ ID NO: 391;
CDR1 is SEQ ID NO: 160, CDR2 is SEQ ID NO: 276 and CDR3 is SEQ ID NO: 392;
CDR1 is SEQ ID NO: 161, CDR2 is SEQ ID NO: 277 and CDR3 is SEQ ID NO: 393;
CDR1 is SEQ ID NO: 162, CDR2 is SEQ ID NO: 278 and CDR3 is SEQ ID NO: 394;
CDR1 is SEQ ID NO: 163, CDR2 is SEQ ID NO: 279 and CDR3 is SEQ ID NO: 395;
CDR1 is SEQ ID NO: 164, CDR2 is SEQ ID NO: 280 and CDR3 is SEQ ID NO: 396;
CDR1 is SEQ ID NO: 165, CDR2 is SEQ ID NO: 281 and CDR3 is SEQ ID NO: 397;
CDR1 is SEQ ID NO: 166, CDR2 is SEQ ID NO: 282 and CDR3 is SEQ ID NO: 398;
CDR1 is SEQ ID NO: 167, CDR2 is SEQ ID NO: 283 and CDR3 is SEQ ID NO: 399;
CDR1 is SEQ ID NO: 168, CDR2 is SEQ ID NO: 284 and CDR3 is SEQ ID NO: 400;
CDR1 is SEQ ID NO: 169, CDR2 is SEQ ID NO: 285 and CDR3 is SEQ ID NO: 401;
CDR1 is SEQ ID NO: 170, CDR2 is SEQ ID NO: 286 and CDR3 is SEQ ID NO: 402;
CDR1 is SEQ ID NO: 171, CDR2 is SEQ ID NO: 287 and CDR3 is SEQ ID NO: 403;
CDR1 is SEQ ID NO: 172, CDR2 is SEQ ID NO: 288 and CDR3 is SEQ ID NO: 404;
CDR1 is SEQ ID NO: 173, CDR2 is SEQ ID NO: 289 and CDR3 is SEQ ID NO: 405; and
CDR1 is SEQ ID NO: 174, CDR2 is SEQ ID NO: 290 and CDR3 is SEQ ID NO: 406.

4. The polypeptide construct according to claim 1, wherein said first ISVD essentially consists of 4 framework regions (FR1 to FR4, respectively) and said 3 CDRs, in which:
(i) CDR1 is chosen from the group consisting of SEQ ID NOs: 131, 132, 134, 140, 144, 146, 150, 151, 152, 153, 155, and 158, and
(ii) CDR2 is chosen from the group consisting of SEQ ID NOs: 247, 248, 250, 256, 260, 262, 266, 267, 268, 269, 271, and 274, and
(iii) CDR3 is chosen from the group consisting of SEQ ID NOs: 363, 364, 366, 372, 376, 378, 382, 383, 384, 385, 387, and 390; and
said second ISVD essentially consists of 4 framework regions (FR1 to FR4, respectively) and said 3 CDRs, in which:
(i) CDR1 is chosen from the group consisting of SEQ ID NOs: 129, 163, 164, 165, and 166, and
(ii) CDR2 is chosen from the group consisting of SEQ ID NOs: 245, 279, 280, 281, and 282, and
(iii) CDR3 is chosen from the group consisting of SEQ ID NOs: 361, 395, 396, 397, and 398; or wherein said first ISVD essentially consists of 4 framework regions (FR1 to FR4, respectively) and said 3 CDRs, in which:
  (i) CDR1 is chosen from the group consisting of SEQ ID NOs: 131, 132, 134, 140, 144, 146, 150, 151, 152, 153, 155, and 158, and
  (ii) CDR2 is chosen from the group consisting of SEQ ID NOs: 247, 248, 250, 256, 260, 262, 266, 267, 268, 269, 271, and 274, and
  (iii) CDR3 is chosen from the group consisting of SEQ ID NOs: 363, 364, 366, 372, 376, 378, 382, 383, 384, 385, 387, and 390; and
said second ISVD essentially consists of 4 framework regions (FR1 to FR4, respectively) and said 3 CDRs, in which:
  (i) CDR1 is chosen from the group consisting of SEQ ID NOs: 117, 119, 120, 125, 126, 136, 159, 160, 161, 162, 167, 168, 169, 170, 171, 172, 173, and 174, and
  (ii) CDR2 is chosen from the group consisting of SEQ ID NOs: 233, 235, 236, 241, 242, 252, 275, 276, 277, 278, 283, 284, 285, 286, 287, 288, 289, and 290, and
  (iii) CDR3 is chosen from the group consisting of SEQ ID NOs: 349, 351, 352, 357, 358, 368, 391, 392, 393, 394, 399, 400, 401, 402, 403, 404, 405, and 406; or
wherein said first ISVD essentially consists of 4 framework regions (FR1 to FR4, respectively) and said 3 CDRs, in which:
  (i) CDR1 is chosen from the group consisting of SEQ ID NOs: 129, 163, 164, 165, and 166, and
  (ii) CDR2 is chosen from the group consisting of SEQ ID NOs: 245, 279, 280, 281, and 282, and
  (iii) CDR3 is chosen from the group consisting of SEQ ID NOs: 361, 395, 396, 397, and 398; and
said second ISVD essentially consists of 4 framework regions (FR1 to FR4, respectively) and said 3 CDRs, in which:
  (i) CDR1 is chosen from the group consisting of SEQ ID NOs: 117, 119, 120, 125, 126, 136, 159, 160, 161, 162, 167, 168, 169, 170, 171, 172, 173, and 174, and
  (ii) CDR2 is chosen from the group consisting of SEQ ID NOs: 233, 235, 236, 241, 242, 252, 275, 276, 277, 278, 283, 284, 285, 286, 287, 288, 289, and 290, and
  (iii) CDR3 is chosen from the group consisting of SEQ ID NOs: 349, 351, 352, 357, 358, 368, 391, 392, 393, 394, 399, 400, 401, 402, 403, 404, 405, and 406.

5. The polypeptide construct according to claim 1, wherein the $EC_{50}$ in a FACS assay is 190 pM or less; and/or
wherein said polypeptide binds to CD38 with an $IC_{50}$ of at most 100 nM as determined by a competition FACS; and/or
wherein said polypeptide binds to CD38 with an $IC_{50}$ which is at least 10% better than the $IC_{50}$ of a benchmark.

6. A pharmaceutical composition comprising a polypeptide construct according to claim 1.

7. The polypeptide construct according to claim 1, wherein the $EC_{50}$ in a FACS assay is less than 16 pM; and/or
wherein said polypeptide binds to CD38 with an $IC_{50}$ of at most 2 nM as determined by a competition FACS; and/or
wherein said polypeptide binds to CD38 with an $IC_{50}$ which is at least 50% better than the $IC_{50}$ of a benchmark.

8. The polypeptide construct according to claim 1, wherein said first and second ISVDs each specifically bind to human CD38 (SEQ ID NO: 465).

9. The polypeptide construct according to claim 1, wherein said first epitope on CD38 does not overlap with said second epitope on CD38.

10. A nucleic acid molecule that encodes a polypeptide construct according to claim 1.

11. An expression vector comprising a nucleic acid molecule according to claim 10.

12. A host cell comprising a nucleic acid molecule according to claim 10.

13. A method for the recombinant production of a polypeptide, comprising (a) culturing the host cell of claim 12 under conditions which allow the expression of the nucleic acid molecule; and (b) isolating the polypeptide from the culture.

14. A method of therapeutic treatment comprising administering, to a subject in need thereof, a pharmaceutically active amount of a polypeptide construct according to claim 1 for therapeutic treatment of a disease which is characterized by increased CD38 expression.

15. The method of claim 14, wherein said disease which is characterized by increased CD38 expression is a hyperproliferative disease or an autoimmune disease.

16. A method of therapeutic treatment comprising administering, to a subject in need thereof, a pharmaceutically active amount of a polypeptide construct according to claim 1 for therapeutic treatment of Burkitt's lymphoma, T-cell lymphoma, hairy cell leukemia, chronic lymphocytic leukemia (CLL), multiple myeloma, chronic myelogenous leukemia (CIVIL), acute myeloid leukemia (AML), acute lymphoblastic leukemia (ALL), CD38-expressing solid tumor, systemic lupus erythematosus (SLE), rheumatoid arthritis, Crohn's disease, ulcerative colitis, Hashimoto's thyroiditis, ankylosing spondylitis, multiple sclerosis, Graves' disease, Sjögren's syndrome, polymyositis, bullous pemphigoid, glomerulonephritis, vasculitis or asthma, Barraquer-Simons Syndrome, autoimmune heart disease, inflammatory bowel disease, paroxysmal nocturnal hemoglobinuria, atypical hemolytic uremic syndrome, ischemia-reperfusion injuries or rejection of transplanted organs.

17. A method for determining competitor polypeptides competing with a polypeptide represented by SEQ ID NOs: 1-58, comprising
  determining binding of said competitor polypeptide in the presence of polypeptide represented by SEQ ID NOs: 1-58 to CD38;
  detecting a competitor polypeptide when the binding to CD38 of said competitor polypeptide is reduced by at least 10% in the presence of a polypeptide represented by SEQ ID NOs: 1-58, compared to the binding to CD38 of the competitor in the absence of the polypeptide represented by SEQ ID NOs: 1-58.

* * * * *